(12) United States Patent
Yamawaki et al.

(10) Patent No.: US 8,883,773 B2
(45) Date of Patent: *Nov. 11, 2014

(54) CEPHEM COMPOUND HAVING PSEUDO-CATECHOL GROUP

(75) Inventors: Kenji Yamawaki, Toyonaka (JP); Hideki Sugimoto, Toyonaka (JP); Masayuki Sano, Toyonaka (JP)

(73) Assignee: Shionogi & Co., Ltd., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/639,427

(22) PCT Filed: Apr. 4, 2011

(86) PCT No.: PCT/JP2011/058497
§ 371 (c)(1), (2), (4) Date: Dec. 6, 2012

(87) PCT Pub. No.: WO2011/125966
PCT Pub. Date: Oct. 13, 2011

(65) Prior Publication Data
US 2013/0079319 A1    Mar. 28, 2013

(30) Foreign Application Priority Data

Apr. 5, 2010    (JP) .................................. 2010-087130

(51) Int. Cl.
*A61K 31/546*    (2006.01)
*C07D 501/46*    (2006.01)

(52) U.S. Cl.
CPC .................................... *C07D 501/46* (2013.01)
USPC .......................................... 514/203; 540/225

(58) Field of Classification Search
USPC ................................. 540/215, 217
See application file for complete search history.

(56) References Cited

U.S. PATENT DOCUMENTS

| 4,906,623 | A | 3/1990 | Matsumura et al. | |
|---|---|---|---|---|
| 5,104,866 | A * | 4/1992 | Sakane et al. | 514/206 |
| 5,143,910 | A | 9/1992 | Onoue et al. | |
| 5,149,803 | A | 9/1992 | Davies et al. | |
| 5,244,890 | A | 9/1993 | Yamanaka et al. | |
| 2005/0153950 | A1 | 7/2005 | Nishitani et al. | |
| 2011/0190254 | A1 | 8/2011 | Nishitani et al. | |
| 2013/0096299 | A1 | 4/2013 | Kusano et al. | |
| 2013/0102583 | A1 | 4/2013 | Hisakawa et al. | |

FOREIGN PATENT DOCUMENTS

| AU | 676218 | 3/1997 |
|---|---|---|
| DE | 25 19 400 | 3/1976 |
| EP | 0 114 752 | 8/1984 |
| EP | 0 168 177 | 1/1986 |
| EP | 0 211 656 | 2/1987 |
| EP | 0 241 901 | 10/1987 |
| EP | 0 305 111 | 3/1989 |
| EP | 0 345 671 | 12/1989 |
| EP | 0 346 465 | 12/1989 |
| EP | 0 474 049 | 3/1992 |
| EP | 0 485 808 | 5/1992 |
| EP | 1 489 084 | 12/2004 |
| EP | 2 341 053 | 7/2011 |
| JP | 57-118588 | 7/1982 |
| JP | 62-30788 | 2/1987 |
| JP | 62-158291 | 7/1987 |
| JP | 2-15090 | 1/1990 |
| JP | 2-28185 | 1/1990 |
| JP | 2-28187 | 1/1990 |
| JP | 2-117678 | 5/1990 |
| JP | 4-364189 | 12/1992 |
| JP | 5-213971 | 8/1993 |
| JP | 6-345776 | 12/1994 |
| WO | WO 86/05183 | 9/1986 |
| WO | WO 92/21683 | 12/1992 |

(Continued)

OTHER PUBLICATIONS

Tashiro, Tatsuo. Macromol. Mater. Eng. 2001, 286, 63-87.*

(Continued)

*Primary Examiner* — Golam M M Shameem
*Assistant Examiner* — Laura Daniel
(74) *Attorney, Agent, or Firm* — Hamre, Schumann, Mueller & Larson, P.C.

(57) ABSTRACT

A compound of the formula:

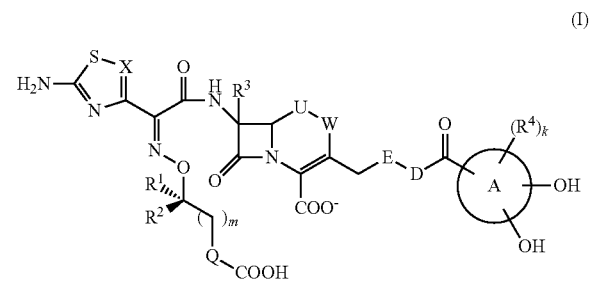

wherein
X is —N=, —CH=, or the like;
W is —CH$_2$— or the like;
U is —S— or the like;
R$^1$ and R$^2$ are each independently hydrogen, halogen, optionally substituted lower alkyl, or the like;
Q is a single bond or the like;
R$^3$ is hydrogen or the like;
Ring A is a 6-membered aromatic heterocyclic group having 1-3 nitrogen atoms;
each R$^4$ is independently hydrogen, halogen, or the like;
m is an integer from 0 to 2;
G is —C(=O)— or the like;
D is a single bond, —NH—, or the like; and
E is a cyclic quaternary ammonium group,
or an ester, a protected compound at the amino on the ring in the 7-side chain, a pharmaceutically acceptable salt, or a solvate thereof.

22 Claims, No Drawings

(56) References Cited

FOREIGN PATENT DOCUMENTS

| WO | WO 99/33839 | 7/1999 |
|---|---|---|
| WO | WO 03/099826 | 12/2003 |
| WO | WO 2006/104141 | 10/2006 |
| WO | WO 2007/096740 | 8/2007 |
| WO | WO 2007/119511 | 10/2007 |

OTHER PUBLICATIONS

Wermuth, Camille G. "Molecular Variations Based on Isoteric Replacements." The Practice of Medicinal Chemistry. Academic Press, 1996. pp. 203-237.*

Takeda et al. "In Vitro Antibacterial Activity of a New Cephalosporin, FR295389, against IMP-type Metallo-β-lactamase-producers". *J. Antibiot.*, vol. 61, No. 1, pp. 36-39 (2008).

Hashizume et al. "Comparison of Transport Pathways of Catechol-Substituted Cephalosporins, BO-1236, and BO-1341, through the Outer Membrane of *Escherichia coli*". *The Journal of Antibiotics*, vol. 43, No. 12, pp. 1617-1620 (1990).

Okita et al. "Synthesis and Antibacterial Activity of Cephalosporins having a Catechol in the C3 Side Chain". *The Journal of Antibiotics*, vol. 46, No. 5, pp. 833-839 (1993).

Imae et al. "Cephalosporins having a Heterocyclic Catechol in the C3 Side Chain". *The Journal of Antibiotics*, vol. 46, pp. 840-849 (1993).

Imura et al. "Cephalosporins having a Heterocyclic Catechol in the C3 Side Chain". *The Journal of Antibiotics*, vol. 46, pp. 850-857 (1993).

Baudart et al. "Synthesis and Biological Activity of C-3' *Ortho* Dihydroxyphthalimido Cephalosporin". *The Journal of Antibiotics*, vol. 46, pp. 1458-1470 (1993).

Choi et al. "Studies on New Catechol containing Cephalosporin". *The Journal of Antibiotics*, vol. 48, No. 11, pp. 1371-1374 (1995).

Arnould et al. "Synthesis and Structure-Activity Relationship of Cephalosporins with C-3' Catechol-Containing Residues". *J. Med. Chem.*, vol. 35, pp. 2631-2642 (1992).

Bird et al. "Pharmacokinetics of Catechol Cephalosporins. The Effect of Incorporating Substituents into the Catechol Moiety on Pharmacokinetics in a Marmoset Model". *J. Med. Chem.*, vol. 35, pp. 2643-2651 (1992).

Tsuji et al. "Synthesis and Antibacterial Activity of Cephalosporins having C-3 Catechol-Containing (Pyridinium-4'-Thio) Methyl Groups". *Bioorganic and Medicinal Chemistry Letters*, vol. 5, No. 9, pp. 963-966 (1995).

Adams et al. "Structure-activity Relationships within a Series of C(7)-Substitutedoxyiminocephalosporins containing the C(3)-Methylaminopyridiniumthiomethyl Substituent Synthesis and Biological Properties of BRL 57342 and Some Close Analogues". *The Journal of Antibiotics*, vol. 48, No. 5, pp. 417-424 (1995).

Mochizuki et al. "Antibacterial and Pharmacokinetic Properties of M14659, A new Injectable Semisynthetic Cephalosporin". *The Journal of Antibiotics*, vol. 41, No. 3, pp. 377-391 (1988).

Kim et al. "Synthesis of Antibacterial Activities of Novel C(7)-Catechol-substituted Cephalosporins". *The Journal of Antibiotics*, vol. 49, pp. 496-498 (1996).

Guest et al. "Synthesis and Biological Activity of 3-(N-Substituted Pyridiuium-4-Thiomethyl)-7α-Formamido Cephalosporins". *The Journal of Antibiotics*, vol. 46, No. 8, pp. 1279-1288 (1993).

Yamano et al. "Ferric iron transport system of *Pseudomonas aeruginosa* PA01 that functions as the uptake pathway of a novel catechol-substituted cephalosporin, S-9096". *Appl. Microbiol. Biotechnol.*, vol. 40, pp. 892-897 (1994).

Yamawaki et al. "A novel series of parenteral cephalosporins exhibiting potent activities against *Pseudomonas aeruginosa* and other Gram-negative pathogens: Synthesis and structure-activity relationships". *Bioorganic of Medicinal Chemistry*, vol. 15, pp. 6716-6732 (2007).

Almeida et al. "Synthesis of N-(2-chloro-3,4-dimethoxybenzylideneamino)guanidinium acetate [α-$^{14}$C]". *Journal of Labelled Compounds and Radiopharmaceuticals*, vol. 45, pp. 371-377 (2002).

Obi et al. "Novel Cephalosporins having a Benzothiopyran Group-Synthesis and Biological Activity of Catecholic Benzothiopyrain Group at the C-3 Side Chain". *The Journal of Antibiotics*, vol. 48, pp. 278-281 (1995).

Yamano et al.. "Ferric iron transport system of *Pseudomonas aeruginosa* PA01 that functions as the uptake pathway of a novel catechol-substituted cephalosporin, S-9096". *Appl. Microbiol. Biotechnol.*, vol. 40, pp. 892-897 (1994).

Takeda et al. "In Vitro Antibacterial Activity of a New Cephalosporin, FR295389, against IMP-type Metallo-β-lactamase-producers". *J. Antibio.*, vol. 61, No. 1., pp. 36-39 (2008).

Hashizume et al. "Comparison of Transport Pathways of Catechol-Substituted Cephalosporins, BO-1236 and BO-1341, Through the Outer Membrane of *Escherichia coli*". *The Journal of Antibiotics*, vol. 43, No. 12, pp. 1617-1620 (1990).

Weissberger et al. "L-658,310, A New Injectable Cephalosporin". *The Journal of Antibiotics*, vol. 42, No. 5, pp. 795-806 (1989).

Branch et al. "Studies on Semi-Synthetic 7 α-Formamidocephalosporins". *The Journal of Antibiotics*, vol. 40, pp. 646-651 (1987).

Bryskier. *Clinical Microbiology and Infection*, vol. 3, Supplement 1, Apr. 1997, pp. S1-S6.

Silley et al. *Antimicrobial Agents and Chemotherapy*, vol. 34, No. 9, Sep. 1990, pp. 1806-1808.

* cited by examiner

CEPHEM COMPOUND HAVING PSEUDO-CATECHOL GROUP

TECHNICAL FIELD

The invention is related to cephem compounds, which have a wide antimicrobial spectrum, and in particular exhibit potent antimicrobial activity against beta-lactamase producing Gram negative bacteria, and pharmaceutical composition comprising the same.

BACKGROUND ART

To date, a variety of beta-lactam drugs have been developed and beta-lactam drugs have become clinically extremely important antimicrobial drugs. However, there are increasing number of bacterial types which have obtained resistance against beta-lactam drugs by producing beta-lactamase, which degrade beta-lactam drugs.

According to the Ambler molecular classification, beta-lactamase are largely classified into four classes. Specifically, those are Class A (TEM type, SHV type, CTX-M type and the like), Class B (IMP type, VIM type, L-1 type and the like), Class C (AmpC type) and Class D (OXA type and the like). Amongst these, Classes A, C and D types are largely classified into serine-beta-lactamase, and on the other hand, Class B type is classified into metallo-beta-lactamase. It has been known that both have respectively different mechanisms to each other in terms of hydrolysis of beta-lactam drugs.

Recently, clinical problem has been occurring due to the existence of Gram negative bacteria which have become highly resistant to a number of beta-lactam drugs including Cephems and Carbapenems by producing Class A (ESBL) and D types serine-beta-lactamases which have an extended substrate spectrum, and Class B type metallo-beta-lactamase which have an extended substrate spectrum. Particularly, metallo-beta-lactamase is known to be one of the causes of obtaining multi-resistance in Gram negative bacteria. Cephem compounds which exhibit intermediate activity against metallo-beta-lactamase producing Gram negative bacteria are known (e.g., Patent Document 1 and Non-Patent Document 1). However, there is a demand for development of Cephem compounds which exhibit more potent antimicrobial activity, in particular more effective against a variety of beta-lactamase producing Gram negative bacteria.

One of the known antimicrobials having high anti-Gram negative bactericidal activity is Cephem compounds having a catechol group intramolecularly (e.g., Non-patent Documents 2-4). The action thereof is that the catechol group forms a chelate with $Fe^{3+}$, thereby the compound is efficiently incorporated into the bacterial body through the $Fe^{3+}$ transportation system on the cellular membrane (tonB-dependent iron transport system). Therefore, research has been conducted on compounds having catechol or similar structure thereto, on the 3-side chain or 7-side chain moiety on the Cephem backbone.

Patent Documents 2-5 describe pseudo-catechol type derivatives having a hydroxypyridone group on the 3-side chain moiety on the Cephem backbone. Non-patent Documents 2-11 and 16 disclose compounds having a catechol group or a structure similar thereto on the 3-side chain moiety of the Cephem backbone.

Patent Document 6 and Non-patent Documents 12-15 disclose compounds having a catechol group or a pseudo-catechol structure on the 7-side chain moiety of the Cephem backbone.

Non-patent Documents 9, 10 and 12-15 describe Cephem compounds which have been Stabilized against beta-lactamase.

However, these documents do not describe the compounds of the subject invention. Furthermore, these documents, which describe Cephem compounds having catechol group intramolecularly, have no specific description regarding metallo-beta-lactamase of Class B type, or antimicrobial activity against wide spectrum of Gram negative bacteria including Class B type.

Patent Documents 7 and 8 do not specifically disclose Cephem compounds having catechol type substituents. On the other hand, the present applicant filed an application of Cephem compounds having catechol type substituents (Patent Document 9).

PRIOR ART DOCUMENT

Patent Documents

Patent Document 1: WO 2007/119511 A1
Patent Document 2: JP 2-15090 A
Patent Document 3: JP 2-28187 A
Patent Document 4: JP 6-510523 A
Patent Document 5: JP 5-213971 A
Patent Document 6: JP 6-345776 A
Patent Document 7: WO 2007/09674
Patent Document 8: WO 2003/078440 A1
Patent Document 9: International Patent Application No. PCT/JP2009/068400

Non-Patent Documents

Non-patent document 1: The Journal of Antibiotics, vol. 61, pp. 36-39 (2008)
Non-patent document 2: The Journal of Antibiotics, vol. 43, pp. 1617-1620 (1990)
Non-patent document 3: The Journal of Antibiotics, vol. 42, pp. 795-806 (1989)
Non-patent document 4: The Journal of Antibiotics, vol. 46, pp. 833-839 (1993)
Non-patent document 5: The Journal of Antibiotics, vol. 46, pp. 840-849 (1993)
Non-patent document 6: The Journal of Antibiotics, vol. 46, pp. 850-857 (1993)
Non-patent document 7: The Journal of Antibiotics, vol. 46, pp. 1458-1470 (1993)
Non-patent document 8: The Journal of Antibiotics, vol. 48, pp. 1371-1374 (1995)
Non-patent document 9: The Journal of Medicinal Chemistry, vol. 35, pp. 2631-2642 (1992)
Non-patent document 10: The Journal of Medicinal Chemistry, vol. 35, pp. 2643-2651 (1992)
Non-patent document 11: Bioorganic & Medicinal Chemistry Letters, vol. 5, pp. 963-966 (1995)
Non-patent document 12: The Journal of Antibiotics, vol. 48, pp. 417-121 (1995)
Non-patent document 13: The Journal of Antibiotics, vol. 41, pp. 377-391 (1988)
Non-patent document 14: The Journal of Antibiotics, vol. 49, pp. 496-498 (1996)
Non-patent document 15: The Journal of Antibiotics, vol. 46, pp. 1279-1288 (1993)
Non-patent document 16: Applied Microbiology and Biotechnology, vol. 40, pp. 892-897 (1994)

SUMMARY OF INVENTION

Problems to be Solved by the Invention

The subject invention provides Cephem compounds which exhibit potent antimicrobial spectrum against a variety of bacteria including Gram negative bacteria and/or Gram positive bacteria.

Preferably, the subject invention provides Cephem compounds which exhibit potent antimicrobial activity against beta-lactamase producing Gram negative bacteria.

More preferably, the subject invention provides Cephem compounds which exhibit potent antimicrobial activity against multi-drug resistant bacteria, in particular, Class B type metallo-beta-lactamase producing Gram negative bacteria.

Still preferably, the subject invention provides Cephem compounds which exhibit effective antimicrobial activity against extended-spectrum beta-lactanae (ESBL) producing bacteria.

Most preferably, the subject invention provides Cephem compounds which do not exhibit cross-resistance against known Cephem drug or Carbapenem drugs.

Means for Solving the Problems

The subject invention provides Cephem compounds which have solved the above-mentioned problems, at least based on the following structural features:

1) The compounds of the subject invention have a cyclic quaternary ammonium group (-E-) on the 3-side chain, and a pseudo-catechol group (ring A) on the terminal thereof. Preferably, they have one chlorine atom on the aromatic heterocycle of ring A;

2) The compounds of the subject invention have a spacer moiety (-D-C(=O)—) between the quaternary ammonium group (-E-) and the pseudo-catechol group (ring A);

3) In the spacer moiety (-D-C(=C)—), it is particularly preferable that D is a chain structure;

4) The compounds of the subject invention have an aminothiadiazole ring or aminothiazole ring on the 7-side chain, and a carboxylic group on the terminus of the oxime moiety; and 5) The feature of another embodiment of the compounds of the subject invention is to have a non-cyclic quaternary ammonium group on the 3-side chain, and a pseudo-catechol group (ring A) on the terminus thereof. In this case, D of the spacer moiety (-D-C(=O)—) is a cyclic group.

Specifically, the subject invention provides the following inventions:

(Item 1)
A compound of the formula:

[Formula I]

or an ester, a protected compound at the amino on the ring in the 7-side chain, a pharmaceutically acceptable salt, or a solvate thereof, wherein X is —N=, —CH=, —C(—$R^5$)=, —C(—Br)= or —C(—Cl)=;

$R^5$ is lower alkyl or halo(lower)alkyl;

W is —$CH_2$—, —S— or —O—;

U is —$CH_2$, —S—, or —O— when W is —$CH_2$—, and U is —$CH_2$— when W is —S— or —O—;

$R^1$ and $R^2$ are independently hydrogen atom, halogen, hydroxy, carboxy, optionally substituted lower alkyl, optionally substituted carbocyclic group or optionally substituted heterocyclic group; or $R^1$ and $R^2$ are taken together with a neighboring atom to form an optionally substituted carbocyclic group or an optionally substituted heterocyclic group;

Q is a single bond, optionally substituted carbocyclic group or optionally substituted heterocyclic group;

Ring A is a 6-membered aromatic heterocyclic group having 1-3 nitrogen atoms;

$R^3$ is a hydrogen atom, —$OCH_3$ or —NH—CH(=O);

k is an integer from 0 to 2;

m is an integer from 0 to 2;

each $R^4$ is independently hydrogen atom, halogen, hydroxy, —CN, —C(=O)—$R^6$, —C(=O)—OH, or —$OR^6$;

$R^6$ is lower alkyl or halo(lower)alkyl;

with regard to D and E, a) D is a single bond, —N($R^8$)— or —$R^7$—N($R^8$)— wherein $R^7$ is an optionally substituted lower alkylene and $R^8$ is hydrogen or lower alkyl, and E is an optionally substituted cyclic group selected from the following formulae (1) to (40); or b) D is the formula:

[Formula 2]

wherein g is 0 or 1, and

E is a group of formula (10) or (41) in the following formulae of Substituent E:

[Formula 3]

(1)

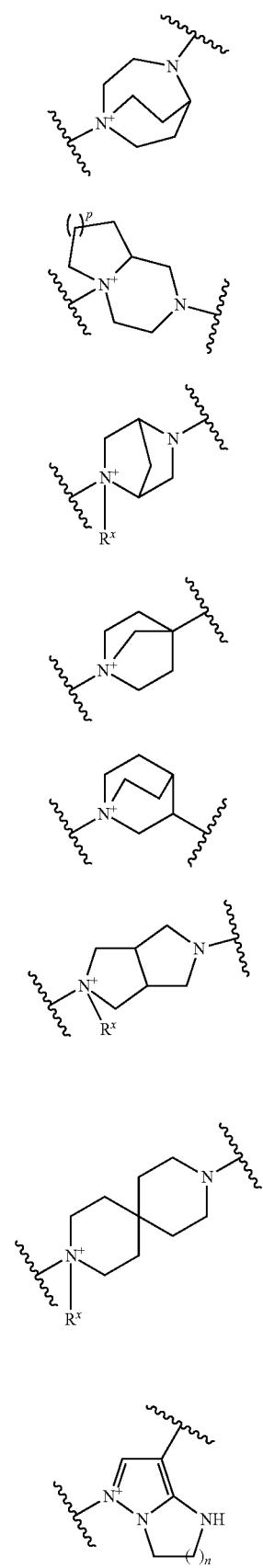
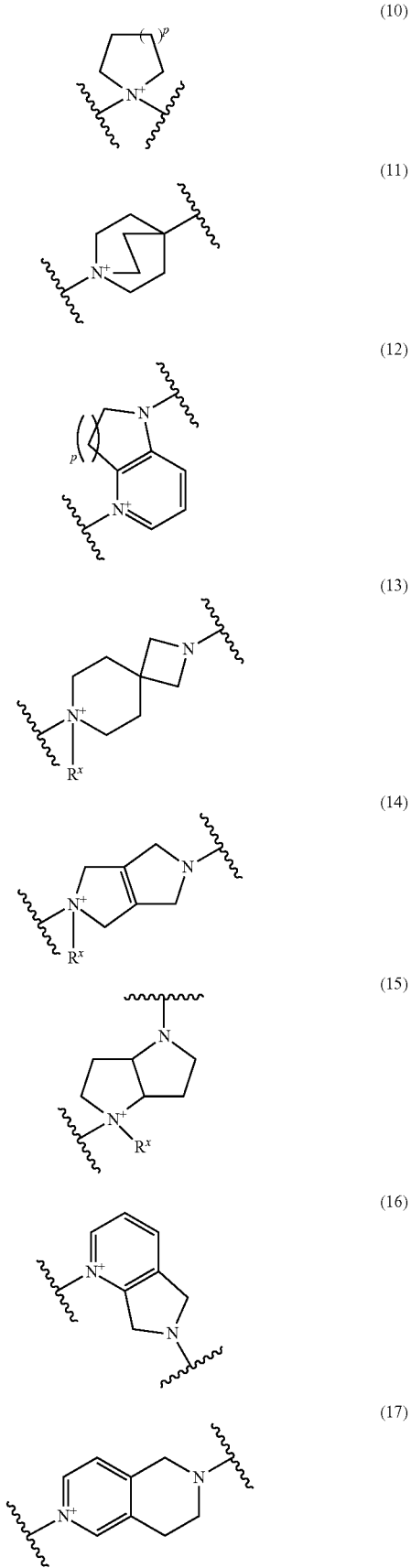

-continued
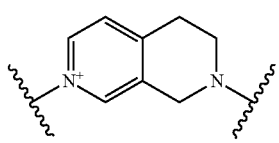 [SMILES: *N1CCc2cc[n+](*)cc2C1]
(18)
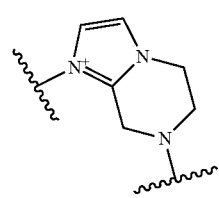
(19)
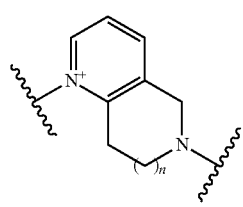 [SMILES: *N1CCc2c(ccc[n+]2*)C1]
(20)
[Formula 4]
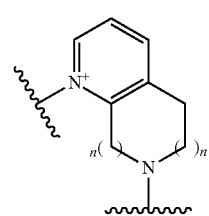
(21)
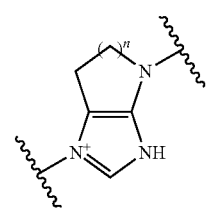
(22)
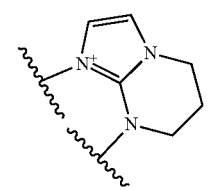
(23)
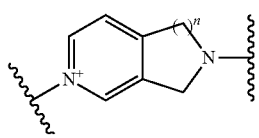
(24)
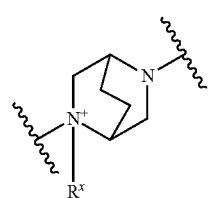
(25)
-continued
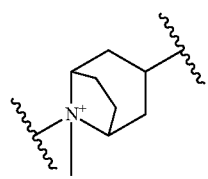
(26)
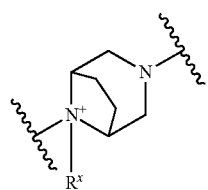
(27)
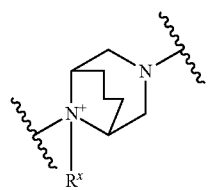
(28)
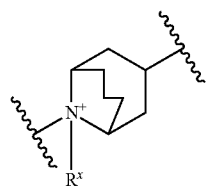
(29)
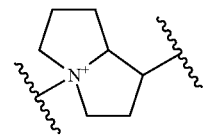
(30)
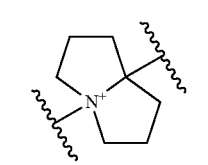
(31)
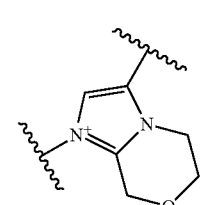
(32)
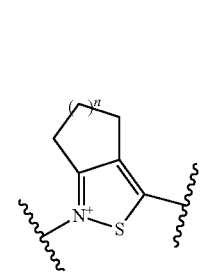
(33)

-continued

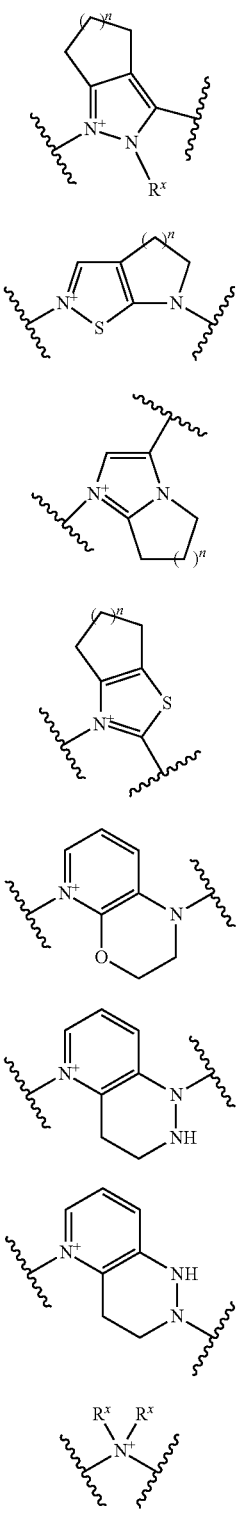

(34)

(35)

(36)

(37)

(38)

(39)

(40)

(41)

wherein p is an integer from 1 to 3; n is 1 or 2; and $R^x$ is an optionally substituted lower alkyl.

(Item 2)

The compound, or an ester, a protected compound at the amino on the ring in the 7-side chain, a pharmaceutically acceptable salt, or a solvate thereof according to item 1, wherein D is a single bond, —NH—, or —$R^7$—NH—, $R^7$ is a lower alkylene, and E is selected from the formulae (1) to (40).

(Item 3)

The compound, or an ester, a protected compound at the amino on the ring in the 7-side chain, a pharmaceutically acceptable salt, or a solvate thereof according to item 2, wherein D is —NH—, —$CH_2$—NH— or —$CH_2$—$CH_2$—NH—.

(Item 4)

The compound, or an ester, a protected compound at the amino on the ring in the 7-side chain, a pharmaceutically acceptable salt, or a solvate thereof according to item 3, wherein E is a group selected from the formulae (5), (6), (10), (11), (26), (29) to (34), (36) and (37)

(Item 5)

The compound, or an ester, a protected compound at the amino on the ring in the 7-side chain, a pharmaceutically acceptable salt, or a solvate thereof according to item 3, wherein E is a group of the formula (26) or (31).

(Item 6)

The compound, or an ester, a protected compound at the amino on the ring in the 7-side chain, a pharmaceutically acceptable salt, or a solvate thereof according to item 2, wherein D is a single bond.

(Item 7)

The compound, or an ester, a protected compound at the amino on the ring in the 7-side chain, a pharmaceutically acceptable salt, or a solvate thereof according to item 6, wherein E is a group selected from the formulae (1) to (4), (7), (12) to (25), (27) and (28).

(Item 8)

The compound, or an ester, a protected compound at the amino on the ring in the 7-side chain, a pharmaceutically acceptable salt, or a solvate thereof according to item 6, wherein E is a group selected from the formulae (1) to (3), (7) and (12).

(Item 9)

The compound, or an ester, a protected compound at the amino on the ring in the 7-side chain, a pharmaceutically acceptable salt, or a solvate thereof according to item 1, wherein D is the formula:

[Formula 5]

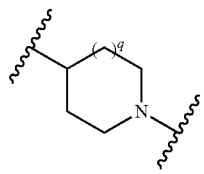

wherein q is as defined in item 1

(Item 10)

The compound, or an ester, a protected compound at the amino on the ring in the 7-side chain, a pharmaceutically acceptable salt, or a solvate thereof according to any one of items 1 to 9, wherein U is —S—.

(Item 11)

The compound, or an ester, a protected compound at the amino on the ring in the 7-side chain, a pharmaceutically acceptable salt, or a solvate thereof according to any one of items 1 to 10, wherein W is —$CH_2$—.

(Item 12)

The compound, or an ester, a protected compound at the amino on the ring in the 7-side chain, a pharmaceutically acceptable salt, or a solvate thereof according to any one of items 1 to 11, wherein $R^3$ is hydrogen atom or —OCH$_3$.

(Item 13)

The compound, or an ester, a protected compound at the amino on the ring in the 7-side chain, a pharmaceutically acceptable salt, or a solvate thereof according to any one of items 1 to 12, wherein X is —N=, —CH= or —C(—Cl)=.

(Item 14)

The compound, or an ester, a protected compound at the amino on the ring in the 7-side chain, a pharmaceutically acceptable salt, or a solvate thereof according to any one of items 1 to 13, wherein the formula:

[Formula 6]

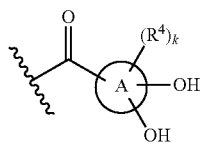

is selected from the formula:

[Formula 7]

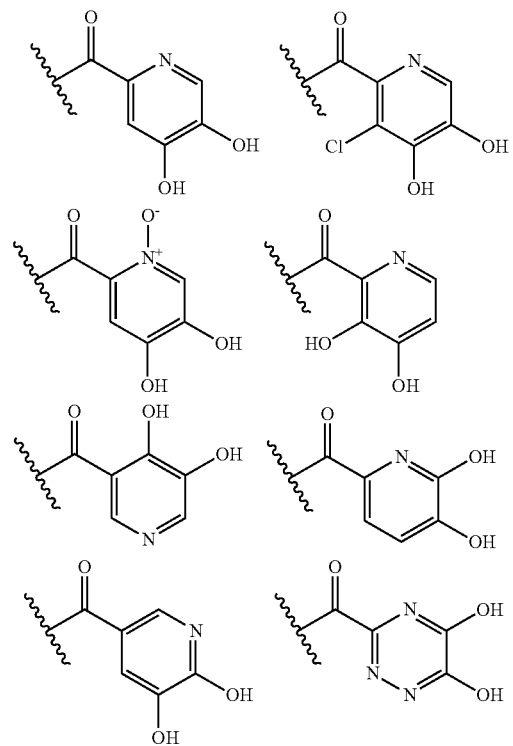

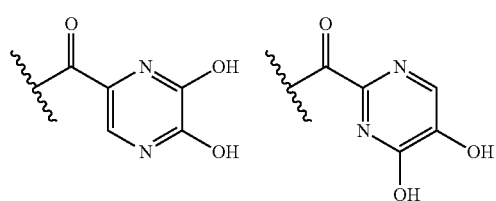

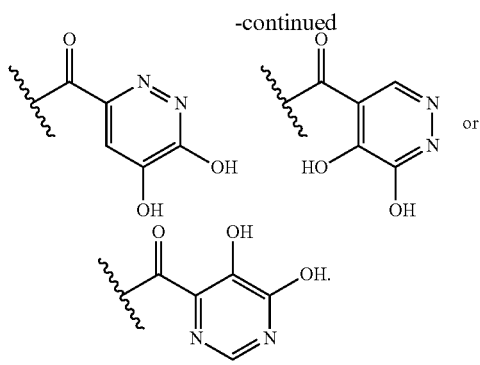

(Item 15)

The compound, or an ester, a protected compound at the amino on the ring in the 7-side chain, a pharmaceutically acceptable salt, or a solvate thereof according to any one of items 1 to 13, wherein the formula:

[Formula 8]

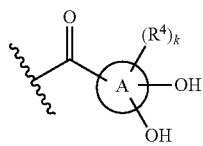

is selected from the formula:

[Formula 9]

(Item 16)

The compound, or an ester, a protected compound at the amino on the ring in the 7-side chain, a pharmaceutically acceptable salt, or a solvate thereof according to any one of items 1 to 15, wherein Q is a single bond or optionally substituted phenylene.

(Item 17)
The compound, or an ester, a protected compound at the amino on the ring in the 7-side chain, a pharmaceutically acceptable salt, or a solvate thereof according to item 16, wherein $R^1$ is an optionally substituted lower alkyl and $R^2$ is a hydrogen atom.
(Item 18)
The compound, or an ester, a protected compound at the amino on the ring in the 7-side chain, a pharmaceutically acceptable salt, or a solvate thereof according to item 16, wherein $R^1$ is hydrogen atom and $R^2$ is an optionally substituted lower alkyl.
(Item 19)
The compound, or an ester, a protected compound at the amino on the ring in the 7-side chain, a pharmaceutically acceptable salt, or a solvate thereof according to item 16, wherein $R^1$ and $R^2$ are independently a lower alkyl.
(Item 20)
The compound, or an ester, a protected compound at the amino on the ring in the 7-side chain, a pharmaceutically acceptable salt, or a solvate thereof according to item 17, wherein m is 0.
(Item 21)
A pharmaceutical composition, which comprises a compound, or an ester, a protected compound at the amino on the ring in the 7-side chain, a pharmaceutically acceptable salt, or a solvate thereof according to any one of items 1 to 18.

(Item 22)
The pharmaceutical composition according to item 20, which possesses antimicrobial activity.
(Item 23)
A method for treating an infectious disease, characterized in that the compound, or an ester, a protected compound at the amino on the ring in the 7-side chain, a pharmaceutically acceptable salt, or a solvate thereof according to any one of items 1 to 20 is administered.
(Item 24)
The compound, or an ester, a protected compound at the amino on the ring in the 7-side chain, a pharmaceutically acceptable salt, or a solvate thereof according to any one of items 1 to 20 for the treatment of an infectious disease.
(Item 25)
Use of the compound, or an ester, a protected compound at the amino on the ring in the 7-side chain, a pharmaceutically acceptable salt, or a solvate thereof according to any one of items 1 to 20 for manufacturing a therapeutic agent for treating an infectious disease.

In another embodiment, the subject invention also provides the following invention:

The compound, or an ester, a protected compound at the amino on the ring in the 7-side chain, a pharmaceutically acceptable salt, or a solvate thereof according to anyone of items 1 to 18, provided that the following compounds (B-1), (B-2), and (B-3) are excluded from Formula (I):

[Formula 10]

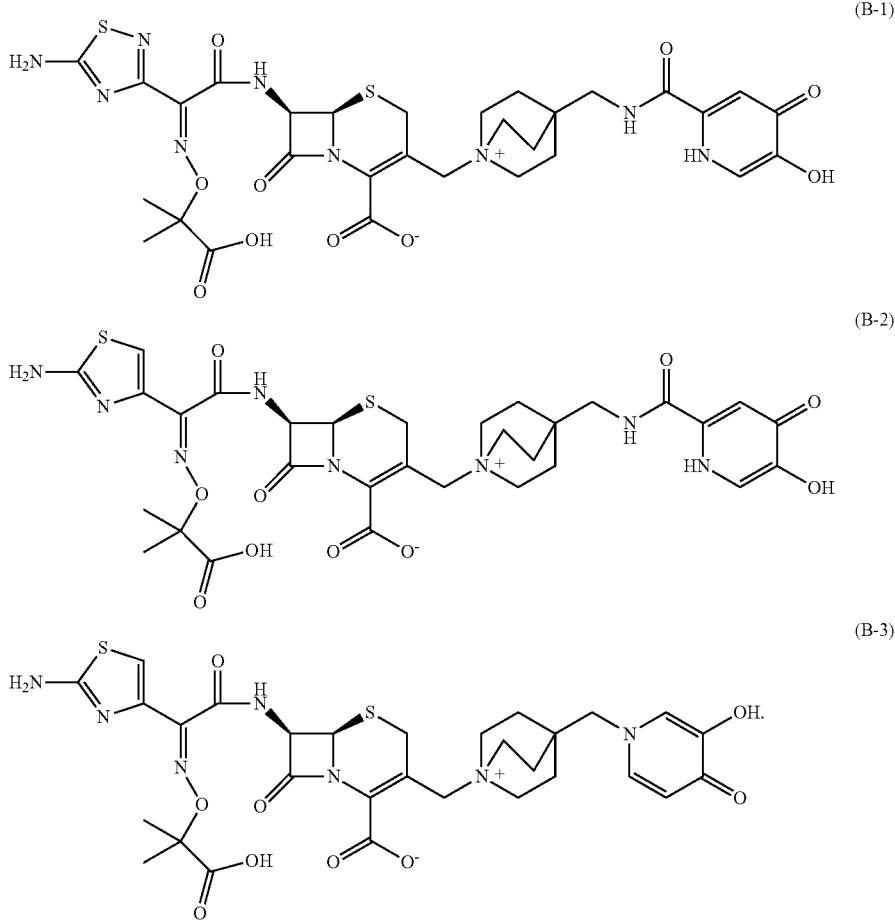

Effects of the Invention

The compounds of the subject invention are useful as a pharmaceutical product in that the compounds have at least one of the following features:
1) The compounds exhibit potent antimicrobial spectrum against a variety of bacteria including Gram negative bacteria and/or Gram positive bacteria;
2) the compounds exhibit potent antimicrobial activity against beta-lactamase producing Gram negative bacteria;
3) the compounds exhibit potent antimicrobial activity against multi drug resistant bacteria, in particular, Class B type, metallo-beta-lactamase producing Gram negative bacteria;
4) the compounds exhibit potent antimicrobial activity against extended-spectrum beta-lactamase (ESBL) producing bacteria;
5) the compounds do not exhibit cross resistance with known Cephem drugs and/or Carbapenem drugs; and
6) the compounds do not exhibit side effects such as fever after administration into the body.

EMBODIMENTS FOR CARRYING OUT THE INVENTION

The respective terms used herein are as defined alone or in combination with other terms as follows:

"Halogen" includes fluorine, chlorine, bromine and iodine. Preferably, halogen is fluorine, chlorine or bromine, and more preferably halogen is chlorine.

"Lower alkyl" includes linear or branched alkyl having 1-8 carbons, preferably 1-6 carbons, and more preferably 1-4 carbons, and includes, for example, methyl, ethyl, n-propyl, isopropyl, n-butyl, isobutyl, sec-butyl, tert-butyl, n-pentyl, isopentyl, neopentyl, hexyl, isohexyl, n-heptyl, isoheptyl, n-octyl, and the like.

"Lower alkylene" includes linear alkylene having 1-8 carbons, preferably 1-6 carbons, more preferably 1-4 carbons, and most preferably one or two carbons, and includes, for example, methylene, ethylene, n-propylene, n-butylene, n-pentylene, n-hexylene, and the like.

"Halo(lower)alkyl" refers to a group in which at least one position of said "lower alkyl" is substituted with the above "halogen", and includes, for example, monofluoromethyl, difluoromethyl, trifluoromethyl, monochloromethyl, dichloromethyl, trichloromethyl, monobromomethyl, monofluoroethyl, monochloromethyl, chlorodifluoromethyl, and the like. Preferably, halo(lower)alkyl is trifluoromethyl, or trichloromethyl.

Substituent groups for "optionally substituted lower alkyl" include at least one group is selected from Substituent Group Alpha. When substitution is carried out with a plurality of the group of Substituent Group Alpha, such groups may be the same or different.

Substituent groups for "optionally substituted lower alkylene" include optionally substituted lower alkyl, and at least one group selected from Substituent Group Alpha. When substitution is carried out with a plurality of substituent groups, such substituent groups may be the same or different.

Substituent groups for "optionally substituted phenylene" include optionally substituted lower alkyl, and at least one group selected from Substituent Group Alpha. When substitution is carried out with a plurality of substituent groups, such substituent groups may be the same or different.

Here, "Substituent Group Alpha." is a q coup consisting of halogen, hydroxy, lower alkoxy, hydroxy(lower)alkoxy, lower alkoxy(lower)alkoxy, carboxy, amino, acylamino, lower alkylamino, imino, hydroxyimino, lower alkoxyimino, lower alkylthio, carbamoyl, lower alkylcarbamoyl, hydroxy (lower)alkylcarbamoyl, sulfamoyl, lower alkylsulfamoyl, lower alkylsulfinyl, cyano, nitro, a carbocyclic group, and a heterocyclic group.

The lower alkyl moiety in "lower alkoxy", "hydroxy(lower)alkoxy", "lower alkoxy(lower)alkoxy", "lower alkylamino", "lower alkoxyimino", "lower alkylthio", "lower alkylcarbamoyl", "hydroxy(lower)alkylcarbamoyl", and "lower alkylsulfamoyl" is as defined above for "lower alkyl".

Preferred embodiments of substituent groups for "optionally substituted lower alkyl" include a fluorine atom, a chlorine atom, a bromine atom, hydroxy, carboxy, methoxy, ethoxy, hydroxymethoxy, hydroxyethoxy, methoxymethoxy, methoxyethoxy, amino, acetylamino, methylamino, dimethylamino, imino, hydroxyimino, methoxyimino, methylthio, carbamoyl, methylcarbamoyl, hydroxymethylcarbamoyl, sulfamoyl, methylsulfamoyl, lower alkylsulfamoyl, cyano, nitro, phenyl, cyclopropyl, cyclobutyl, cyclohexyl, pyridyl, morpholinyl, and the like.

Preferred embodiments of "optionally substituted lower alkyl" include methyl, ethyl, isopropyl, tert-butyl, monofluoromethyl, difluoromethyl, trifluoromethyl, carboxymethyl, carboxyethyl, carbamoylmethyl, carbamoylethyl, hydroxymethyl, hydroxyethyl, methoxymethyl, ethoxymethyl, methoxyethyl, ethoxyethyl, methylthiomethyl, ethylthiomethyl, benzyl, phenethyl, 4-hydroxybenzyl, 4-methoxybenzyl, 4-carboxybenzyl, and the like.

"Carbocyclic group" includes cycloalkyl, cycloalkenyl, aryl and non-aromatic fused carbocyclic groups, and the like. The term includes divalent radical (for example, cycloalkylene, cycloalkenylene, arylene), as well as aforementioned monovalent group.

"Cycloalkyl" is a carbocyclic group having 3-10 carbons, preferably 3-8 carbons, more preferably 4-8 carbons, and includes, for example, cyclopropyl, cyclobutyl, cyclopentyl, cyclohexyl, cycloheptyl, cyclooctyl, cyclononyl, cyclodecyl, and the like.

"Cycloalkenyl" includes those having at least one double bond at any position in a cycloalkyl ring, and specifically includes, for example, cyclopropenyl, cyclobutenyl, cyclopentenyl, cyclohexenyl, cycloheptynyl, cyclooctynyl, and cyclohexadienyl, and the like.

"Aryl" includes phenyl, naphthyl, anthryl, phenanthryl, and the like, and in particular, phenyl is preferable.

"Non-aromatic fused carbocyclic group" includes a group in which two or more cyclic groups selected from the "cycloalkyl", "cycloalkenyl," and "aryl" are fused, and specifically includes, for example, indanyl, indenyl, tetrahydronaphthyl, and fluorenyl, and the like.

"Heterocyclic group" includes heterocyclic groups having at least one hetero atom selected from O, S and N, in the ring thereof, and specifically includes, for example, 5- or 6-membered heteroaryl such as pyrrolyl, imidazolyl, pyrazolyl, pyridyl, pyridazinyl, pyrimidinyl, pyrazinyl, triazolyl, triazinyl, tetrazolyl, isoxazolyl, oxazolyl, oxadiazolyl, isothiazolyl, thiazolyl, thiadiazolyl, furyl, thienyl, and the like; bicyclic fused heterocyclic groups such as indolyl, isoindolyl, indazolyl, indolizinyl, indolinyl, isoindolinyl, quinolyl, isoquinolyl, cinnolinyl, phthalazinyl, quinazolinyl, naphthyridinyl, quinoxalinyl, purinyl, pteridinyl, benzopyranyl, benzimidazolyl, benzotriazolyl, benzisoxazolyl, benzoxazolyl, benzoxadiazolyl, benzisothiazolyl, benzothiazolyl, benzothiadiazolyl, benzofuryl, isobenzofuryl, benzothienyl, benzotriazolyl, imidazopyridyl, pyrazolopyridine, triazolopyridyl, imidazothiazolyl, pyrazinopyridazinyl, quinazolinyl, quinolyl, isoquinolyl, naphthyridinyl, dihydrobenzofuryl, tetrahydroquinolyl, tetrahydroisoquinolyl, dihydrobenzoxazine, tetrahydrobenzothienyl, and the like; tricyclic fused heterocyclic groups such as carbazolyl, acridinyl, xanthenyl, phenothiadinyl, phenoxathiinyl, phenoxazinyl, dibenzofuryl, imidazoquinolyl, and the like; non-aromatic heterocyclic groups such as dioxanyl, thiiranyl, oxiranyl, oxathiolanyl, azetidinyl, thianyl, thiazolidine, pyrrolidinyl, pyrrolinyl, imidazolidinyl, imidazolinyl, pyrazolidinyl, pyrazolinyl, piperidyl, piperazinyl, morpholinyl, thiomorpholinyl, thiomorpholino, dihydropyridyl, dihyrobenzimidazolyl, tetrahydropyridyl, tetrahydrofuryl, tetrahydropyranyl, tetrahydrothiazolyl, tetrahydroisothiazolyl, dihydrooxazinyl, hexahydroazepinyl, tetrahydrodiazepinyl, and the like. Preferably, heterocyclic group is a 5- or 6-membered heteroaryl or non-aromatic heterocyclic group, and more preferably, a 5- or 6-membered heteroaryl These include divalent heterocyclic group, as well as aforementioned monovalent heterocyclic group.

Substituents groups for "optionally substituted carbocyclic group" and "optionally substituted heterocyclic group" include optionally substituted lower alkyl and at least one group selected from Substituent Group Alpha.

Preferred embodiments of substituent groups for "optionally substituted carbocyclic group" and "optionally substituted heterocyclic group" include methyl, ethyl, isopropyl, tert-butyl, a fluorine atom, a chlorine atom, a bromine atom, hydroxy, carboxy, methoxy, ethoxy, hydroxymethoxy, hydroxyethoxy, methoxymethoxy, methoxyethoxy, amino, acetylamino, methylamino, dimethylamino, hydroxyimino, methoxyimino, methylthio, carbamoyl, methylcarbamoyl, hydroxymethylcarbamoyl, sulfamoyl, methylsulfamoyl, lower alkylsulfamoyl, cyano, nitro, phenyl, cyclopropyl, cyclobutyl, cyclohexyl, pyridyl, morpholinyl, and the like.

"6-membered aromatic heterocyclic group having 1-3 nitrogen atoms" includes pyridine, pyrimidine, pyridazine, pyrazine, 1,3,5-triazine, 1,2,4-triazine, 1,2,3-triazine, and the like.

Examples of the case that "$R^1$ and $R^2$ taken together with a neighboring atom forms an optionally substituted carbocyclic group or optionally substituted heterocyclic group" include the cases where the following formula:

[Formula 11]

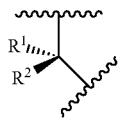

wherein each symbol is as defined in item 1, is cycloalkyl, cycloalkenyl, or non-aromatic heterocyclic group, for example, groups of the following formulae:

[Formula 12]

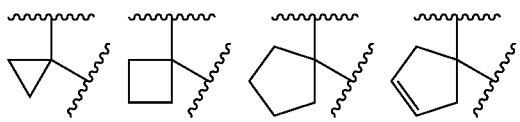

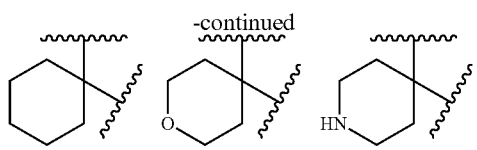
-continued optionally having a substituent group selected from Substituent Group Alpha on the ring.

In the moiety "E", "optionally substituted cyclic group selected from the formulae (1) to (40)" includes groups in which a hydrogen atom on a carbon atom of each cyclic group is substituted with one or more groups which are the same or different and are selected from optionally substituted lower alkyl or Substituent Group Alpha. Preferred embodiments of the substituent groups include methyl, ethyl-isopropyl, text-butyl, a fluorine atom, a chlorine atom, a bromine atom, hydroxy, carboxy, methoxy, ethoxy, hydroxymethoxy, hydroxyethoxy, methoxymethoxy, methoxyethoxy, amino, acetylamino, methylamino, dimethylamino, imino, hydroxyimino, methoxyimino, methylthio, carbamoyl, methylcarbamoyl, hydroxymethylcarbamoyl, sulfamoyl, methylsulfamoyl, lower alkylsulfamoyl, cyano, nitro, phenyl, cyclopropyl, cyclobutyl, cyclohexyl, pyridyl, morpholinyl, and the like. More preferred embodiment non-substitution.

Examples or embodiments for each moiety in Formula (I) are shown below. However, the scope of the subject invention is not limited to those described below.

Examples of "X" include —N=, —CH=, —C(—CH$_3$)=, —C(—CF$_3$)=, —C(—Br)=, —C(—Cl)=, and the like. Preferably, "X" is —N=, —CH=, and —C(—Cl)=.

In a preferred embodiment, "W" is —CH$_2$—, and "U" is —CH$_2$—, —S— or —O—. More preferably, "W" is —CH$_2$—, and "U" is —S— or —O—. Still more preferably, "W" is —CH$_2$—, and "U" is —S—.

Examples of "$R^1$ and $R^2$" include a hydrogen atom, a fluorine atom, a chlorine atom, hydroxy, carboxy, methyl, ethyl, isopropyl, tert-butyl, monofluoromethyl, difluoromethyl, trifluoromethyl, carboxymethyl, carboxyethyl, carbamoylmethyl, carbamoylethyl, hydroxymethyl, hydroxyethyl methoxymethyl, ethoxymethyl, methoxyethyl, ethoxyethyl, methylthiomethyl, ethylthiomethyl, benzyl, 4-hydroxybenzyl, 4-methoxybenzyl, 4-carboxybenzyl, phenyl, naphthyl, cyclopropyl, cyclobutyl, cyclopentyl, pyrrolyl, pyrazolyl, pyridyl, pyridazinyl, pyrimidinyl, pyrazinyl, triazolyl, triazinyl, tetrazolyl, isoxazolyl, oxazolyl, oxadiazolyl, isothiazolyl, thiazolyl, thiadiazolyl, furyl, thienyl, and the like.

Preferred combinations of $R^1$ and $R^2$ include, ($R^1$, $R^2$) is (hydrogen atom, hydrogen atom), (methyl, hydrogen atom), (hydrogen atom, methyl), (methyl, methyl), (ethyl, hydrogen atom), (hydrogen atom, ethyl), (ethyl, ethyl), (phenyl, hydrogen atom), (hydrogen atom, phenyl), (carboxymethyl, hydrogen atom), (hydrogen atom, carboxymethyl), (carboxyethyl, hydrogen atom), (hydrogen atom, carboxyethyl), (hydroxyethyl, hydrogen atom), (hydrogen atom, hydroxylethyl), (carbamoylmethyl, hydrogen atom), (hydrogen atom, carbamoylmethyl), (trifluoromethyl, hydrogen atom), (carboxy, hydrogen atom), (carbamoylethyl, hydrogen atom), (benzyl, hydrogen atom), (4-hydroxybenzyl, hydrogen atom), and the like.

Preferred embodiments of the cases where "$R^1$ and $R^2$ taken together with a neighboring atom forms an optionally substituted carbocyclic group, or optionally substituted heterocyclic group" include optionally substituted 3-8 membered cycloalkyl, optionally substituted 3-8 membered cycloalkenyl, or 3-8 membered non-aromatic heterocyclic groups. More preferred embodiments include the case where the following formula:

[Formula 13]

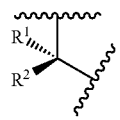

wherein each symbol is as defined in item 1, is any one of the following formulae:

[Formula 14]

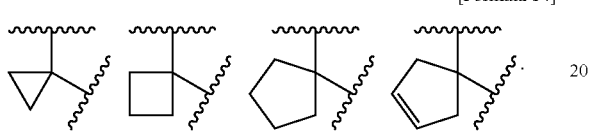

"$R^3$" is preferable to be a hydrogen atom or —OCH$_3$.

Examples of "$R^4$" include hydrogen atom, chlorine atom, fluorine atom, bromine atom, cyano, hydroxy, acetyl, methoxy, ethoxy, trifluoromethyl, and the like. Preferably, $R^4$ is hydrogen atom, hydroxy, or chlorine atom.

Examples of "-E-D-(C=O)—" include the following formulae (1A)-(41A):

[Formula 15]

(1A)

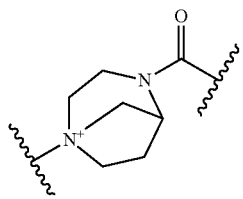

(2A)

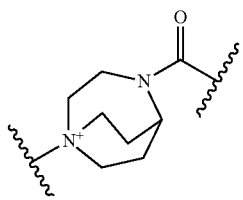

(3A)

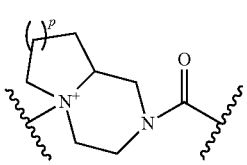

(4A)

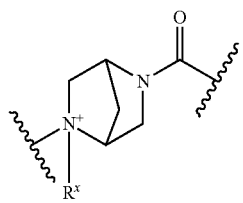

(5A)

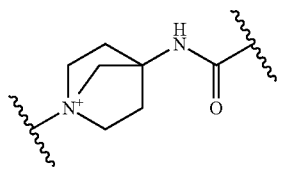

(6A)

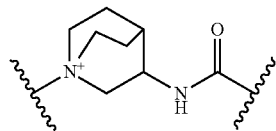

(7A)

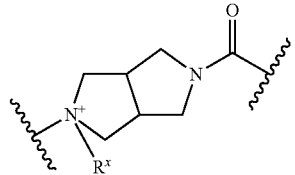

(8A)

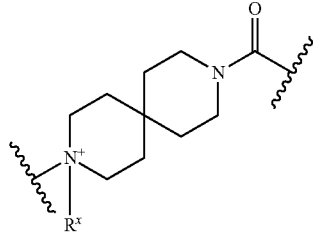

(9A)

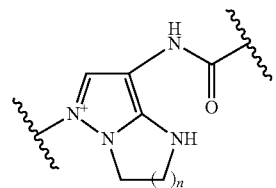

(10A)

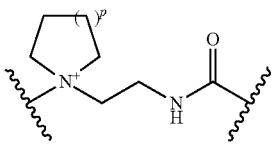

(11A)

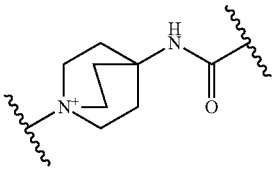

(12A)

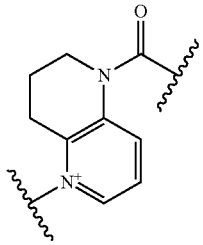

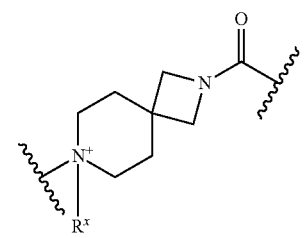 (13A)
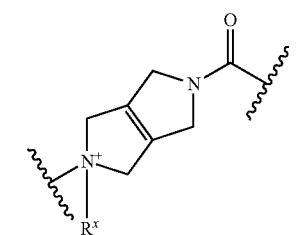 (14A)
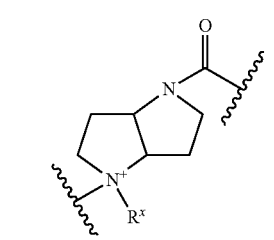 (15A)
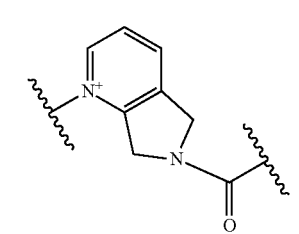 (16A)
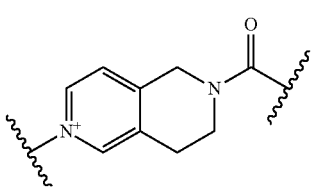 (17A)
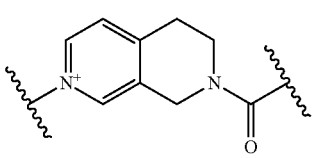 (18A)
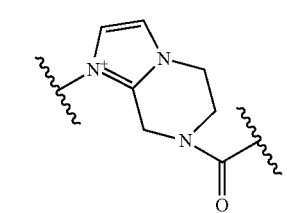 (19A)
[Formula 16]
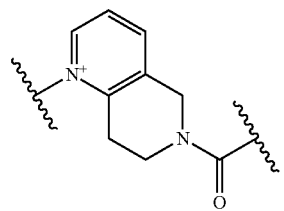 (20A)
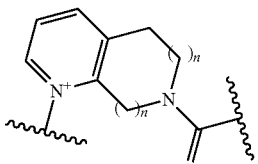 (21A)
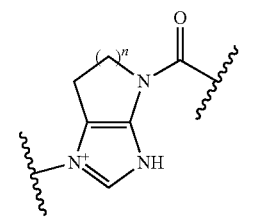 (22A)
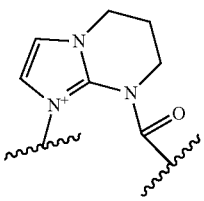 (23A)
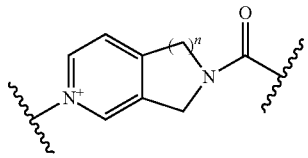 (24A)
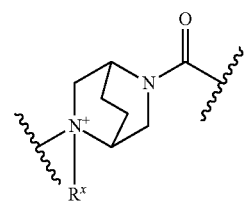 (25A)
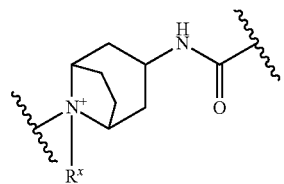 (26A)

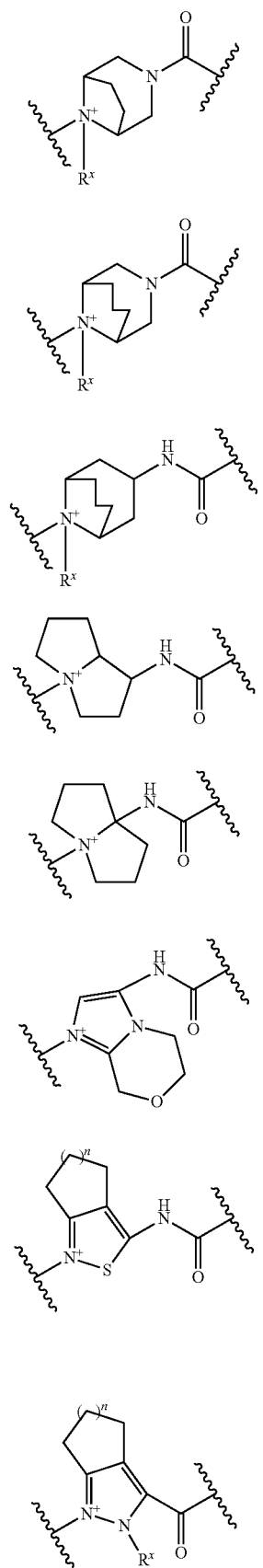
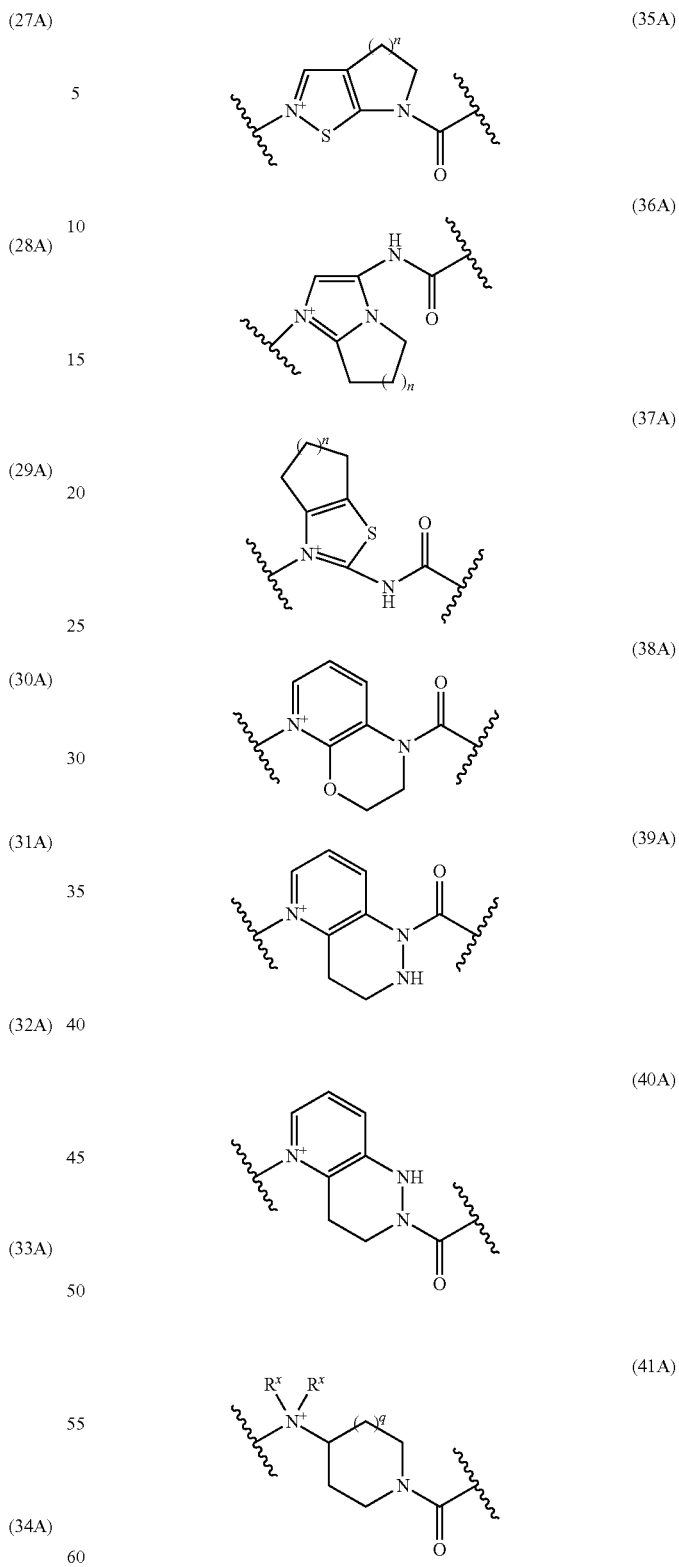
wherein p is an integer from 1 to 3; n is 1 or 2; and $R^x$ is an optionally substituted lower alkyl.
Here, preferred examples of include methyl, ethyl, fluoromethyl, carboxymethyl, carbamoylmethyl, hydroxyethyl, and the like.

Preferred embodiments of "-E-D-(C=O)—" include the following formulae (18)-(41B):
[Formula 17]
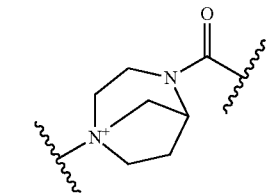
(1B)
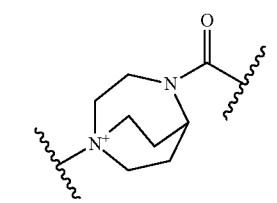
(2B)
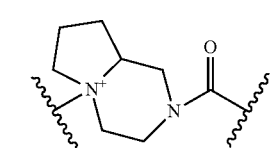
(3B)
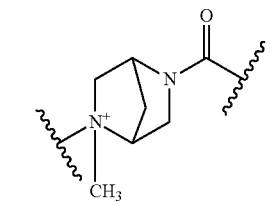
(4B)
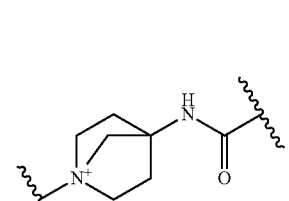
(5B)
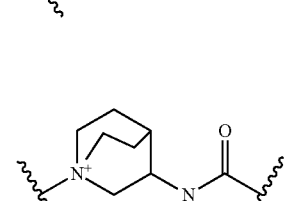
(6B)
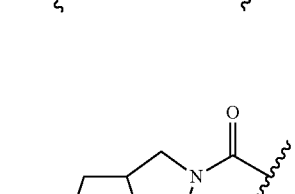
(7B)
-continued
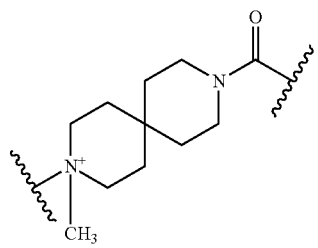
(8B)
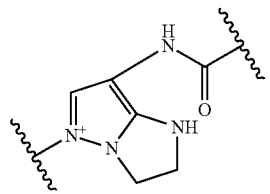
(9B)
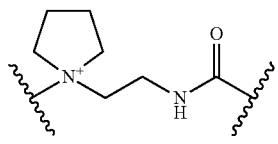
(10B)
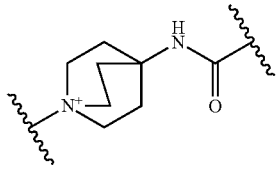
(11B)
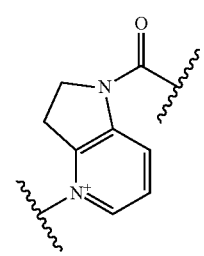
(12B)
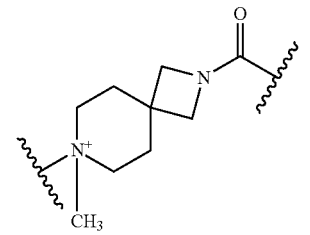
(13B)
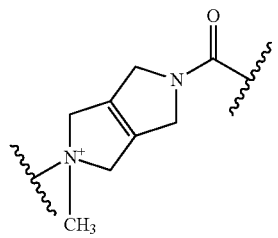
(14B)

-continued
(15B) 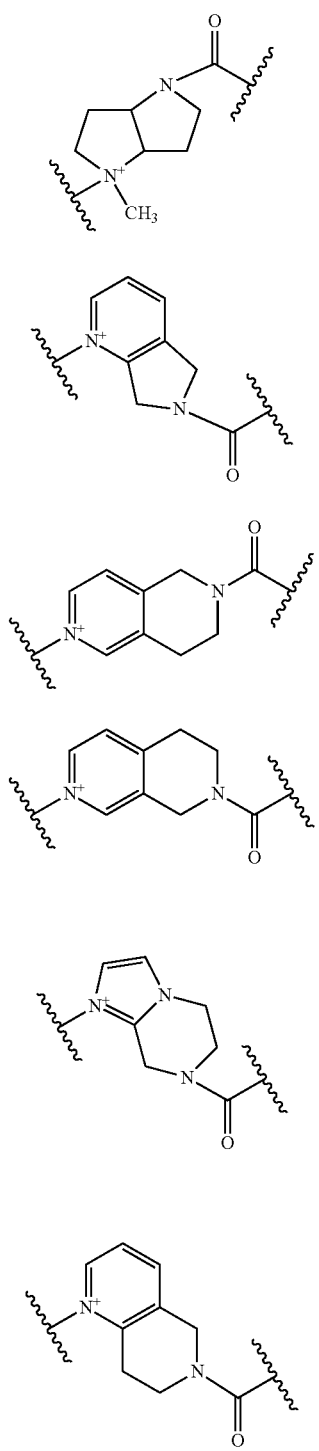
(16B)
(17B)
(18B)
(19B)
(20B)
[Formula 18]
(21B) 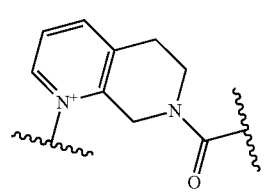
-continued
(22B) 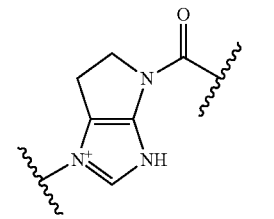
(23B) 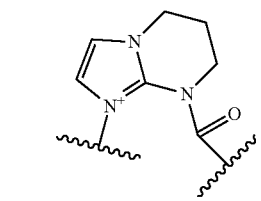
(24B) 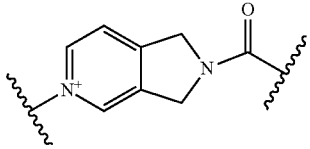
(25B) 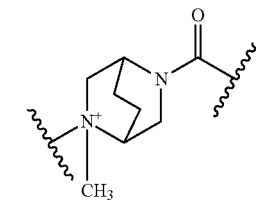
(26B) 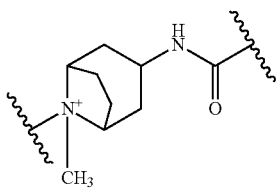
(27B) 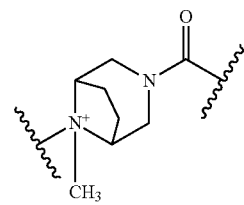
(28B) 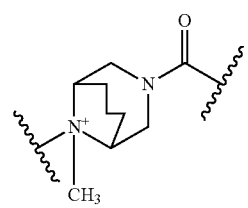
(29B) 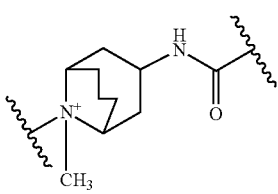

(30B) 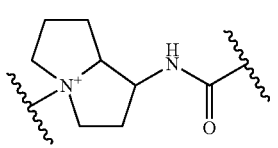
(31B) 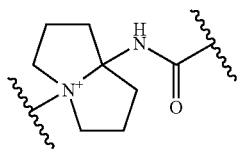
(32B) 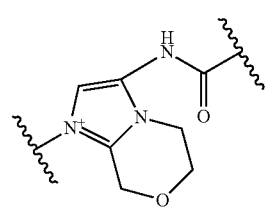
(33B) 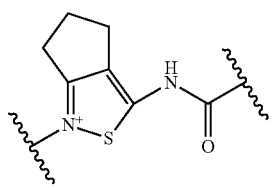
(34B) 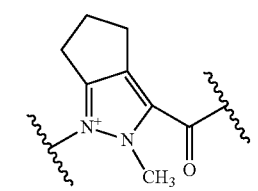
(35B) 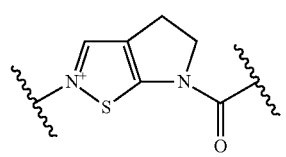
(36B) 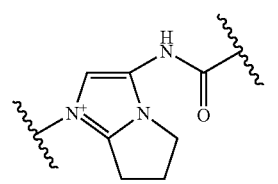
(37B) 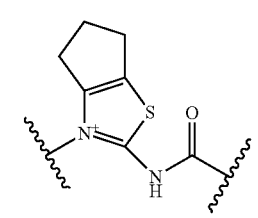
(38B) 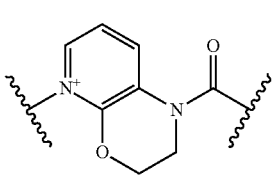
(39B) 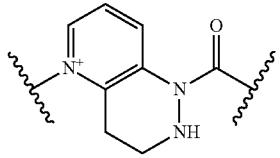
(40B) 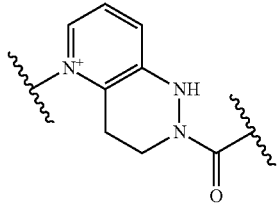
(41B) 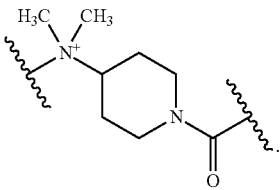
Still more preferred embodiments of "-E-D-(C=O)—" include the following formulae:
[Formula 19]
(1B) 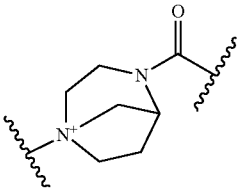
(2B) 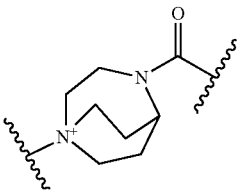
(3B) 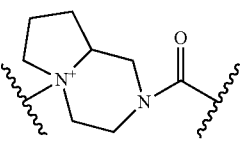
(4B) 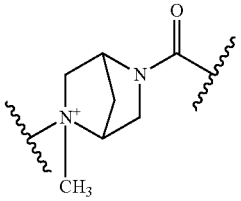

-continued (7B)
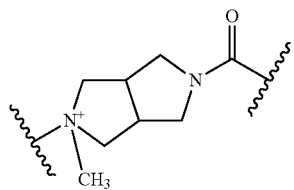

(12B)
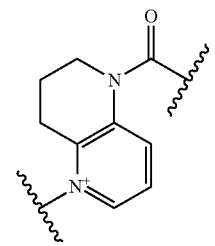

(31B')
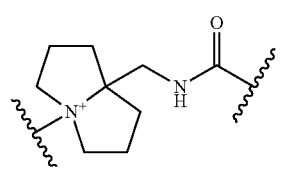

(41B)
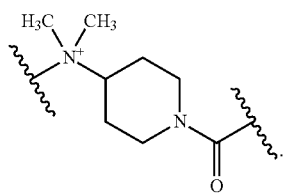

In a preferred embodiment, Ring A of the formula:

[Formula 20]
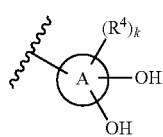

wherein each symbol is as defined in item 1,
is a 6-membered aromatic heterocyclic group having 1-3 nitrogen atoms.

In a preferred embodiment, $R^4$ is hydrogen atom, chlorine atom or hydroxy.

It is preferable that k is 0 or 1.

In a more preferred embodiment, the formula:

[Formula 21]
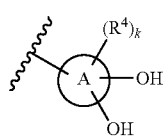

wherein each symbol is as defined in item 1, has the formula:

[Formula 22]
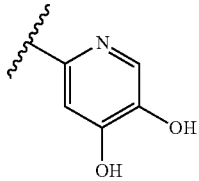

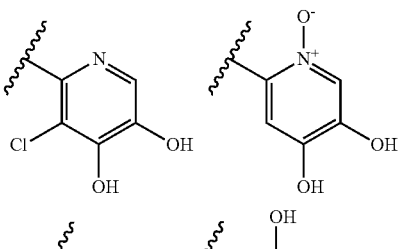

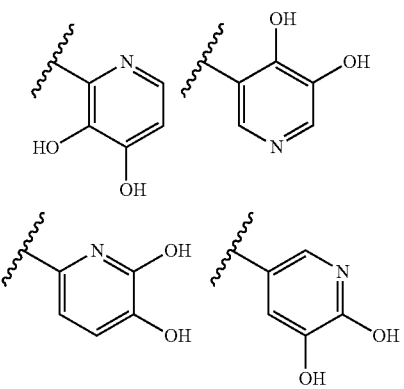

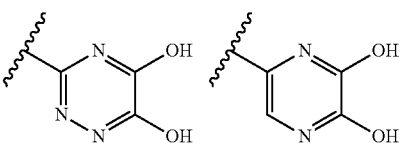

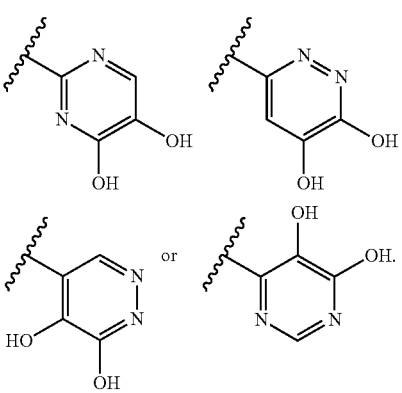

In a still more preferred embodiment, the formula:

[Formula 23]
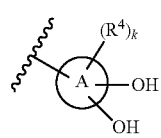

wherein each symbol is as defined in item 1, has the formula:

[Formula 24]

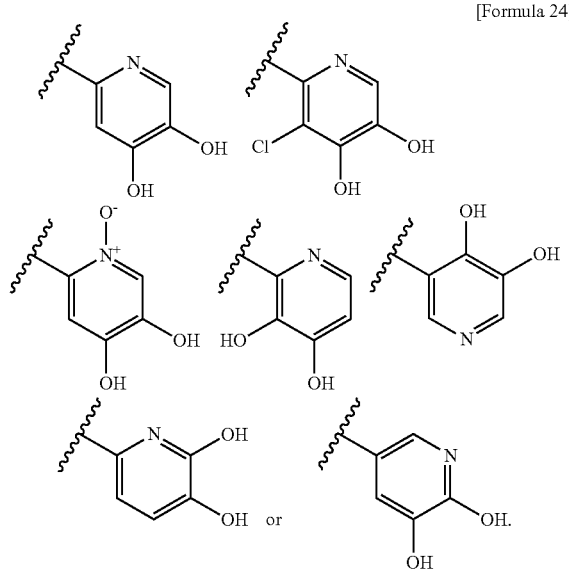

In a preferred embodiment, Q is a single bond or phenylene. In a more preferred embodiment, Q is a single bond.

The nomenclature of the substitution position on the Cephem skeleton of Formula (I) is as follows. As used herein, 7-side chain and 3-side chain refer to groups binding to the 7-position and the 3-position of the Cephem skeleton as shown below, respectively.

[Formula 25]

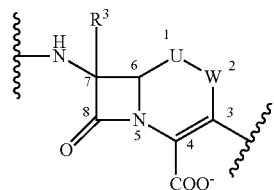

Esters of Formula (I) preferably include those esters at the carboxyl on the 7-side chain and/or at the 4-position. Esters at the carboxyl group on the 7-side chain refer to compounds having a structure in which the carboxyl group at the of the oxime group is esterified as shown in the formula:

[Formula 26]

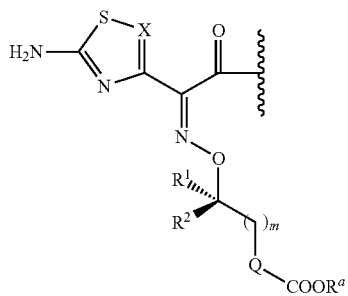

wherein each symbol is as defined in item 1 and $R^a$ represents an ester residue such as a carboxyl-protecting group. Such esters include those esters that are readily metabolized in the body to form a carboxylic state.

Esters at the carboxyl group at the 4-position of Formula (I) refer to compounds having a structure in which the carboxyl group at the 4-position of the cephem skeleton is esterified as shown in the formula:

[Formula 27]

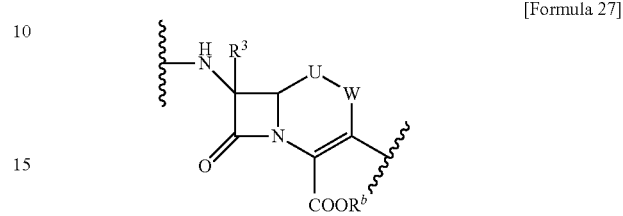

wherein each symbol is as defined in item 1 and $R^b$ is an ester residue such as a carboxyl-protecting group. Such esters include those esters that are easily metabolized in the body to form a carboxylic state.

The aforementioned carboxyl-protecting group may be of any group as long as it can be used for protection and/or deprotection by a method such as described in Protective Groups in Organic Synthesis, Theodora. W Green (John Wiley & Sons) and for examples include lower alkyl (e.g., methyl, ethyl, t-butyl), lower alkylcarbonyloxymethyl (e.g., pivaloyl), optionally substituted aralkyl (e.g., benzyl, benzhydryl, phenethyl, p-methoxybenzyl, p-nitrobenzyl), silyl groups (t-butyldimethylsilyl, diphenyl(t-butyl)silyl), and the like.

A compound protected at the amino on the 7-side chain of Formula (I) refers to a structure in which the amino on the ring has been protected, as shown in the formula:

[Formula 28]

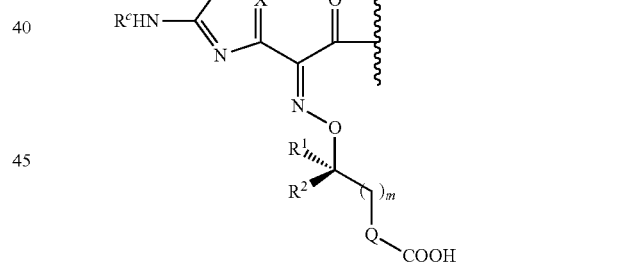

wherein each symbol is as defined in item 1, and $R^c$ represents an amino-protecting group. Such amino-protecting groups include those groups that are readily metabolized in the body to form amino. The aforementioned amino-protecting group may be of any group as long as it can be used for protection and/or deprotection by a method such as described in Protective Groups in Organic Synthesis, Theodora W Green (John Wiley & Sons) and for examples include lower alkoxycarbonyl (e.g., t-butoxycarbonyl, benzyloxycarbonyl, p-nitrobenzyloxycarbonyl), optionally substituted aralkanoyl (e.g., benzoyl, p-nitrobenzoyl) acyl (e.g., formyl, chloroacetyl), and the like.

Salts of Formula (I) include those formed with a counter cation (s) after the hydrogen atom(s) of the carboxyl group at the 4-position, the carboxyl group at the 7-position side chain, and/or the hydroxyl group of the pyridone derivative is dissociated; those formed by the amino group in the 7-position side chain with an inorganic or organic acid; and those formed by the quaternary amine moiety in the 3-side chain with a counter anion.

Pharmaceutically acceptable salts of Formula (I) include, for example, salts or intramolecular salts formed with inorganic base, ammonia, organic base, inorganic acid, organic acid, basic amino acid, halogen ions, and the like. Such inorganic bases include, for example, alkali metal (Na, K, etc.) and alkali earth metal (Mg, etc.). Organic bases include, for example, procaine, 2-phenylethylbenzylamine, dibenzylethylenediamine, ethanolamine, diethanolamine, trishydroxymethylaminomethane, polyhydroxyalkylamine, N-methyl glucosamine, and the like. Inorganic acids include, for example, hydrochloric acid, hydrobromic acid, sulfuric acid, nitric acid, phosphoric acid, and the like. Organic acids include, for example, p-toluene sulfonic acid, methane sulfonic acid, formic acid, acetic acid, trifluoroacetic acid, maleic acid and the like. Basic amino acids include, for example, lysine, arginine, ornithine, histidine, and the like.

As used herein, "solvate" refers to a solvate with water or organic solvent (for example, methanol, ethanol, isopropyl alcohol, acetone), and preferably a hydrate.

The Compound (I) of the subject invention is not limited to particular isomers, but includes any possible isomers, racemates, and resonance structures as exemplified below:

For example, the formula in Formula (I):

[Formula 29]

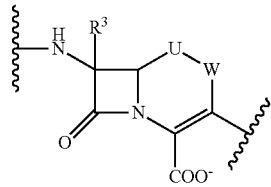

wherein each symbol is as defined in item 1, includes:

[Formula 30]

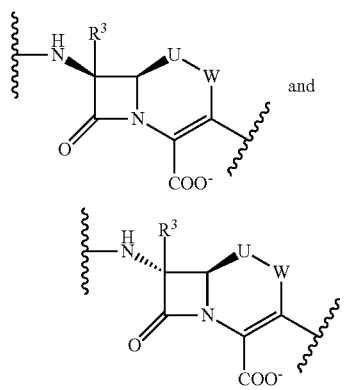

wherein each symbol is as defined in item 1.

For example, the formula in Formula (I):

[Formula 31]

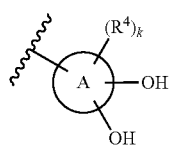

wherein each symbol is as defined in item 1, includes the following resonance structures:

[Formula 32]

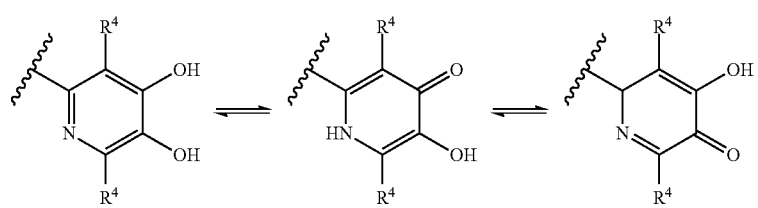

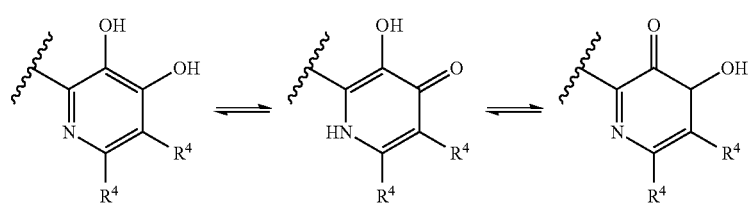

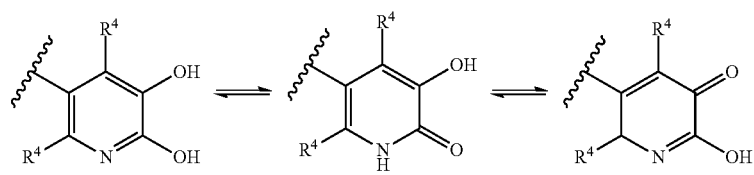

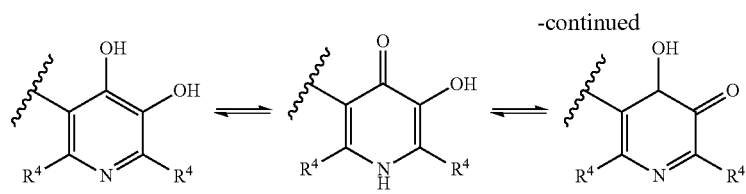
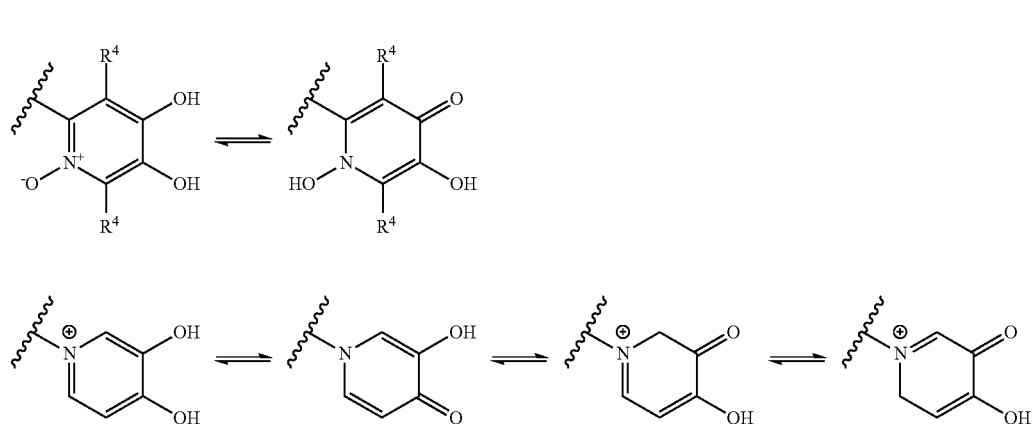
wherein $R^4$ defined in item 1,
and the like.
The compounds represented by Formula (I) of the subject invention can be manufactured, for example, by a general synthesis method described below.
[Formula 33]
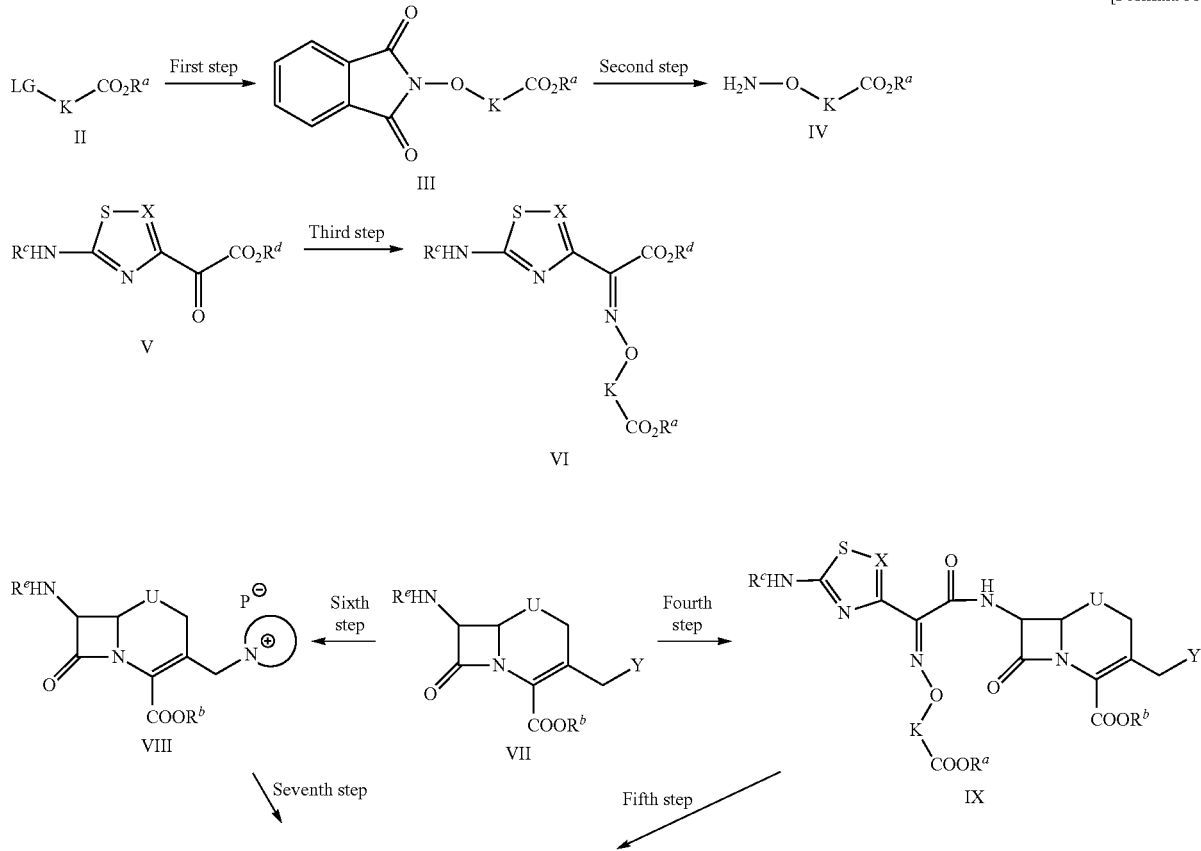

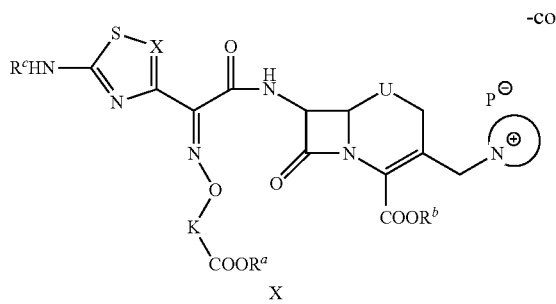 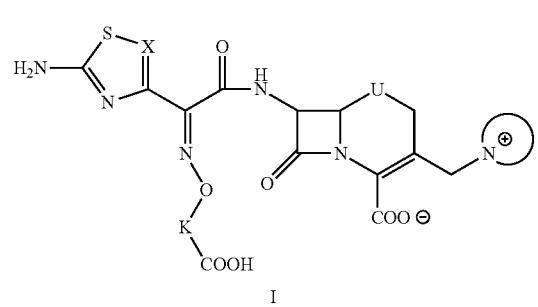

Eighth step wherein X, U, $R^a$, $R^b$, and $R^c$ are as defined above; $P^-$ is a counter anion of a quaternary amine;
K has the formula:

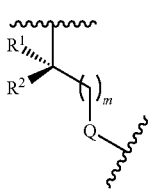

[Formula 34]

wherein each symbol is as defined above;
the formula:

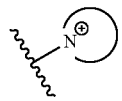

[Formula 35]

is the following moiety in Formula (I) including a quaternary ammonium group moiety of 3-side chain:

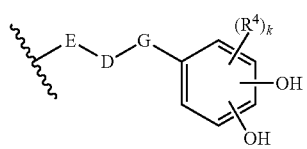

[Formula 36]

wherein each symbol is as defined above;
LG and Y are leaving groups (fox example, hydroxy, halogen (Cl, Br, I), optionally substituted carbamoyloxy, acyloxy, methanesulfonyloxy, and toluenesulfonyloxy, etc.);
$R^d$ is a hydrogen or a carboxy protecting group; and
$R^e$ is a hydrogen or an amino protecting group.

1) Starting Materials for the 7-Side Chain: Synthesis of Compound (VI)

The First Step:

Compound (III) is obtained by reacting N-hydroxyphthalimide in the presence of Compound (II) (LG is hydroxy) and a Mitsunobu reagent, or in the presence of Compound (II) (LG is another leaving group) and a base (such as sodium hydroxide, sodium methoxide).

The amount of N-hydroxyphthalimide used is generally 1-5 molar equivalents, preferably, 1-2 molar equivalents, relative to Compound (II).

Examples of reaction solvents include ethers (e.g., dioxane, tetrahydrofuran, diethyl ether, tert-butyl methyl ether, diisopropyl ether), halogenated hydrocarbons (e.g., dichloromethane, chloroform, carbon tetrachloride), hydrocarbons (e.g., n-hexane, benzene, toluene), amides (e.g., formamide, N,N-dimethylformamide, N,N-dimethylacetamide, N-methylpyrrolidone), and the like, and mixed solvents and the like thereof.

The reaction temperature is in a range of, generally, about −50 to 100° C., preferably about −40 to 50° C., and more preferably about −30 to 0° C.

The Second Step:

N-Methylhydrazine or hydrazine is added and reacted to Compound (III) to provide Compound (IV).

The amount of N-methylhydrazine or hydrazine used is in a range of about 1-10 molar equivalents, preferably 1-5 molar equivalents, more preferably 1-2 molar equivalents, relative to Compound (III).

Examples of reaction solvents include ethers (e.g., dioxane, tetrahydrofuran, diethyl ether, tert-butyl methyl ether, diisopropyl ether), esters (e.g., ethyl formate, ethyl acetate, isopropyl acetate), halogenated hydrocarbons (e.g., dichloromethane, chloroform, carbon tetrachloride), hydrocarbons (e.g., n-hexane, benzene, toluene), alcohols (e.g., methanol, ethanol, isopropanol), amides (e.g., formamide, N,N-dimethylformamide, N,N-dimethylacetamide, N-methylpyrrolidone), ketones (e.g., acetone, methyl ethyl ketone) nitriles (e.g., MeCN, propionitrile), dimethylsulfoxide, water, and the like, and mixed solvents thereof.

The reaction temperature is in a range of, generally, about 0 to 100° C., preferably about 0 to 50° C., more preferably about 10 to 30° C.

The Third Step:

Compound (V), which is commercially available or obtained by a known method, is added and reacted with Compound (IV) to provide Compound (VI). (e.g., as described in Bioorganic & Medicinal Chemistry, vol. 15, pp. 6716-6732 (2007)).

Compound (III) is added and reacted with N-Methylhydrazine or hydrazine to provide Compound (IV).

Examples of reaction solvents include ethers (e.g., dioxane, tetrahydrofuran, diethyl ether, tert-butyl methyl ether, diisopropyl ether), esters (e.g., ethyl formate, ethyl acetate, isopropyl acetate), halogenated hydrocarbons (e.g., dichloromethane, chloroform, carbon tetrachloride), hydrocarbons (e.g. n-hexane, benzene, toluene), alcohols (e.g., methanol, ethanol, isopropanol), amides (e.g., formamide, N,N-dimethylformamide, N,N-dimethylacetamide, N-methylpyrrolidone), ketones (e.g., acetone, methyl ethyl ketone), nitriles (e.g., MeCN, propionitrile), dimethylsulfoxide, water and the like, and mixed solvents thereof.

The reaction temperature is in a range of, generally, about 0 to 100° C., preferably about 0 to 50° C., more preferably about 10 to 30° C.

2) 7-Amidation and Formation of the 3-Side Chain; Synthesis of Compound (X)

The Fourth Step (7-Amidation Reaction):

Compound (IX) is obtained by reacting Compound (VI) with Compound (VII), which are commercially available or synthesized according to methods described in a document (e.g., JP 60-231684 A, LIP 62-119682 A, etc.). In this case, preferably, $R^a$ and $R^b$ are carboxy protecting groups, $R^c$ is an amino protecting group, and $R^d$ and $R^e$ are hydrogen.

The amount of Compound (VI) used is in a range of, generally, about 1-5 moles, preferably 1-2 moles, relative to 1 mole of Compound (VII).

Examples of reaction solvents include ethers (e.g., dioxane, tetrahydrofuran, diethyl ether, tert-butyl methyl ether, diisopropyl ether), esters (e.g., ethyl formate, ethyl acetate, isopropyl acetate), halogenated hydrocarbons (e.g., dichloromethane, chloroform, carbon tetrachloride), hydrocarbons (e.g., n-hexane, benzene, toluene), amides (e.g., formamide, N,N-dimethylformandde, N,N-dimethylacetamide, N-methylpyrrolidone), ketones (e.g., acetone, methyl ethyl ketone), nitriles (e.g., MeCN, propionitrile), dimethylsulfoxide, water, and the like, and mixed solvents and the like thereof.

The reaction temperature is in a range of, generally, about −40 to 80° C., preferably about −20 to 50° C., more preferably about −10 to 30° C.

The above-described amidation reaction may be carried out after the carboxy moiety is converted into a reactive derivative (e.g., inorganic base salt, organic base salt, acid halide, acid azide, acid anhydride, mixed acid anhydride, active amide, active ester, and active thioester). Examples of such inorganic bases include alkali metal (e.g., Na, K, etc.), alkali earth metal (e.g., Ca, Mg), and the like. Examples of organic bases include trimethylamine, triethylamine, tert-butyldimethylamine, dibenzylmethylamine, benzyldimethylamine, N-methylmorpholine, diisopropylethylamine, and the like. Examples of acid halides include acid chlorides, acid bromides, and the like. Examples of mixed acid anhydrides include mixed acid anhydrides of mono-alkyl carbonates, mixed acid anhydrides of aliphatic carboxylic acid, mixed acid anhydrides of aromatic carboxylic acid, mixed acid anhydrides of organic sulfonic acid, and the like. Examples of active amides include amides with nitrogen-containing heterocyclic compound, and the like. Examples of active esters include organic phosphoric esters (e.g., diethoxyphosphoric ester, diphenoxyphosphoric ester, and the like), p-nitrophenyl ester, 2,4-dinitrophenyl ester, cyanomethyl ester, and the like. Examples of active thioesters include esters with aromatic heterocyclic thiol compound (e.g., 2-pyridylthiol esters), and the like. Furthermore, in the above-described reaction, a suitable condensing agent may be used as desired. For example, hydrochloric acid salt of 1-dimethylaminopropyl-3-ethylcarbodiimide (WSCD.HCl), N,N'-dicyclohexylcarbodiimide, N,N'-carbonyldiimidazole, N,N'-thiocarbonyldiimidazole, N-ethoxycarbonyl-2-ethoxy-1,2-dihydroquinoline, phosphorus oxychloride, alkoxyacetylene, 2-chloromethylpyridinium iodide, 2-fluoromethylpyridinium iodide, trifluoroacetic anhydride, and the like can be used as a condensing agent.

The Fifth Step (3-Side Chain Forming Reaction):

Compound (X) is obtained by reacting Compound (IX) and a corresponding tertiary amine. In this case, preferably, $R^a$ and $R^b$ are carboxy protecting groups, and $R^c$ is an amino protecting group.

The amount of the corresponding tertiary amine used is in a range of, generally, 1-5 moles, preferably 1-2 moles, relative to 1 mole of Compound (IX).

Examples of reaction solvents include ethers (e.g., dioxane, tetrahydrofuran, diethyl ether, tert-butyl methyl ether, diisopropyl ether), esters (e.g., ethyl formate, ethyl acetate, isopropyl acetate), halogenated hydrocarbons (e.g., dichloromethane, chloroform, carbon tetrachloride), hydrocarbons (e.g., n-hexane, benzene, toluene), amides (e.g., formamide, N,N-dimethylformamide, N,N-dimethylacetamide, N-methylpyrrolidone), ketones (e.g., acetone, methyl ethyl ketone), nitriles (e.g., MeCN, propionitrile) dimethylsulfoxide, water, and the like, and mixed solvents and the like thereof.

The reaction temperature is in a range of, generally, −20 to 60° C., preferably −10 to 40° C., more preferably 0 to 20° C.

Furthermore, Compound (X) wherein U is SO can be obtained by reducing Compound (X) wherein U is SO. Examples of reducing agents include potassium iodide-acetyl chloride, and the like.

3) 3-Side Chain Formation and 7-Amidation; Synthesis of Compound (X)

The Sixth Step (3-side chain forming reaction):

Compound (VIII) is obtained by reacting Compound (VII) with a corresponding tertiary amine. In this case, preferably, $R^b$ is a carboxy protecting group, and $R^c$ is an amino protecting group.

The amount of the corresponding tertiary amine used is in a range of, generally, 1-5 moles, preferably 1-2 moles, relative to 1 mole of Compound (VII).

Examples of reaction solvents include ethers (e.g., dioxane, tetrahydrofuran, diethyl ether, tert-butyl methyl ether, diisopropyl ether), esters (e.g., ethyl formate, ethyl acetate, isopropylacetate), halogenated hydrocarbons (e.g., dichloromethane, chloroform, carbon tetrachloride), hydrocarbons (e.g., n-hexane, benzene, toluene), amides (e.g., formamide, N,N-dimethylformamide, N,N-dimethylacetamide, N-methylpyrrolidone), ketones (e.g., acetone, methyl ethyl ketone), nitriles (e.g., MeCN, propionitrile), dimethylsulfoxide, water, and the like, and mixed solvents thereof.

The reaction temperature is in a range of, generally, −20 to 60° C., preferably −10 to 40° C., more preferably 0 to 20° C.

Both tertiary amine moieties used in the 3-side chain forming reactions of the fifth and the sixth steps (corresponding to the moiety E in item 1) can be obtained as a commercially available reagent, by a known method, and/or by a method described herein.

The Seventh Step (7-amidation reaction):

Compound (X) is obtained by reacting Compound (VIII) and Compound (VI). In this case, preferably, $R^a$ and $R^b$ are carboxy protecting groups, $R^c$ is an amino protecting group, $R^d$ and $B^e$ are hydrogen.

The amount Compound (VI) used is in a range of, generally, about 1-5 moles, preferably 1-2 moles, relative to 1 mole of Compound (VIII).

Examples of reaction solvents include ethers (e.g., dioxane, tetrahydrofuran, diethyl ether, tert-butyl methyl ether, diisopropyl ether), esters (e.g., ethyl formate, ethyl acetate, isopropyl acetate), halogenated hydrocarbons (e.g., dichloromethane, chloroform, carbon tetrachloride), hydrocarbons (e.g., n-hexane, benzene, toluene), amides (e.g., formamide, N,N-dimethylformamide, N,N-dimethylacetamide, N-methylpyrrolidone), ketones (e.g., acetone, methyl ethyl ketone), nitriles (e.g., MeCN, propionitrile), dimethylsulfoxide, water, and the like, and mixed solvents thereof.

The reaction temperature is in a range of, generally, about −40 to 80° C., preferably about −20 to 50° C., more preferably about −10 to 30° C.

The above-described amidation reaction may be carried out after a carboxyl moiety is converted to a reactive derivative (e.g., inorganic base salt, organic base salt, acid halide, acid azide, acid anhydride, mixed acid anhydride, active amide, active ester, and active thioester). Examples of such inorganic bases include alkali metal (e.g., Na, K, etc.), alkali earth metal (e.g., Ca, Mg), and the like. Examples of organic bases include trimethylamine, triethylamine, tert-butyldimethylamine, dibenzylmethylamine, benzyldimethylamine, N-methylmorpholine, diisopropylethylamine, and the like. Examples of acid halides include acid chlorides, acid bromides, and the like. Examples of mixed acid anhydrides include mixed acid anhydrides of mono-alkyl carbonate, mixed acid anhydrides of aliphatic carboxylic acid, mixed acid anhydrides of aromatic carboxylic acid, mixed acid anhydrides of organic sulfonic acid, and the like. Examples of active amides include amides with nitrogen-containing heterocyclic compound, and the like. Examples of active esters include organic phosphoric esters (e.g., diethoxyphosphoric ester, diphenoxyphosphoric ester, and the like), p-nitrophenyl ester, 2,4-dinitrophenyl ester, cyanomethyl ester, and the like. Examples of active thioesters include esters with aromatic heterocyclic thiol compound (e.g., 2-pyridylthiol esters), and the like. Examples of active thioesters include esters with aromatic heterocyclic thiol compound (e.g., 2-pyridylthiol esters), and the like. Furthermore, in the above-described reaction, a suitable condensing agent may be used as desired. For example, hydrochloric acid salt of 1-dimethylaminopropyl-3-ethylcarbodiimide (WSCD.HCl) N,N'-dicyclohexylcarbodiimide, N,N'-carbonyldiimidazole, N,N'-thiocarbonyldiimidazole, N-ethoxycarbonyl-2-ethoxy-1,2-dihydroquinoline, phosphorus oxychloride, alkoxyacetylene, 2-chloromethylpyridinium 2-fluoromethylpyridinium iodide, trifluoroacetic anhydride, and the like can be used as a condensing agent.

Furthermore, Compound (X) wherein U is O can be obtained using Compound (VII) wherein U is O.

4) Deprotection Reaction

The Eighth Step:

Compound (I) is obtained by subjecting Compound (X) to a deprotection reaction according to a method well known to those skilled in the art.

Examples of reaction solvents include ethers (e.g., anisole, dioxane, tetrahydrofuran, diethyl ether, tert-butyl methyl ether, diisopropyl ether), esters (e.g., ethyl formate, ethyl acetate, n-butyl acetate), halogenated hydrocarbons (e.g., dichloromethane, chloroform, carbon tetrachloride) hydrocarbons (e.g., n-hexane, benzene, toluene), amides (e.g., formamide, N,N-dimethylformamide, N,N-dimethylacetamide, N-methylpyrrolidone), ketones (e.g., acetone, methyl ethyl ketone), nitriles (e.g., MeCN, propionitrile), nitrous (e.g., nitromethane, nitroethane, nitrobenzene), dimethylsulfoxide, water, and the like. These solvents may be used alone or in a combination using two or more of such solvents.

The reaction temperature is in a range of, generally, about −30 to 100° C., preferably about 0 to 50° C., more preferably about 0 to 10° C.

As a catalyst, Lewis acid (e.g., $AlCl_3$, $SnCl_4$, $TiCl_4$), protonic acid (e.g., HCl, HBr, $H_2SO_4$, HCOOH), and the like can be used.

The obtained Compound (I) is further chemically modified to obtain an ester, or a compound wherein the amino on the thiazole ring at the 7-position is protected, or a pharmaceutically acceptable salt, or a solvate thereof.

The compounds of the subject invention have a wide antimicrobial activity spectrum, and may be used for the prevention or treatment of a variety of diseases caused by pathogenic bacteria in mammals including humans, for example, airway infectious diseases, urinary system infectious diseases, respiratory system infectious diseases, sepsis, nephritis, cholecystitis, oral cavity infectious diseases, endocarditis, pneumonia, bone marrow membrane myelitis, otitis media, enteritis, empyema, wound infectious diseases, opportunistic infection and the like.

The compounds of the subject invention exhibit high antimicrobial activity in particular against Gram negative bacteria, preferably, Gram negative bacteria of enterobacteria (*E. coli, Serratia, Enterobacter, Citrobacter, Morganella, Providencia, Proteus* and the like), Gram negative bacteria colonized in respiratory system (*Haemophilus, Moraxella* and the like), and Gram negative bacteria of glucose non-fermentable (*Pseudomonas aeruginosa, Pseudomonas* other than *P. aeruginosa, Stenotrophomonas, Burkholderia, Acinetobacter* and the like). The compounds are table against beta-lactamase Classes A, B, C and D which beta-lactamase are produced by these Gram negative bacteria, and have high antimicrobial activity against a variety of beta-lactam drug resistant Gram negative bacteria, such as ESBL producing bacteria and the like. These are extremely stable against metallo-beta-lactamase belonging to Class B including in particular IMP type, VIM type, L-1 type and the like, and thus, these are effective against Gram negative bacteria resistant to a variety of beta-lactam drug including Cephem and Carbapenem. Moreover, the compounds of the subject invention have antimicrobial activity against Gram positive bacteria including methicillin-resistant *Staphylococcus aureus* (MRSA), penicillin-resistant *Streptococcus pneumoniae* (PRSP), and the like. Still more preferable compounds have features regarding kinetics in the body, such as high blood concentration, long duration of effects, and/or significant tissue migration. More preferable compounds are safe in terms of side effects. Also, more preferable compounds have high water solubility, and thus particularly suitable for injectable formulations.

Compounds (I) may be administered parenterally or orally as injectable formulations, capsules, tablets, and granules, and preferably, administered as an injectable formulation. The dosage may usually be about 0.1 to 100 mg/day, preferably, about 0.5 to 50 mg/day, per 1 kg of body weight of a patient or animal, and optionally be divided into 2 to 4 times per day. The carriers for use in injectable formulation may be, for example, distilled water, saline and the like, and further bases may be used for pH adjustment. The carriers for used in capsules, granules or tablets, carriers include known excipients (e.g., starch, lactose, sucrose, calcium carbonate, calcium phosphate and the like), binders (e.g., starch, acacia gum, carboxymethyl cellulose, hydroxypropyl cellulose, crystalline cellulose, and the like), lubricants (e.g., magnesium stearate, talc and the like), and the like.

EXAMPLES

Hereinafter, the subject invention is described in more details with working examples and experimental examples. However, the subject invention is not limited to them.

In the Examples, the meaning of each abbreviation is as described below.

ODS: Octadodecylsilyl
MeCN: Acetonitrile
WSCD.HCl: Hydrochloric acid salt of N-ethyl-N'-(3-dimethylaminopropyl)carbodilmide
Me: Methyl
Et: Ethyl
Pr: Propyl
Ph: Phenyl
PMB: para-Methoxybenzyl
L-Bu: tert-Butyl
i-Pr: Isopropyl
Boc: tert-Butoxycarbonyl
BH: Benzhydryl
Ms: Methanesulfonyl
Trt: Trityl
TBS: tert-Butyldimethylsilyl
Bn: Benzyl

Example 1

Synthesis of Compound (I-1)

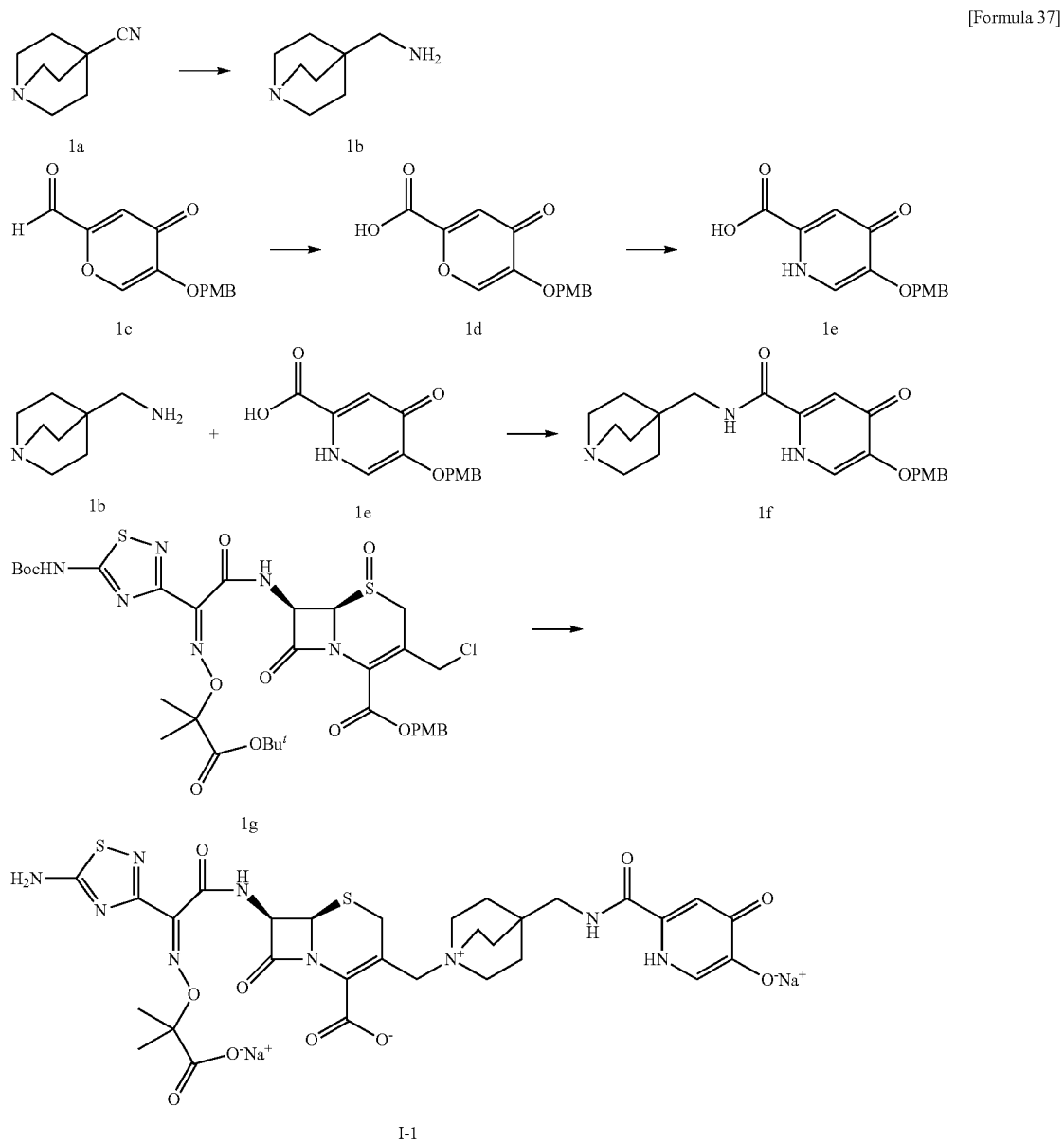

[Formula 37]

Step (1): Compound 1a→Compound 1b

To ice-cooled tetrahydrofuran (40 mL), lithium aluminum hydride (1.52 g, 40 mmol) followed by compound 1a (2.72 g, 20 mmol) were added. After heating at reflux for 45 minutes, the reaction solution was cooled in an ice bath. Sodium sulfate decahydrate was then added thereto until effervescence ceased. Anhydrous sodium sulfate (5.0 g) was then added, subsequently stirring at room temperature for 1 hour. After the insoluble was filtered off through a Celite, the resulting filtrate was Concentrated and then dried to yield Compound 1b (2.61 g, 93% yield) as a colorless liquid.

$^1$H-NMR (CDCl$_3$) δ: 1.36 (6H, t, J=7.5 Hz), 2.43 (2H, s), 2.91 (6H, q, J=7.5 Hz).

Step (2): Compound 1c→Compound 1d

Sodium chlorite (3.87 g, 42.7 mmol) was dissolved in water (20 mL). Under ice-cooling, a solution of amidosulfuric acid (9.15 g, 42.7 mmol) and Compound 1c (4.45 g, 17.1 mmol) in methanol (50 mL) was added thereto, and then stirred at the same temperature for 3 hours. After the reaction solution was diluted with water (150 mL) the insoluble was filtered, and then washed with isopropanol/diethylether (1/1). The filtered residue was dried under reduced pressure to yield Compound 1d (3.98 g, 84% yield).

$^1$H-NMR (d$_6$-DMSO) δ: 3.76 (3H, s), 4.90 (2H, s), 6.92-6.97 (3H, m), 7.50 (2H, d, J=8.7 Hz), 8.33 (1H, s).

Step (3): Compound 1d→Compound 1e

To a solution of Compound 1d (829 mg, 3.0 mmol) in ethanol (6.0 mL), aqueous 28% ammonium solution (3.46 mL, 45 mmol) was added. After stirring at room temperature for 12 hours, the mixture was left to stand overnight at room temperature. The solvent was evaporated in vacuo, and then water was added thereto. Subsequently, pH was adjusted to 2.5 with 1 N hydrochloric acid, and the precipitated insoluble was filtered. The filtered residue was dried in vacuo to yield Compound 1e (79% mg, 97% yield).

$^1$H-NMR (d$_6$-DMSO) δ: 3.75 (3H, s), 5.09 (2H, s), 6.94 (2H, d, J=8.4 Hz), 7.18 (1H, brs), 7.37 (2H, d, J=8.4 Hz), 7.90 (1H, brs).

Step (4): Compound 1e→Compound 1f

To a solution of Compound 1e (1.69 g, 6.19 mmol) in N,N-dimethylformamide (18 mL), while stirring under ice-cooling, hydrochloric acid salt of N-ethyl-N'-(3-dimethylaminopropyl) carbodiimide (1.69 g, 6.14 mmol) and 1-hydroxybenzotriazole (954 mg, 7.06 mmol) were added. After stirring at room temperature for 1 hour, the mixture was ice-cooled again, a solution of Compound 1b (1.03 g, 7.37 mmol) in N,N-dimethylformamide (6 mL) was added thereto over 5 minutes. After stirring at the same temperature for 2 hours, the solvent was evaporated in vacuo. The residue was added into cooled water, and then the pH was adjusted to 10 with aqueous 20% sodium carbonate solution. The precipitates were filtered, and then dried in vacuo to yield Compound 1f (1.38 g, 57% yield).

$^1$H-NMR (d$_6$-DMSO) δ: 0.90 (6H, t, J=8.1 Hz), 2.34 (6H, t, J=8.1 Hz), 2.63 (2H, d, J=6.6 Hz), 3.33 (3H, s), 4.72 (2H, s), 6.52 (28, d, J=8.7 Hz), 6.95-6.98 (3H, m), 7.62 (1H, s), 7.89 (1H, t, J=6.6 Hz).

Step (5): Compound 1g→Compound (I-1)

To a solution of Compound 1g (506 mg, 0.6 mmol) in N,N-dimethylformamide (2.0 mL), Compound 1f (262 mg, 0.66 mmol) and sodium bromide (123 mg, 1.2 mmol) were added under ice-cooling. After the reaction solution was stirred for 3 hours in a water bath at 15° C., N,N-dimethylformamide (4 mL) was added thereto, and then cooled to −40° C. At −40° C., phosphorus tribromide (113 µl, 1.2 mmol) was added thereto, and then stirred at the same temperature for 1 hour. The reaction solution was poured into 5% brine (100 mL), and stirred for 15 minutes, and then the precipitate was filtered. The precipitate was dried in vacuo to yield a pale brown solid A solution of this solid in methylene chloride (5 mL) was added to an ice-cooled solution of anisole (553 mL) in trifluoroacetic acid (7.0 mL) while stirring. The reaction solution was stirred at room temperature for 1.5 hours and the solvent was evaporated in vacuo. At this time, the temperature in the water bath was set to not more than 25° C. The residue was added to ice-cooled diisopropyl ether (80 mL) while stirring, and then the precipitate was filtered. The resulting solid was dried, dissolved in aqueous sodium bicarbonate solution, and then subjected to ODS column chromatography, eluting with water-acetonitrile. The eluted fractions containing the intended compound were concentrated in vacuo and the concentrated solution was lyophilized to yield Compound I-1 (185 mg, 30% yield) as a powder.

$^1$H-NMR (D$_2$O) δ: 1.52 (3H, s), 1.53 (3H, s), 1.92 (6H, m), 3.36-3.49 (9H, m), 3.84-3.91 (2H, m), 4.59 (1H, m), 5.34 (1H, d, J=5.1 Hz), 5.88 (1H, d, J=5.1 Hz), 7.09 (1H, s), 7.70 (1H, s).

Elemental analysis for C$_{30}$H$_{33}$N$_9$Na$_2$O$_{10}$S$_2$.8.7H$_2$O
Calcd.: C, 37.96; H, 5.21; N, 13.13; S, 7.80; Na, 4.51(%).
Found.: C, 37.07; H, 5.37; N, 13.32; S, 6.78; Na, 4.86(%).

Example 2

Synthesis of Compound (I-2)

[Formula 38]

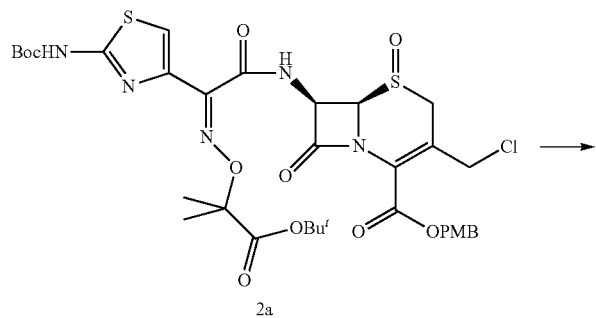

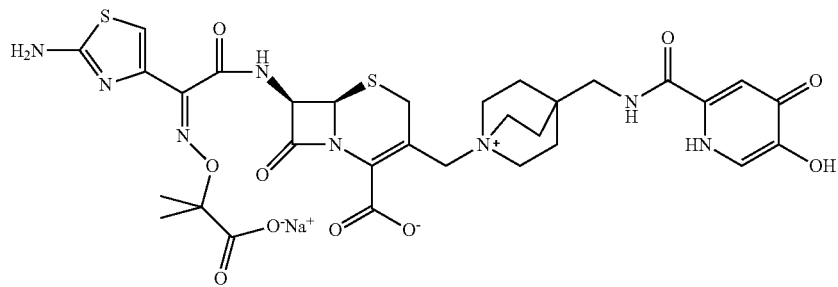

I-2

Step (1): Compound 2a→Compound (I-2)

Compound I-2 (305 mg, 52% yield) was obtained as described in Example 1 using Compound 2a (637 mg, 0.80 mmol).

$^1$H-NMR (D$_2$O) δ: 1.48 (3H, s), 1.50 (3H, s), 1.92 (6H, t, J=7.5 Hz), 3.36-3.49 (9H, m), 3.85-3.91 (1H, m), 4.57 (1H, d, J=13.5 Hz), 5.34 (1H, d, J=5.1 Hz), 5.86 (1H, d, J=5.1 Hz), 6.96 (1H, s), 7.09 (1H, s), 7.72 (1H, s).

Elemental analysis for C$_{31}$H$_{35}$N$_8$NaO$_{10}$S$_2$.6.1H$_2$O.0.4NaHCO$_3$ Calcd.: C, 41.38; H, 5.33; N, 12.55; 5, 7.29; Na, 3.68(%).
Found.: C, 41.43; H, 5.27; N, 12.31; S, 7.05; Na, 3.54(%).

Example 3

Synthesis of Compound (I-3)

[Formula 39]

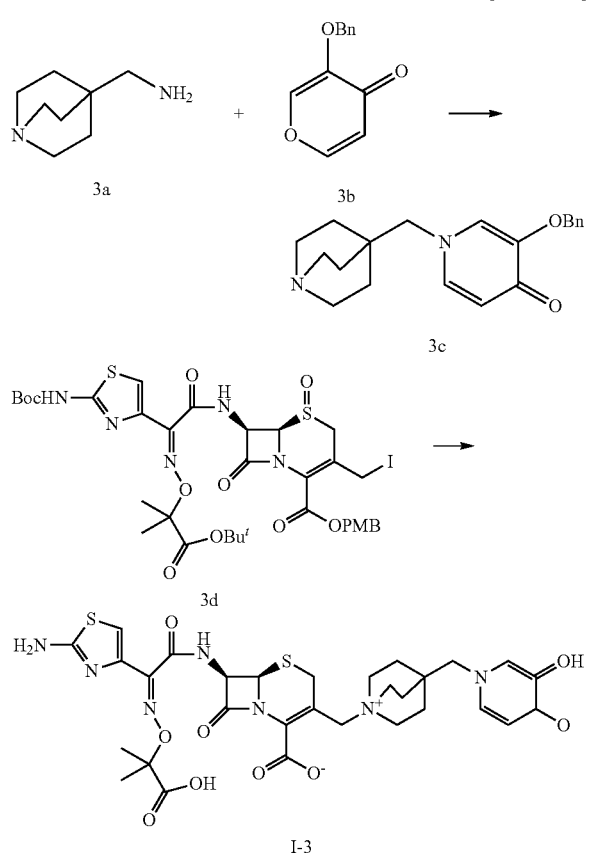

Step (1): Compound 3a→Compound 3c

To a solution of Compound 3a (561 mg, 4.0 mmol) in ethanol (0.5 mL), Compound 3b (404 mg) was added, and then heated at reflux for 20 hours. After the solvent was evaporated, the residue was diluted with chloroform, and then washed with water. The organic layer was dried with anhydrous magnesium sulfate, filtered, and then concentrated. Isopropyl acetate was added to the residue. The resulting precipitated solid was filtered, and then dried to yield Compound 3c (312 mg, 48% yield).

$^1$H-NMR (CDCl$_3$) δ: 1.22 (6H, t, J=8.4 Hz), 2.91 (6H, t, J=8.4 Hz), 3.44 (2H, s), 5.22 (2H, s), 6.41 (1H, d, J=7.5 Hz), 6.66 (1H, d, J=2.1 Hz), 6.98 (1H, dd, J=2.1, 7.5 Hz), 7.26-7.39 (5H, m).

Step (2): Compound 3d→Compound (I-3)

To a solution of Compound 3d (444 mg, 0.50 mmol) in N,N-dimethylformamide (2.0 mL), Compound 3c (162 mg, 0.50 mmol) was added under ice-cooling. After the reaction solution was stirred for 3 hours in a water bath at 15° C., N,N-dimethylformamide (4 mL) was added thereto, and then ice-cooled at −40° C. At −40° C., phosphorus tribromide (47 μl, 0.50 mmol) was added thereto, and then stirred at the same temperature for 1 hour. The reaction solution was poured into 5% brine (100 mL). After stirring for 15 minutes, the precipitate was filtered. The filtered residue was dried in vacuo to yield a pale brown solid. To a solution of the solid in methylene chloride (10 mL), anisole (657 μl) was added, and then cooled to −40° C. Subsequently, to this solution, aluminum chloride (3.01 mL, 2.0 M solution in nitromethane) was added at the same temperature, and then stirred at room temperature for 3 hours. The reaction solution was poured into an ice-cooled, mixed solution of water (30 mL), acetonitrile (30 mL), and diisopropyl ether (50 mL) while stirring. The aqueous layer was separated, and then the organic layer was extracted with a mixed solution of water/acetonitrile/diluted hydrochloric acid. To the combined aqueous layer, HP20SS was added, and then concentrated to 20 mL. The concentrated suspension was subjected to HP20SS column chromatography, eluting with water-acetonitrile. The eluted fractions containing the intended compound were concentrated in vacuo, the concentrated solution was lyophilized to yield Compound I-3 (201 mg, 42% yield) as a powder.

$^1$H-NMR (D$_2$O) δ: 1.48 (3H, s), 1.99 (3H, s), 1.90 (6H, m), 3.38-3.49 (7H, m), 3.81-4.10 (4H, m), 4.58 (1H, d, J=13.2 Hz), 5.34 (1H, brs), 5.80 (1H, brs), 6.70 (1H, d, J=6.31 Hz), 6.92 (1H. Brs), 7.30 (1H, brs), 7.58 (1H, d, J=6.3 Hz).

Elemental analysis for C$_{30}$H$_{35}$N$_7$O$_{10}$S$_2$.9.3H$_2$O
Calcd.: C, 41.17; H, 5.52; N, 11.59; 5, 8.21(%).
Found.: C, 41.45; H, 6.21; N, 11.28; 5, 7.38(%).

Example 4

Synthesis of Compound (I-4)

[Formula 40]

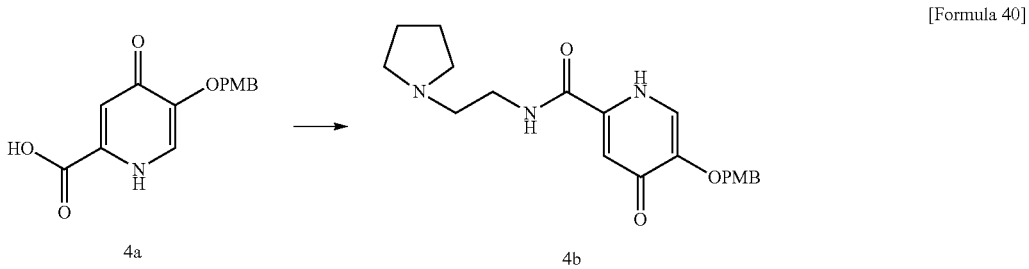

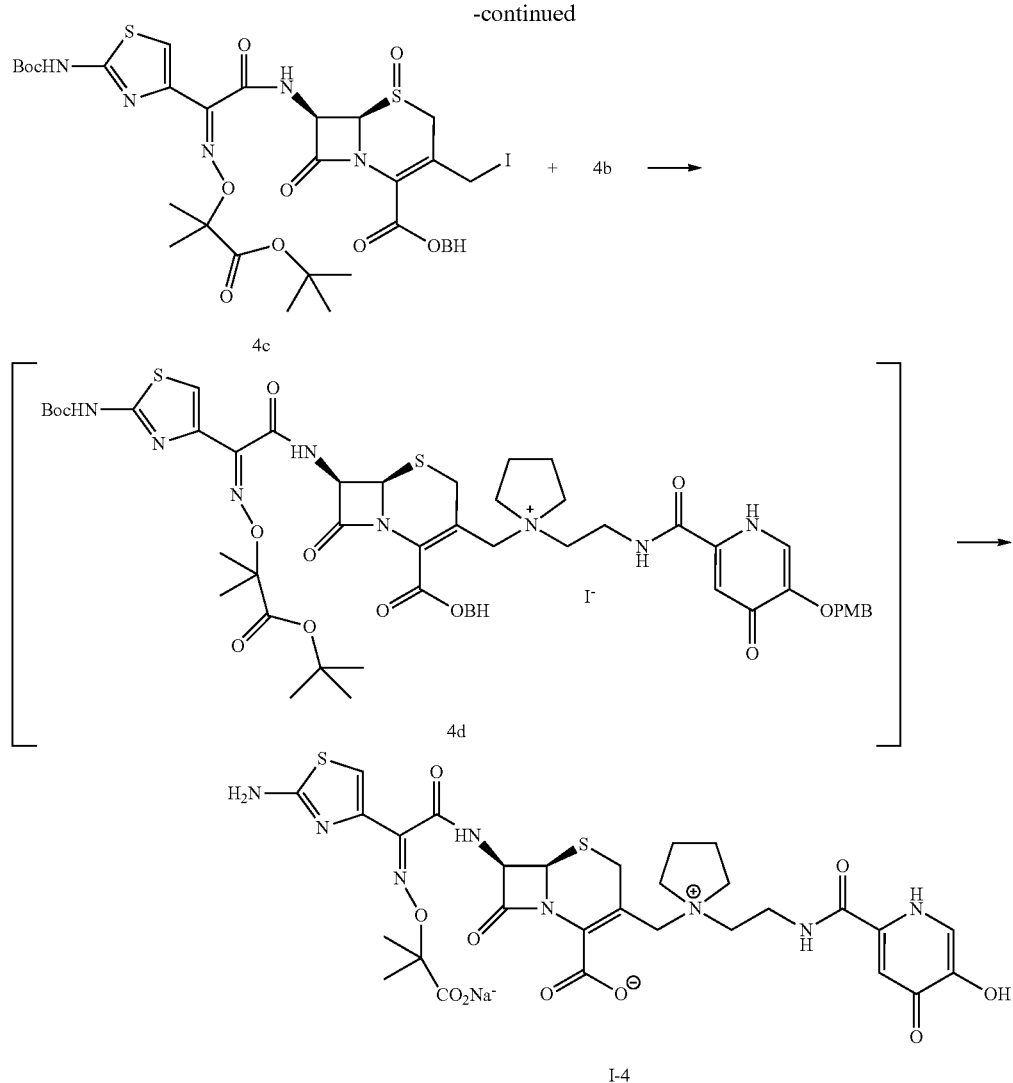

Step (3): Compound 4a→Compound 4b

A solution of Compound 4a (963 mg, 3.5 mmol) in N,N-dimethylformamide (7 mL) was cooled to 0° C., and then N-(2-aminoethyl)-pyrrolidine (480 mg, 4.20 mmol), hydrochloric acid salt of N-ethyl-W (3-dimethylaminopropyl)carbodiimide (738 mg, 3.85 mmol), and 1-hydroxybenzotriazole (520 mg, 3.85 mmol) were added, followed by stirring at room temperature for 1 hour. The solvent was evaporated, and then was subjected to HP20SS column chromatography, eluting with water-acetonitrile. The eluted fractions containing the intended compound were concentrated in vacuo to yield Compound 4b (256 mg, 20% yield).

$^1$H-NMR (DMSO) δ: 1.66-1.70 (4H, m), 2.40-2.60 (4H, m), 3.10-3.80 (4H, m), 3.75 (3H, s), 5.15 (2H, s), 6.92-7.00 (2H, m) 7.37-7.39 (2H, m), 7.44 (1H, s), 8.11 (1H, s), 8.43-8.50 (1H, br)

Step (4): Compound 4c+Compound 4b→Compound 4d→Compound (I-4)

After a solution of Compound 4c (635 mg, 0.68 mmol) in N,N-dimethylformamide (3 mL) was cooled to 0° C., Compound 4b (253 mg, 0.68 mmol) was added thereto, and then stirred at room temperature for 1 hour. The react ion solution was diluted with N,N-dimethylformamide (6 mL), and then cooled to −40° C. Subsequently, phosphorus tribromide (0.189 mL, 2 mmol) was added thereto, followed by stirring for 1 hour. The reaction solution was added to cooled 5% brine, the precipitated solid was filtered, washed with water, and then air-dried to yield Compound 4d.

Compound 4d was dissolved in methylene chloride (10 ml) and anisole (0.7 ml), and then cooled to −40° C. 2 mol/L-aluminum chloride/nitromethane solution (3.4 ml) was added thereto, and then stirred at 0° C. for 50 minutes. To the reaction solution, aqueous 2 N hydrochloric acid (60 mL), acetonitrile (50 mL) and diethyl ether (100 mL) were added. The separated aqueous layer was washed with diethyl ether, concentrated in vacuo, and then subjected to ODS column chromatography, eluting with acetonitrile-water. The eluted fractions containing the desired compound were concentrated under reduced pressure. To the concentrated solution, aqueous 7% sodium bicarbonate was added, and then subjected again to ODS column chromatography, eluting with acetonitrile-water. The eluted fractions containing the desired compound were concentrated under reduced pressure. The concentrated solution was further subjected to ODS column chromatography, eluting with acetonitrile-aqueous 0.02 N hydrochloric acid. The eluted fractions containing the desired compound were concentrated under reduced pressure. The concentrated solution was further subjected to ODS column chromatography, eluting with acetonitrile-water. To the fractions containing the desired compound, aqueous 0.02 N sodium hydroxide solution was added to adjust pH=6 and to form a sodium salt. The resulting solution was concentrated under reduced pressure, and then lyophilized to yield Compound I-4 as a white powder. Yield 69.9 mg (14%).

$^1$H-NMR (D$_2$O) δ: 1.47 (3H, s), 1.48 (3H, s), 2.00-2.15 (1H, m), 3.40-4.18 (12H, m), 5.34 (1H, d, J=5.1 Hz), 5.85 (1H, d, J=5.1 Hz), 6.94 (1H, s), 7.01 (1H, s), 7.74 (1H, s)

Elemental analysis for C$_{29}$H$_{33}$N$_8$O$_{10}$S$_2$Na.7.8H$_2$O
Calcd.: C, 39.36; H, 5.42; N, 12.73; S, 7.61; Na, 2.88(%)
Found.: C, 39.52; H, 5.56; N, 12.72; S, 7.28; Na, 2.61(%)

Example 5

Synthesis of Compound (I-5)

Step (1): Compound 5a→Compound 5b

To Compound 5a (6.94 g, 30 mmol), acetonitrile (120 mL) was added. N-Chlorosuccinimide (6.01 g, 45 mmol) was added thereto, and then stirred at 80° C. for 90 minutes. The precipitated solid was filtered, washed with acetonitrile then water, and then air-dried to yield Compound 5b. Yield 5.21 g (65%).

$^1$H-NMR (CDCl$_3$) δ: 3.15-3.70 (1H, br), 4.34 (1H, s), 5.03 (1H, s), 7.22-7.50 (6H, m)

Step (2): Compound 5b→Compound 5c

Compound 5b (5.21 g, 19.61 mmol) was dissolved in chloroform (80 mL). Manganese dioxide (6.82 g, 78 mmol) was added thereto, and then refluxed for 3 hours. After standing overnight, manganese dioxide (13.6 g, 156 mmol) was further added, and then refluxed for 4 hours. After filtration through

[Formula 41]

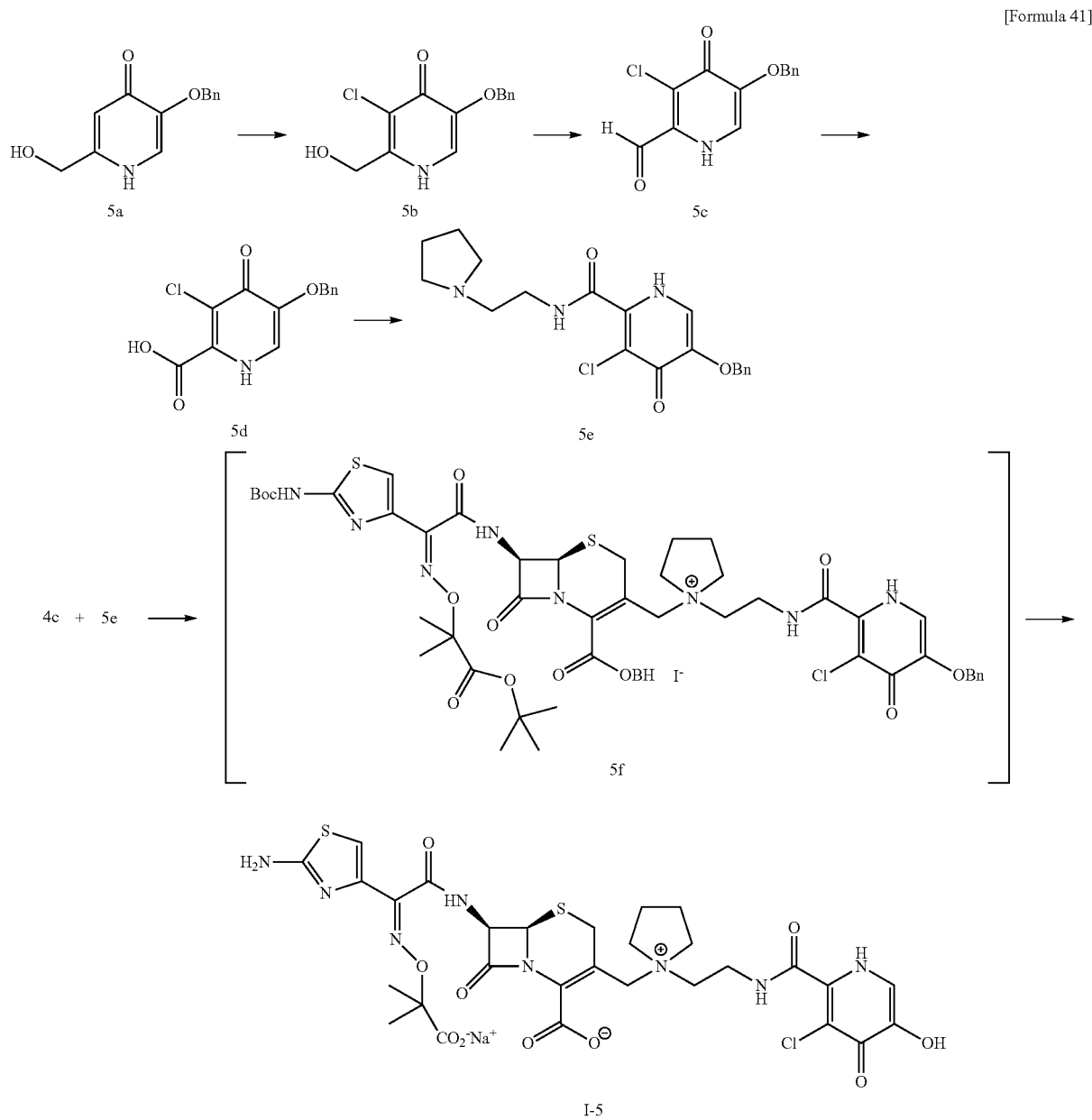

a Celite, methanol/chloroform were added thereto. Manganese dioxide (6.82 g, 78 mmol) was added thereto, and then further refluxed for 3 hours. After filtration through a Celite, the solvent was evaporated under reduced pressure to yield Compound 5c. Yield 4.0 g (77%).

Step (3): Compound 5c→Compound 5d

Compound 5c (4 g, 15.17 mmol) was suspended in water (5 mL), and then amidosulfuric acid (3.68 g, 37.9 mmol) was added thereto. After cooling to 0° C., a solution of methanol (40 mL) and sodium chlorite (3.43 g, 37.9 mmol) in water (35 mL) was added dropwise thereto. After stirring at room temperature for 1 hour, the solvent was evaporated under reduced pressure. The residue was subjected to HP20SS chromatography, eluting with water-acetonitrile. The eluted fractions containing the desired compound were concentrated to yield Compound 5d. Yield 2.34 g (55.2%).

$^1$H-NMR (DMSO) δ: 5.17 (2H, s), 7.30-7.50 (6H, m), 7.60-7.80 (1H, br)

Step (4): Compound 5d→Compound 5e

To a solution of Compound 5d (839 mg, 3 mmol) and N-(2-aminoethyl)-pyrrolidine (514 mmol) mg, 4.5 in N,N-dimethylformamide (8 mL), O-(7-azabenzotriazol-1-yl)-N,N,N',N'-tetramethyluronium hexafluorophosphite (1.37 g, 3.60 mmol) and triethylamine (0.499 mL, 3.60 mmol) were added, and then stood overnight. After the solvent was evaporated in vacuo, HP20SS column chromatography was performed, eluting with acetonitrile-water. The fractions containing the desired compound were collected, and concentrated to yield Compound 5e. Yield 530 mg (47%).

$^1$H-NMR (DMSO) δ: 1.80-2.00 (4H, m), 3.00-4.00 (8H, m), 5.24 (2H, s), 7.12-7.50 (5H, m), 7.90 (1H, s), 8.79-8.82 (1H, br)

Step (5): Compound 4c+Compound 5e→Compound 5f→Compound (I-5)

A solution of Compound 4c (934 mg, 1.0 mmol) in N,N-dimethylformamide (3 mL) was cooled to 0° C. Compound 5e (376 mg, 1.0 mmol) was added thereto, and then stirred at room temperature for 2 hours. The reaction solution was diluted with N,N-dimethylformamide (6 mL), and then cooled to −40° C. Subsequently, phosphorus tribromide (0.189 mL, 2 mmol) was added thereto, and then stirred for 1 hour. After the reaction solution was added to 5% brine pre-cooled to 0° C., the precipitated solid was filtered, washed with water, and air-dried to yield Compound 5f.

Compound 5f was dissolved in methylene chloride (10 ml) and anisole (1.1 ml), and then cooled to −40° C. Subsequently, 2 mol/L-aluminum chloride/nitromethane solution (5 ml) was added thereto, and then stirred at 0° C. for 50 minutes. To the reaction solution, aqueous 2 N hydrochloric acid (60 mL), acetonitrile (50 ml), and diethyl ether (100 mL) were added. The separated aqueous layer was washed with diethyl ether, concentrated under reduced pressure, and then subjected to HP-20SS column chromatography, eluting with acetonitrile-water. To the eluted fractions containing the desired compound, aqueous 0.02 N sodium hydroxide solution was added to adjust pH=6. The resulting solution was concentrated in vacuo, and then lyophilized to yield Compound I-5 as a white powder. Yield 26 mg (3%).

$^1$H-NMR (D$_2$O) δ: 1.48 (3H, s), 1.50 (3H, s), 2.00-2.20 (4H, m), 3.20-4.00 (11H, m), 5.20 (1H, d, J=4.5 Hz), 5.28 (1H, d, 16.2 Hz), 5.84 (1H, d, J=4.5 Hz), 6.98 (s, 1H), 7.75 (s, 1H)

Elemental analysis for $C_{29}H_{32}ClN_8O_{10}S_2Na \cdot 7.4H_2O$ $(NaHCO_3)_{0.4}$ Calcd.: C, 37.30; H, 4.86; Cl, 3.90; N, 11.80; S, 7.39; Na, 3.75(%).

Found.: C, 37.48; H, 5.05; Cl, 3.76; N, 11.89; 8, 6.81; Na, 3.42(%).

Example 6

Synthesis of Compound (I-6)

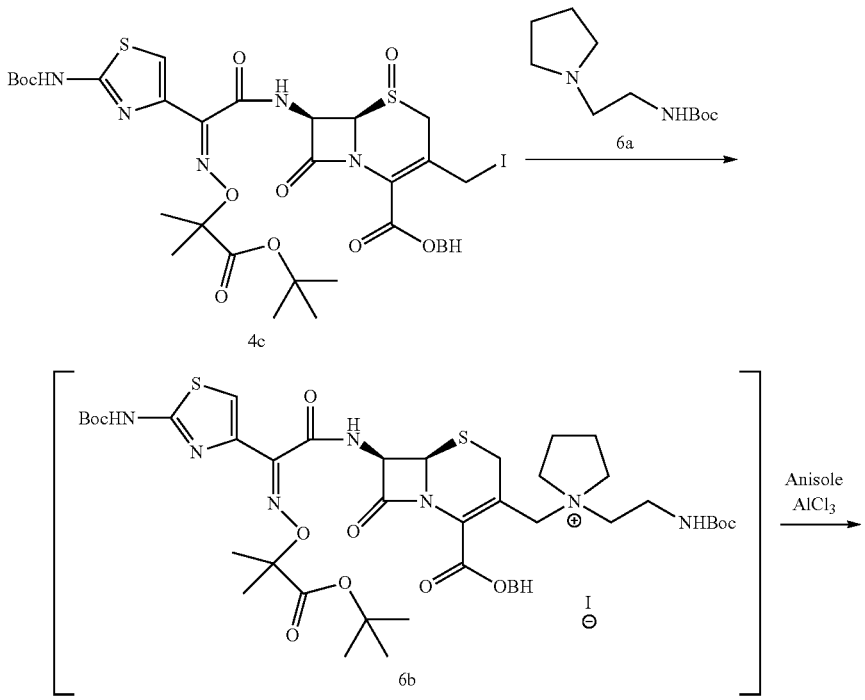

[Formula 42]

-continued

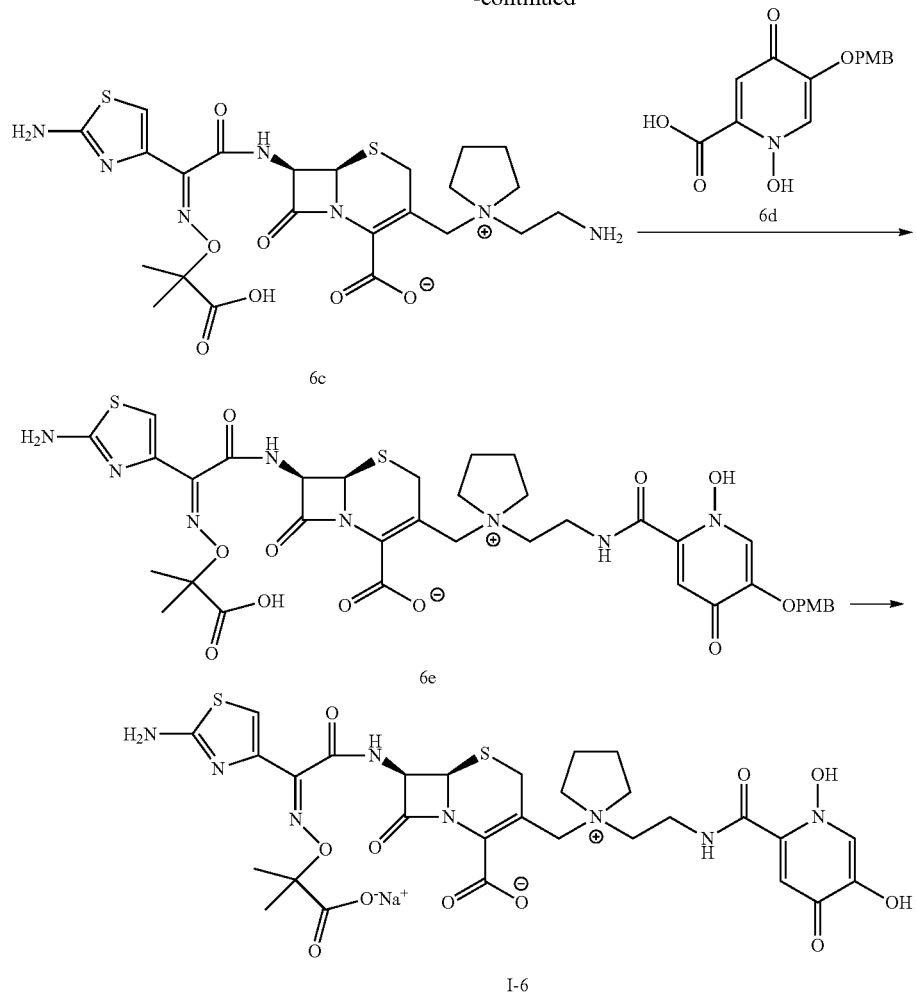

Step (1): Compound 4c+Compound 6a→Compound 6b→Compound 6c

To a solution of Compound 4a (28.0 g, 30 mmol) in N,N-dimethylacetamide (45 mL), at 15° C., a solution of Compound 6a (8.04 g, 30 mmol) in N,N-dimethylformamide (45 mL) was added dropwise After stirring at room temperature for 2 hours, N,N-dimethylformamide (180 mL) was added thereto, and then cooled to −40° C. Subsequently, to the reaction solution, phosphorus tribromide (5.66 mL, 60 mmol) was added, and then stirred for 1 hour. The reaction solution was added to aqueous 5% sodium sulfite solution pre-cooled to 0° C., and then the precipitated solid was filtered. The filtered residue was suspended in water and then lyophilized.

The resulting Compound 6b was treated similarly as 4d of Example 4 to obtain Compound 6c.

Compound 6b was dissolved in methylene chloride (300 ml) and anisole (33 ml), and then cooled to −40° C. 2 mol/L-aluminum chloride/nitromethane solution (150 ml, 300 mmol) was added thereto, and then stirred at 0° C. for 50 minutes. To the reaction solution, aqueous 2 N hydrochloric acid (60 mL), acetonitrile (50 mL), and diethyl ether (100 mL) were added. The separated aqueous layer was washed with diethyl ether, concentrated in vacuo, and subjected to ODS column chromatography, eluting with acetonitrile-water. The eluted fractions containing the desired compound were concentrated under reduced pressure, and then lyophilized to yield Compound 6c as a white powder. Yield 4.84 g (28%).

$^1$H-NMR (D$_2$O) δ: 1.50 (3H,s), 1.51 (3H, s), 2.10-2.40 (4H, m), 3.40-3.80 (10H, m), 3.90 (1H, d, J=16.8 Hz), 4.11 (1H, d, J=16.8 Hz), 5.37 (1H, d, J=5.1 Hz), 5.86 (1H, d, J=5.1 Hz), 6.98 (1H, s)

Step (2): Compound 6c+Compound 6d→Compound 6e

To a solution of Compound 6d in tetrahydrofuran (8 mL), triethylamine (0.22 mL, 1.59 mmol) was added. After cooling to 15° C., phosphorus pentachloride (267 mg, 1.28 mmol) was added, and then stirred for 1 hour to prepare an acid chloride. Meanwhile, to a solution of Compound 6c (582 mg, 1 mmol) in water (8 mL) and tetrahydrofuran (8 mL), triethylamine (1.25 mL, 9 mmol) was added, and then cooled to 0° C. To the resulting solution, the previously prepared acid chloride was added in one portion, and then stirred at 0° C. for 1 hour. After diluted hydrochloric acid was added and the mixture was confirmed to be acidic, the mixture was subjected to HP-20SS column chromatography, eluting the desired compound with acetonitrile-water. Aqueous 0.02 N sodium hydroxide solution was added to adjust pH=6 to form a sodium salt. The solution was concentrated in vacuo, and then lyophilized to yield Compound 6e as a white powder. Yield 226 mg (26%).

$^1$H-NMR (DMSO) δ: 1.39 (3H, s), 1.46 (3H, s), 1.90-2.20 (4H, m), 3.00-3.60 (12H, m), 3.75 (3H, s), 5.04 (2H, s), 5.11-5.12 (1H, m), 5.70-5.80 (1H, m), 6.73 (1H, s), 6.80-7.50 (6H, m)

Step (3): Compound 6e→Compound (I-6)

To trifluoroacetic acid (5.5 mL), anisole (0.38 mL) was added, and cooled to 0° C., and then a solution of Compound 6e in methylene chloride was added. After stirring at 0° C. for 1 hour, the solvent was evaporated under reduced pressure. To the reaction solution, aqueous 2 N hydrochloric acid (60 mL), acetonitrile (50 mL), and diethyl ether (100 mL) were then added. The separated aqueous layer was washed with diethyl ether, concentrated under reduced pressure, and then subjected to RP-20SS column chromatography, eluting the desired compound with acetonitrile-water. To the solution, aqueous 0.02 N sodium hydroxide solution was added to adjust pH=6 to form a sodium salt. The solution was concentrated under reduced pressure, and then lyophilized to yield Compound I-6 as a white powder. Yield 115 mg (43%).

$^1$H-NMR (D$_2$O) δ: 1.50 (3H, s), 1.51 (3H, s), 2.00-2.15 (4H, m), 3.40-4.20 (12H, m), 5.37 (1H, d, J=4.6 Hz), 5.89 (1H, d, J=4.8 Hz), 6.99 (1H, s), 7.38 (1H, s), 7.99 (1H, s)

Elemental analysis for C$_{29}$H$_{33}$N$_8$O$_{11}$S$_2$Na.6H$_2$O (NaHCO$_3$)

Calcd.: C, 38.20; H, 5.08; N, 12.12; S, 7.29; Na, 5.17(%).
Found.: C, 37.98; H, 4.89; N, 11.81; S, 6.76; Na, 4.85(%).

Example 7

Synthesis of Compound (I-7)

[Formula 43]

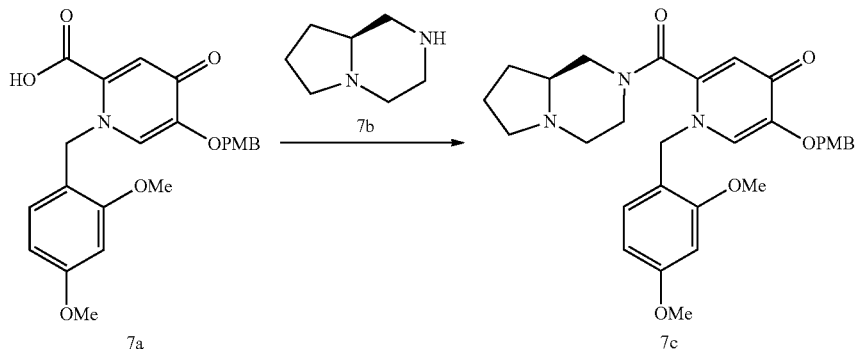

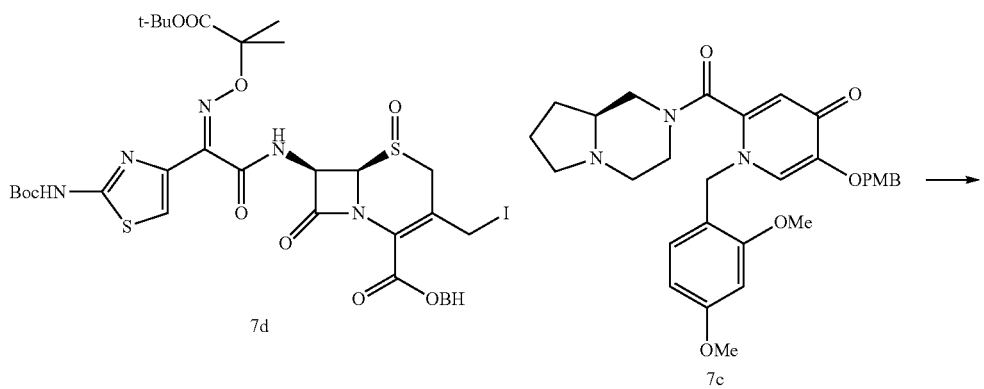

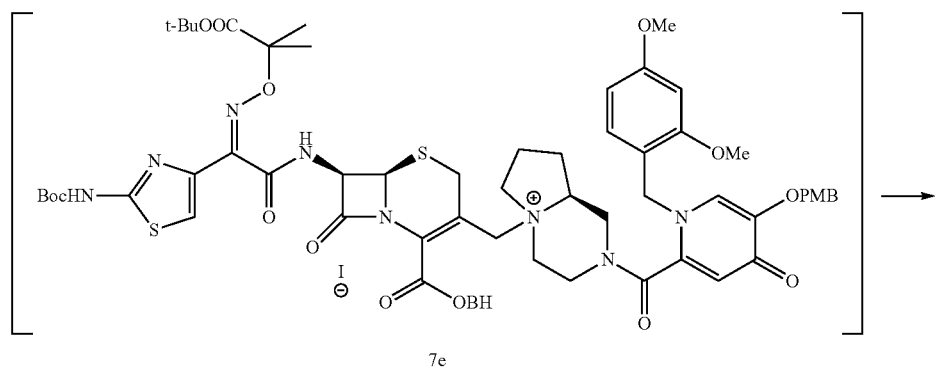

-continued

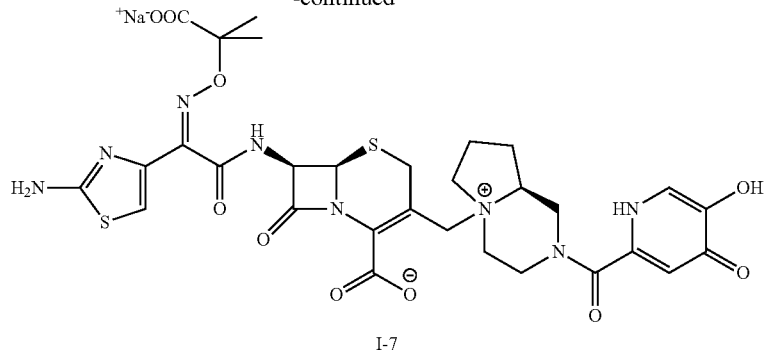

I-7

Step (1): Compound 7a→Compound 7c

To a solution of compound 7a (851 mg, 2.0 mmol) in N,N-dimethylacetamide (8 mL), triethylamine (665 μl, 4.8 mmol) was added. After cooling to −15° C., methanesulfonyl chloride (187 μl, 2.4 mmol) was added. After stirring at −15° C. for 1 hour, compound 7b (303 mg, 2.4 mmol) was added thereto, and then stirred at −15° C. for 3.5 hours. The solvent was evaporated in vacuo, and then aqueous 5% sodium bicarbonate was added to the resulting concentrated residue, followed by extraction with ethyl acetate. The organic layer was washed with aqueous 5% sodium bicarbonate, then saturated brine, and then dried with anhydrous sodium sulfate. The inorganic substance was removed by filtration, followed by concentration in vacuo. The resulting crude product was purified by silica gel column chromatography to yield compound 7c as a brown foam. Yield 373 mg, (35%).

MS (m+1)=534.25

Step (2): Compound 7d+Compound 7c→Compound 7e→Compound (I-7)

After a solution of compound 7d (648 mg, 0.69 mmol) in N,N-dimethylacetamide (2 mL) was cooled to 1.5° C., a solution of 7c (370 mg, 0.69 mmol) N,N-dimethylacetamide (1 mL) was added dropwise thereto over 10 minutes, and then stirred at 15° C. for 7.5 hours. To the reaction solution, N,N-dimethylformamide (1.6 mL) was added, and then cooled to −40° C. Subsequently, phosphorus tribromide (131 μl, 1.4 mmol) was added, and then stirred at −40° C. for 30 minutes. The reaction mixture was slowly added to pre-ice-cooled 5% brine. The precipitated solid was filtered, and then washed with water. The residue was suspended in water, and then lyophilized to yield compound 7e as a brown solid. The obtained compound 7e was used in the next reaction without purification.

The whole amount of compound 7e obtained was dissolved in methylene chloride (7 ml), and then cooled to −40° C. Anisole (757 μl, 6.9 mmol) followed by 2 mol/L-aluminum chloride/nitromethane solution (3.45 ml, 6.9 mmol) were added thereto, and then stirred at 0° C. for 45 minutes. To the reaction solution, aqueous 2 N hydrochloric acid, acetonitrile, and diisopropyl ether were added, and then stirred. The insoluble was separated from the supernatant by decantation, and then an aqueous layer was separated from the supernatant. Meanwhile, water and acetonitrile were added to the insoluble attached to the container, and then stirred. After the insoluble was completely dissolved, diisopropyl ether was added thereto, and then the aqueous layer was separated. The organic layer was then extracted with water. All the aqueous layers were combined, HP20-SS resin was added thereto, and then the acetonitrile containing solution was concentrated under reduced pressure. The resulting mixed suspension was purified by ODS column chromatography. To the resulting fractions containing the intended compound, aqueous 0.2 N sodium hydroxide solution was added to adjust pH=6.0, and then a piece of dry ice was added. The resulting solution was concentrated in vacuo, and then lyophilized to yield Compound I-7 as a yellow powder. Yield 111 mg, (21%).

$^1$H-NMR (D$_2$O) δ: 1.43 (3H, s), 1.45 (3H, s), 2.16 (4H, br), 3.40-4.26 (13H, m), 5.29 (1H, d, J=4.5 Hz), 5.82 (1H, d, J=4.8 Hz), 6.71 (1H, br), 6.91 (1H, s), 7.71 (1H, s)

MS (m+1)=731.33

Example 8

Synthesis of Compound (I-8)

[Formula 44]

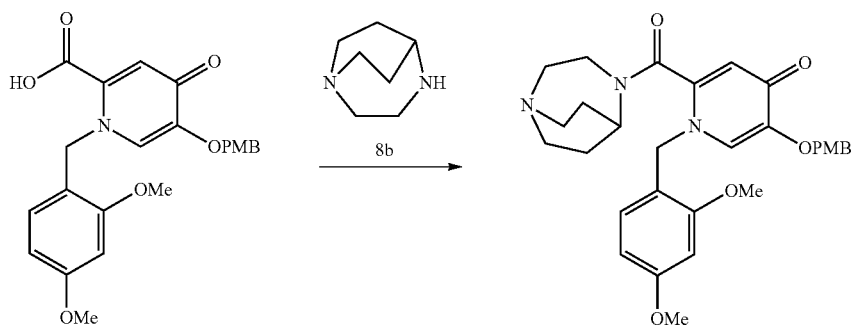

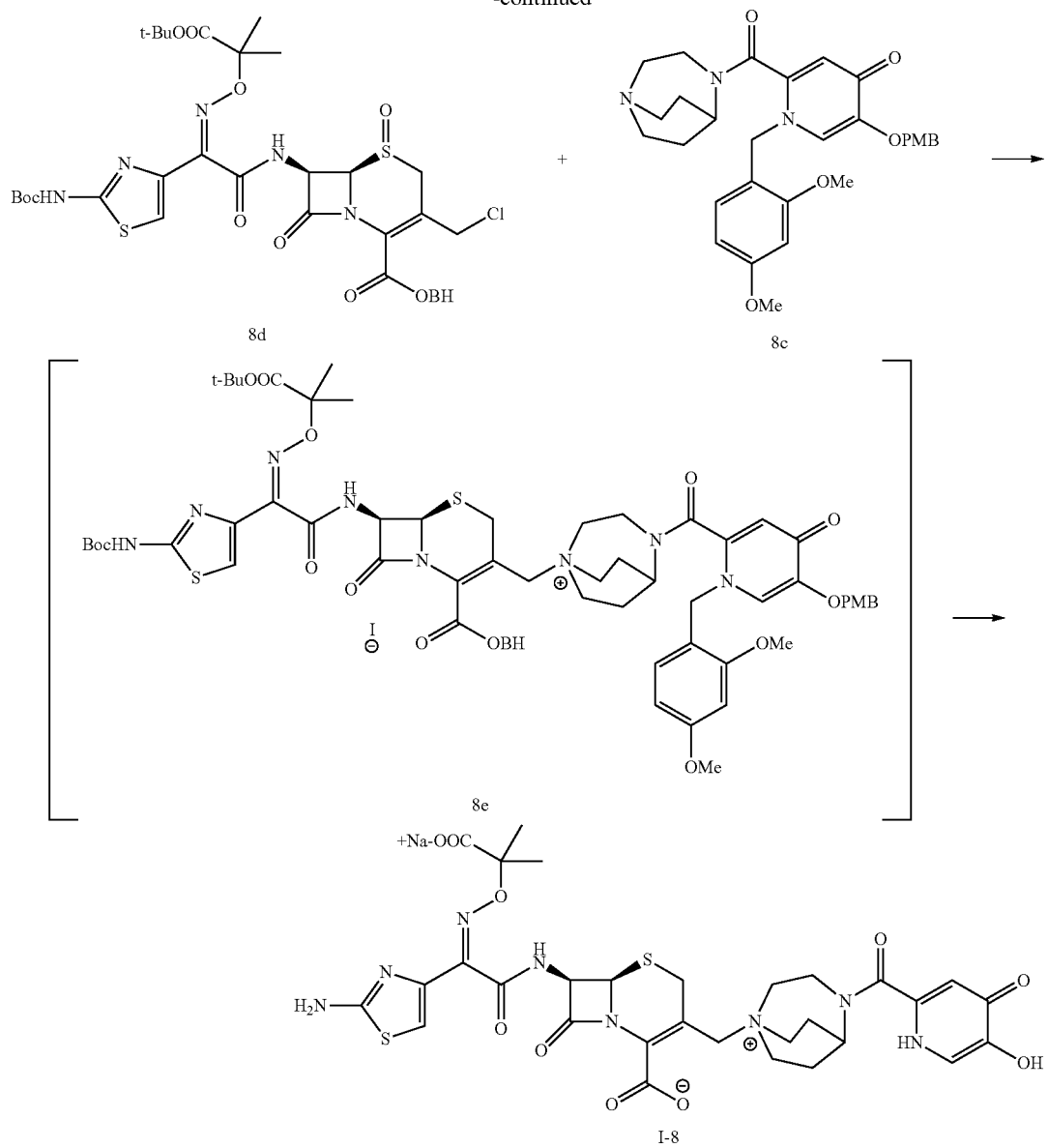

Step (1): Compound 8a→Compound 8c

To a solution of compound 8a (851 mg, 2.0 mmol) in N,N-dimethylacetamide (9 ml), triethylamine (665 μl, 4.8 mmol) and compound 8b (252 mg, 2.0 mmol) were added, under ice-cooling, O-(7-azabenzotriazol-1-yl)-N,N,N',N'-tetramethyluronium hexafluorophosphite (913 mg, 2.4 mmol) was added, and then stirred at room temperature for 45 minutes. After the solvent was evaporated under reduced pressure, aqueous 5% sodium bicarbonate was added to the resulting concentrated residue, followed by extraction with mixed solvent of ethyl acetate and tetrahydrofuran. The organic layer was washed with aqueous 5% sodium bicarbonate, then saturated brine, and then dried with anhydrous sodium sulfate. The inorganic substance was removed by filtration, followed by concentration under reduced pressure. The resulting crude product was purified by silica gel column chromatography to yield compound 8c as a brown foam. Yield 565 mg, (53%).

MS (m+1)=534.25

Step (2): Compound 8d+Compound 8c→Compound 8e→Compound (I-8)

To a solution of compound 8d (1.02 g, 1.0 mmol) in N,N-dimethylacetamide (3 mL), sodium bromide (204 mg, 2.0 mmol) was added, and then stirred at room temperature for 30 minutes. After the reaction solution was cooled to 15° C., a solution of compound 8c (534 mg, 1.0 mmol) in N,N-dimethylacetamide (1.5 mL) was added dropwise over 10 minutes, and then stirred at the same temperature for 7 hours. To the reaction solution, N,N-dimethylformamide (2.5 mL) was added, and then cooled to −40° C. Subsequently, phosphorus tribromide (189 μl, 2.0 mmol) was added, and then stirred at −40° C. for 30 minutes. The reaction mixture was slowly added to pre-ice-cooled 5% brine. The precipitated solid was filtered, washed with water, suspended in water, and then lyophilized to yield compound 8e as a brown solid. The obtained compound 8e was used in the next reaction without purification.

The whole amount of compound 8e obtained was dissolved in methylene chloride (10 ml), and then cooled to −40°

C. Anisole (1.09 ml, 10 mmol) followed by 2 mol/L-aluminum chloride/nitromethane solution (5.0 ml, 10 mmol) were added thereto, and then stirred at −40° C. for 1 hour. To the reaction solution, aqueous 2 N hydrochloric acid, acetonitrile, and diisopropyl ether were added, and then stirred. The insoluble was separated from the supernatant by decantation. An aqueous layer was separated from the supernatant. Meanwhile, water and acetonitrile were added to the insoluble attached to the container, and then stirred. After the insoluble was completely dissolved, diisopropyl ether was added thereto, and then the aqueous layer was separated. The organic layer was then extracted with water. All the aqueous layers were combined, HP20-SS resin was added thereto, and then concentrated. The resulting mixed suspension was purified by ODS column chromatography. To the resulting fractions containing the intended compound, aqueous 0.2 N sodium hydroxide solution was added to adjust pH=5.2, and then the solution was concentrated in vacuo. The concentrated solution was lyophilized to yield Compound I-8 as a yellow powder. Yield 122 mg, (16%).

$^1$H-NMR (D$_2$O) δ: 1.42 (3H, s), 1.44 (3H, s), 2.29 (4H, br), 3.36-4.32 (13H, m), 5.29 (1H, d, J=4.8 Hz), 5.80 (1H, d, J=4.8 Hz), 6.70 (1H, s), 6.90 (1H, s), 7.69 (1H, s)

MS (m+1)=731.22

Elemental analysis for: $C_{30}H_{33}N_3O_{10}S_2Na \cdot 0.1NaHCO_3 \cdot 6.6H_2O$ Calcd.: C, 41.08; H, 5.30; N, 12.73; S, 7.29; Na, 2.87(%).
Found.: C, 40.89; H, 5.19; N, 12.78; S, 8.08; Na, 3.02(%).

Example 9

Synthesis of Compound (I-9)

[Formula 45]

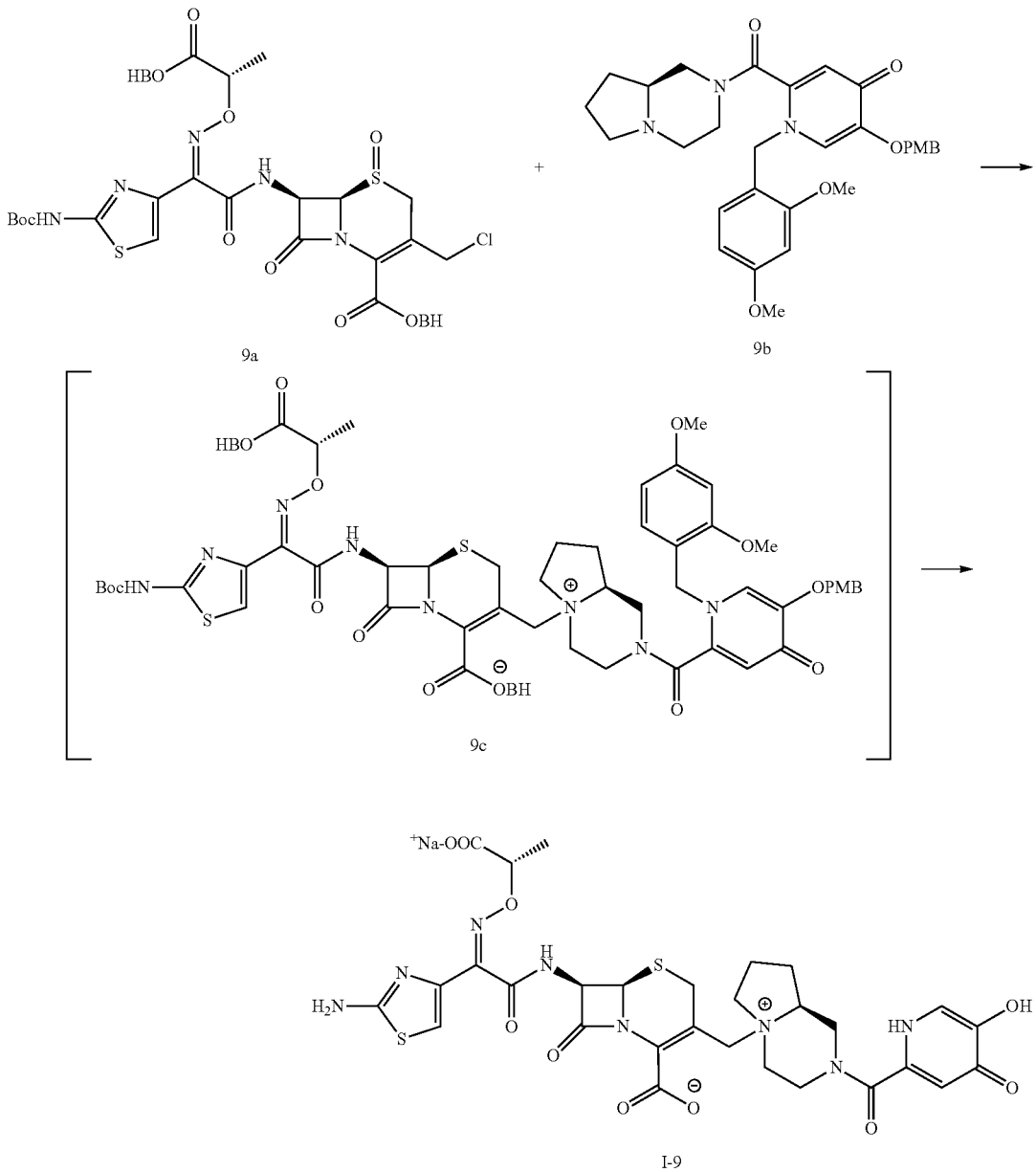

Step (1): Compound 9a 4→Compound 9b-Compound 9c→Compound (I-9)

To a solution of compound 9a (720 mg, 0.75 mmol) in N,N-dimethylacetamide (2 ml), sodium iodide (225 mg, 1.5 mmol) was added, and then stirred at room temperature for 10 minutes. After cooling to 15° C., a solution of compound 9b (534 mg, 1.0 mmol) in N,N-dimethylacetamide (1 mL) was added dropwise thereto over 5 minutes, and then stirred at room temperature for 6 hours. To the reaction solution, N,N-dimethylformamide (2 ml) was added, and then cooled to −40° C. Subsequently, phosphorus tribromide (141 μl, 1.5 mmol) was added thereto, and then stirred at −40° C. for 30 minutes. The reaction mixture was slowly added to pre-ice-cooled 5% brine. The precipitated solid was filtered, washed with water, suspended in water, and then lyophilized to yield compound 9c as a pale orange solid. The obtained compound 9c was used in the next reaction without purification.

The whole amount of compound 9c obtained was dissolved in methylene chloride (10 ml), and then cooled to −40° C. Anisole (735 μl, 6.73 mmol) followed by 2 mol/L-aluminum chloride/nitromethane solution (3.36 ml, 6.73 mmol) were added thereto, and then stirred at 0° C. for 1 hour. To the reaction solution, aqueous 2 N hydrochloric acid, acetonitrile, and diisopropyl ether were added, and then stirred. The aqueous layer was then separated. The organic layer was extracted with a mixed solution of water/acetonitrile/diluted hydrochloric acid. All the aqueous layers were combined, HP20-SS resin was added thereto, and than the acetonitrile containing solution was concentrated under reduced pressure. The resulting mixed suspension was purified by ODS column chromatography. To the resulting fractions containing the intended compound, aqueous 0.2 N sodium hydroxide solution was added to adjust pH=6.0, and then a piece of dry ice was added. The resulting solution was concentrated in vacuo, and then lyophilized to yield Compound I-9 as a yellow powder. Yield 45.6 mg, (8%).

$^1$H-NMR (D$_2$O) δ: 7.79 (1H, s), 7.03 (1H, s), 6.78 (1H, s), 5.91 (1H, d, J=5.20 Hz), 5.37 (1H, d, J=4.70 Hz), 4.38-3.86 (7H, m), 3.72-3.47 (5H, m), 2.14 (4H, d, J=51.53 Hz), 1.47 (3H, d, J=7.05 Hz).

Elemental analysis for: C$_{29}$H$_{31}$N$_8$O$_{10}$S$_2$Na.0.15NaHCO$_3$.6.5H$_2$O Calcd.: C, 40.32; H, 5.12; N, 12.90; S, 7.38; Na, 3.04(%).
Found.: C, 40.53; H, 4.90; N, 12.65; S, 7.52; Na, 3.04(%).

Example 10

Synthesis of Compound (I-10)

[Formula 46]

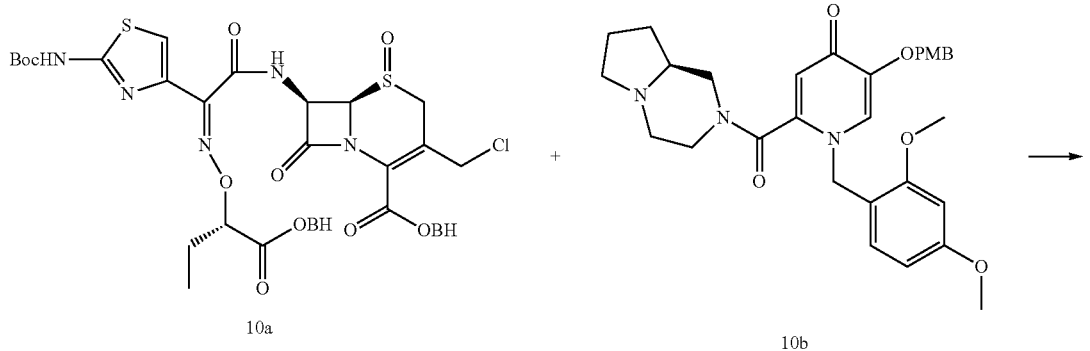

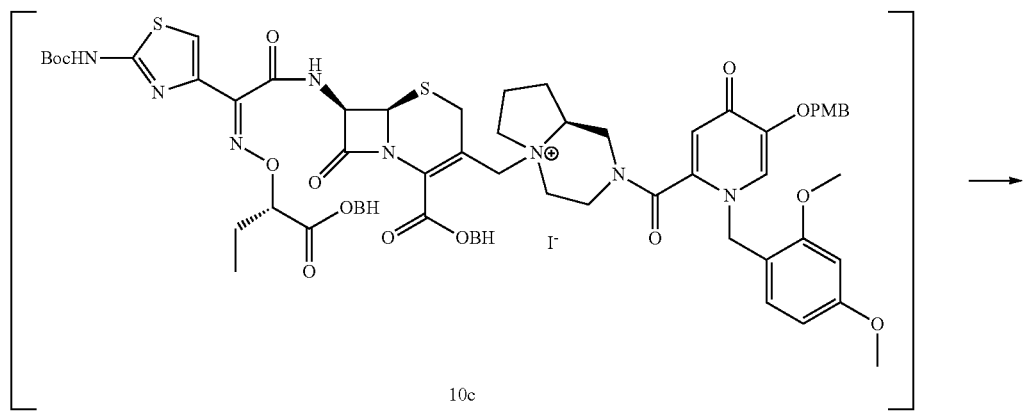

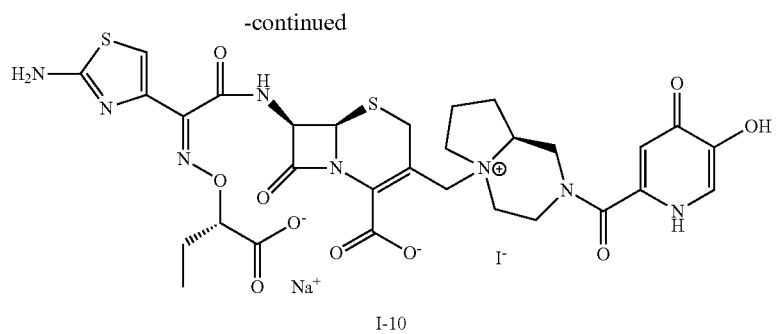

I-10

Step (1) Compound 10a+Compound 10b→Compound 10c

To a solution of compound 10a (952 mg, 1 mmol) in N,N-dimethylacetoamide (3 mL) was added sodium iodide (300 mg, 2 mmol) and the mixture was stirred at rt for 10 min. The mixture was cooled to 0° C., and compound 10b (539 mg, 1 mmol) and sodium hydrogen carbonate (336 mg, 4 mmol) were added. The mixture was stirred at 15° C. for 1.5 h. To the resulting mixture was added DMF (6 mL) and cooled to −40° C. Acetyl chloride (0.5 mL, 7 mmol), potassium iodide (830 mg, 5 mmol) and phosphorous tribromide (0.189 mL, 2 mmol) were added and the mixture was stirred for 1 h. The resulting mixture was poured into a cooled 5% aqueous solution of sodium hydrogensulfite (30 mL), and then the precipitated material was collected by filtration, m washed with water and dried to afford compound 10c which was used for the next step without further purification.

Step (2): Compound 10c→Compound (I-10)

To a solution of compound 10c in methylene chloride (10 mL) was added anisole (1.0 mL, 10 mmol) and then the mixture was cooled to −40° C. To the mixture was added 2 mol/L aluminum chloride/nitromethane solution (5.0 mL). The mixture was stirred at 0° C. for 50 min and then stirred at rt for further 1 h. To the resulting mixture was added 2 mol/L HCl/water (60 mL), acetonitrile (50 mL) and diethyl ether (100 mL). The organic layer was concentrated, and then the residual mixture was purified by column chromatography on HP-20SS eluting with water-acetonitrile. Aqueous 0.2 N solution of sodium hydroxide was added to fractions containing the desired compound to adjust them to pH=6 and form a sodium salt thereof. Concentration in vacuo and subsequent lyophilization yielded compound I-10 (196 mg, 26%) as a powder.

$^1$H-NMR (D2O) δ: 0.97 (3H, t), 1.80-2.60 (6H, m), 3.40-4.40 (13H, 5.36 (1H, d, J=5.1 Hz), 5.88 (1H, d, J=5.1 Hz,), 6.85-6.95 (1H, br), 7.00 (1H, s), 7.79 (1H, s).

Elemental analysis for C30H33N8O10S2Na.5.8H$_2$O. (NaHCO3) 0.2

Calcd.: C, 41.50; H, 5.17; N, 12.82; S, 7.34; Na, 3.16(%).
Found.: C, 41.40; H, 5.10; N, 12.81; S, 7.49; Na, 3.36(%).

Example 11

Synthesis of Compound (I-11)

[Formula 47]

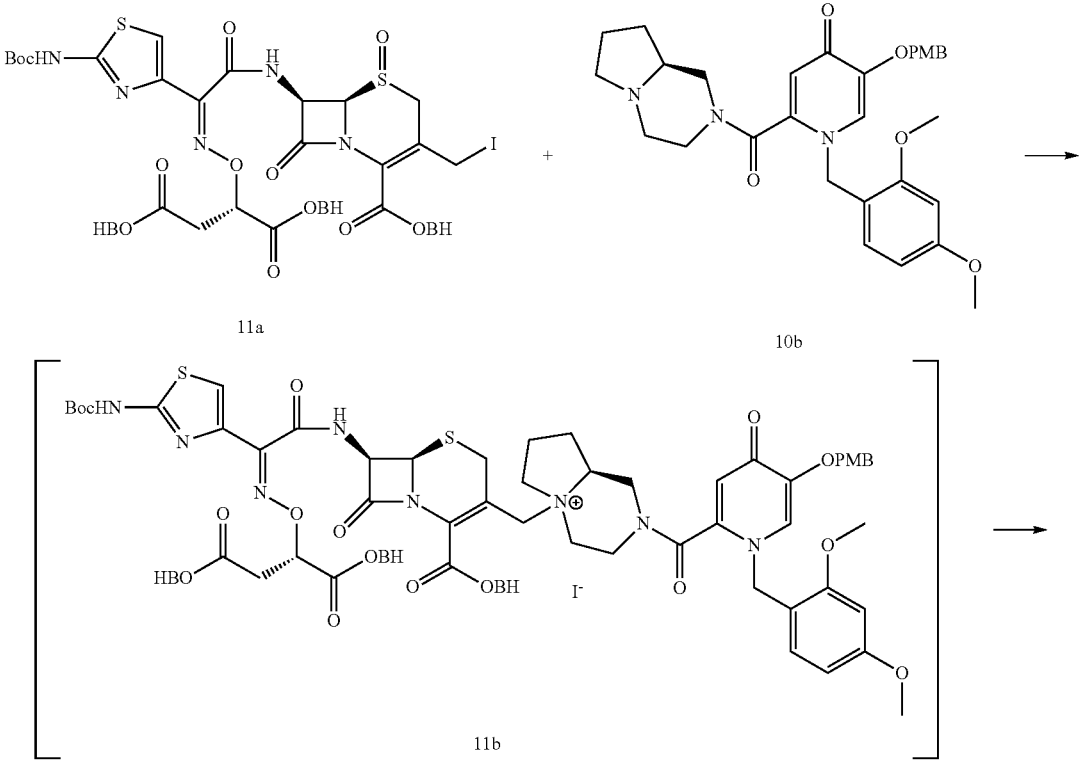

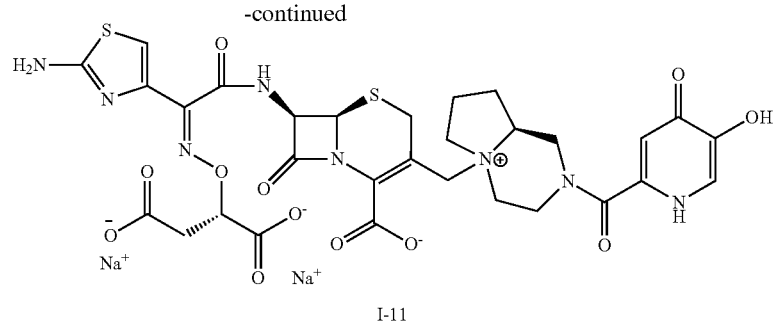
I-11
Step: Compound 11a+Compound 10b→Compound (I-11)
Compound I-11 was obtained from Compound 11a and Compound 10b by a procedure as described for the synthesis of compound I-10 (yield: 283 mg, 35%).
$^1$H-NMR (D2O) δ: 1.90-4.20 (20H, m), 5.33 (1H, J=4.8 Hz, d), 5.82 (1H, J=4.6 Hz, d), 6.79-6.80 (1H, br), 7.01 (1H, s), 7.80 (1H, s).
Elemental analysis for C30H30N8O12S2Na2·7H2O
Calcd.: C, 38.71; H, 4.76; N, 12.04; S, 6.89; Na, 4.94(%).
Found.: C, 38.67; H, 4.78; N, 11.93; S, 6.88; Na, 4.67(%).
Example 12
Synthesis of Compound (I-12)
[Formula 48]
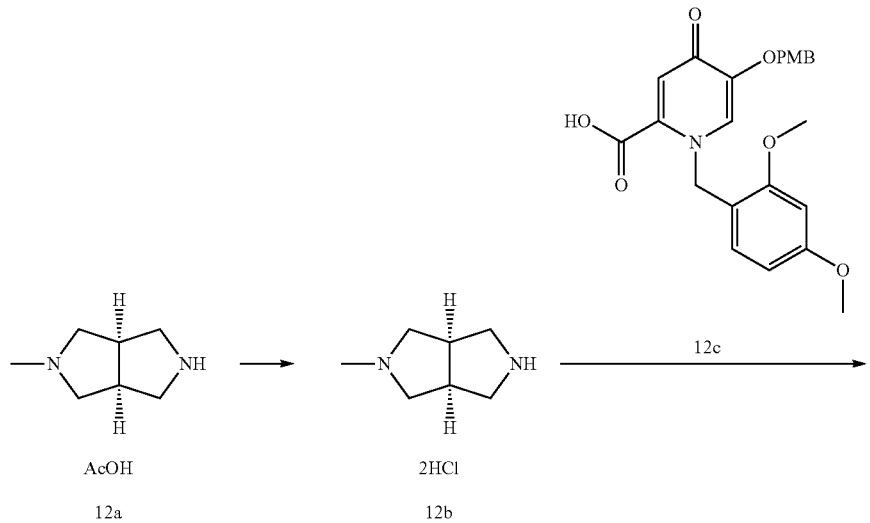
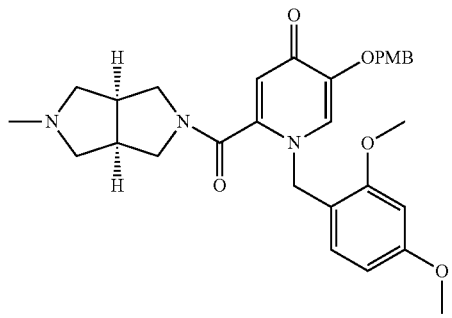
12d

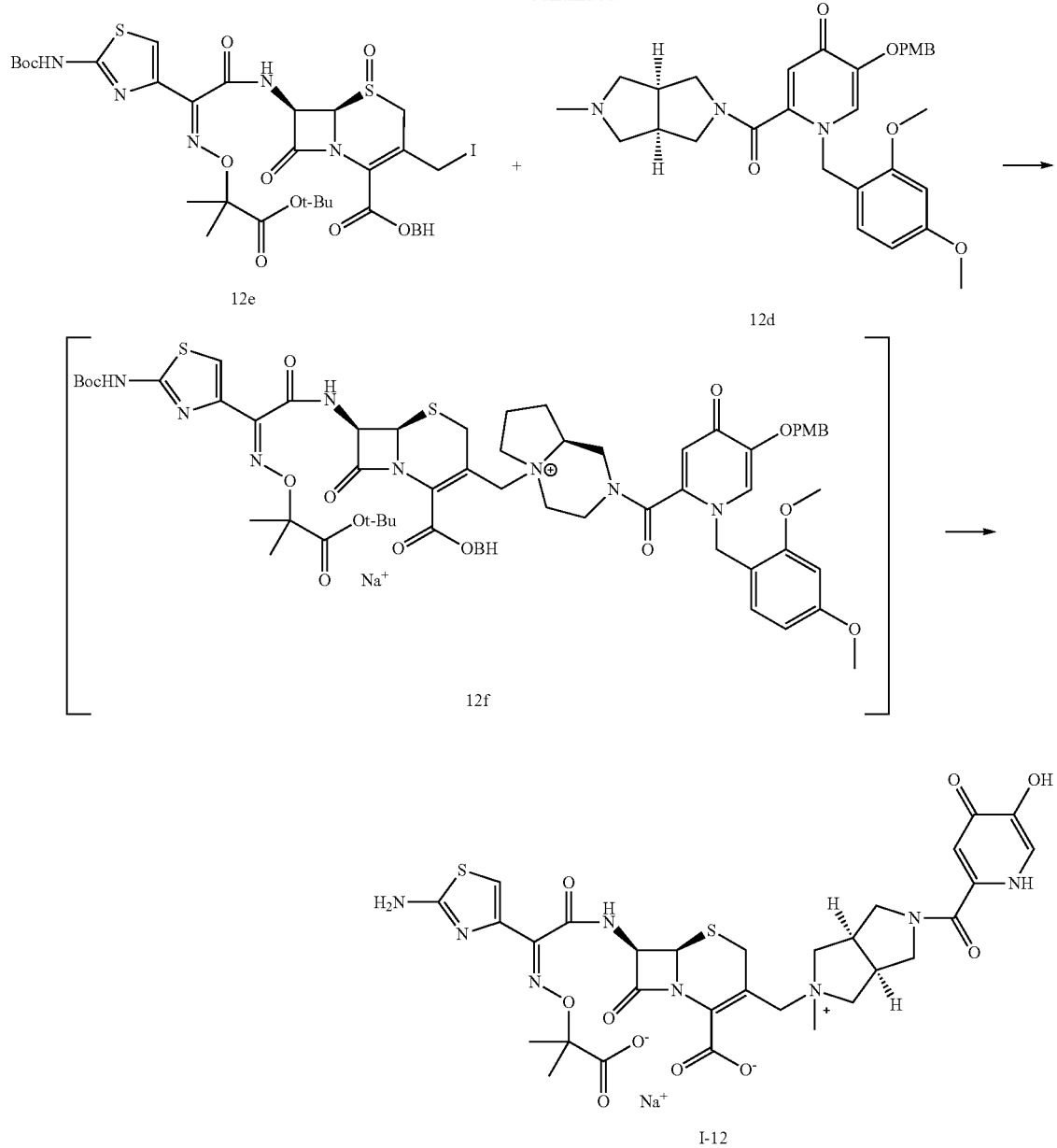

Step (1): Compound 12a→Compound 12b

Compound 12a (1.03 g, 2.5 mmol) was dissolved in ethyl acetate (10 mL) and added with 4 mol/L hydrochloric acid/ethyl acetate solution (3.75 mmol, 15 mmol). Diethyl ether was added and the solvent was removed by decantation. Azeotropic distillation with toluene and dried in vacuo afforded the residue, compound 12b (550 mg, quant.).

$^1$H-NMR (D2O) δ: 2.98 (3H, s), 2.99-4.20 (10H, m).

Step (2): Compound 12b+Compound 12c→Compound 12d

To a solution of compound 12c (2.55 g, 6 mmol) in DMF (25 mL) was added WSCD-HCl (1.38 g, 7.20 mmol) and HOBt hydrate (1.10 g, 7.20 mmol). The mixture was stirred at rt for 30 min. The resulting mixture was cooled to 0° C., and then a solution of compound 12b (1.49 g, 7.5 mmol) in DMF (25 mL) and triethylamine (1.66 mL, 12 mmol) were added. The solvent was removed by evaporation. Ethyl acetate and tetrahydrofuran were added, and the organic layer was washed with water and brine, and then dried over MgSO4 and filtered. The solvent was removed under reduced pressure. Purification on silica gel column chromatography afforded compound 12d (2.44 g, 76%).

$^1$H-NMR (CDCl3) δ: 1.80-2.80 (9H, m), 3.0-4.20 (15H, m), 5.08 (1H, s), 6.25-7.35 (9H, m).

Step (3): Compound 12e Compound 12d→Compound (I-12)

Compound I-12 was prepared from Compound 12e and Compound 12d by a procedure similar to that of Compound I-10 (yield: 39%).

$^1$H-NMR (D2O) δ: 1.49 (3H, s), 1.51 (3H, s), 3.00-4.20 (17H, m), 5.37-5.39 (1H, m), 5.86-5.89 (1H, m), 6.82 (1H, s), 6.98 (1H, s), 7.77 (1H, s).

Elemental analysis for C30H33N8O10S2Na.6.7H2O

Calcd.: C, 41.25; H, 5.35; N, 12.83; S, 7.34; Na, 2.63(%).

Found.: C, 41.22; H, 5.26; N, 12.80; S, 7.48; Na, 2.74(%).

Example 13
Synthesis of Compound (I-13)
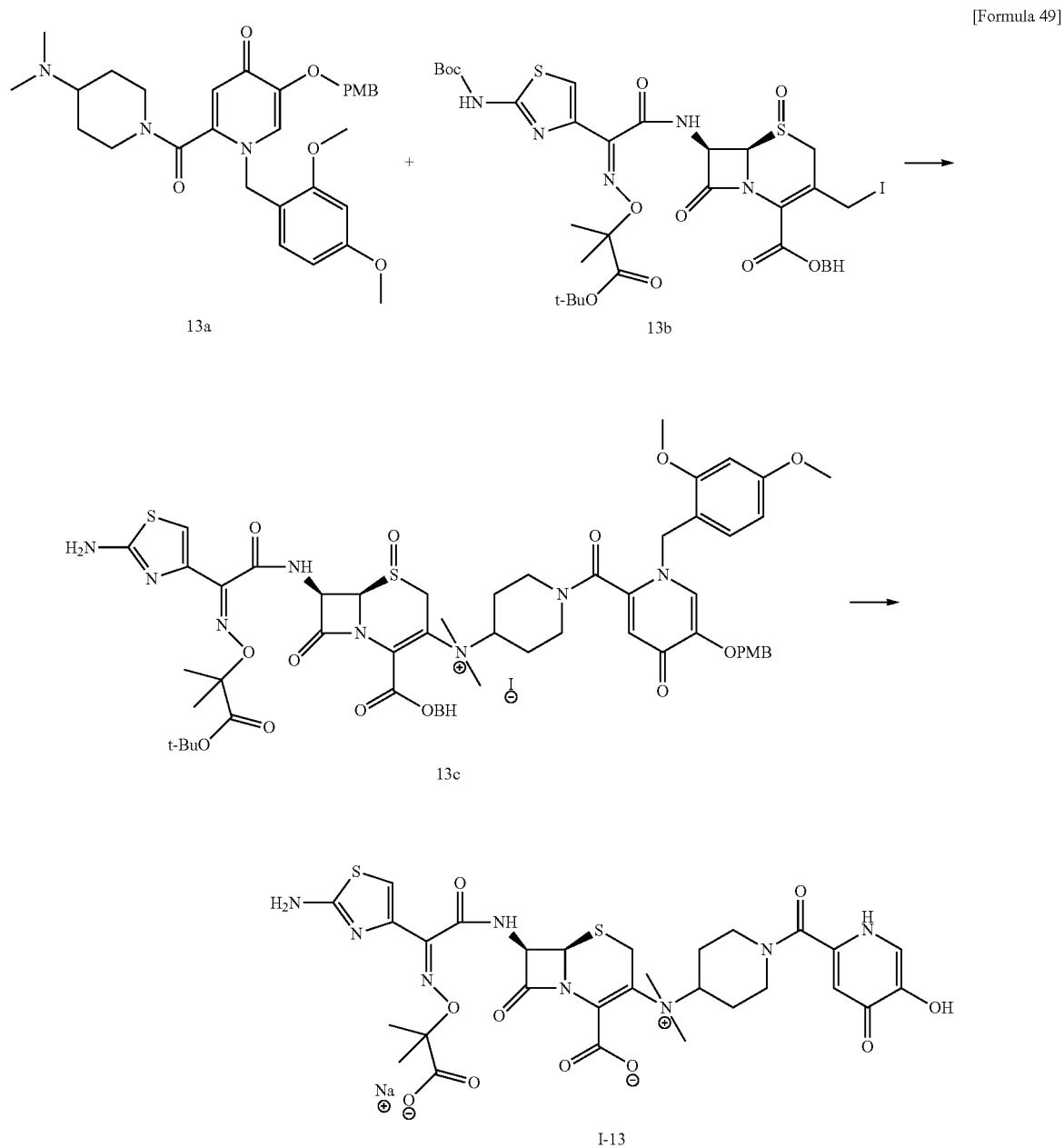
Step: Compound 13a+Compound 13b→Compound 13c→Compound (I-13)
Compound I-13 was obtained from Compound 13a and Compound 13b by a procedure as described for the synthesis of compound I-10 (yield: 480 mg, 34%).
$^{1}$H-NMR (D2O) δ: 7.75 (1H, s), 6.97 (1H, s), 6.72 (1H, s), 5.85 (1H, s), 5.38 (1H, d, J=5.0 Hz), 4.08-3.88 (4H, m), 3.72 (1H, t, J=12.0 Hz), 3.49 (1H, d, J=16.6 Hz), 3.39-3.25 (1H, m), 3.08 (3H, br s), 2.98 (3H, br s), 2.46-2.17 (2H, m), 2.03-1.80 (2H, m), 1.51 (3H, s), 1.50 (3H, s).
Elemental analysis for C30H35N8O10S2Na 7.2H2O 0.2NaOH
Calcd.: C, 40.37; H, 5.60; N, 12.56; Na, 3.09; S, 7.19(%).
Found.: C, 40.29; H, 5.44; N, 12.66; Na, 3.20; S, 7.44(%).

Example 14
Synthesis of Compound (I-14)
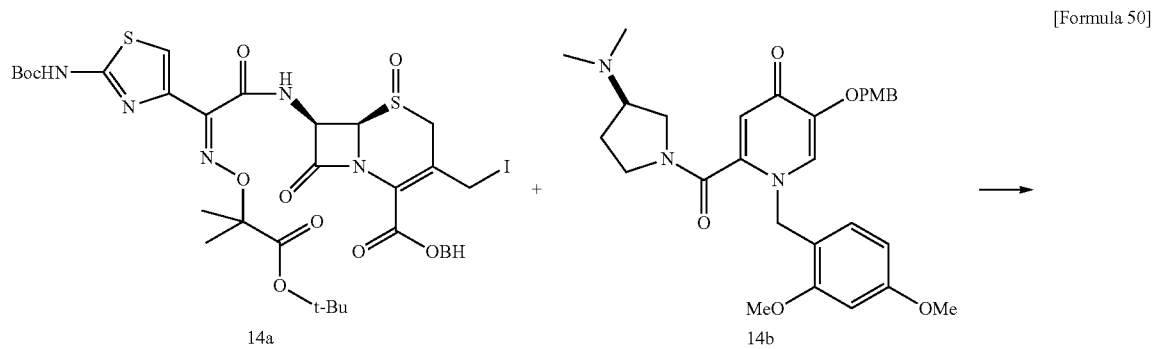
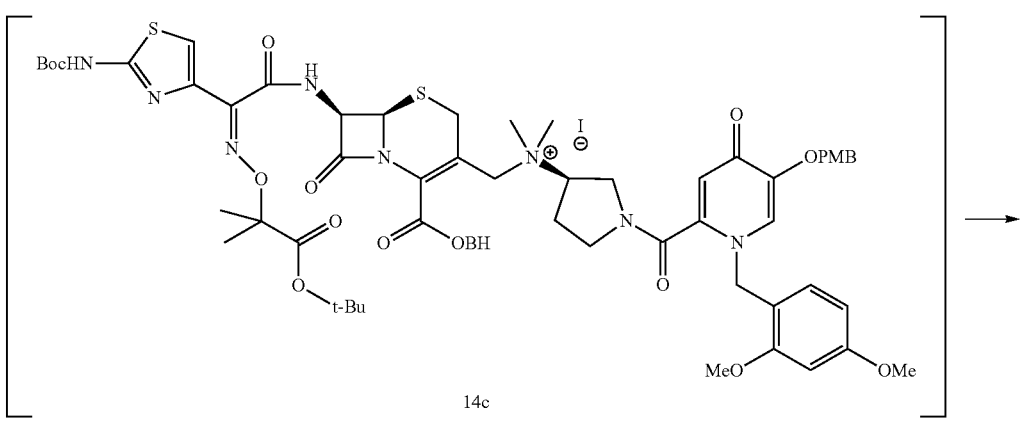
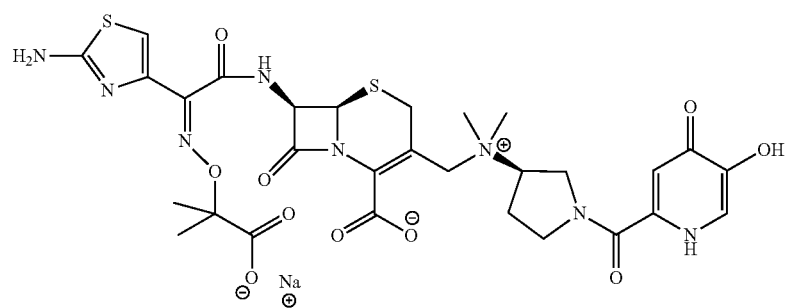
Step: Compound 14a+Compound 14b→Compound 14c→Compound (I-14)
Compound I-14 was obtained from Compound 14a and Compound 14b by a procedure as described for the synthesis of compound I-10 (yield: 560 mg, 27%).
$^1$H-NMR (D2O) δ: 7.77-7.75 (1H, m), 6.96 (1H, s), 6.90-6.81 (1H, m), 5.92-5.83 (1H, m), 5.38 (1H, dd, J=13.2, 5.0 Hz), 4.97-4.60 (OH, m), 4.50-3.60 (7H, m), 3.49 (18, t, J=14.7 Hz), 3.25-2.87 (7H, m), 2.65-2.31 (2H, m), 1.59-1.39 (6H, m).
Elemental analysis for C29H33N8O10S2Na (H2O) 7.1
Calcd.: C, 40.10; H, 5.48; N, 12.90; S, 7.38; Na, 2.65(%).
Found.: C, 40.04; H, 5.34; N, 12.89; S, 7.42; Na, 2.81(%).

Example 15
Synthesis of Compound (I-15)
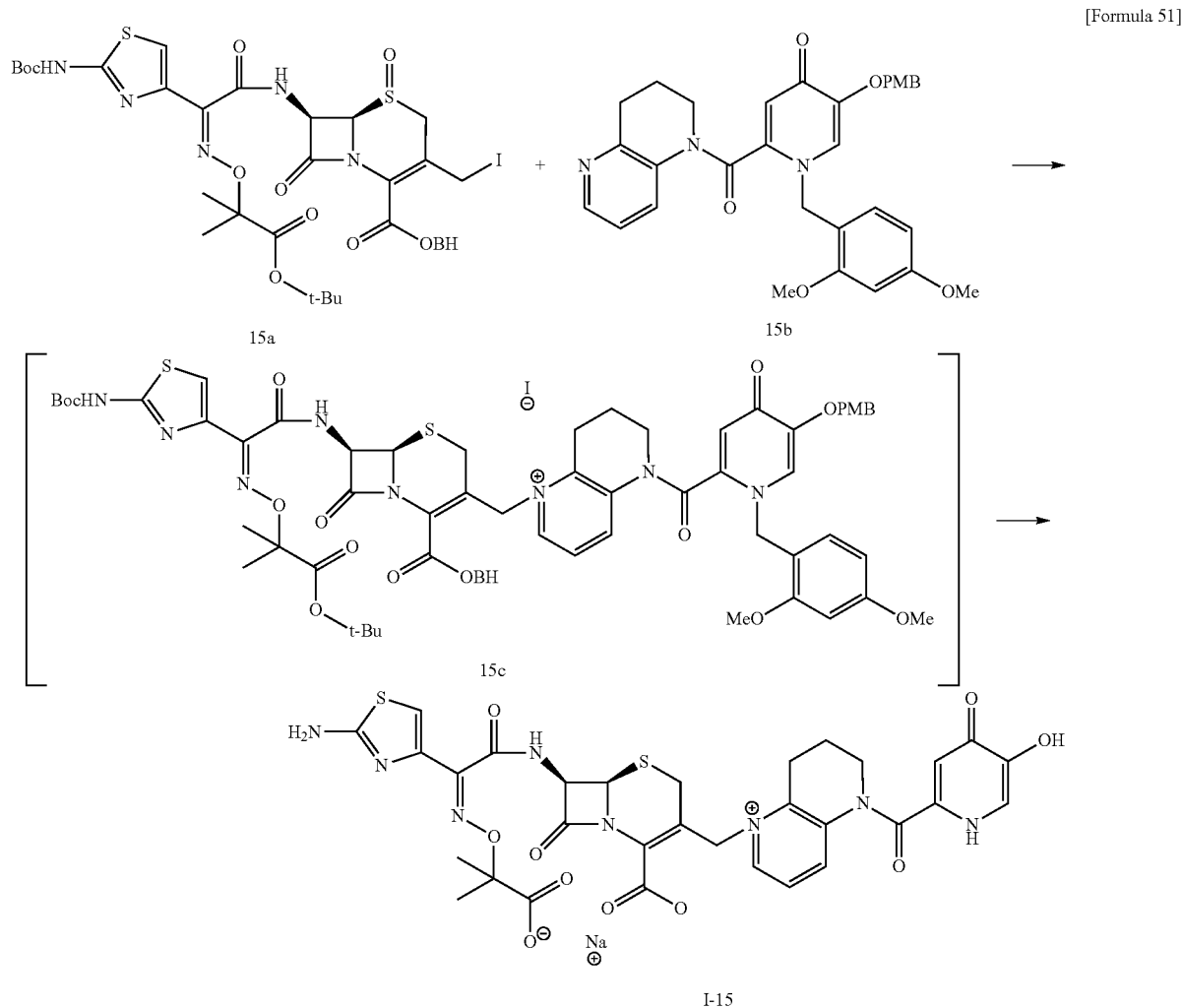
Step: Compound 15a+Compound 15b→Compound 15c→Compound (I-15)
Compound I-15 was obtained from Compound 15a and Compound 15b by a procedure as described for the synthesis of compound I-10 (yield: 27 mg, 3%).
Mass:
Calcd.: 738.15.
Found.: [M+1]=739.39.
Example 16
Synthesis of Compound (I-16)
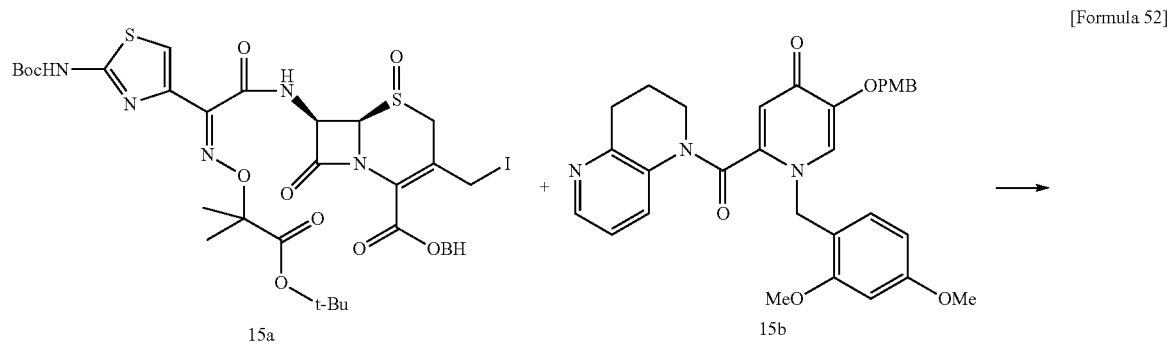

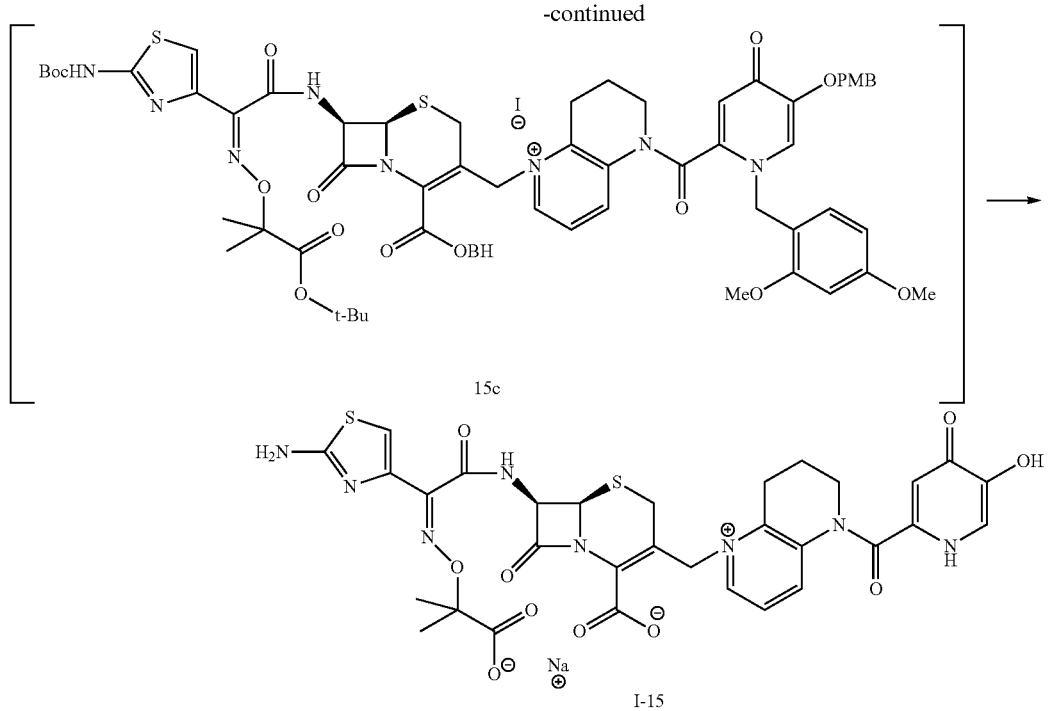

Step (1): Compound 16a→Compound 16b

Known Compound 16a (Bioorganic & Medicinal Chemistry 17 (2009) 6106-6122)) was dissolved in N,N-dimethylforamide (30 mL) and added with potassium carbonate (2.99 g, 21.62 mmol), p-methoxy benzyl chloride (2.99 g, 21.62 mmol), and sodium iodide (3.24 g, 21.62 mmol). The mixture was stirred under room temperature until the reaction was finished, and then water was added to the reaction mixture. The aqueous layer was extracted with ethyl acetate. The organic layer was washed with water and brine, dried over magnesium sulfate, filtered, and concentrated in vacuo. The residue was purified by silica gel chromatography to afford compound 16b (4.44 g, 15.35 mmol).

$^1$H-NMR (CDCl$_3$) δ: 7.98 (1H, d, J=2.5 Hz), 7.79 (1E, dd, J=9.4, 2.5 Hz), 7.34 (2H, dt, J=9.5, 2.5 Hz), 6.89 (2H, dt, J=9.2, 2.5 Hz), 6.64 (1H, d, J=9.5 Hz), 5.24 (2H, s), 3.81 (3H, s), 3.81 (3H, s).

Step (2): Compound 16b→Compound 16c→Compound 16d

Compound 16b (4.4 g, 14 mmol) was dissolved in tetrahydrofuran (20 mL) and methanol (20 mL) and added with 2 mol/L sodium hydroxide aqueous solution (23 mL). The mixture was stirred at room temperature for 1 hr. To the reaction mixture 2 mol/L hydrochloric acid aqueous solution (22 mL) was added, and the solvent was removed under reduced pressure. The resulting precipitate was collected by filtration, washed with water, and dried in vacuo to afford compound 16c (3.98 g, 14.46 mmol).

Compound 16c (1.376 g, 5 mmol) was dissolved in methylene chloride. 2-(pyrrolidin-1-yl)ethanamine) (0.685 g, 6 mmol), 1-hydroxybenzotriazole and 1-ethyl-3-(3-dimethylaminopropyl)carbodiimide hydrochloride (1.15 g, 6 mmol) were added, and the mixture was stirred at room temperature. Water was added to the mixture, and the aqueous layer was basified with 2 mol/L sodium hydroxide aqueous solution and extracted with ethyl acetate. The organic layer was washed with water and brine, dried over magnesium sulfate, filtered, and removed the solvent in vacuo. The residue was purified by chromatography to afford compound 16d.

$^1$H-NMR (CDCl$_3$) δ: 7.95 (1H, d, J=2.6 Hz), 7.62 (1H, dd, J=9.6, 2.5 Hz), 7.35 (2H, dt, J=9.6, 2.5 Hz), 6.89 (2H, dt, J=8.7, 2.4 Hz), 6.67-6.64 (2H, m), 5.23 (2H, s), 3.81 (3H, s), 3.45 (2H, dd, J=4.7, 10.9 Hz), 2.65 (2H, t, J=6.4 Hz), 2.58-2.50 (4H, m), 2.22 (2H, br s), 1.84-1.77 (4H, m).

Step (3): Compound 16e→Compound 16f→Compound (I-16)

Compound 16e (0.842 g, 1 mmol) was dissolved in N,N-dimethylacetamide (3.3 mL). Sodium iodide (0.3 g, 2 mmol) and compound 16d (659 mg, 1 mmol) were added and the mixture was stirred at 10° C. The mixture was added with water and extracted with ethyl acetate. The organic layer was washed with water and brine, dried over magnesium sulfate, filtered, and removed the solvent in vacuo to afford Compound 16f. Compound 16f was dissolved in dichloromethane (15 mL) and cooled to −40° C. Phosphorous tribromide (0.189 mL, 21=01) was added and stirred at same temperature for 1 hr. Then the mixture was added with anisole (1.09 mL, 10 mmol) and 2 mol/L-aluminum chloride/nitromethane solution (5.0 mL, 10 mmol) and stirred at 0° C. To the solution water (30 mL) and diisopropyl ether (50 mL) were added. Acetnitrile and 2 mol/L hydrochloric acid were added to solubilize the precipitate, and the aqeuous layer was separated. The organic layer was extracted with water/acetritrile/diluted HCl mixture. HP-20SS resin was added to the aqueous layer, concentrated, and then subjected to HP20SS/ODS column chromatography, eluting with water-acetonitrile. Aqueous 0.2 mol/L solution of sodium hydroxide was added to fractions containing the desired compound to form a sodium salt. Concentrating in vacuo and subsequent lyophilization yielded Compound I-16 (178 mg, 24%) as a powder.

$^1$H-NMR (D2O) δ: 8.62 (1H, s), 8.04 (1H, d, J=9.9 Hz), 7.7-6.94 (2H, m), 5.84-5.76 (1H, m), 5.40-5.29 (1H, m), 4.79 (1H, d, J=14.1 Hz), 3.99-3.47 (11H, m), 2.21 (4H, s), 1.55-1.44 (6H, m).

Elemental Analysis

Calcd.: C, 39.93; H, 5.50; N, 12.85; 8, 7.35; Na, 2.64(%).
Found.: C, 39.91; H, 5.22; N, 12.80; S, 7.39; Na, 2.92(%).

Example 17

Synthesis of Compound (I-17)

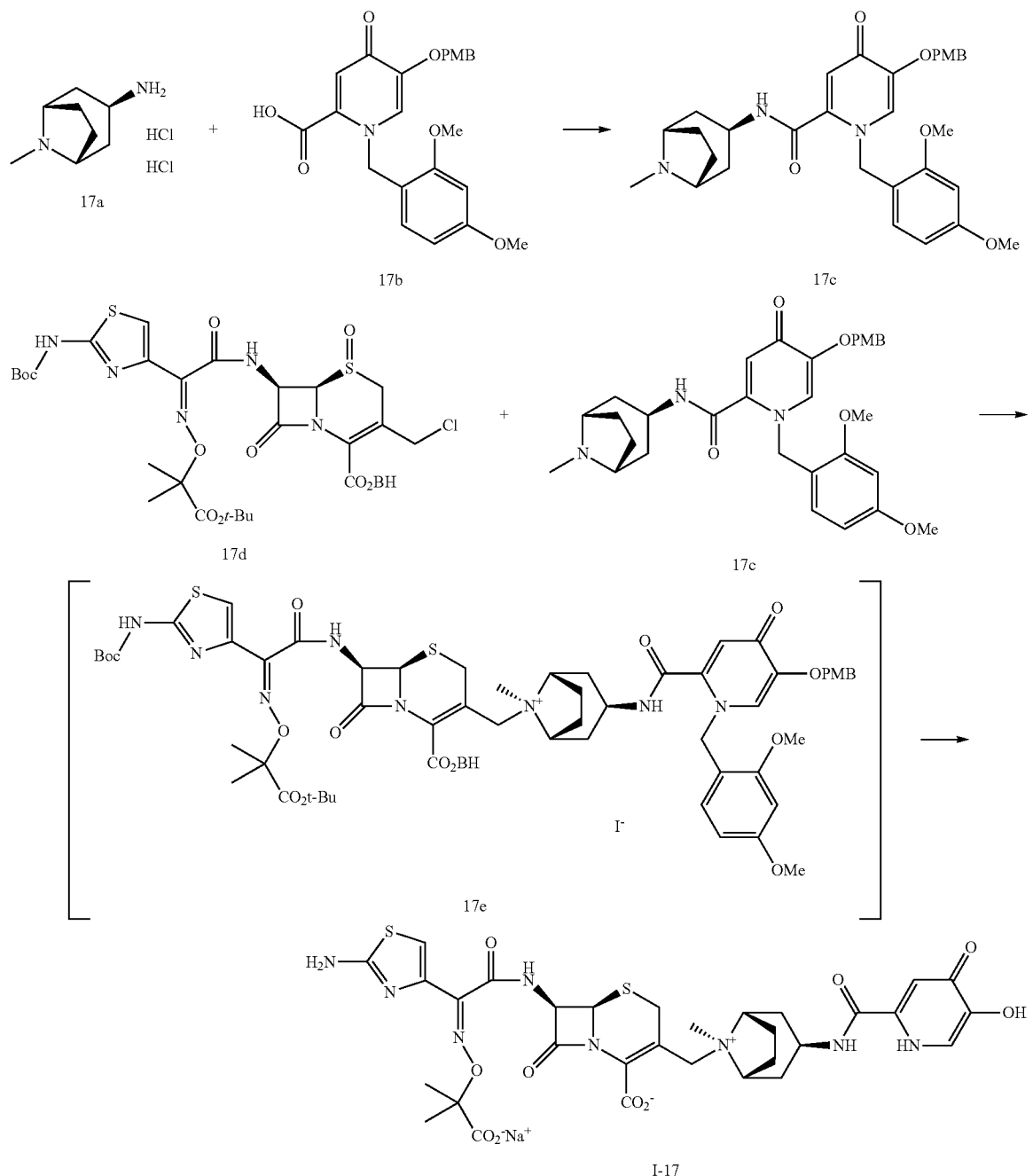

Step (1): Compound 17a+Compound 17b→Compound 17c

Compound 17a (1.28 g, 6.00 mmol) and compound 17b (2.13 g, 5.00 mmol) were reacted using 1-hydroxybenzotriazole, 1-ethyl-3-(3-dimethylaminopropyl)carbodiimide hydrochloride, and diisopropylethylamine. The compound-containing liquid was subjected to amino silica gel column chromatography, eluting with chloroform. The fractions containing desired compound were concentrated under reduced pressure to yield compound 17c (1.43 g, 52%).

$^1$H-NMR (DMSO-d6) δ: 8.37 (1H, d, J=4.70 Hz), 7.55 (1H, s), 7.29 (2H, d, J=8.73 Hz), 6.90 (2H, d, J=8.73 Hz), 6.85 (1H, d, J=8.39 Hz), 6.52 (1H, d, J=2.43 Hz), 6.41 (1H, dd, J=8.39, 2.43 Hz), 6.15 (1H, s), 5.10 (2H, s), 4.95 (2H, s), 3.75 (3H, s), 3.74 (3H, s), 3.70 (3H, s), 2.93 (2H, br s), 2.11 (3H, s), 2.00-1.69 (6H, m), 1.60 (1H, br s), 1.56 (1H, br s).

Step (2): Compound 17d+Compound 17c→Compound (1-17)

Compound I-17 was prepared using Compound 17d (796 mg, 1.000 mmol) and compound 17c (602 mg, 1.100 mmol) in the same way as described above.

Yielded amount: 221.2 mg, (23%)

$^1$H-NMR (D2O) δ: 7.78 (1H, s), 7.10 (1H, s), 6.98 (1H, s), 5.89 (1H, d, J=4.88 Hz), 5.38 (1H, d, J=4.88 Hz), 4.63 (1H, d, J=14.18 Hz), 4.25 (1H, t, J=7.02 Hz), 4.10-3.94 (4H, m), 3.51 (1H, d, J=16.93 Hz), 3.10 (3H, br s), 2.81-2.70 (2H, m), 2.59-2.36 (4H, m), 2.25 (1H, br s), 2.19 (1H, br s), 1.52 (3H, s), 1.50 (3H, s).

Elem. Anal.: C31H35N8O10S2Na (H2O) 8.4

Calcd.: C, 40.55; H, 5.69; N, 12.20; S, 6.99; Na, 2.50(%).
Found.: C, 40.59; H, 5.62; N, 12.05; S, 6.80; Na, 2.57(%).

Example 18

Synthesis of Compound (I-18)

Step: Compound 18a+Compound 17c→Compound (I-18)

Compound I-18 was prepared using Compound 18a (1.26 g, 1.000 mmol) and Compound 17c (602 mg, 1.100 mmol) in the same way as described above.

Yielded amount: 268.1 mg, (26%)

$^1$H-NMR (D2O) δ: 7.76 (1H, s), 7.08 (1H, s), 6.99 (1H, s), 5.84 (111, d, J=4.88 Hz), 5.34 (1H, d, J=4.88 Hz), 4.98 (1H, dd, J=8.16, 5.11 Hz), 4.61 (1H, d, J=14.03 Hz), 4.24 (1H, t, J=7.17 Hz), 4.13-3.89 (4H, m), 3.50 (1H, d, J=16.62 Hz), 3.10 (3H, brs), 2.79-2.71 (4H, m), 2.59-2.32 (4H, m), 2.24 (1H, br s), 2.18 (1H, br s).

Elem. Anal.: C31H32.1N8O12S2Na1.9 (H2O) 9.2

Calcd.: C, 37.90; H, 5.18; N, 11.41; S, 6.53; Na, 4.45(%).
Found.: C, 38.14; H, 5.20; N, 11.16; S, 6.38; Na, 4.46(%).

[Formula 54]

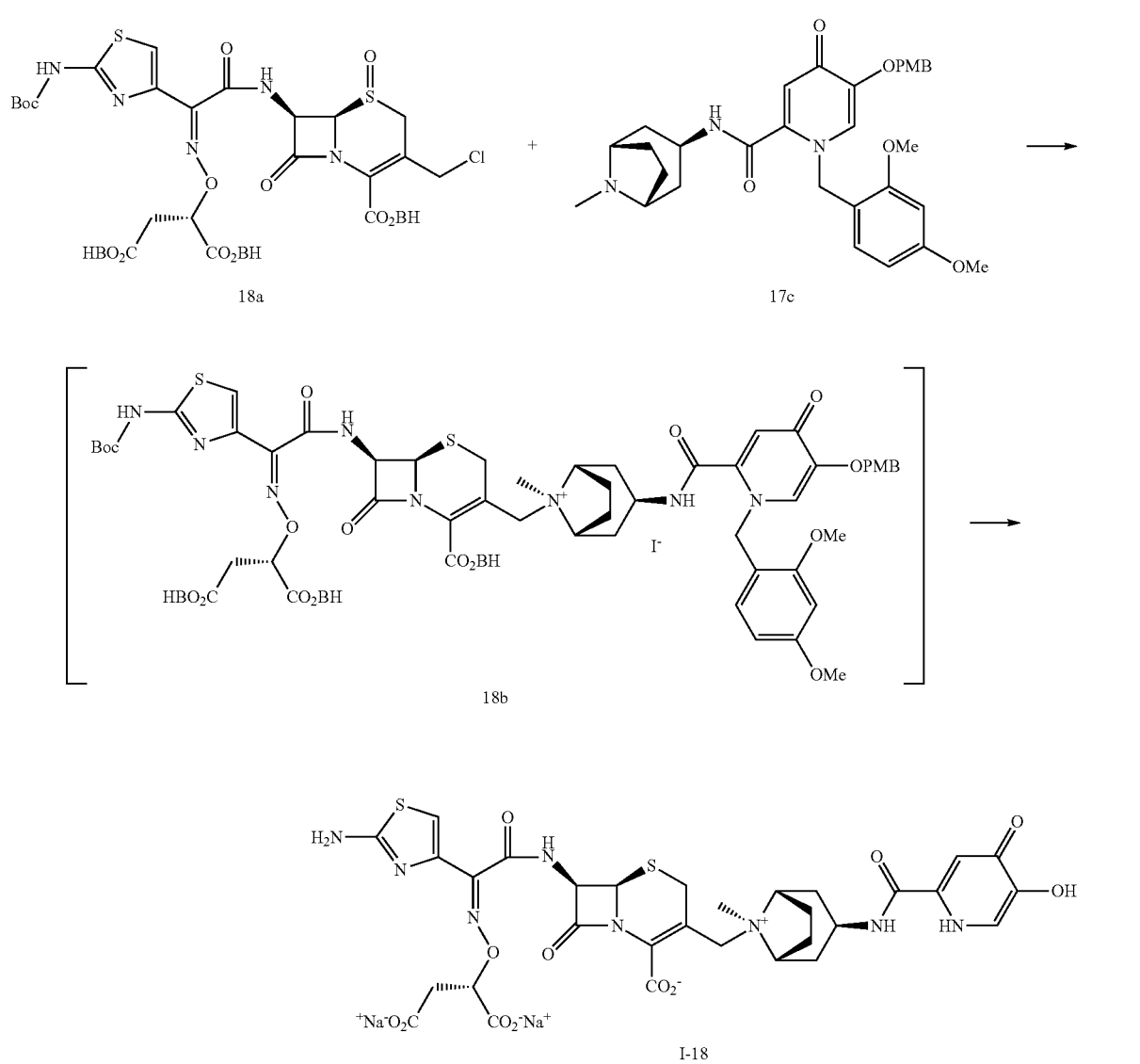

Example 19

Synthesis of Compound (I-19)

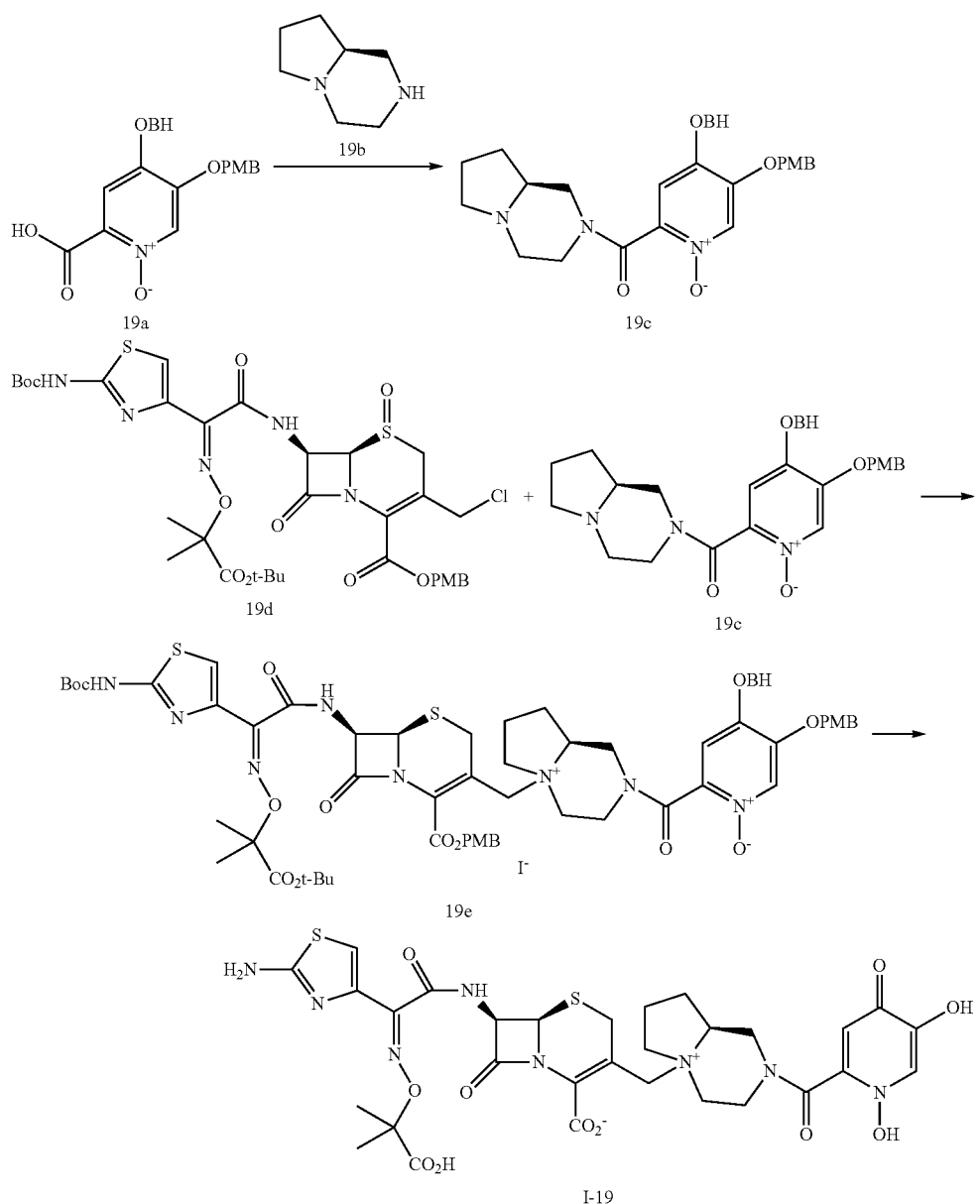

[Formula 55]

Step (1): Compound 1a+Compound 19b→Compound 19c

Compound 19c was synthesized from 19a (0.147 g, 0.32 mmol) in the same way as described above (0.122 g, 68%).

$^1$H-NMR (DMSO-d6) δ: 8.14 (1H, s), 7.52-7.25 (12H, m), 7.10-7.07 (1H, m), 6.99 (2H, d, J=8.6 Hz), 6.77-6.71 (1H, m), 5.19 (2H, s), 3.77 (3H, s), 3.05-1.62 (13H, m).

Step (2): Compound 19d+Compound 1c→Compound 19e→Compound (I-19)

Compound I-19 was synthesized from 19d (0.155 g, 0.194 mmol) and 19c (0.110 g, 0.194 mmol) in the same way as described above (0.021 g, 22%).

HPLC purity: 97.1%,
MS: 747.18 (M+H)

$^1$H-NMR (DMSO-d6) δ: 9.48 (1H, d, J=6.9 Hz), 7.78-7.76 (1H, m), 7.31 (2H, s), 6.83-6.77 (1H, m), 6.71 (1H, s), 5.89-5.84 (1H, m), 5.24-5.20 (1H, m), 4.83-3.37 (16H, m), 2.18-2.03 (4H, m), 1.45-1.43 (6H, m).

Example 20

Synthesis of Compound (I-20)

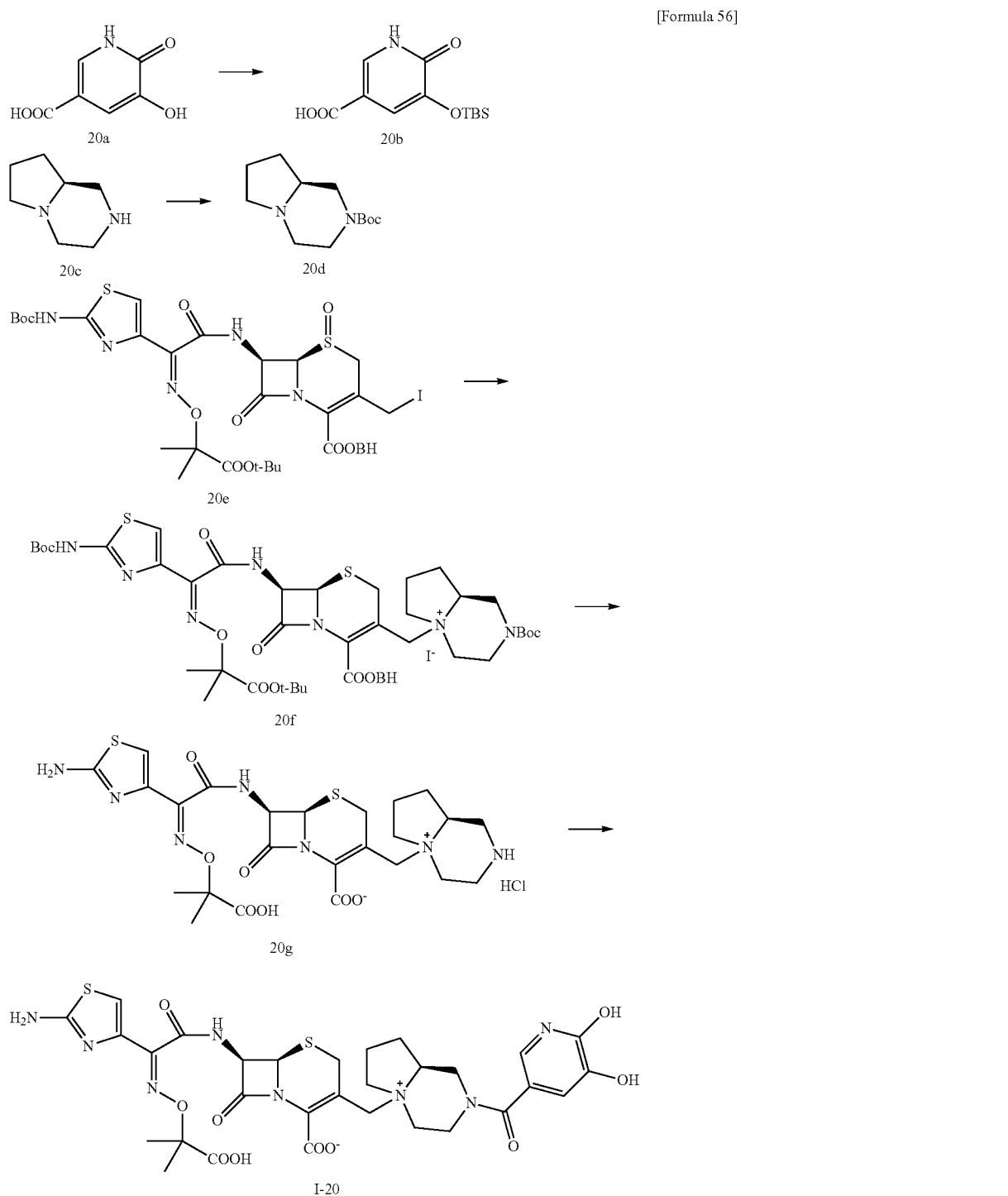

[Formula 56]

Step (1): Compound 20a→Compound 20b

To a solution of compound 20a (1.87 g) in dimethylformamide (20 mL) in ice bath was added imidazole and tert-Butyldimethylsilyl chloride (6.0 g), and the mixture was stirred and then left standing at r.t. overnight. The solvent was removed by evaporation. The residue was diluted with water and ethyl acetate. The organic layer was washed with water and brine, dried over MgSO$_4$, filtered and concentrated. The residue was crystallized from methanol to afford Compound 20b (2.34 g, 72% yield).

$^1$H-NMR (DMSO-d6) δ: 0.18 (6H, s), 0.94 (9H, s), 7.12 (1H, d, J=2.4 Hz), 7.65 (1H, brs), 12.1 (1H, brs), 12.7 (1H, brs).

Step (2): Compound 20c→Compound 20d

To a solution of Compound 20c (1.26 g) in dichloromethane (20 mL) in ice bath was added a solution of di-tert-butyl dicarbonate (2.40 g) in dichloromethane (10 mL). The mixture was stirred at r.t. for 2 hr. The solvent was removed by evaporation and the residue was purified by column chromatography on silica gel to afford Compound 20d (1.83 g, 81% yield).

$^1$H-NMR (CDCl$_3$) δ: 1.46 (9H, s), 1.81 (4H, m), 2.11 (2H, m), 2.55 (1H, m), 3.02 (3H, m), 4.05 (3H, m), 12.7 (1H, brs).

Step (3): Compound 20e+Compound 20d→Compound 20g→Compound (I-20)

Compound 20g was prepared from Compound 20e and Compound 20d by the similar procedure as described above.

To a solution of Compound 20b (189 mg) in N,N-dimethylformamide (5 mL) in ice bath was added N-methylmorphorine (0.165 mL) and 1-hydroxybenzotriazole (73 mg) and WSCD-HCl (104 mg). The mixture was stirred at r.t. for 30 min. Compound 20g was added to the mixture under ice-cooling, and then the whole mixture was stirred in ice bath for 2.5 hr. The resulting mixture was poured into diethylether.

The precipitated material was collected by filtration. The solid was dissolved with diluted HCl/acetonitrile. HP20SS was added, and the mixture was concentrated to 20 mL. The residue was purified by HP20SS reverse-phase column chromatography and lyophilized to afford I-20 (102 mg).

$^1$H-NMR (D$_2$O+NaHCO3) δ: 1.53 (3H, s), 1.55 (3H, s), 2.01-2.45 (5H, m), 3.40-3.85 (5H, m), 3.80-4.35 (6H, m), 5.36 (1H, d, J=5.1 Hz), 5.86 (1H, d, J=5.1 Hz), 7.07 (1H, m), 7.39 (1H, m).

Example 21

Synthesis of Compound (I-21)

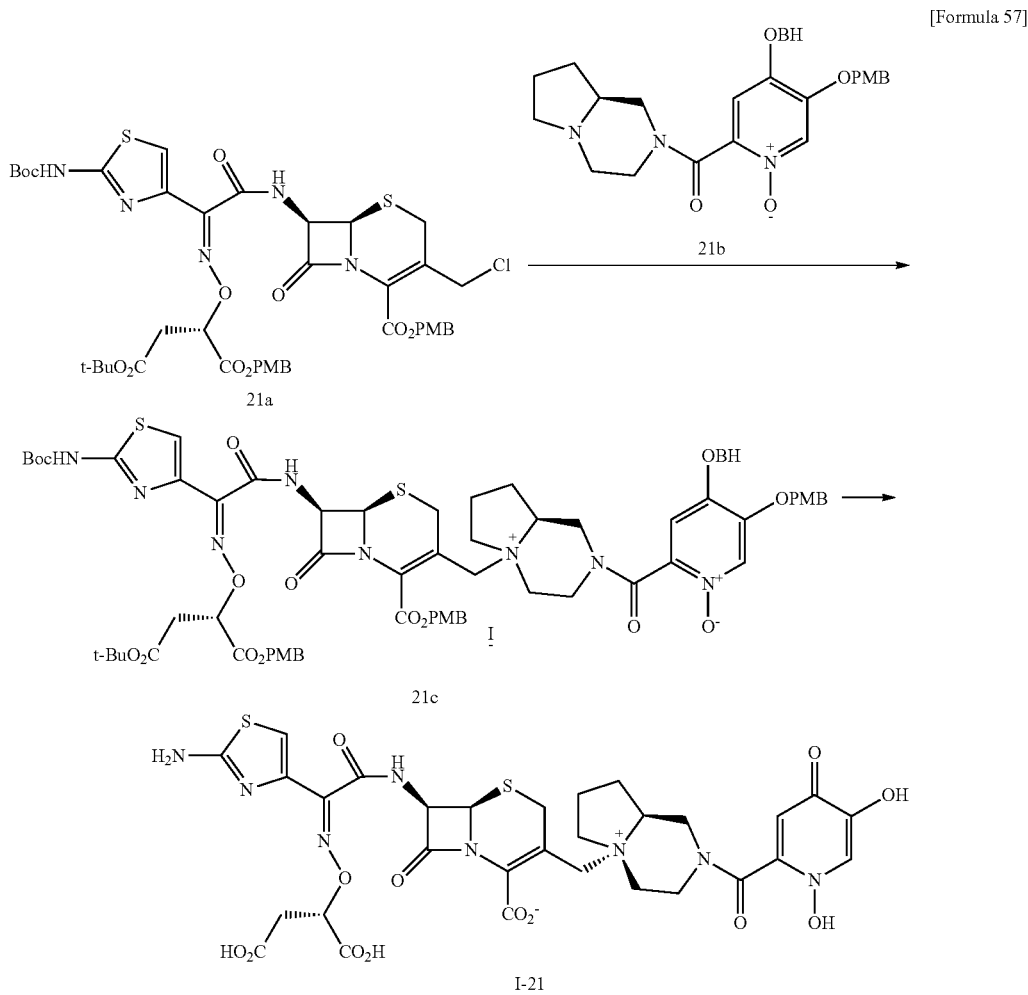

[Formula 57]

Step (I): Compound 21a→Compound (I-21)

Compound 21a (0.627 g, 0.633 mmol) was treated in a similar manner as described above to obtain Compound I-21. yield 0.086 g, (16%).

MS: 777.20 (M+H)

$^1$H-NMR (D$_2$O) δ: 7.68-7.66 (1H, m), 7.01 (1H, s), 6.71-6.64 (1H, m), 5.85-5.82 (1H, m), 5.35-5.31 (1H, m), 4.98-4.94 (1H, m), 4.40-4.35 (1H, m), 3.94-3.49 (12H, m), 2.74-2.70 (2H, m), 2.39-2.22 (4H, m).

Example 22

Synthesis of Compound (I-22)

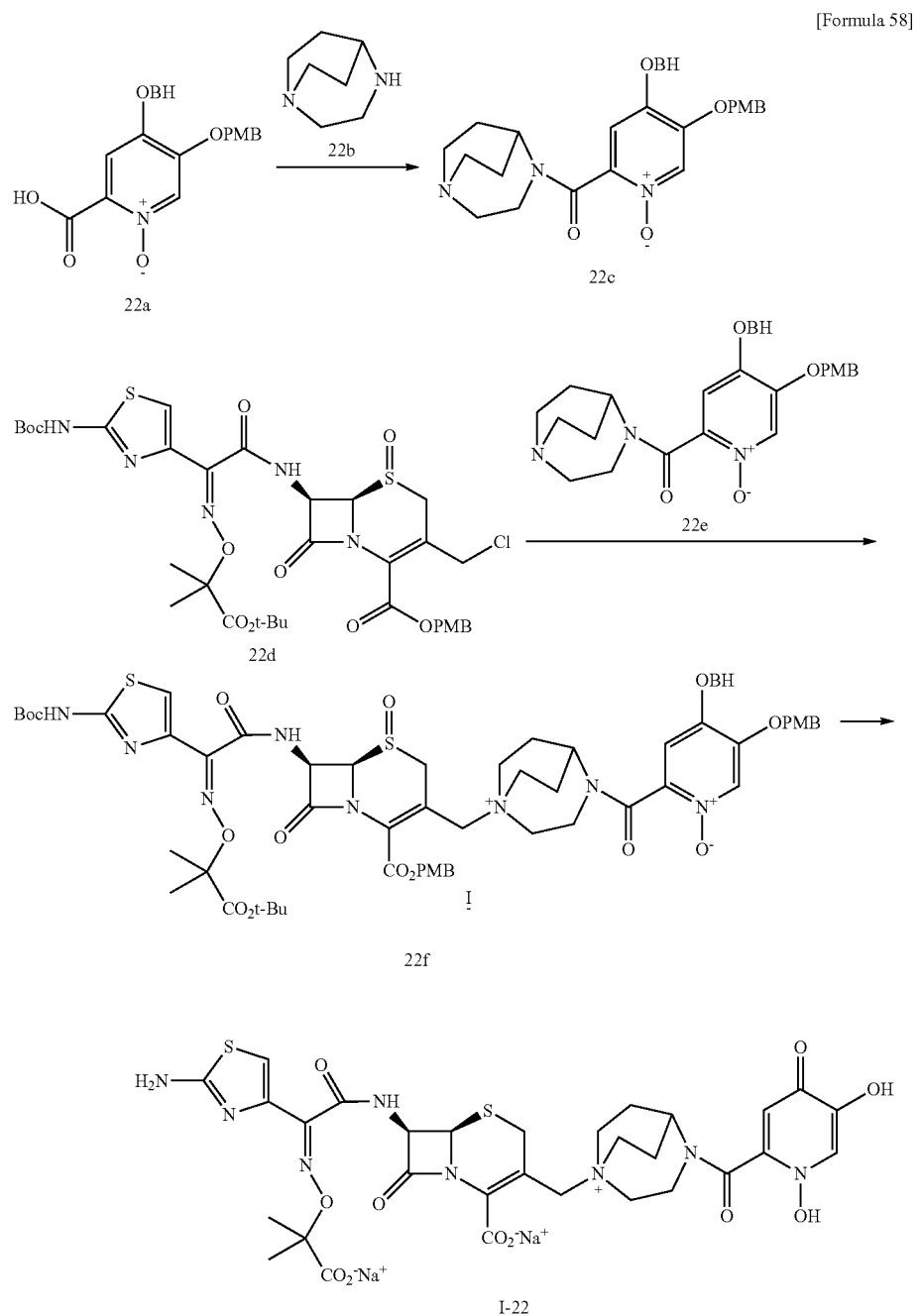

[Formula 58]

Step (1): Compound 22a+Compound 22b→Compound 22c

Compound 22a (1.10 g, 2.40 mmol) and Compound 22b (0.424 g, 3.36 mmol) was treated in a similar manner as described above to obtain Compound 22c.

Yield 0.895 g, (66%).

$^1$H-NMR (DMSO-d6) δ: 8.13-8.11 (1H, m), 7.44-7.22 (12H, m), 7.12-7.07 (1H, m), 6.99 (2H, d, J=8.7 Hz), 6.76-6.75 (1H, m), 5.77-5.75 (2H, m), 5.18 (2H, s), 4.39 (1H, s), 4.13-4.10 (2H, m), 3.77 (3H, s), 3.18-1.44 (8H, m).

Step (2): Compound 22d→Compound 22f→Compound (I-22)

Compound 22d (0.637 g, 0.800 mmol) was treated as the similar procedure described above to obtain Compound I-22.

Yield 0.075 g, (12%).

MS: 747.25 (M+H)

$^1$H-NMR (D2O) δ: 7.66-7.64 (1H, m), 6.98-6.98 (1H, m), 6.66-6.63 (1H, m), 5.90-5.87 (1H, m), 5.38-5.36 (1H, m), 4.21-3.43 (13H, m), 2.37-2.23 (4H, m), 1.51-1.50 (7H, m).

Example 23
Synthesis of Compound (I-23)
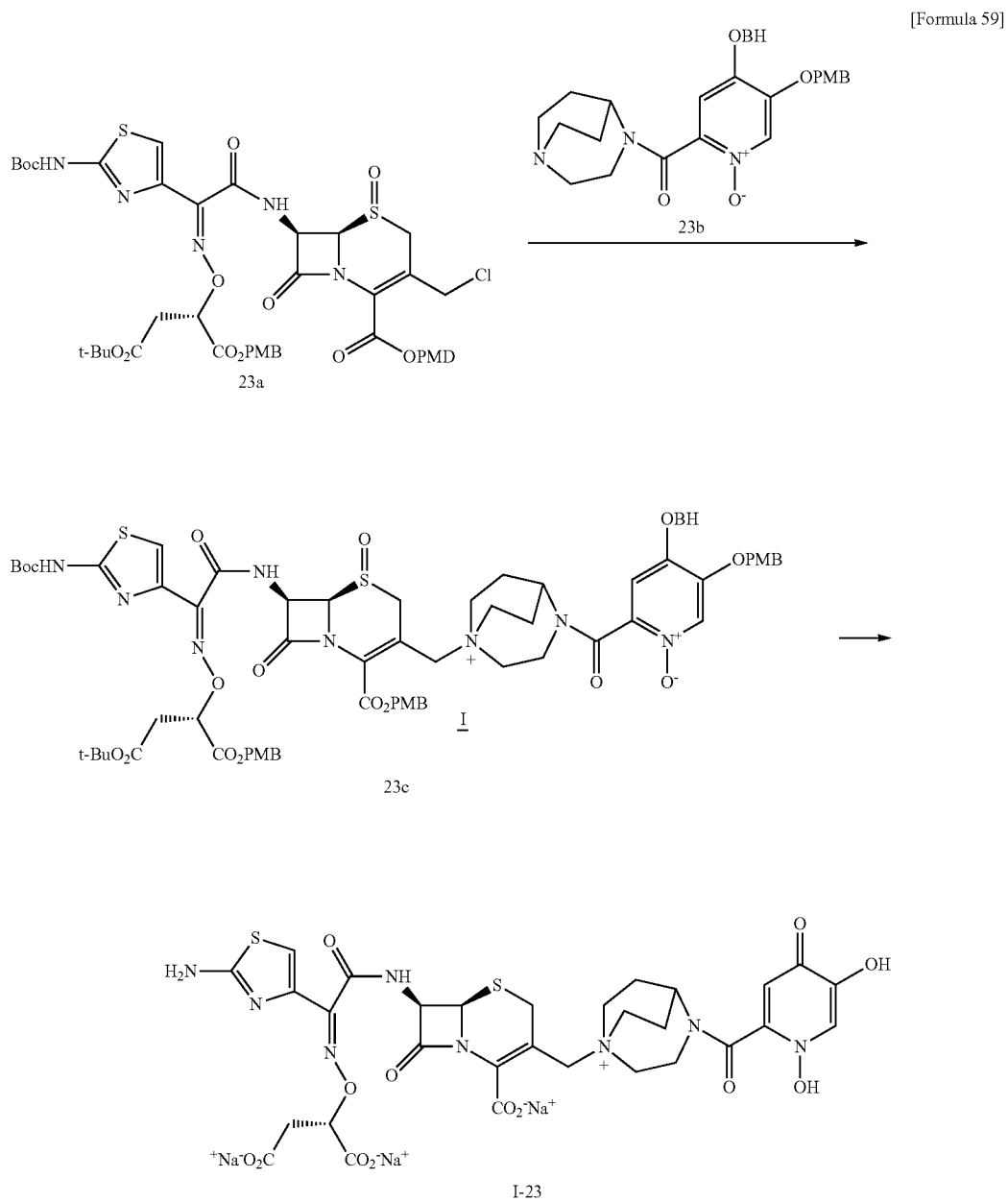
[Formula 59]
Step: Compound 23a→Compound 23c→Compound I-23
Compound 23a (0.757 g, 0.800 mmol) was treated in a similar manner as described above to obtain Compound I-23.
Yield 0.035 g, (5%)
MS: 777.17 (M+H)
1H-NMR (D2O) δ: 7.66-7.63 (1H, m), 7.02 (1H, s), 6.64 (1H, s), 5.85-5.82 (1H, m) 5.37-5.33 (1H, m), 4.96-4.90 (2H, m), 4.23-3.42 (12H, m), 2.74-2.70 (2H, m), 2.39-2.24 (4H, m).

Example 24
Synthesis of Compound (I-24)
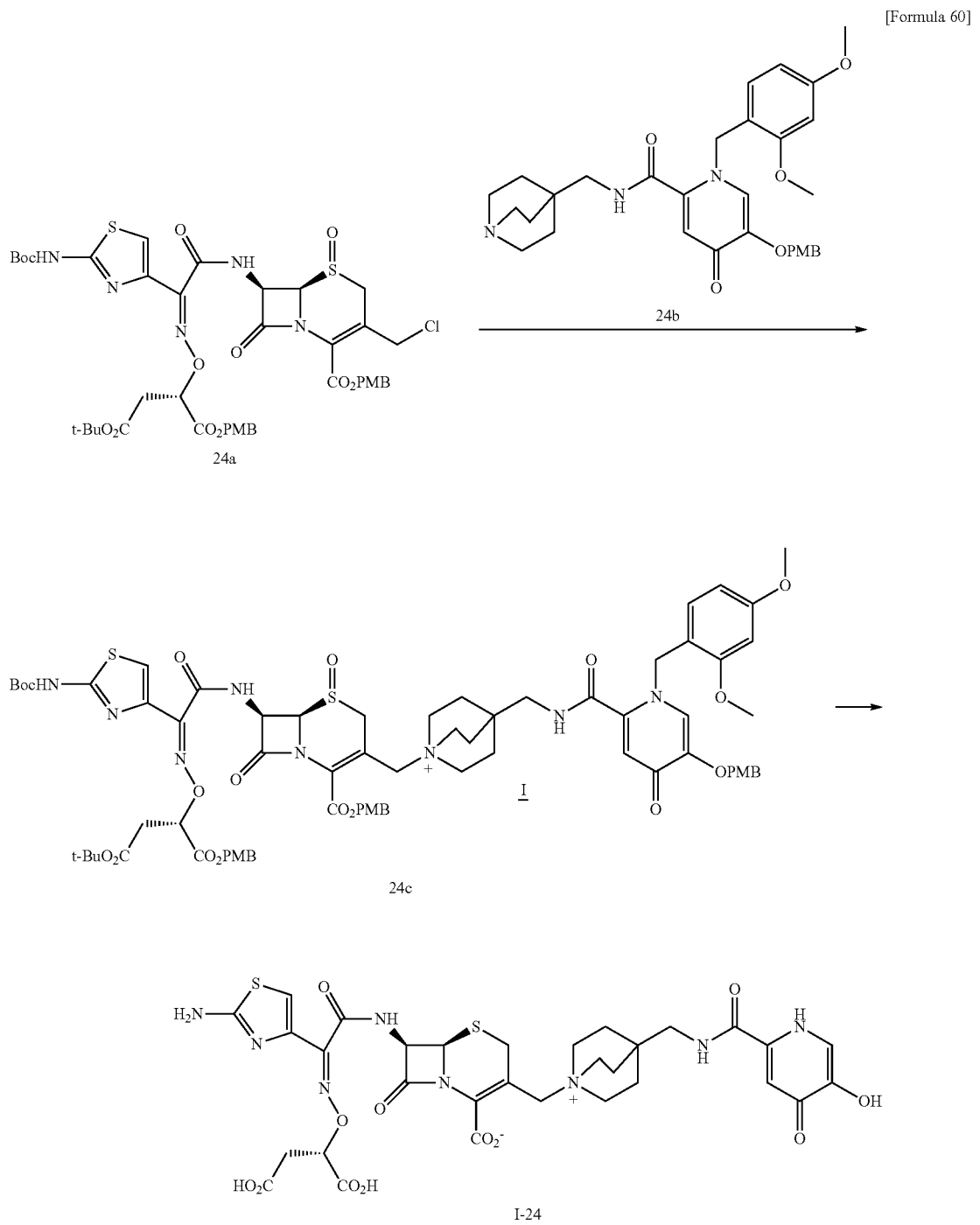
[Formula 60]
Step: Compound 24a→Compound 24c→Compound (I-24)
Compound 24a was treated in a similar manner as described above to obtain Compound I-24.
Yield 0.097 g, (13%).
$^1$H-NMR (DMSO-d6) δ: 9.54-9.52 (1H, m), 8.64 (1H, s), 7.92 (1H, s), 7.47 (1H, s), 7.29-7.27 (2H, m), 6.81 (1H, s), 5.71 (1H, dd, J=8.2, 4.9 Hz), 5.08 (1H, d, J=4.9 Hz), 4.84-4.73 (2H, m), 3.82-2.68 (17H, m), 1.78-1.74 (6H, m).
Elemental analysis: C31H34N8O12S2 (H2O) 5.9
Calculated value: C, 42.26; H, 5.24; N, 12.72; S, 7.28(%).
Experimental value: C, 42.20; H, 5.13; N, 12.85; S, 7.37 (%).

Example 25
Synthesis of Compound (I-25)
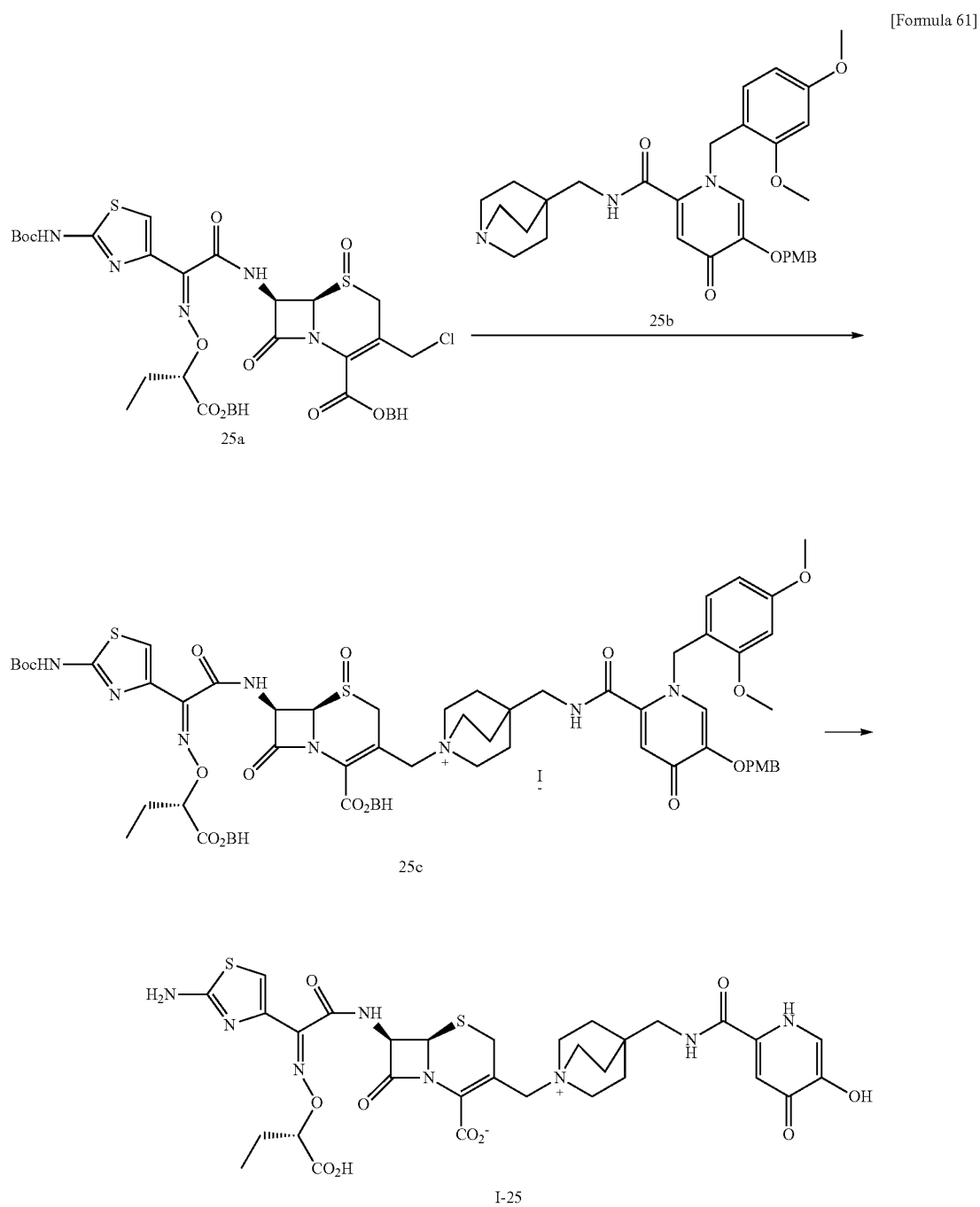
Step: Compound 25a→Compound 25c→Compound (I-25)
Compound 25a (0.726 g, 0.800 mmol) was treated in a similar manner as described above to obtain Compound I-25.
Yield 0.025 g, (4%)
$^1$H-NMR (DMSO-d6) δ: 9.48 (1H, d, J=8.4 Hz), 8.63 (1H, s), 7.96-7.93 (1H, m), 7.48-7.43 (1H, m), 7.29-7.26 (2H, m), 6.75 (1H, s), 5.80-5.75 (1H, m), 5.12-5.10 (1H, m), 4.84-4.71 (1H, m), 4.44 (18, t, 6.3 Hz), 3.84-3.20 (14H, m), 1.85-1.71 (OH, m), 0.95 (3H, t, J=7.5 Hz).
Elemental analysis C31H36N8O10S2 (H2O) 6.6 (NaCl) 0.2
Calculated value: C, 42.53; H, 5.67; N, 12.80; S, 7.33; Cl, 0.81(%).
Experimental value: C, 42.47; H, 5.42; N, 12.27; S, 7.53; Cl, 0.74(%).

Example 26
Synthesis of Compound (I-26)
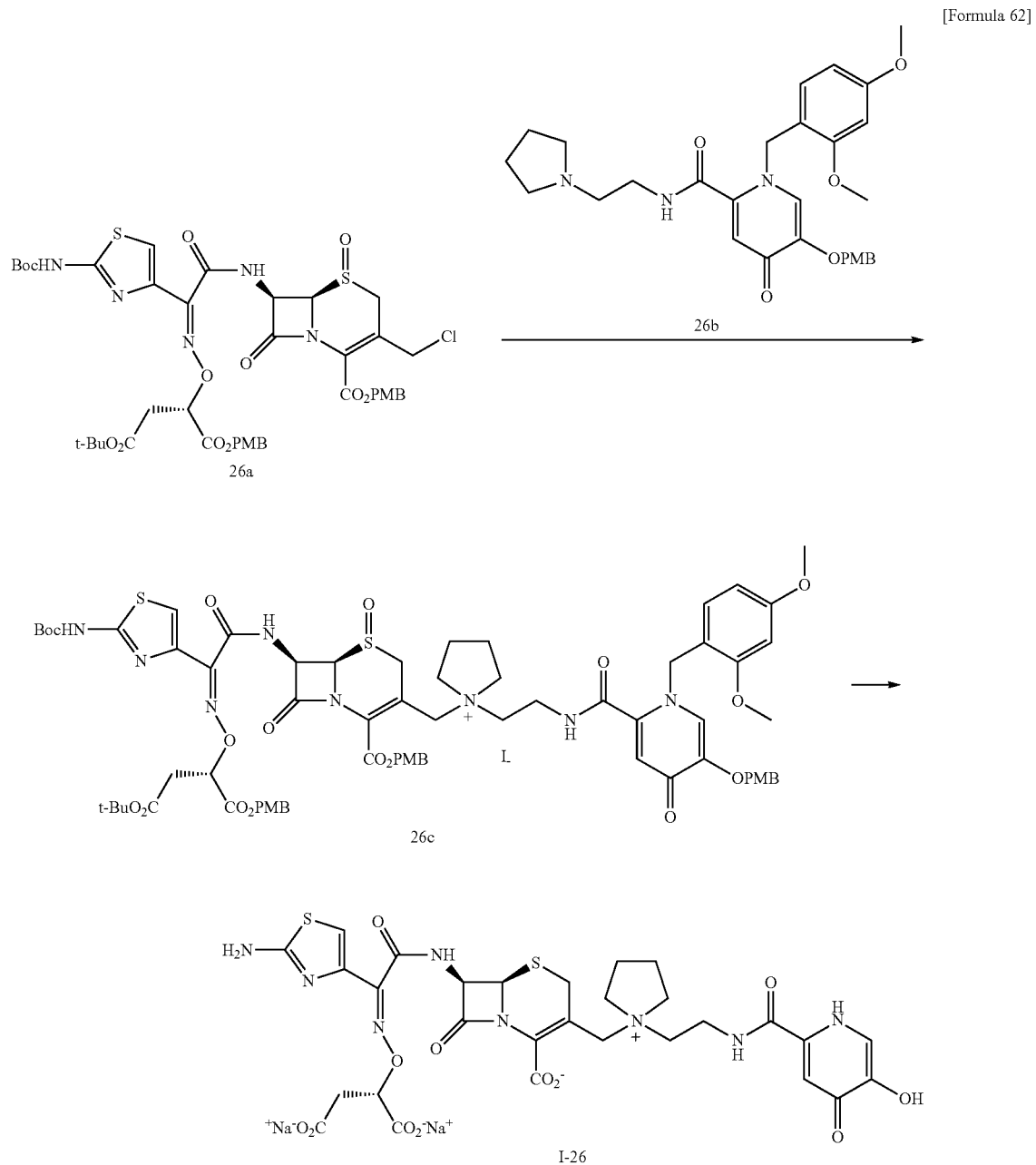
[Formula 62]
Step: Compound 26a→Compound 26c→Compound (I-26)
Compound 26a (0.852 g, 0.900 mmol) was treated in a similar manner as described above to obtain Compound I-26.
Yield 0.093 g, (13%)
MS: 749.12 (M+H)
$^1$H-NMR (D2O) δ: 7.77 (1H, s), 7.09 (1H, s), 7.00 (1H, s), 5.85-5.81 (1H, m), 5.36-5.33 (1H, m), 5.00-4.95 (1H, m), 4.16 (1H, d, J=14.5 Hz), 3.95-3.52 (11H, m), 2.78-2.66 (2H, m), 2.23-2.07 (4H, m).

Example 27
Synthesis of Compound (I-27)
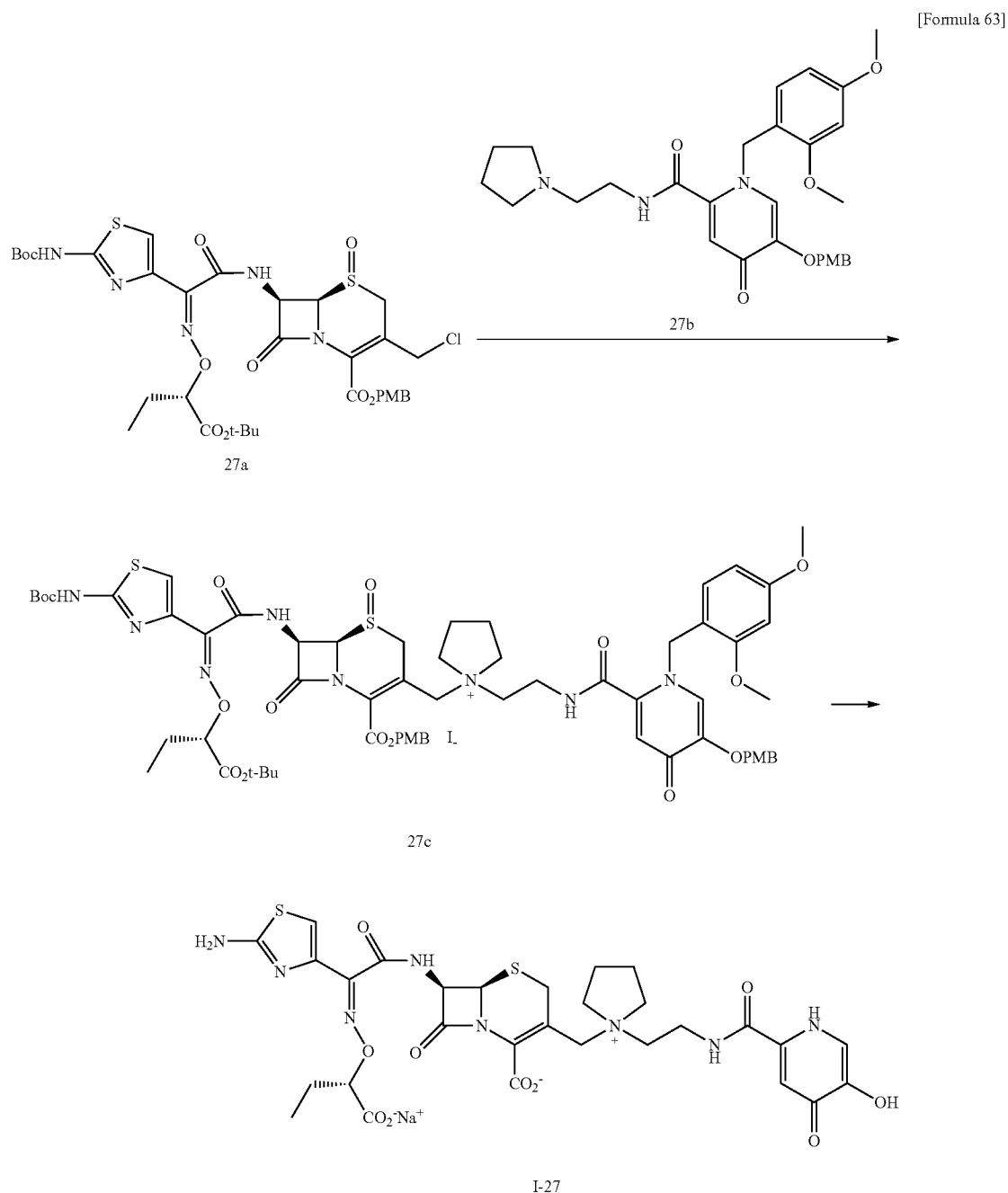
Step: Compound 27a→Compound 27c→Compound (I-27)
Compound 27a (0.726 g, 0.800 mmol) was treated in a similar manner as described above to obtain Compound I-27.
Yield 0.192 g, (32%)
MS: 719.17 (M+H)
$^1$H-NMR (D2O) δ: 7.77 (1H, s), 7.09 (1H, s), 6.99 (1H, s), 5.88 (1H, d, J=5.3 Hz), 5.37 (1H, s), 4.53 (1H, t, J=5.9 Hz), 4.12 (1H, d, J=13.6 Hz), 4.00-3.43 (11H, m), 2.24-2.20 (4H, m), 1.92-1.82 (2H, m), 0.97 (3H, t, J=7.2 Hz)

Example 28

Synthesis of Compound I-28

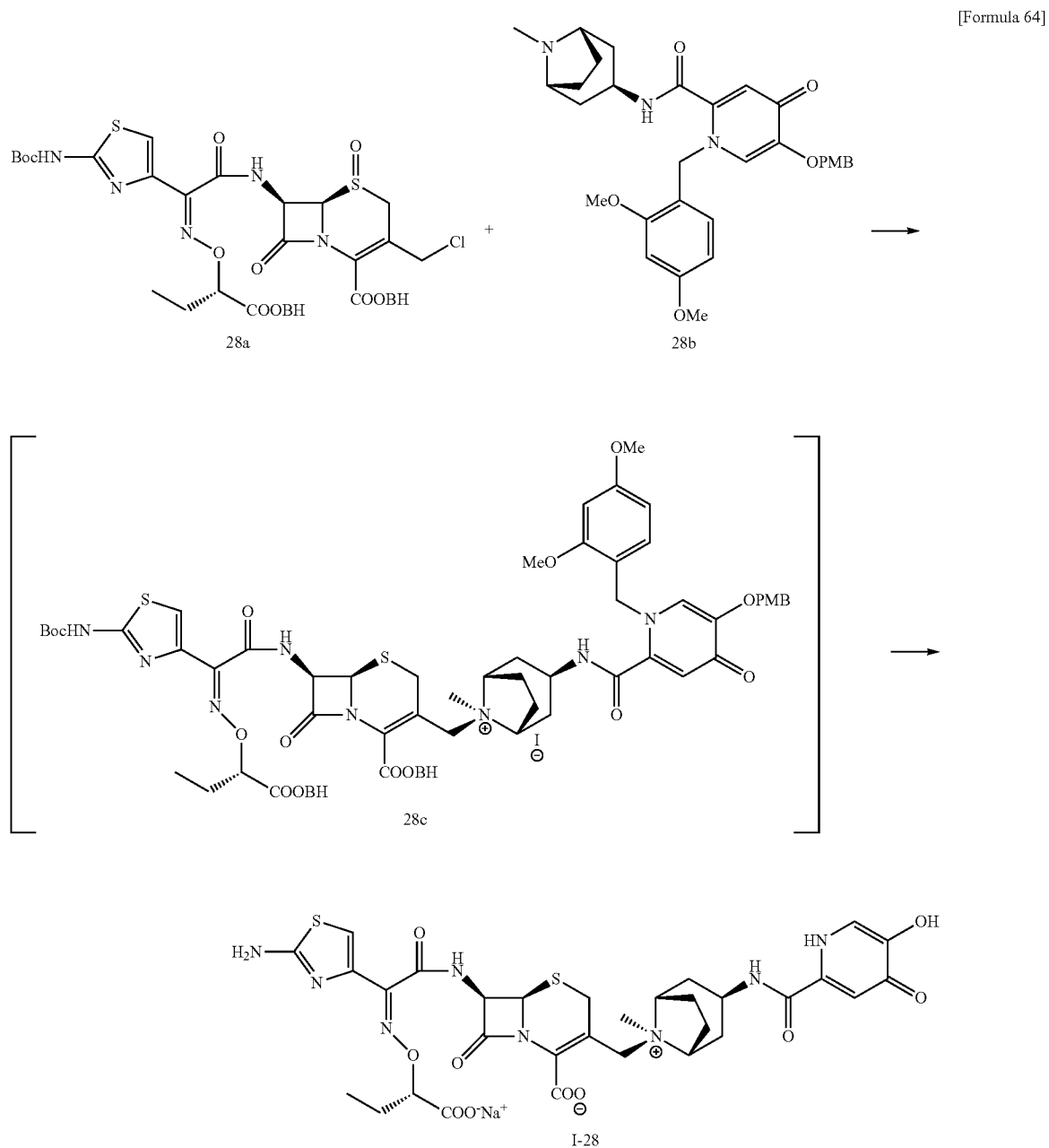

[Formula 64]

Step: Compound 28a→Compound 28b→Compound 28c→Compound (I-28)

Compound I-28 was obtained from Compound 28a (952 mg, 1.0 mmol) and Compound 28b (548 mg, 1.0 mmol) by the similar procedure described above as a white powder.

Yield 125 mg, (16%)

$^1$H-NMR (D2O) δ: 0.98 (3H, t, J=7.3 Hz), 1.83-1.92 (2H, m), 2.21 (2H, d, J=16.8 Hz), 2.44-2.58 (3H, m), 2.71-2.80 (2H, m), 3.10 (3H, s), 3.49 (1H, d, J=16.8 Hz), 3.93-4.10 (4H, m), 4.24 (1H, t, J=7.4 Hz), 4.53 (1H, t, J=6.2 Hz), 4.62 (1H, d, J=14.2 Hz), 5.37 (1H, d, J=5.0 Hz), 5.89 (1H, d, J=5.0 Hz), 7.00 (1H, s), 7.09 (1H, s), 7.77 (1H, s).

MS (m+1)=745.34

Elemental analysis: C31E35N8O10S2Na.6.2H2O

Calculated value: C, 42.38; H, 5.44; N, 12.76; S, 7.30; Na, 2.62(%).

Experimental value: C, 42.32; H, 5.22; N, 12.74; S, 7.26; Na, 2.78(%)

Example 29

Synthesis of Compound I-29

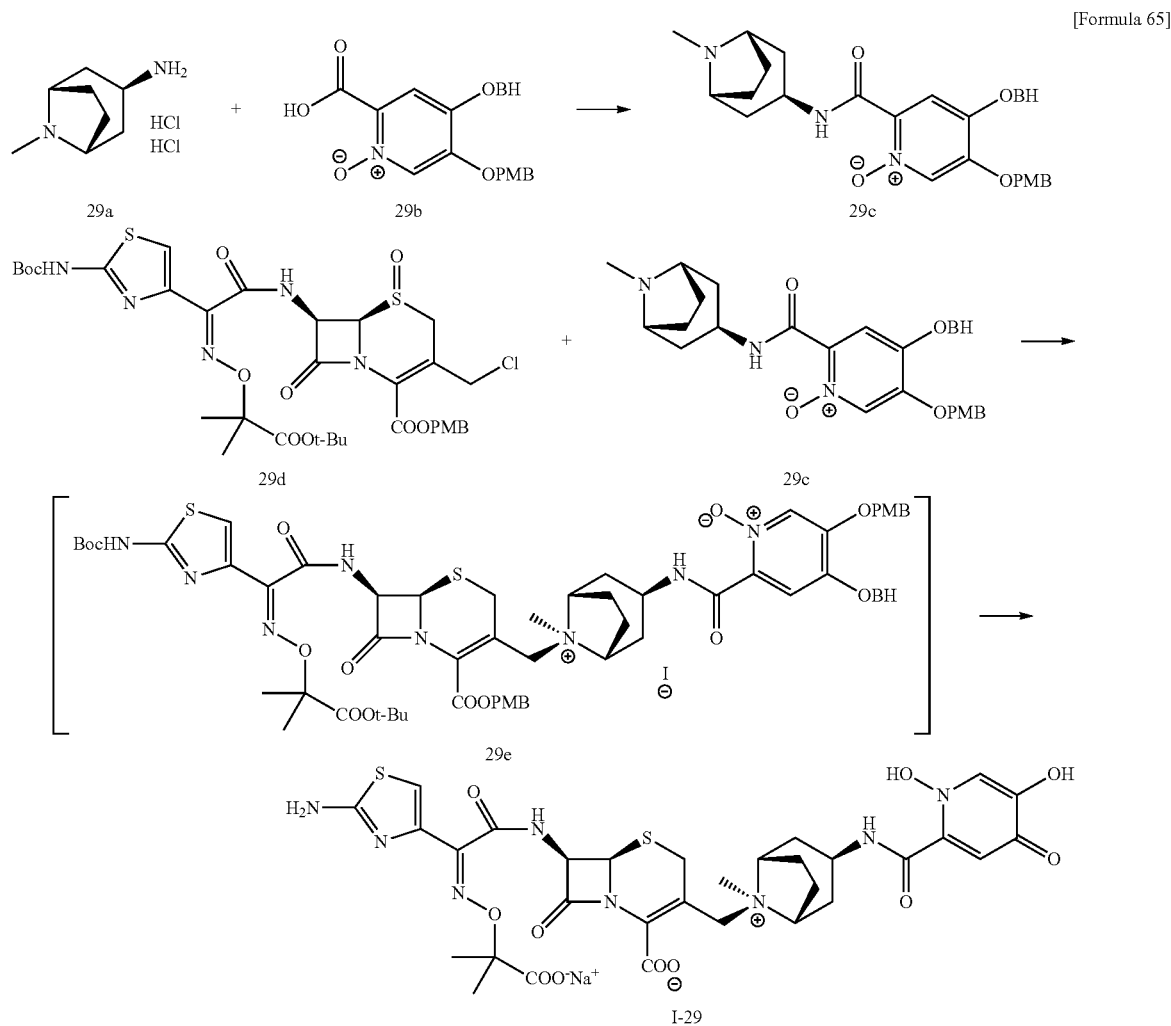

Step (1): Compound 29a+Compound 29b→Compound 29c

To a solution of Compound 29b (1.37 g, 3.0 mmol) in N,N-dimethylformamide (14 ml), 1-hydroxybenzotriazole (486 mg, 3.6 mmol), WSCD-HCl (633 mg, 3.3 mmol), Compound 29a (1.41 g, 6.6 mmol) and diisopropylethylamine (1.26 ml, 7.2 mmol) were added, and then stirred at 70° C. over night. N,N-dimethylformamide was removed by evaporation, then to the residue was added 1N sodium hydroxide aqueous solution and extracted with ethyl acetate. The organic phase was washed with water and brine, and dried over magnesium sulfate anhydride. The inorganic substance was removed by filtration, and the filtrate was concentrated in vacuo. The obtained crude product was purified by silica gel chromatography to obtain Compound 29c as a brown powder.

Yield 526 mg, (30%)

$^1$H-NMR (CDCl$_3$) δ: 1.69-2.21 (8H, m), 2.30 (3H, s), 3.16 (2H, br s), 3.83 (3H, s), 4.21 (1H, g, J=7.1 Hz), 5.12 (2H, s), 6.40 (1H, s), 6.91 (2H, d, J=8.7 Hz), 7.27-7.44 (12H, m), 7.85 (1H, s), 7.86 (1H, s), 12.02 (1H, d, J=7.5 Hz).

MS (m+1)=580.41

Step (2): Compound 29d+Compound 29c→Compound (I-29)

A solution of Compound 29c (290 mg, 0.50 mmol) in N,N-dimethylformamide (1 ml) was cooled to 15° C., to which was added Compound 29d (398 mg, 0.50 mmol) and degassed in vacuo. To the reaction mixture was added sodium iodide (150 mg, 1.0 mmol), and the mixture was stirred at 15° C. for two hours, and then stood over night in a refrigerator. To the reaction mixture was added N,N-dimethylformamide (3.0 mL) and the mixture was cooled at 0° C., to which were added potassium iodide (581 mg, 3.5 mmol) and acetyl chloride (143 μL, 2.0 mmol) by sequence, and stirred at 0° C. for three hours. The reaction mixture was added into iced 5% brine slowly. The precipitates were filtered, washed with water, suspended in water and then lyophilized to obtain Compound 29e as yellow solid. The obtained Compound 29e was used for next step without purification. The whole amount of Compound 29e obtained was dissolved in dichloromethane (8 mL) and cooled to −40° C., and then anisole (546 μL, 5.0 mmol) and 2 mol/L aluminum chloride/nitromethan solution (2.5 mL, 5.0 mmol) were added in sequence, and the mixture was stirred at 0° C. for 30 minutes. To the reaction solution was added diisopropylether and a drop of water and stirred to stimulate precipitates, and removed supernatant liquid by decantation. To the insoluble matter attached in the flask was added dilute hydrochloride acid and acetonitrile and stirred and dissolved completely, to which was added isopropyl ether and an aqueous layer was separated from the supernatant. The organic phase was extracted with water again, all the aqueous Experimental value: C, 41.04; H, 5.29; N, 12.56; S, 7.00; Cl, 0.72; Na, 3.24(%).

Example 30

Synthesis of Compound (I-30)

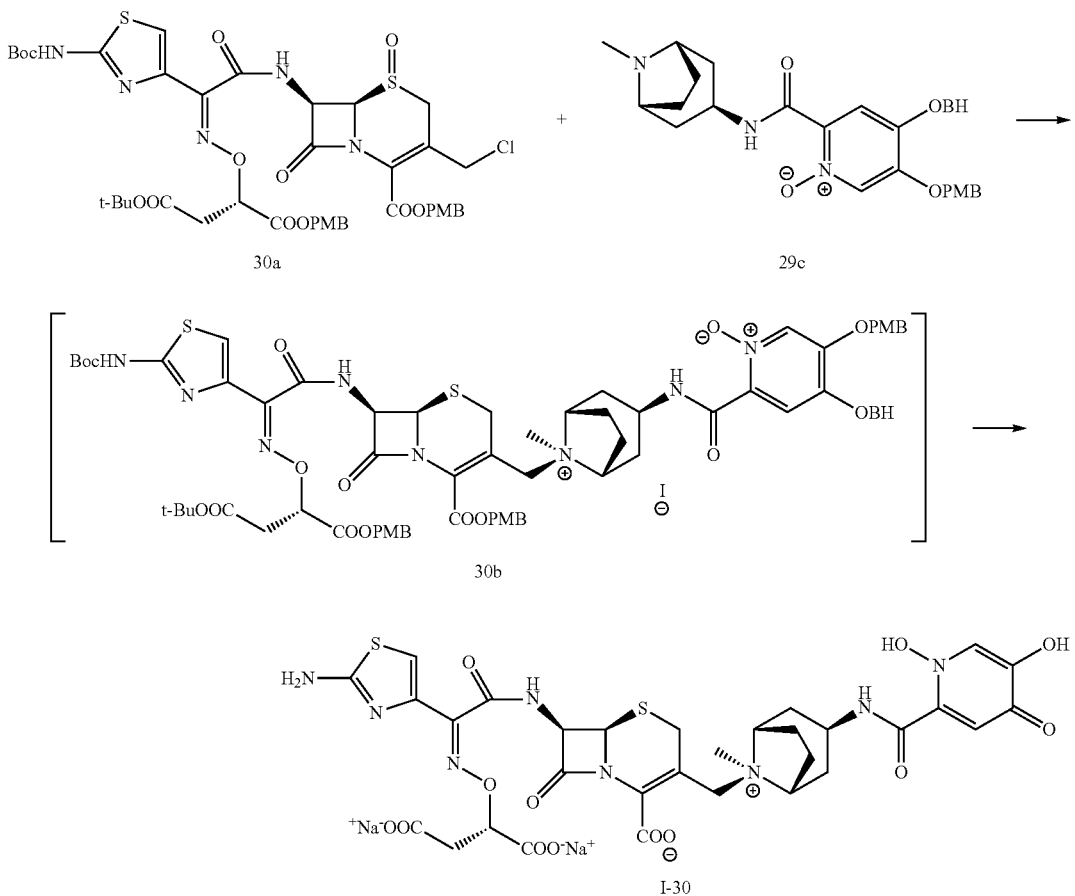

[Formula 66]

Phases were combined, HP20-SS resin was added thereto, and then the acetonitrile-containing solution was concentrated under reduced pressure. The obtained mixed solution was purified by ODS column chromatography. To the fractions containing the intended compound was added 0.2 mol/L sodium hydroxide aqueous solution to adjust pH=6.0, and then a piece of dry ice was added thereto. The resulting solution was concentrated in vacuo, and then lyophilized to obtain Compound I-29 as a white powder.

Yield 61 mg, (16%)

$^1$H-NMR (D2O) δ: 1.50 (3H, s), 1.52 (3H, s), 2.21 (2H, d, J=17.2 Hz), 2.45-2.58 (3H, m), 2.72-2.80 (2H, m), 3.10 (3H, s), 3.50 (1H, d, J=16.6 Hz), 3.93-4.10 (4H, m), 4.24 (1H, t, J=6.9 Hz), 4.63 (1H, d, J=14.3 Hz), 5.37 (1H, d, J=4.8 Hz), 5.89 (1H, d, J=4.8 Hz), 6.98 (1H, s), 7.09 (1H, s), 7.78 (1H, s).

Elemental analysis: C31H35N8O11S2Na (H2O) 6.2 (NaCl) 0.2

Calculated value: C, 41.09; H, 5.27; N, 12.37; S, 7.08; Cl, 0.78; Na, 3.04(%).

Step: Compound 30a+Compound 29c→Compound (I-30)

Compound I-30 was prepared from Compound 30a (398 mg, 0.50 mmol) and Compound 29c (290 mg, 0.50 mmol) as the similar procedure described above as a pale yellow powder.

Yield 130 mg, (31%)

$^1$H-NMR (D2O) δ: 2.08 (2H, d, J=16.8 Hz), 2.37 (2H, d, J=9.5 Hz), 2.60-2.81 (6H, m), 3.11 (3H, s), 3.51 (1H, d, J=16.6 Hz), 3.90-4.16 (4H, m), 4.34 (1H, t, J=6.9 Hz), 4.61 (1H, d, J=13.7 Hz), 4.97 (1H, dd, J=8.2, 5.0 Hz), 5.34 (1H, d, J=5.0 Hz), 5.84 (1H, d, J=5.0 Hz), 7.02 (1H, s), 7.42 (1H, s), 7.64 (1H, s).

MS (m+1)=791.36

Elemental analysis: C31H32N8O13S2Na2.(H2O) 7.0.NaHCO3 (0.9)

Calculated value: C, 36.97; H, 4.56; N, 10.81; S, 6.19; Na, 6.43(%).

Experimental value: C, 36.79; H, 4.73; N, 11.38; S, 6.32; Na, 6.52(%).

Example 31

Synthesis of Compound (I-31)

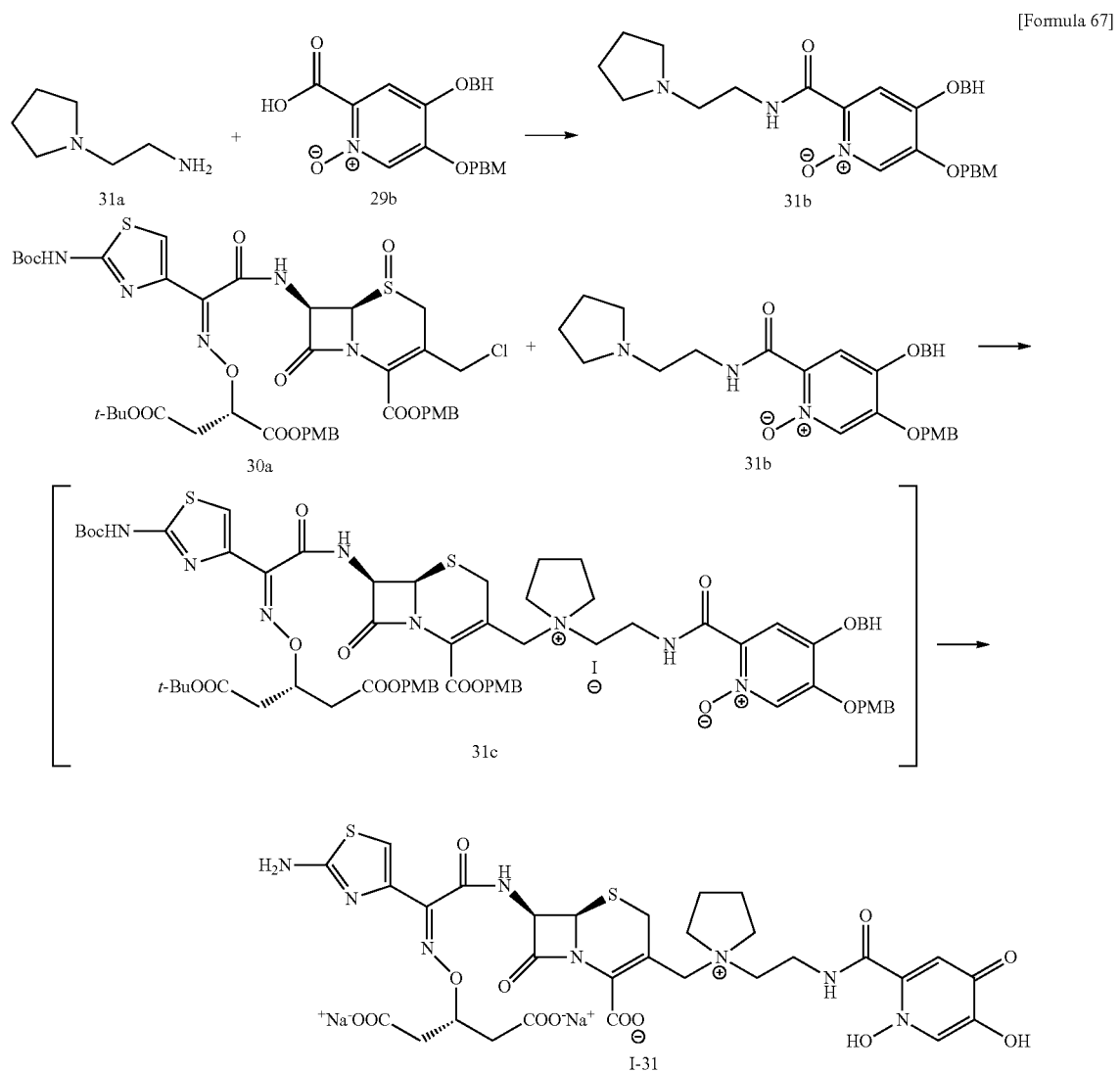

[Formula 67]

Step (1): Compound 31a+Compound 29b→Compound 31b

To a solution of Compound 29b (915 mg, 2.0 mmol) in N,N-dimethylformamide (9 ml), 1-hydroxybenzotriazole (324 mg, 2.4 mmol), WSCD-HCl (422 mg, 2.2 mmol) and Compound 31a (502 mg, 4.4 mmol) were added, and then stirred at 70° C. over night. N,N-dimethylformamide was removed by evaporation. To the residue was added 1N sodium hydroxide aqueous solution and extracted with ethyl acetate. The organic phase was washed with water and brine, and dried over magnesium sulfate anhydride. The inorganic substance was removed by filtration, and the filtrate was concentrated in vacuo. The obtained crude product was purified by silica gel chromatography to obtain Compound 31b as a brown powder.

Yield 400 mg, (36%)

$^1$H-NMR (CDCl$_3$) δ: 1.75-1.79 (4H, m), 2.55 (4δ, br s), 2.67 (2H, t, J=6.6 Hz), 3.55 (2H, dd, J=12.2, 6.6 Hz), 3.82 (3H, s), 5.11 (2H, s), 6.40 (1H, s), 6.91 (2H, d, J=8.7 Hz), 7.27-7.44 (12H, m), 7.96 (2H, s), 11.43 (1H, br s).

Step (2): Compound 30a+Compound 31b→Compound 31c→Compound (I-31)

Compound I-31 was prepared from Compound 30a (710 mg, 0.75 mmol) and Compound 31b (415 mg, 0.75 mmol) by the similar procedure described above as an orange powder.

Yield 70 mg, (12%)

$^1$H-NMR (D2O) δ: 2.21 (4H, b s), 2.70-2.73 (2H, m), 3.03-3.08 (2H, m), 3.39-3.64 (6H, m), 3.84-4.01 (3H, m), 4.14 (1H, d, J=14.5 Hz), 4.97 (1H, dd, J=8.1, 4.9 Hz), 5.35 (1H, d, J=4.9 Hz), 5.85 (1H, d, J=4.9 Hz), 7.02 (1H, s), 7.41 (1H, s), 7.63 (1H, s).

MS (m+1)=765.35

Elemental analysis: C29H30N8O13S2Na2.(H2O) 8.3

Calculated value: C, 36.35; H, 4.90; N, 11.69; S, 6.69(%).

Experimental value: C, 36.29; H, 4.65; N, 11.75; S, 6.50 (%).

Example 32

Synthesis of Compound I-32

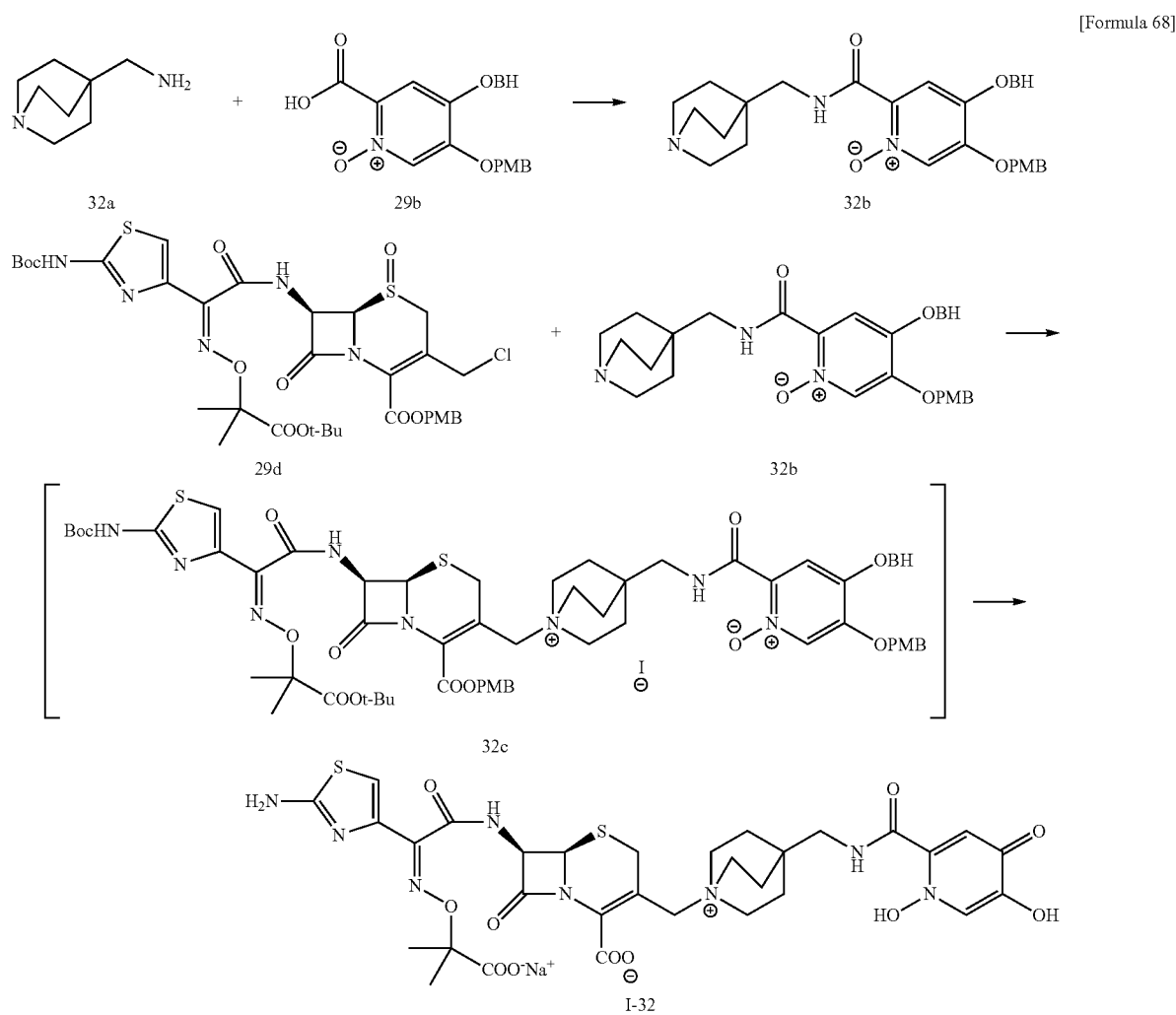

Step (1): Compound 32a+Compound 29b→Compound 32b

To a solution of Compound 29b (1.83 g, 4.0 mmol) in N,N-dimethylformamide (18 ml), 1-hydroxybenzotriazole (619 mg, 4.8 mmol), WSCD-HCl (843 mg, 4.4 mmol) and Compound 32a (1.23 g, 8.8 mmol) were added, and the mixture was stirred at 70° C. over night. N,N-dimethylformamide was removed by evaporation, then to the residue was added 1N sodium hydroxide aqueous solution and extracted with ethyl acetate. The organic phase was washed with water and brine, and dried over magnesium sulfate anhydride. The inorganic substance was removed by filtration, and the filtrate was concentrated in vacuo. The obtained crude product was purified by silica gel chromatography to obtain Compound 32b as a brown powder.

Yield 218 mg, (9%)

$^1$H-NMR (CDCl$_3$) δ: 1.45 (6H, t, J=7.6 Hz), 2.89 (6H, t, J=7.6 Hz), 3.21 (2H, d, J=5.9 Hz), 3.83 (3H, s), 5.13 (2H, s), 6.41 (1H, s), 6.91 (2H, d, J=8.7 Hz), 7.27-7.44 (12H, m), 7.85 (1H, s), 7.86 (1H, s), 11.53 (1H, br s).

MS (m+1)=580.41

Step (2): Compound 29d+Compound 32b→Compound 32c→Compound (I-32)

A solution of Compound 32b (261 mg, 0.45 mmol) in N,N-dimethylformamide (1 ml) was cooled to 15° C., and to which was added Compound 29d (358 mg, 0.45 mmol) and degassed under reduced pressure. To the reaction solution was added sodium bromide (93 mg, 0.90 mmol), and the mixture was stirred at 15° C. for 2 hours, and then stood over night in a refrigerator. To the reaction solution was added N,N-dimethylformamide (3.0 mL), and the mixture was cooled to 0° C., and added potassium iodide (523 mg, 3.15 mmol) and acetyl chloride (128 µL, 1.8 mmol) in sequence, and the mixture was stirred at 0° C. for 3 hours. The reaction mixture was slowly added into pre-iced-cooled 5% brine. The precipitated solid was filtered, washed with water, suspended in water, and then lyophilized to obtain Compound 32c as a yellow solid. The obtained Compound 32c was used in the next reaction without purification.

The whole amount of Compound 32c obtained was dissolved in dichloromethane (8 mL), and the Solution was cooled −40° C., to which added anisole (492 μL, 4.5 mmol) and 2 mol/L-aluminum chloride/nitromethane solution (2.25 mL, 4.5 mmol) in sequence, and the mixture was stirred at 0° C. for 30 minutes. To the reaction solution was added diisopropyl ether and a drop of water, and the mixture was stirred to stimulate precipitates, and the supernatant liquid was removed by decantation. The insoluble matter which attached in the flask was added dilute hydrochloride acid and acetonitrile, and the mixture was stirred and dissolved completely, Experimental value: C, 41.40; H, 5.10; N, 12.55; S, 7.00; Na, 3.68(%)

Example 33

Synthesis of Compound (I-33)

[Formula 69]

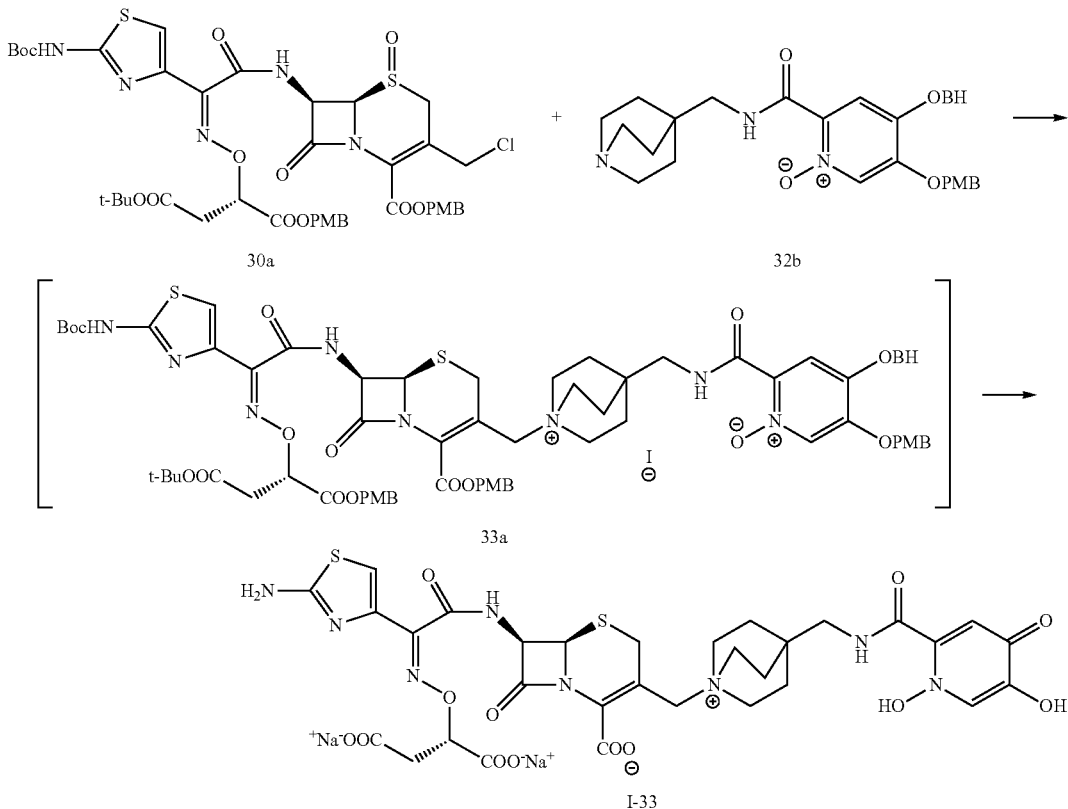

and then to which was added isopropyl ether, then an aqueous layer was separated from the supernatant. The organic phase was extracted with water again, all the aqueous phases were combined, HP20-SS resin was added thereto, and then acetonitrile containing solution was concentrated under reduced pressure. The obtained mixed solution was purified by ODS column chromatography. The fractions containing the intended compound were added 0.2 mol/L sodium hydroxide aqueous solution to adjust pH=6.0, and then a piece of dry ice was added thereto. The resulting solution was concentrated in vacuo, and then lyophilized to obtain Compound I-32 as a white powder.

Yield 134 mg, (38%)

$^1$H-NMR (D2O) δ: 1.50 (3H, s), 1.52 (3H, s), 1.93 (6H, t, J=7.2 Hz), 3.40-3.53 (9H, m), 3.87 (1H, s), 3.92 (1H, d, J=4.1 Hz), 4.60 (1H, d, J=13.7 Hz), 5.36 (1H, d, J=5.0 Hz), 5.88 (1H, d, J=5.0 Hz), 6.98 (1H, s), 7.45 (1H, s), 7.75 (1H, s).

MS (m+1)-761.33

Elemental analysis: C31H35N8O11S2Na (H2O) 5.2 (NaHCO3) 0.4

Calculated value: C, 41.44; H, 5.07; N, 12.31; S, 7.05; Na, 3.54(%).

Step: Compound 30a+Compound 32b→Compound 33a→Compound (I-33)

Compound I-33 was prepared from Compound 30a (142 mg, 0.15 mmol) and Compound 32b (87 mg, 0.15 mmol) by the similar procedure described above as a white powder.

Yield 60 mg, (48%)

$^1$H-NMR (D2O) δ: 1.94 (6I-1, t, J=7.6 Hz), 2.71 (1H, d, J=3.5 Hz), 2.73 (1H, s), 3.38-3.57 f 9H, m), 3.84-3.93 (2H, m), 4.59 (1H, d, J=14.0 Hz), 4.96 (1H, dd, J=8.2, 4.9 Hz), 5.32 (1H, d, J=5.0 Hz), 5.83 (1H, d, 5.0 Hz), 7.01 (1H, s), 7.91 (1H, s), 7.68 (1H, s).

MS (m+1)=791.28

Elemental analysis: C31H32N8O13S2Na2 (H2O) 7.0 (NaHCO3) 0.8

Calculated value: C, 37.15; H, 9.59; N, 10.90; S, 6.24; Na, 6.26(%)

Experimental value: C, 37.04; H, 4.60; N, 11.26; S, 6.54; Na, 6.23(%).

The subject invention includes compounds of the following formulae (II-A), (II-B), (II-C), (II-D), (II-E), (II-F), (II-G), (II-H), (II-I), (II-J), (II-K), (II-L) and (II-M):

[Formula 70]
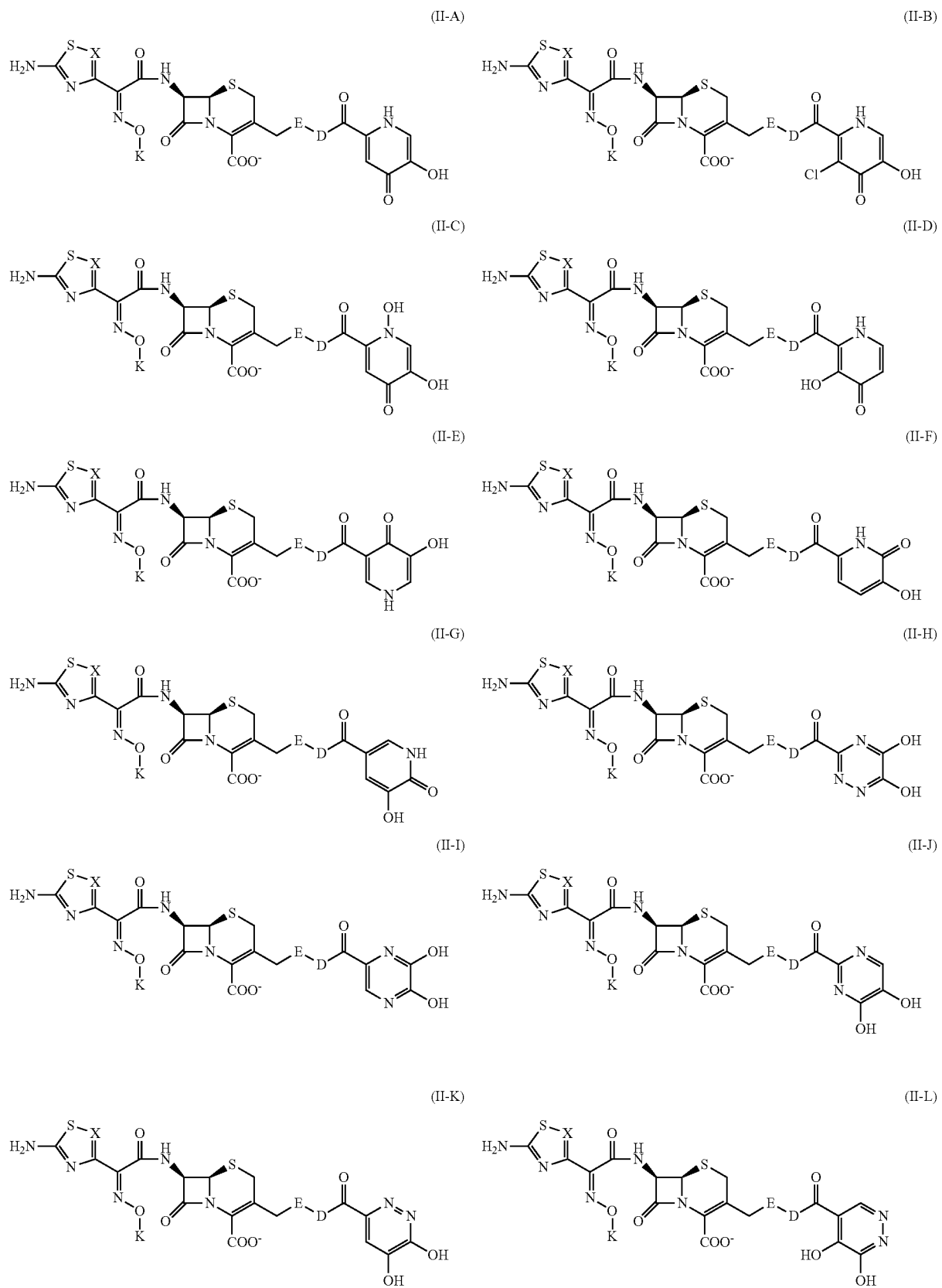

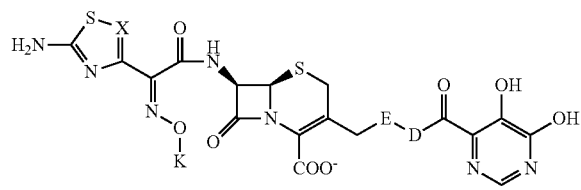
(II-M)
wherein X, K and -E-D- are selected from X1 to X3, K1 to K29, and ED1 to ED92 respectively from the following Tables 1 to 9:
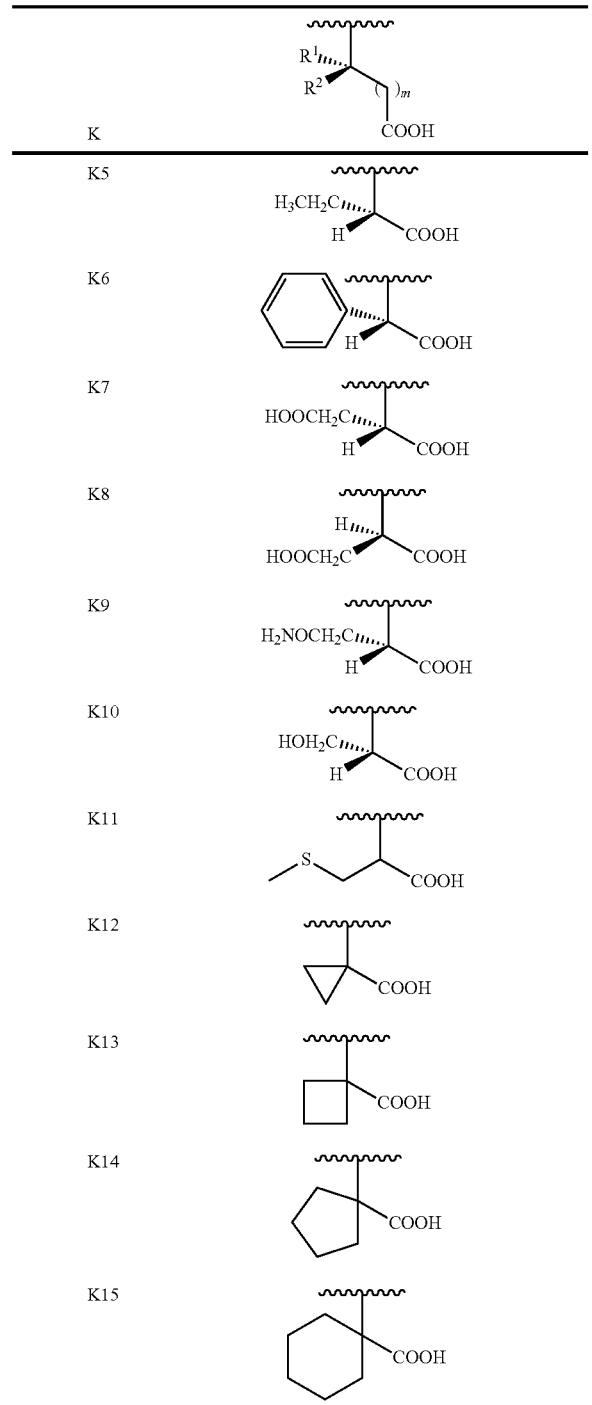

TABLE 2-continued

| K | ![structure with R1, R2, (CH2)m, COOH] |
|---|---|
| K16 | cyclopent-3-ene with COOH |
| K17 | (CH3)2C-CH2-COOH |
| K18 | -(CH2)3-COOH |
| K19 | -CH(CH3)-CH2-COOH |
| K20 | -CH(CH2COOH)-CH2-COOH |
| K21 | HOOC-(CH2)2-CH(-)-COOH |
| K22 | CH3O-CH2-CH(-)-COOH |

TABLE 3

| K23 | H2NOC-(CH2)2-CH(-)-COOH |
|---|---|
| K24 | HOOC-CH(-)-COOH |
| K25 | HO-CH(CH3)-CH(-)-COOH |
| K26 | FH2C-CH(-)-COOH |
| K27 | F3C-CH(-)-COOH |

TABLE 3-continued

| K28 | -CH(COOH)-CH2-C6H5 |
|---|---|
| K29 | -CH(COOH)-CH2-C6H4-OH |

TABLE 4

—E—D—

| ED1 | bicyclic diamine structure (N-methyl bridged) |
|---|---|
| ED2 | bicyclic diamine structure |
| ED3 | bicyclic diamine structure |
| ED4 | pyrrolidinium-piperazine structure |
| ED5 | pyrrolidinium-diamine structure |

TABLE 4-continued

—E—D—

| | |
|---|---|
| ED6 | (structure) |
| ED7 | (structure) |
| ED8 | (structure) |
| ED9 | (structure) |
| ED10 | (structure) |
| ED11 | (structure) |
| ED12 | (structure) |
| ED13 | (structure) |

TABLE 4-continued

—E—D—

| | |
|---|---|
| ED14 | (structure) |
| ED15 | (structure) |
| ED16 | (structure) |
| ED17 | (structure) |
| ED18 | (structure) |

TABLE 5

| | |
|---|---|
| ED19 | (structure) |
| ED20 | (structure) |

TABLE 5-continued
ED21 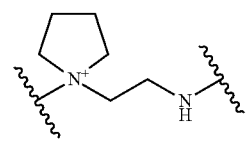 [SMILES: *NCC[N+]1(*)CCCC1]
ED22 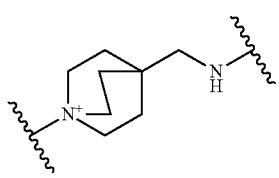 [SMILES: *NCC12CC[N+](*)(CC1)CC2]
ED23 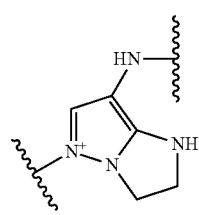 [SMILES: *Nc1c[n+](*)n2c1NCC2]
ED24 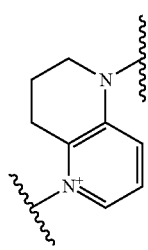 [SMILES: *N1CCCc2c1ccc[n+]2*]
ED25 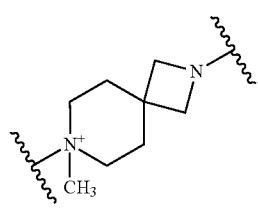 [SMILES: *N1CC2(CC[N+](*)(C)CC2)C1]
ED26 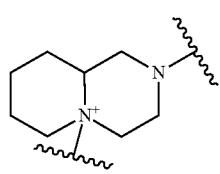 [SMILES: *N1CC[N+]2(*)CCCCC2C1]
ED27 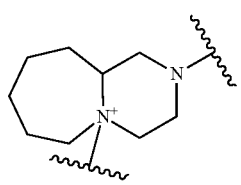 [SMILES: *N1CC[N+]2(*)CCCCCC2C1]
ED28 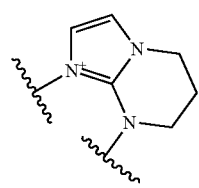 [SMILES: *N1CCCn2cc[n+](*)c21]
ED29 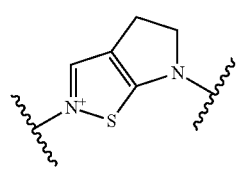 [SMILES: *N1CCc2c[n+](*)sc21]
ED30 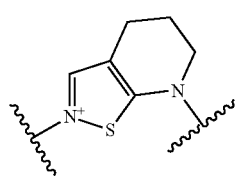 [SMILES: *N1CCCc2c[n+](*)sc21]
ED31 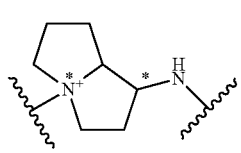
ED32 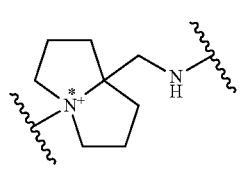
ED33 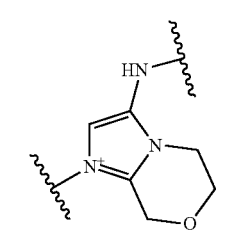 [SMILES: *Nc1c[n+](*)c2n1CCOC2]
ED34 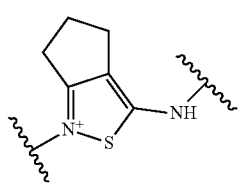 [SMILES: *Nc1s[n+](*)c2c1CCC2]
ED35 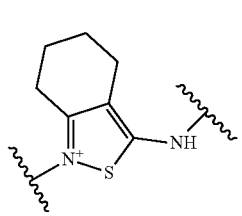 [SMILES: *Nc1s[n+](*)c2c1CCCC2]
ED36 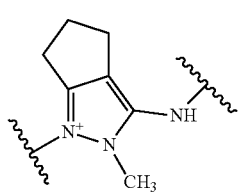 [SMILES: *Nc1c2c([n+](*)n1C)CCC2]

TABLE 6
| | | | | |
|---|---|---|---|---|
| ED37 | 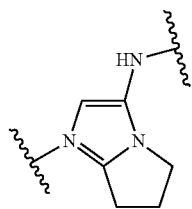 | | ED44 | 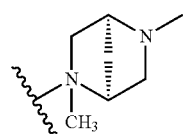 |
| ED38 | 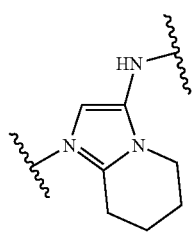 | | ED45 | 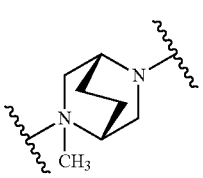 |
| ED39 | 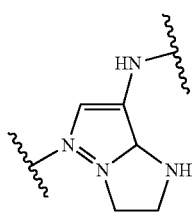 | | ED46 | 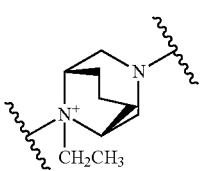 |
| ED40 | 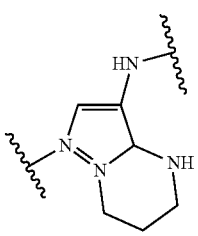 | | ED47 | 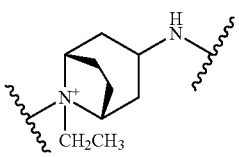 |
| ED41 | 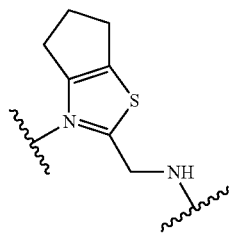 | | ED48 | 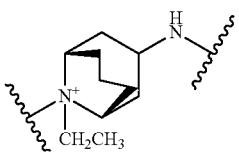 |
| ED42 | 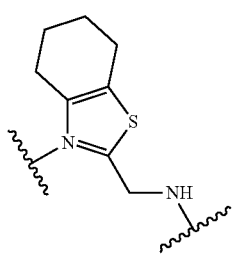 | | ED49 | 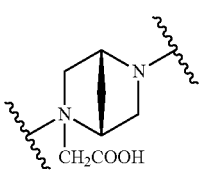 |
| ED43 | 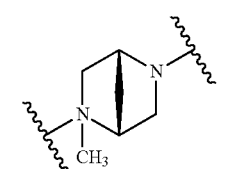 | | ED50 | 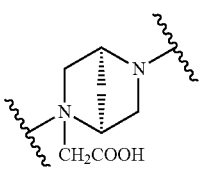 |
| | | | ED51 | 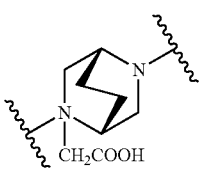 |
| | | | ED52 | 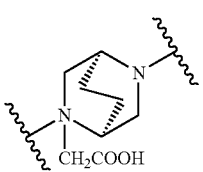 |

TABLE 6-continued
ED53 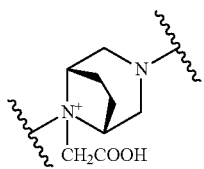
ED54 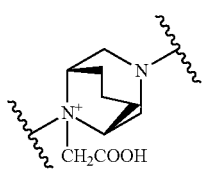
TABLE 7
ED55 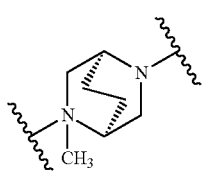
ED56 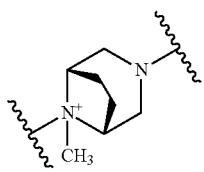 [SMILES: *N1C[C@H]2CC[C@@H](C1)[N+]2(*)C]
ED57 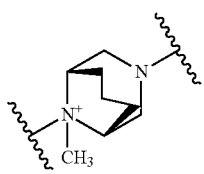 [SMILES: *N1C[C@H]2CCC[C@@H](C1)[N+]2(*)C]
ED58 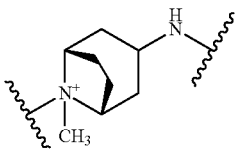 [SMILES: *NC1C[C@H]2CC[C@@H](C1)[N+]2(*)C]
ED59 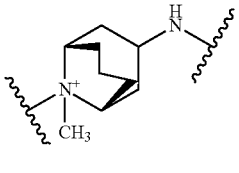 [SMILES: *NC1C[C@H]2CCC[C@@H](C1)[N+]2(*)C]
ED60 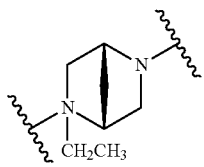
TABLE 7-continued
ED61 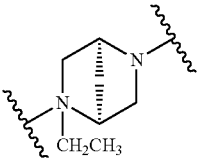
ED62 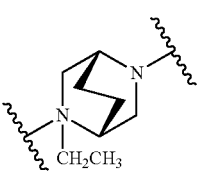
ED63 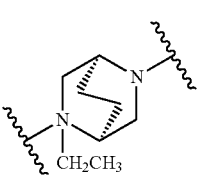
ED64 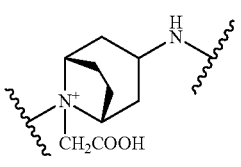
ED65 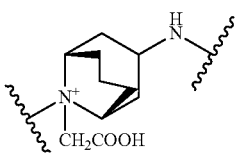
ED66 
ED67 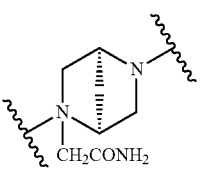
ED68 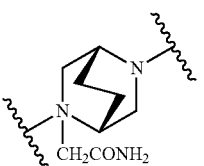
ED69 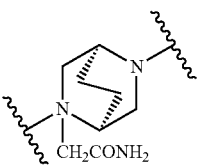

TABLE 7-continued
| ED70 | 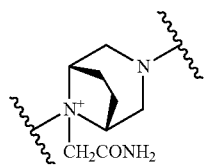 |
| --- | --- |
| ED71 | 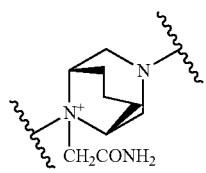 |
| ED72 | 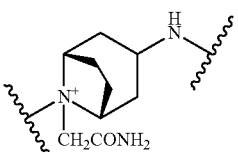 |
TABLE 8
| ED73 | 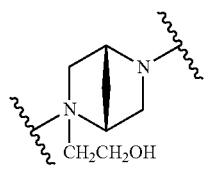 |
| --- | --- |
| ED74 | 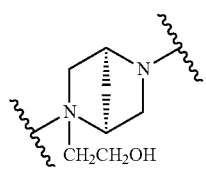 |
| ED75 | 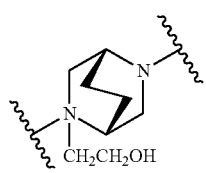 |
| ED76 | 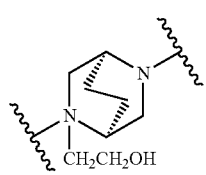 |
| ED77 | 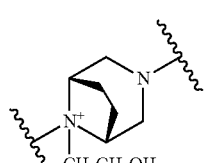 |
TABLE 8-continued
| ED78 | 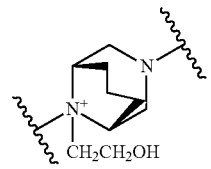 |
| --- | --- |
| ED79 | 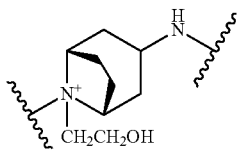 |
| ED80 | 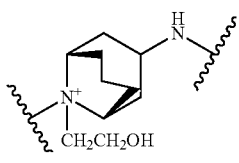 |
| ED81 | 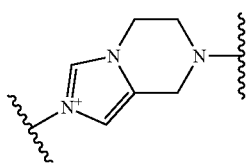 [SMILES: *N1CCn2c[n+](*)cc2C1] |
| ED82 | |
| ED83 | |
| ED84 | |
| ED85 | |
| ED86 | |

TABLE 8-continued

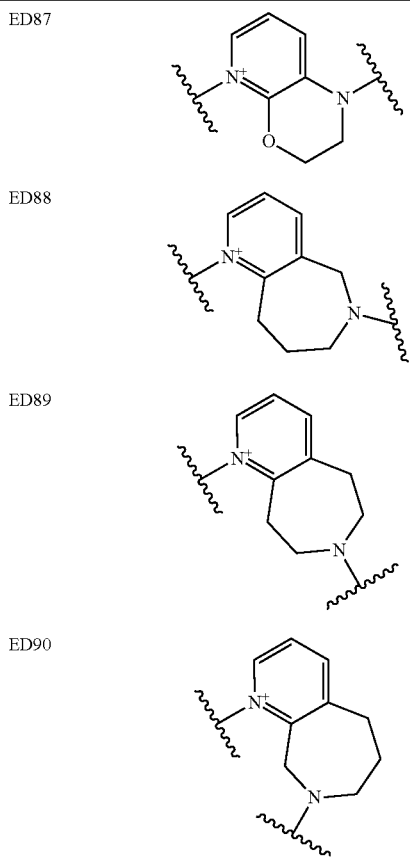

TABLE 9

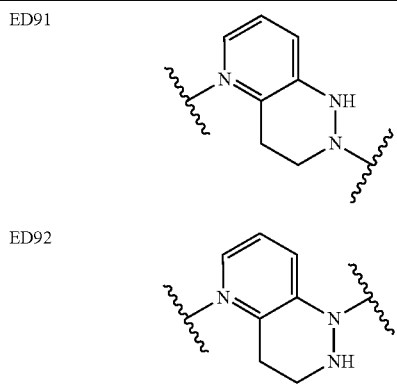

(X, K, ED)=
(X1, K1, ED1), (X1, K1, ED2), (X1, K1, ED3), (X1, K1, ED4), (X1, K1, ED5), (X1, K1, ED6), (X1, K1, ED7), (X1, K1, ED8), (X1, K1, ED9), (X1, K1, ED10), (X1, K1, ED11), (X1, K1, ED12), (X1, K1, ED13), (X1, K1, ED14), (X1, K1, ED15), (X1, K1, ED16), (X1, K1, ED17), (X1, K1, ED18), (X1, K1, ED19), (X1, K1, ED20), (X1, K1, ED21), (X1, K1, ED22), (X1, K1, ED23), (X1, K1, ED24), (X1, K1, ED25), (X1, K1, ED26), (X1, K1, ED27), (X1, K1, ED28), (X1, K1, ED29), (X1, K1, ED30), (X1, K1, ED31), (X1, K1, ED32), (X1, K1, ED33), (X1, K1, ED34), (X1, K1, ED35), (X1, K1, ED36), (X1, K1, ED37), (X1, K1, ED38), (X1, K1, ED39), (X1, K1, ED40), (X1, K1, ED41), (X1, K1, ED42), (X1, K1, ED43), (X1, K1, ED44), (X1, K1, ED45), (X1, K1, ED46), (X1, K1, ED47), (X1, K1, ED48), (X1, K1, ED49), (X1, K1, ED50), (X1, K1, ED51), (X1, K1, ED52), (X1), K1, ED53), (X1, K1, ED54), (X1, K1, ED55), (X1, K1, ED56), (X1, K1, ED57), (X1, K1, ED58), (X1, K1, ED59), (X1, K1, ED60), (X1, K1, ED61), (X1, K1, ED62), (X1, K1, ED63), (X1, K1, ED64), (X1, K1, ED65), (X1, K1, ED66), (X1, K1, ED67), (X1, K1, ED68), (X1, K1, ED69), (X1, K1, ED70), (X1, K1, ED71), (X1, K1, ED72), (X1, K1, ED73), (X1, K1, ED74), (X1, K1, ED75), (X1, K1, ED76), (X1, K1, ED77), (X1, K1, ED78), (X1, K1, ED79), (X1, K1, ED80), (X1, K1, ED81), (X1, K1, ED82), (X1, K1, ED83), (X1, K1, ED84), (X1, K1, ED85), (X1, K1, ED86), (X1, K1, ED87), (X1, K1, ED88), (X1, K1, ED89), (X1, K1, ED90), (X1, K1, ED91), (X1, K1, ED92), (X1, K2, ED1), (X1, K2, ED2), (X1, K2, ED3), (X1, K2, ED4), (X1, K2, ED5), (X1, K2, ED6), (X1, K2, ED7), (X1, K2, ED8), (X1, K2, ED9), (X1, K2, ED10), (X1, K2, ED11), (X1, K2, ED12), (X1, K2, ED13), (X1, K2, ED14), (X1, K2, ED15), (X1, K2, ED16), (X1, K2, ED17), (X1, K2, ED18), (X1, K2, ED19), (X1, K2, ED20), (X1, K2, ED21), (X1, K2, ED22), (X1, K2, ED23), (X1, K2, ED24), (X1, K2, ED25), (X1, K2, ED26), (X1, K2, ED27), (X1, K2, ED28), (X1, K2, ED29), (X1, K2, ED30), (X1, K2, ED31), (X1, K2, ED32), (X1, K2, ED33), (X1, K2, ED34), (X1, K2, ED35), (X1, K2, ED36), (X1, K2, ED37), (X1, K2, ED38), (X1, K2, ED39), (X1, K2, ED40), (X1, K2, ED41), (X1, K2, ED42), (X1, K2, ED43), (X1, K2, ED44), (X1, K2, ED45), (X1, K2, ED46), (X1, K2, ED47), (X1, K2, ED48), (X1, K2, ED49), (X1, K2, ED50), (X1, K2, ED51), (X1, K2, ED52), (X1, K2, ED53), (X1, K2, ED54), (X1, K2, ED55), (X1, K2, ED56), (X1, K2, ED57), (X1, K2, ED58), (X1, K2, ED59), (X1, K2, ED60), (X1, K2, ED61), (X1, K2, ED62), (X1, K2, ED63), (X1, K2, ED64), (X1, K2, ED65), (X1, K2, ED66), (X1, K2, ED67), (X1, K2, ED68), (X1, K2, ED69), (X1, K2, ED70), (X1, K2, ED71), (X1, K2, ED72), (X1, K2, ED73), (X1, K2, ED74), (X1, K2, ED75), (X1, K2, ED76), (X1, K2, ED77), (X1, K2, ED78), (X1, K2, ED79), (X1, K2, ED80), (X1, K2, ED81), (X1, K2, ED82), (X1, K2, ED83), (X1, K2, ED84), (X1, K2, ED85), (X1, K2, ED86), (X1, K2, ED87), (X1, K2, ED88), (X1, K2, ED89), (X1, K2, ED90), (X1, K2, ED91), (X1, K2, ED92), (X1, K3, ED1), (X1, K3, ED2), (X1, K3, ED3), (X1, K3, ED4), (X1, K3, ED5), (X1, K3, ED6), (X1, K3, ED7), (X1, K3, ED8), (X1, K3, ED9), (X1, K3, ED10), (X1, K3, ED11), (X1, K3, ED12), (X1, K3, ED13), (X1, K3, ED14), (X1, K3, ED15), (X1, K3, ED16), (X1, K3, ED17), (X1, K3, ED18), (X1, K3, ED19), (X1, K3, ED20), (X1, K3, ED21), (X1, K3, ED22), (X1, K3, ED23), (X1, K3, ED24), (X1, K3, ED25), (X1, K3, ED26), (X1, K3, ED27), (X1, K3, ED28), (X1, K3, ED29), (X1, K3, ED30), (X1, K3, ED31), (X1, K3, ED32), (X1, K3, ED33), (X1, K3, ED34), (X1, K3, ED35), (X1, K3, ED36), (X1, K3, ED37), (X1, K3, ED38), (X1, K3, ED39), (X1, K3, ED40), (X1, K3, ED41), (X1, K3, ED42), (X1, K3, ED43), (X1, K3, ED44), (X1, K3, ED45), (X1, K3, ED46), (X1, K3, ED47), (X1, K3, ED48), (X1, K3, ED49), (X1, K3, ED50), (X1, K3, ED51), (X1, K3, ED52), (X1, K3, ED53), (X1, K3, ED54), (X1, K3, ED55), (X1, K3, ED56), (X1, K3, ED57), (X1, K3, ED58), (X1, K3, ED59), (X1, K3, ED60), (X1, K3, ED61), (X1, K3, ED62), (X1, K3, ED63), (X1, K3, ED64), (X1, K3, ED65), (X1, K3, ED66), (X1, K3, ED67), (X1, K3, ED68), (X1, K3, ED69), (X1, K3, ED70), (X1, K3, ED71), (X1, K3, ED72), (X1, K3, ED73), (X1, K3, ED74), (X1, K3, ED75), (X1, K3, ED76), (X1, K3, ED77), (X1, K3, ED78), (X1, K3, ED79), (X1, K3, ED80), (X1, K3, ED81), (X1, K3, ED82), (X1, K3, ED83), (X1, K3, ED84), (X1, K3, ED85), (X1, K3, ED86), (X1, K3, ED87), (X1, K3, ED88), (X1, K3, ED89), (X1, K3, ED90), (X1, K3, ED91), (X1, K3, ED92), (X1, K4, ED1), (X1, K4, ED2), (X1,

K4, ED3), (X1, K4, ED4), (X1, K4, ED5), (X1, K4, ED6), (X1, K4, ED7), (X1, K4, ED8), (X1, K4, ED9), (X1, K6, ED10), (X1, K4, ED11), (X1, K4, ED12), (X1, K4, ED13), (X1, K4, ED14), (X1, K4, ED15), (X1, K4, ED16), (X1, K4, ED17), (X1, K4, ED18), (X1, K4, ED19), (X1, K4, ED20), (X1, K4, ED21), (X1, K4, ED22), (X1, K4, ED23), (X1, K4, ED24), (X1, K4, ED25), (X1, K4, ED26), (X1, K4, ED27), (X1, K4, ED28), (X1, K6, ED29), (X1, K4, ED30), (X1, K4, ED31), (X1, K4, ED32), (X1, K6, ED33), (X1, K6, ED34), (X1, K6, ED35), (X1, K6, ED36), (X1, K4, ED37), (X1, K4, ED38), (X1, K4, ED39), (X1, K4, ED40), (X1, K4, ED41), (X1, K4, ED42), (X1, K4, ED43), (X1, K4, ED44), (X1, K4, ED45), (X1, K4, ED46), (X1, K4, ED47), (X1, K4, ED48), (X1, K4, ED49), (X1, K4, ED50), (X1, K4, ED51), (X1, K4, ED52), (X1, K4, ED53), (X1, K4, ED54), (X1, K4, ED55), (X1, K4, ED56), (X1, K4, ED57), (X1, K4, ED58), (X1, K4, ED59), (X1, K4, ED60), (X1, K4, ED61), (X1, K4, ED62), (X1, K4, ED63), (X1, K4, ED64), (X1, K4, ED65), (X1, K4, ED66), (X1, K4, ED67), (X1, K4, ED68), (X1, K4, ED69), (X1, K6, ED70), (X1, K4, ED71), (X1, K4, ED72), (X1, K4, ED73), (X1, K4, ED74), (X1, K4, ED75), (X1, K4, ED76), (X1, K4, ED77), (X1, K4, ED78), (X1, K4, ED79), (X1, K4, ED80), (X1, K4, ED81), (X1, K4, ED82), (X1, K4, ED83), (X1, K4, ED84), (X1, K4, ED85), (X1, K4, ED86), (X1, K4, ED87), (X1, K4, ED88), (X1, K4, ED89), (X1, K4, ED90), (X1, K4, ED91), (X1, K4, ED92), (X1, K5, ED1), (X1, K5, ED2), (X1, K5, ED3), (X1, K5, ED4), (X1, K5, ED5), (X1, K5, ED6), (X1, K5, ED7), (X1, K5, ED8), (X1, K5, ED9), (X1, K5, ED10), (X1, K5, ED11), (X1, K5, ED12), (X1, K5, ED13), (X1, K5, ED14), (X1, K5, ED15), (X1, K5, ED16), (X1, K5, ED17), (X1, K5, ED18), (X1, K5, ED19), (X1, K5, ED20), (X1, K5, ED21), (X1, K5, ED22), (X1, K5, ED23), (X1, K5, ED24), (X1, K5, ED25), (X1, K5, ED26), (X1, K5, ED27), (X1, K5, ED28), (X1, K5, ED29), (X1, K5, ED30), (X1, K5, ED31), (X1, K5, ED32), (X1, K5, ED33), (X1, K5, ED34), (X1, K5, ED35), (X1, K5, ED36), (X1, K5, ED37), (X1, K5, ED38), (X1, K5, ED39), (X1, K5, ED40), (X1, K5, ED41), (X1, K5, ED42), (X1, K5, ED43), (X1, K5, ED44), (X1, K5, ED45), (X1, K5, ED46), (X1, K5, ED47), (X1, K5, ED48), (X1, K5, ED49), (X1, K5, ED50), (X1, K5, ED51), (X1, K5, ED52), (X1, K5, ED53), (X1, K5, ED54), (X1, K5, ED55), (X1, K5, ED56), (X1, K5, ED57), (X1, K5, ED58), (X1, K5, ED59), (X1, K5, ED60), (X1, K5, ED61), (X1, K5, ED62), (X1, K5, ED63), (X1, K5, ED64), (X1, K5, ED65), (X1, K5, ED66), (X1, K5, ED67), (X1, K5, ED68), (X1, K5, ED69), (X1, K5, ED70), (X1, K5, ED71), (X1, K5, ED72), (X1, K5, ED73), (X1, K5, ED74), (X1, K5, ED75), (X1, K5, ED76), (X1, K5, ED77), (X1, K5, ED78), (X1, K5, ED79), (X1, K5, ED80), (X1, K5, ED91), (X1, K5, ED82), (X1, K5, ED83), (X1, K5, ED84), (X1, K5, ED85), (X1, K5, ED86), (X1, K5, ED87), (X1, K5, ED88), (X1, K5, ED89), (X1, K5, ED90), (X1, K5, ED91), (X1, K5, ED92), (X1, K6, ED1), (X1, K6, ED2), (X1, K6, ED3), (X1, K6, ED4), (X1, K6, ED5), (X1, K6, ED6), (X1, K6, ED7), (X1, K6, ED8), (X1, K6, ED9), (X1, K6, ED10), (X1, K6, ED11), (X1, K6, ED12), (X1, K6, ED13), (X1, K6, ED14), (X1, K6, ED15), (X1, K6, ED16), (X1, K6, ED17), (X1, K6, ED18), (X1, K6, ED19), (X1, K6, ED20), (X1, K6, ED21), (X1, K6, ED22), (X1, K6, ED23), (X1, K6, ED24), (X1, K6, ED25), (X1, K6, ED26), (X1, K6, ED27), (X1, K6, ED28), (X1, K6, ED29), (X1, K6, ED30), (X1, K6, ED31), (X1, K6, ED32), (X1, K6, ED33), (X1, K6, ED34), (X1, K6, ED35), (X1, K6, ED36), (X1, K6, ED37), (X1, K6, ED38), (X1, K6, ED39), (X1, K6, ED40), (X1, K6, ED41), (X1, K6, ED42), (X1, K6, ED43), (X1, K6, ED44), (X1, K6, ED45), (X1, K6, ED46), (X1, K6, ED47), (X1, K6, ED48), (X1, K6, ED49), (X1, K6, ED50), (X1, K6, ED51), (X1, K6, ED52), (X1, K6, ED53), (X1, K6, ED54), (X1, K6, ED55), (X1, K6, ED56), (X1, K6, ED57), (X1, K6, ED58), (X1, K6, ED59), (X1, K6, ED60), (X1, K6, ED61), (X1, K6, ED62), (X1, K6, ED63), (X1, K6, ED64), (X1, K6, ED65), (X1, K6, ED66), (X1, K6, ED67), (X1, K6, ED68), (X1, K6, ED69), (X1, K6, ED70), (X1, K6, ED71), (X1, K6, ED72), (X1, K6, ED73), (X1, K6, ED74), (X1, K6, ED75), (X1, K6, ED76), (X1, K6, ED77), (X1, K6, ED78), (X1, K6, ED79), (X1, K6, ED80), (X1, K6, ED81), (X1, K6, ED82), (X1, K6, ED83), (X1, K6, ED84), (X1, K6, ED85), (X1, K6, ED86), (X1, K6, ED87), (X1, K6, ED88), (X1, K6, ED89), (X1, K6, ED90), (X1, K6, ED91), (X1, K6, ED92), (X1, K7, ED1), (X1, K7, ED2), (X1, K7, ED3), (X1, K7, ED4), (X1, K7, ED5), (X1, K7, ED6), (X1, K7, ED7), (X1, K7, ED8), (X1, K7, ED9), (X1, K7, ED10), (X1, K7, ED11), (X1, K7, ED12), (X1, K7, ED13), (X1, K7, ED14), (X1, K7, ED15), (X1, K7, ED16), (X1, K7, ED17), (X1, K7, ED18), (X1, K7, ED19), (X1, K7, ED20), (X1, K7, ED21), (X1, K7, ED22), (X1, K7, ED23), (X1, K7, ED24), (X1, K7, ED25), (X1, K7, ED26), (X1, K7, ED27), (X1, K7, ED28), (X1, K7, ED29), (X1, K7, ED30), (X1, K7, ED31), (X1, K7, ED32), (X1, K7, ED33), (X1, K7, ED34), (X1, K7, ED35), (X1, K7, ED36), (X1, K7, ED37), (X1, K7, ED38), (X1, K7, ED39), (X1, K7, ED40), (X1, K7, ED41), (X1, K7, ED42), (X1, K7, ED43), (X1, K7, ED44), (X1, K7, ED45), (X1, K7, ED46), (X1, K7, ED47), (X1, K7, ED48), (X1, K7, ED49), (X1, K7, ED50), (X1, K7, ED51), (X1, K7, ED52), (X1, K7, ED53), (X1, K7, ED54), (X1, K7, ED55), (X1, K7, ED56), (X1, K7, ED57), (X1, K7, ED58), (X1, K7, ED59), (X1, K7, ED60), (X1, K7, ED61), (X1, K7, ED62), (X1, K7, ED63), (X1, K7, ED64), (X1, K7, ED65), (X1, K7, ED66), (X1, K7, ED67), (X1, K7, ED68), (X1, K7, ED69), (X1, K7, ED70), (X1, K7, ED71), (X1, K7, ED72), (X1, K7, ED73), (X1, K7, ED74), (X1, K7, ED75), (X1, K7, ED76), (X1, K7, ED77), (X1, K7, ED78), (X1, K7, ED79), (X1, K7, ED80), (X1, K7, ED81), (X1, K7, ED82), (X1, K7, ED83), (X1, K7, ED84), (X1, K7, ED85), (X1, K7, ED86), (X1, K7, ED87), (X1, K7, ED88), (X1, K7, ED89), (X1, K7, ED90), (X1, K7, ED91), (X1, K7, ED92), (X1, K8, ED1), (X1, K8, ED2), (X1, K8, ED3), (X1, K8, ED4), (X1, K8, ED5), (X1, K8, ED6), (X1, K8, ED7), (X1, K8, ED8), (X1, K8, ED9), (X1, K8, ED10), (X1, K8, ED11), (X1, K8, ED12), (X1, K8, ED13), (X1, K8, ED14), (X1, K8, ED15), (X1, K8, ED16), (X1, K8, ED17), (X1, K8, ED18), (X1, K8, ED19), (X1, K8, ED20), (X1, K8, ED21), (X1, K8, ED22), (X1, K8, ED23), (X1, K8, ED24), (X1, K8, ED25), (X1, K8, ED26), (X1, K8, ED27), (X1, K8, ED28), (X1, K8, ED29), (X1, K8, ED30), (X1, K8, ED31), (X1, K8, ED32), (X1, K8, ED33), (X1, K8, ED34), (X1, K8, ED35), (X1, K8, ED36), (X1, K8, ED37), (X1, K8, ED38), (X1, K8, ED39), (X1, K8, ED40), (X1, K8, ED41), (X1, K8, ED42), (X1, K8, ED43), (X1, K8, ED44), (X1, K8, ED45), (X1, K8, ED46), (X1, K8, ED47), (X1, K8, ED48), (X1, K8, ED49), (X1, K8, ED50), (X1, K8, ED51), (X1, K8, ED52), (X1, K8, ED53), (X1, K8, ED54), (X1, K8, ED55), (X1, K8, ED56), (X1, K8, ED57), (X1, K8, ED58), (X1, K8, ED59), (X1, K8, ED60), (X1, K8, ED61), (X1, K8, ED62), (X1, K8, ED63), (X1, K8, ED64), (X1, K8, ED65), (X1, K8, ED66), (X1, K8, ED67), (X1, K8, ED68), (X1, K8, ED69), (X1, K8, ED70), (X1, K8, ED71), (X1, K8, ED72), (X1, K8, ED73), (X1, K8, ED74), (X1, K8, ED75), (X1, K8, ED76), (X1, K8, ED77), (X1, K8, ED78), (X1, K8, ED79), (X1, K8, ED80), (X1, K8, ED81), (X1, K8, ED82), (X1, K8, ED83), (X1, K8, ED84), (X1, K8, ED85), (X1, K8, ED86), (X1, K8, ED87), (X1, K8, ED88), (X1, K8, ED89), (X1, K8, ED90), (X1, K8, ED91), (X1, K8, ED92), (X1, K9, ED1), (X1, K9, ED2), (X1, K9, ED3), (X1, K9, ED4), (X1, K9, ED5), (X1, K9, ED6), (X1, K9, ED7), (X1, K9, ED8), (X1, K9, ED9), (X1, K9, ED10), (X1, K9, ED11), (X1, K9, ED12), (X1, K9, ED13), (X1, K9, ED14), (X1, K9, ED15), (X1, K9, ED16), (X1, K9, ED17), (X1, K9, ED18), (X1, K9, ED19), (X1, K9, ED20), (X1, K9, ED21), (X1, K9, ED22), (X1, K9, ED23), (X1, K9, ED24), (X1, K9, ED25), (X1, K9, ED26), (X1, K9, ED27), (X1, K9, ED28), (X1, K9, ED29), (X1, K9, ED30), (X1, K9, ED31), (X1, K9, ED32), (X1, K9, ED33), (X1, K9, ED34), (X1, K9, ED35), (X1, K9, ED36), (X1, K9, ED37), (X1, K9, ED38), (X1, K9, ED39), (X1, K9, ED40), (X1, K9, ED41), (X1, K9, ED42), (X1, K9, ED43), (X1, K9, ED44), (X1, K9, ED45), (X1, K9, ED46), (X1, K9, ED47), (X1, K9, ED48), (X1, K9, ED49), (X1, K9, ED50), (X1, K9, ED51), (X1, K9, ED52), (X1, K9, ED53), (X1, K9, ED54), (X1, K9, ED55), (X1, K9, ED56), (X1, K9, ED57), (X1, K9, ED58), (X1, K9, ED59), (X1, K9, ED60), (X1, K9, ED61), (X1, K9, ED62), (X1, K9, ED63), (X1, K9, ED64), (X1, K9, ED65), (X1, K9, ED66), (X1, K9, ED67), (X1, K9, ED68), (X1, K9, ED69), (X1, K9, ED70), (X1, K9, ED71), (X1, K9, ED72), (X1, K9, ED73), (X1, K9, ED74), (X1, K9, ED75), (X1, K9, ED76), (X1, K9, ED77), (X1, K9, ED78), (X1, K9, ED79), (X1, K9, ED80), (X1, K9, ED81), (X1, K9, ED82), (X1, K9, ED83), (X1, K9, ED84), (X1, K9, ED85), (X1, K9, ED86), (X1, K9, ED87), (X1, K9, ED88), (X1, K9, ED89), (X1, K9, ED90), (X1, K9, ED91), (X1, K9, ED92), (X1, K10, ED1), (X1, K10, ED2), (X1, K10, ED3), (X1, K10, ED4), (X1, K10, ED5), (X1, K10, ED6), (X1, K10, ED7), (X1, K10, ED8), (X1, K10, ED9), (X1, K10, ED10), (X1, K10, ED11), (X1, K10, ED12), (X1, K10, ED13), (X1, K10, ED14), (X1, K10, ED15), (X1, K10, ED16), (X1, K10, ED17), (X1, K10, ED18), (X1, K10, ED19), (X1, K10, ED20), (X1, K10, ED21), (X1, K10, ED22), (X1, K10, ED23), (X1, K10, ED24), (X1, K10, ED25), (X1, K10, ED26), (X1, K10, ED27), (X1, K10, ED28), (X1, K10, ED29), (X1, K10, ED30), (X1, K10, ED31), (X1, K10, ED32), (X1, K10, ED33), (X1, K10, ED34), (X1, K10, ED35), (X1, K10, ED36), (X1, K10, ED37), (X1, K10, ED38), (X1, K10, ED39), (X1, K10, ED40), (X1, K10, ED41), (X1, K10, ED42), (X1, K10, ED43), (X1, K10, ED44), (X1, K10, ED45), (X1, K10, ED46), (X1, K10, ED47), (X1, K10, ED48), (X1, K10, ED49), (X1, K10, ED50), (X1, K10, ED51), (X1, K10, ED52), (X1, K10, ED53), (X1, K10, ED54), (X1, K10, ED55), (X1, K10, ED56), (X1, K10, ED57), (X1, K10, ED58), (X1, K10, ED59), (X1, K10, ED60), (X1, K10, ED61), (X1, K10, ED62), (X1, K10, ED63), (X1, K10, ED64), (X1, K10, ED65), (X1, K10, ED66), (X1, K10, ED67), (X1, K10, ED68), (X1, K10, ED69), (X1, K10, ED70), (X1, K10, ED71), (X1, K10, ED72), (X1, K10, ED73), (X1, K10, ED74), (X1, K10, ED75), (X1, K10, ED76), (X1, K10, ED77), (X1, K10, ED78), (X1, K10, ED79), (X1, K10, ED80), (X1, K10, ED81), (X1, K10, ED82), (X1, K10, ED83), (X1, K10, ED84), (X1, K10, ED85), (X1, K10, ED86), (X1, K10, ED87), (X1, K10, ED88), (X1, K10, ED89), (X1, K10, ED90), (X1, K10, ED91), (X1, K10, ED92), (X1, K11, ED1), (X1, K11, ED2), (X1, K11, ED3), (X1, K11, ED4), (X1, K11, ED5), (X1, K11, ED6), (X1, K11, ED7), (X1, K11, ED8), (X1, K11, ED9), (X1, K11, ED10), (X1, K11, ED11), (X1, K11, ED12), (X1, K11, ED13), (X1, K11, ED14), (X1, K11, ED15), (X1, K11, ED16), (X1, K11, ED17), (X1, K11, ED18), (X1, K11, ED19), (X1, K11, ED20), (X1, K11, ED21), (X1, K11, ED22), (X1, K11, ED23), (X1, K11, ED24), (X1, K11, ED25), (X1, K11, ED26), (X1, K11, ED27), (X1, K11, ED28), (X1, K11, ED29), (X1, K11, ED30), (X1, K11, ED31), (X1, K11, ED32), (X1, K11, ED 33), (X1, K11, ED34), (X1, K11, ED35), (X1, K11, ED36), (X1, K11, ED37), (X1, K11, ED38), (X1, K11, ED39), (X1, K11, ED40), (X1, K11, ED41), (X1, K11, ED42), (X1, K11, ED43), (X1, K11, ED44), (X1, K11, ED45), (X1, K11, ED46), (X1, K11, ED47), (X1, K11, ED48), (X1, K11, ED49), (X1, K11, ED50), (X1, K11, ED51), (X1, K11, ED52), (X1, K11, ED53), (X1, K11, ED54), (X1, K11, ED55), (X1, K11, ED56), (X1, K11, ED57), (X1, K11, ED58), (X1, K11, ED59), (X1, K11, ED60), (X1, K11, ED61), (X1, K11, ED62), (X1, K11, ED63), (X1, K11, ED64), (X1, K11, ED65), (X1, K11, ED66), (X1, K11, ED67), (X1, K11, ED68), (X1, K11, ED69), (X1, K11, ED70), (X1, K11, ED71), (X1, K11, ED72), (X1, K11, ED73), (X1, K11, ED74), (X1, K11, ED75), (X1, K11, ED76), (X1, K11, ED77), (X1, K11, ED78), (X1, K11, ED79), (X1, K11, ED80), (X1, K11, ED81), (X1, K11, ED82), (X1, K11, ED83), (X1, K11, ED84), (X1, K11, ED85), (X1, K11, ED86), (X1, K11, ED87), (X1, K11, ED88), (X1, K11, ED89), (X1, K11, ED90), (X1, K11, ED91), (X1, K11, ED92), (X1, K12, ED1), (X1, K12, ED2), (X1, K12, ED3), (X1, K12, ED4), (X1, K12, ED5), (X1, K12, ED6), (X1, K12, ED7), (X1, K12, ED8), (X1, K12, ED9), (X1, K12, ED10), (X1, K12, ED11), (X1, K12, ED12), (X1, K12, ED13), (X1, K12, ED14), (X1, K12, ED15), (X1, K12, ED16), (X1, K12, ED17), (X1, K12, ED18), (X1, K12, ED19), (X1, K12, ED20), (X1, K12, ED21), (X1, K12, ED22), (X1, K12, ED23), (X1, K12, ED24), (X1, K12, ED25), (X1, K12, ED26), (X1, K12, ED27), (X1, K12, ED28), (X1, K12, ED29), (X1, K12, ED30), (X1, K12, ED31), (X1, K12, ED32), (X1, K12, ED33), (X1, K12, ED34), (X1, K12, ED35), (X1, K12, ED36), (X1, K12, ED37), (X1, K12, ED38), (X1, K12, ED39), (X1, K12, ED40), (X1, K12, ED41), (X1, K12, ED42), (X1, K12, ED43), (X1, K12, ED44), (X1, K12, ED45), (X1, K12, ED46), (X1, K12, ED47), (X1, K12, ED48), (X1, K12, ED49), (X1, K12, ED50), (X1, K12, ED51), (X1, K12, ED52), (X1, K12, ED53), (X1, K12, ED54), (X1, K12, ED55), (X1, K12, ED56), (X1, K12, ED57), (X1, K12, ED58), (X1, K12, ED59), (X1, K12, ED60), (X1, K12, ED61), (X1, K12, ED62), (X1, K12, ED63), (X1, N12, ED64), (X1, K12, ED65), (X1, K12, ED66), (X1, K12, ED67), (X1, K12, ED68), (X1, K12, ED69), (X1, K12, ED70), (X1, K12, ED71), (X1, K12, ED72), (X1, K12, ED73), (X1, K12, ED74), (X1, K12, ED75), (X1, K12, ED76), (X1, K12, ED77), (X1, K12, ED78), (X1, K12, ED79), (X1, K12, ED80), (X1, K12, ED81), (X1, K12, ED82), (X1, K12, ED83), (X1, K12, ED84), (X1, K12, ED85), (X1, K12, ED86), (X1, K12, ED87), (X1, K12, ED88), (X1, K12, ED89), (X1, K12, ED90), (X1, K12, ED91), (X1, K12, ED92), (X1, K13, ED1), (X1, K13, ED2), (X1, K13, En), (X1, K13, ED4), (X1, K13, ED5), (X1, K13, ED6), (X1, K13, ED7), (X1, K13, ED8), (X1, K13, ED9), (X1, K13, ED10), (X1, K13, ED11), (X1, K13, ED12), (X1, K13, ED13), (X1, K13, ED14), (X1, K13, ED15), (X1, K13, ED16), (X1, K13, ED17), (X1, K13, ED18), (X1, K13, ED19), (X1, K13, ED20), (X1, K13, ED21), (X1, K13, ED22), (X1, K13, ED23), (X1, K13, ED24), (X1, K13, ED25), (X1, K13, ED26), (X1, K13, ED27), (X1, K13, ED28), (X1, K13, ED29), (X1, K13, ED30), (X1, K13, ED31), (X1, K13, ED32), (X1, K13, ED33), (X1, K13, ED34), (X1, K13, ED35), (X1, K13, ED36), (X1, K13, ED37), (X1, K13, ED38), (X1, K13, ED39), (X1, K13, ED40), (X1, K13, ED41), (X1, K13, ED42), (X1, K13, ED43), (X1, K13, ED44), (X1, K13, ED45), (X1, K13, ED46), (X1, K13, ED47), (X1, K13, ED42), (X1, K13, ED49), (X1, K13, ED50), (X1, K13, ED51), (X1, K13, ED52), (X1, K13, ED53), (X1, K13, ED54), (X1, K13, ED55), (X1, K13, ED56), (X1, K13, ED57), (X1, K13, ED58), (X1, K13, ED59), (X1, K13, ED60), (X1, K13, ED61), (X1, K13, ED62), (X1, K13, ED63), (X1, K13, ED64), (X1, K13,

ED65), (X1, K13, ED66), (X1, K13, ED67), (X1, K13, ED68), (X1, K13, ED69), (X1, K13, ED70), (X1, K13, ED71), (X1, K13, ED72), (X1, K13, ED73), (X1, K13, ED74), (X1, K13, ED75), (X1, K13, ED76), (X1, K13, ED77), (X1, K13, ED78), (X1, K13, ED79), (X1, K13, ED80), (X1, K13, ED81), (X1, K13, ED82), (X1, K13, ED83), (X1, K13, ED84), (X1, K13, ED85), (X1, K13, ED86), (X1, K13, ED87), (X1, K13, ED88), (X1, K13, ED89), (X1, K13, ED90), (X1, K13, ED91), (X1, K13, ED92), (X1, K14, ED1), (X1, K14, ED2), (X1, K14, ED3), (X1, K14, ED4), (X1, K14, ED5), (X1, K14, ED6), (X1, K14, ED7), (X1, K14, ED8), (X1, K14, ED9), (X1, K14, ED10), (X1, K14, ED11), (X1, K14, ED12), (X1, K14, ED13), (X1, K14, ED14), (X1, K14, ED15), (X1, K14, ED16), (X1, K14, ED17), (X1, K14, ED18), (X1, K14, ED19), (X1, K14, ED20), (X1, K14, ED21), (X1, K14, ED22), (X1, K14, ED23), (X1, K14, ED24), (X1, K14, ED25), (X1, K14, ED26), (X1, K14, ED27), (X1, K14, ED28), (X1, K14, ED29), (X1, K14, ED30), (X1, K14, ED31), (X1, K14, ED32), (X1, K14, ED33), (X1, K14, ED34), (X1, K14, ED35), (X1, K14, ED36), (X1, K14, ED37), (X1, K14, ED38), (X1, K14, ED39), (X1, K14, ED40), (X1, K14, ED41), (X1, K14, ED42), (X1, K14, ED43), (X1, K14, ED44), (X1, K14, ED45), (X1, K14, ED46), (X1, K14, ED47), (X1, K14, ED48), (X1, K14, ED49), (X1, K14, ED50), (X1, K14, ED51), (X1, K14, ED52), (X1, K14, ED53), (X1, K14, ED54), (X1, K14, ED55), (X1, K14, ED56), (X1, K14, ED57), (X1, K14, ED58), (X1, K14, ED59), (X1, K14, ED60), (X1, K14, ED61), (X1, K14, ED62), (X1, K14, ED63), (X1, K14, ED64), (X1, K14, ED65), (X1, K14, ED66), (X1, K14, ED67), (X1, K14, ED68), (X1, K14, ED69), (X1, K14, ED70), (X1, K14, ED71), (X1, K14, ED72), (X1, K14, ED73), (X1, K14, ED74), (X1, K14, ED75), (X1, K14, ED76), (X1, K14, ED77), (X1, K14, ED78), (X1, K14, ED79), (X1, K14, ED80), (X1, K14, ED81), (X1, K14, ED82), (X1, K14, ED83), (X1, K14, ED84), (X1, K14, ED85), (X1, K14, ED86), (X1, K14, ED87), (X1, K14, ED88), (X1, K14, ED89), (X1, K14, ED90), (X1, K14, ED91), (X1, K14, ED92), (X1, K15, ED1), (X1, K15, ED2), (X1, K15, ED3), (X1, K15, ED4), (X1, K15, ED5), (X1, K15, ED6), (X1, K15, ED7), (X1, K15, ED8), (X1, K15, ED9), (X1, K15, ED10), (X1, K15, ED11), (X1, K15, ED12), (X1, K15, ED13), (X1, K15, ED14), (X1, K15, ED15), (X1, K15, ED16), (X1, K15, ED17), (X1, K15, ED18), (X1, K15, ED19), (X1, K15, ED20), (X1, K15, ED21), (X1, K15, ED22), (X1, K15, ED23), (X1, K15, ED24), (X1, K15, ED25), (X1, K15, ED26), (X1, K15, ED27), (X1, K15, ED28), (X1, K15, ED29), (X1, K15, ED30), (X1, K15, ED31), (X1, K15, ED32), (X1, K15, ED33), (X1, K15, ED34), (X1, K15, ED35), (X1, K15, ED36), (X1, K15, ED37), (X1, K15, ED38), (X1, K15, ED39), (X1, K15, ED40), (X1, K15, ED41), (X1, K15, ED42), (X1, K15, ED43), (X1, K15, ED44), (X1, K15, ED45), (X1, K15, ED46), (X1, K15, ED47), (X1, K15, ED48), (X1, K15, ED49), (X1, K15, ED50), (X1, K15, ED51), (X1, K15, ED52), (X1, K15, ED53), (X1, K15, ED54), (X1, K15, ED55), (X1, K15, ED56), (X1, K15, ED57), (X1, K15, ED58), (X1, K15, ED59), (X1, K15, ED60), (X1, K15, ED61), (X1, K15, ED62), (X1, K15, ED63), (X1, K15, ED64), (X1, K15, ED65), (X1, K15, ED66), (X1, K15, ED67), (X1, K15, ED68), (X1, K15, ED69), (X1, K15, ED70), (X1, K15, ED71), (X1, K15, ED72), (X1, K15, ED73), (X1, K15, ED74), (X1, K15, ED75), (X1, K15, ED76), (X1, K15, ED77), (X1, K15, ED78), (X1, K15, ED79), (X1, K15, ED80), (X1, K15, ED81), (X1, K15, ED82), (X1, K15, ED83), (X1, K15, ED84), (X1, K15, ED85), (X1, K15, ED86), (X1, K15, ED87), (X1, K15, ED88), (X1, K15, ED89), (X1, K15, ED90), (X1, K15, ED91), (X1, K15, ED92), (X1, K16, ED1), (X1, K16, ED2), (X1, K16, ED3), (X1, K16, ED4), (X1, K16, ED5), (X1, K16, ED6), (X1, K16, ED7), (X1, K16, ED8), (X1, K16, ED9), (X1, K16, ED10), (X1, K16, ED11), (X1, K16, ED12), (X1, K16, ED13), (X1, K16, ED14), (X1, K16, ED15), (X1, K16, ED16), (X1, K16, ED17), (X1, K16, ED18), (X1, K16, ED19), (X1, K16, ED20), (X1, K16, ED21), (X1, K16, ED22), (X1, K16, ED23), (X1, K16, ED24), (X1, K16, ED25), (X1, K16, ED26), (X1, K16, ED27), (X1, K16, ED28), (X1, K16, ED29), (X1, K16, ED30), (X1, K16, ED31), (X1, K16, ED32), (X1, K16, ED33), (X1, K16, ED34), (X1, K16, ED35), (X1, K16, ED36), (X1, K16, ED37), (X1, K16, ED38), (X1, K16, ED39), (X1, K16, ED40), (X1, K16, ED41), (X1, K16, ED42), (X1, K16, ED43), (X1, K16, ED44), (X1, K16, ED45), (X1, K16, ED46), (X1, K16, ED47), (X1, K16, ED48), (X1, K16, ED49), (X1, K16, ED50), (X1, K16, ED51), (X1, K16, ED52), (X1, K16, ED53), (X1, K16, ED54), (X1, K16, ED55), (X1, K16, ED56), (X1, K16, ED57), (X1, K16, ED58), (X1, K16, ED59), (X1, K16, ED60), (X1, K16, ED61), (X1, K16, ED62), (X1, K16, ED63), (X1, K16, ED64), (X1, K16, ED65), (X1, K16, ED66), (X1, K16, ED67), (X1, K16, ED68), (X1, K16, ED69), (X1, K16, ED70), (X1, K16, ED71), (X1, K16, ED72), (X1, K16, ED73), (X1, K16, ED74), (X1, K16, ED75), (X1, K16, ED76), (X1, K16, ED77), (X1, K16, ED78), (X1, K16, ED79), (X1, K16, ED80), (X1, K16, ED81), (X1, K16, ED82), (X1, K16, ED83), (X1, K16, ED84), (X1, K16, ED85), (X1, K16, ED86), (X1, K16, ED87), (X1, K16, ED88), (X1, K16, ED89), (X1, K16, ED90), (X1, K16, ED91), (X1, K16, ED92), (X1, K17, ED1), (X1, K17, ED2), (X1, K17, ED3), (X1, K17, ED4), (X1, K17, ED5), (X1, K17, ED6), (X1, K17, ED7), (X1, K17, ED8), (X1, K17, ED9), (X1, K17, ED10), (X1, K17, ED11), (X1, K17, ED12), (X1, K17, ED13), (X1, K17, ED14), (X1, K17, ED15), (X1, K17, ED16), (X1, K17, ED17), (X1, K17, ED18), (X1, K17, ED19), (X1, K17, ED20), (X1, K17, ED21), (X1, K17, ED22), (X1, K17, ED23), (X1, K17, ED24), (X1, K17, ED25), (X1, K17, ED26), (X1, K17, ED27), (X1, K17, ED28), (X1, K17, ED29), (X1, K17, ED30), (X1, K17, ED31), (X1, K17, ED32), (X1, K17, ED33), (X1, K17, ED34), (X1, K17, ED35), (X1, K17, ED36), (X1, K17, ED37), (X1, K17, ED38), (X1, K17, ED39), (X1, K17, ED40), (X1, K17, ED41), (X1, K17, ED42), (X1, K17, ED43), (X1, K17, ED44), (X1, K17, ED45), (X1, K17, ED46), (X1, K17, ED47), (X1, K17, ED48), (X1, K17, ED49), (X1, K17, ED50), (X1, K17, ED51), (X1, K17, ED52), (X1, K17, ED53), (X1, K17, ED54), (X1, K17, ED55), (X1, K17, ED56), (X1, K17, ED57), (X1, K17, ED58), (X1, K17, ED59), (X1, K17, ED60), (X1, K17, ED61), (X1, K17, ED62), (X1, K17, ED63), (X1, K17, ED64), (X1, K17, ED65), (X1, K17, ED66), (X1, K17, ED67), (X1, K17, ED68), (X1, K17, ED69), (X1, K17, ED70), (X1, K17, ED71), (X1, K17, ED72), (X1, K17, ED73), (X1, K17, ED74), (X1, K17, ED75), (X1, K17, ED76), (X1, K17, ED77), (X1, K17, ED78), (X1, K17, ED79), (X1, K17, ED80), (X1, K17, ED81), (X1, K17, ED82), (X1, K17, ED83), (X1, K17, ED84), (X1, K17, ED85), (X1, K17, ED86), (X1, K17, ED87), (X1, K17, ED88), (X1, K17, ED89), (X1, K17, ED90), (X1, K17, ED91), (X1, K17, ED92), (X1, K18, ED1), (X1, K18, ED2), (X1, K18, ED3), (X1, K18, ED4), (X1, K18, ED5), (X1, K18, ED6), (X1, K18, ED7), (X1, K18, ED8), (X1, K18, ED9), (X1, K18, ED10), (X1, K18, ED11), (X1, K18, ED12), (X1, K18, ED13), (X1, K18, ED14), (X1, K18, ED15), (X1, K18, ED16), (X1, K18,

ED17), (X1, K18, ED18), (X1, K18, ED19), (X1, K18, ED20), (X1, K18, ED21), (X1, K18, ED22), (X1, K18, ED23), (X1, K18, ED24), (X1, K18, ED25), (X1, K18, ED26), (X1, K18, ED27), (X1, K18, ED28), (X1, K18, ED29), (X1, K18, ED30), (X1, K18, ED31), (X1, K18, ED32), (X1, K18, ED33), (X1, K18, ED34), (X1, K18, ED35), (X1, K18, ED36), (X1, K18, ED37), (X1, K18, ED38), (X1, K18, ED39), (X1, K18, ED40), (X1, K18, ED41), (X1, K18, ED42), (X1, K18, ED43), (X1, K18, ED44), (X1, K18, ED45), (X1, K18, ED46), (X1, K18, ED47), (X1, K18, ED48), (X1, K18, ED49), (X1, K18, ED50), (X1, K18, ED51), (X1, K18, ED52), (X1, K18, ED53), (X1, K18, ED54), (X1, K18, ED55), (X1, K18, ED56), (X1, K18, ED57), (X1, K18, ED58), (X1, K18, ED59), (X1, K18, ED60), (X1, K18, ED61), (X1, K18, ED62), (X1, K18, ED63), (X1, K18, ED64), (X1, K18, ED65), (X1, K18, ED66), (X1, K18, ED67), (X1, K18, ED68), (X1, K18, ED69), (X1, K18, ED70), (X1, K18, ED71), (X1, K18, ED72), (X1, K18, ED73), (X1, K18, ED74), (X1, K18, ED75), (X1, K18, ED76), (X1, K18, ED77), (X1, K18, ED78), (X1, K18, ED79), (X1, K18, ED80), (X1, K18, ED81), (X1, K18, ED82), (X1, K18, ED83), (X1, K18, ED84), (X1, K18, ED85), (X1, K18, ED86), (X1, K18, ED87), (X1, K18, ED88), (X1, K18, ED89), (X1, K18, ED90), (X1, K18, ED91), (X1, K18, ED92), (X1, K19, ED1), (X1, K19, ED2), (X1, K19, ED3), (X1, K19, ED4), (X1, K19, ED5), (X1, K19, ED6), (X1, K19, ED7), (X1, K19, ED8), (X1, K19, ED9), (X1, K19, ED10), (X1, K19, ED11), (X1, K19, ED12), (X1, K19, ED13), (X1, K19, ED14), (X1, K19, ED15), (X1, K19, ED16), (X1, K19, ED17), (X1, K19, ED18), (X1, K19, ED19), (X1, K19, ED20), (X1, K19, ED21), (X1, K19, ED22), (X1, K19, ED23), (X1, K19, ED24), (X1, K19, ED25), (X1, K19, ED26), (X1, K19, ED27), (X1, K19, ED28), (X1, K19, ED29), (X1, K19, ED30), (X1, K19, ED31), (X1, K19, ED32), (X1, K19, ED33), (X1, K19, ED34), (X1, K19, ED35), (X1, K19, ED36), (X1, K19, ED37), (X1, K19, ED38), (X1, K19, ED39), (X1, K19, ED40), (X1, K19, ED41), (X1, K19, ED42), (X1, K19, ED43), (X1, K19, ED44), (X1, K19, ED45), (X1, K19, ED46), (X1, K19, ED47), (X1, K19, ED48), (X1, K19, ED49), (X1, K19, ED50), (X1, K19, ED51), (X1, K19, ED52), (X1, K19, ED53), (X1, K19, ED54), (X1, K19, ED55), (X1, K19, ED56), (X1, K19, ED57), (X1, K19, ED58), (X1, K19, ED59), (X1, K19, ED60), (X1, K19, ED61), (X1, K19, ED62), (X1, K19, ED63), (X1, K19, ED64), (X1, K19, ED65), (X1, K19, ED66), (X1, K19, ED67), (X1, K19, ED68), (X1, K19, ED69), (X1, K19, ED70), (X1, K19, ED71), (X1, K19, ED72), (X1, K19, ED73), (X1, K19, ED74), (X1, K19, ED75), (X1, K19, ED76), (X1, K19, ED77), (X1, K19, ED78), (X1, K19, ED79), (X1, K19, ED80), (X1, K19, ED81), (X1, K19, ED82), (X1, K19, ED83), (X1, K19, ED84), (X1, K19, ED85), (X1, K19, ED86), (X1, K19, ED87), (X1, K19, ED88), (X1, K19, ED89), (X1, K19, ED90), (X1, K19, ED91), (X1, K19, ED92), (X1, K20, ED1), (X1, K20, ED2), (X1, K20, ED3), (X1, K20, ED4), (X1, K20, ED5), (X1, K20, ED6), (X1, K20, ED7), (X1, K20, ED8), (X1, K20, ED9), (X1, K20, ED10), (X1, K20, ED11), (X1, K20, ED12), (X1, K20, ED13), (X1, K20, ED14), (X1, K20, ED15), (X1, K20, ED16), (X1, K20, ED17), (X1, K20, ED18), (X1, K20, ED19), (X1, K20, ED20), (X1, K20, ED21), (X1, K20, ED22), (X1, K20, ED23), (X1, K20, ED24), (X1, K20, ED25), (X1, K20, ED26), (X1, K20, ED27), (X1, K20, ED28), (X1, K20, ED29), (X1, K20, ED30), (X1, K20, ED31), (X1, K20, ED32), (X1, K20, ED33), (X1, K20, ED34), (X1, K20, ED35), (X1, K20, ED36), (X1, K20, ED37), (X1, K20, ED38), (X1, K20, ED39), (X1, K20, ED40), (X1, K20, ED41), (X1, K20, ED42), (X1, K20, ED43), (X1, K20, ED44), (X1, K20, ED45), (X1, K20, ED46), (X1, K20, ED47), (X1, K20, ED48), (X1, K20, ED49), (X1, K20, ED50), (X1, K20, ED51), (X1, K20, ED52), (X1, K20, ED53), (X1, K20, ED54), (X1, K20, ED55), (X1, K20, ED56), (X1, K20, ED57), (X1, K20, ED58), (X1, K20, ED59), (X1, K20, ED60), (X1, K20, ED61), (X1, K20, ED62), (X1, K20, ED63), (X1, K20, ED64), (X1, K20, ED65), (X1, K20, ED66), (X1, K20, ED67), (X1, K20, ED68), (X1, K20, ED69), (X1, K20, ED70), (X1, K20, ED71), (X1, K20, ED72), (X1, K20, ED73), (X1, K20, ED74), (X1, K20, ED75), (X1, K20, ED76), (X1, K20, ED77), (X1, K20, ED78), (X1, K20, ED79), (X1, K20, ED80), (X1, K20, ED81), (X1, K20, ED82), (X1, K20, ED83), (X1, K20, ED84), (X1, K20, ED85), (X1, K20, ED86), (X1, K20, ED87), (X1, K20, ED88), (X1, K20, ED89), (X1, K20, ED90), (X1, K20, ED91), (X1, K20, ED92), (X1, K21, ED1), (X1, K21, ED2), (X1, K21, ED3), (X1, K21, ED4), (X1, K21, ED5), (X1, K21, ED6), (X1, K21, ED7), (X1, K21, ED8), (X1, K21, ED9), (X1, K21, ED10), (X1, K21, ED11), (X1, K21, ED12), (X1, K21, ED13), (X1, K21, ED14), (X1, K21, ED15), (X1, K21, ED16), (X1, K21, ED17), (X1, K21, ED18), (X1, K21, ED19), (X1, K21, ED20), (X1, K21, ED21), (X1, K21, ED22), (X1, K21, ED23), (X1, K21, ED24), (X1, K21, ED25), (X1, K21, ED26), (X1, K21, ED27), (X1, K21, ED28), (X1, K21, ED29), (X1, K21, ED30), (X1, K21, ED31), (X1, K21, ED32), (X1, K21, ED33), (X1, K21, ED34), (X1, K21, ED35), (X1, K21, ED36), (X1, K21, ED37), (X1, K21, ED38), (X1, K21, ED39), (X1, K21, ED40), (X1, K21, ED41), (X1, K21, ED42), (X1, K21, ED43), (X1, K21, ED44), (X1, K21, ED45), (X1, K21, ED46), (X1, K21, ED47), (X1, K21, ED48), (X1, K21, ED49), (X1, K21, ED50), (X1, K21, ED51), (X1, K21, ED52), (X1, K21, ED53), (X1, K21, ED54), (X1, K21, ED55), (X1, K21, ED56), (X1, K21, ED57), (X1, K21, ED58), (X1, K21, ED59), (X1, K21, ED60), (X1, K21, ED61), K21, ED62), (X1, K21, ED63), (X1, K21, ED64), (X1, K21, ED65), (X1, K21, ED66), (X1, K21, ED67), (X1, K21, ED68), (X1, K21, ED69), (X1, K21, ED70), (X1, K21, ED71), (X1, K21, ED72), (X1, K21, ED73), (X1, K21, ED74), (X1, K21, ED75), (X1, K21, ED76), (X1, K21, ED77), (X1, K21, ED78), (X1, K21, ED79), (X1, K21, ED80), (X1, K21, ED81), (X1, K21, ED82), (X1, K21, ED83), (X1, K21, ED84), (X1, K21, ED85), (X1, K21, ED86), (X1, K21, ED87), (X1, K21, ED88), (X1, K21, ED89), (X1, K21, ED90), (X1, K21, ED91), (X1, K21, ED92), (X1, K22, ED1), (X1, K22, ED2), (X1, K22, ED3), (X1, K22, ED4), (X1, K22, ED5), (X1, K22, ED6), (X1, K22, ED7), (X1, K22, ED8), (X1, K22, ED9), (X1, K22, ED10), (X1, K22, ED11), (X1, K22, ED12), (X1, K22, ED13), (X1, K22, ED14), (X1, K22, ED15), (X1, K22, ED16), (X1, K22, ED17), (X1, K22, ED18), (X1, K22, ED19), (X1, K22, ED20), (X1, K22, ED21), (X1, K22, ED22), (X1, K22, ED23), (X1, K22, ED24), (X1, K22, ED25), (X1, K22, ED26), (X1, K22, ED27), (X1, K22, ED28), (X1, K22, ED29), (X1, K22, ED30), (X1, K22, ED31), (X1, K22, ED32), (X1, K22, ED33), (X1, K22, ED34), (X1, K22, ED35), (X1, K22, ED36), (X1, K22, ED37), (X1, K22, ED38), (X1, K22, ED39), (X1, K22, ED40), (X1, K22, ED41), (X1, K22, ED42), (X1, K22, ED43), (X1, K22, ED44), (X1, K22, ED45), (X1, K22, ED46), (X1, K22, ED47), (X1, K22, ED48), (X1, K22, ED49), (X1, K22, ED50), (X1, K22, ED51), (X1, K22, ED52), (X1, K22, ED53), (X1, K22, ED54), (X1, K22, ED55), (X1, K22, ED56), (X1, K22,

ED57), (X1, K22, ED58), (X1, K22, ED59), (X1, K22, ED60), (X1, K22, ED61), (X1, K22, ED62), (X1, K22, ED63), (X1, K22, ED64), (X1, K22, ED65), (X1, K22, ED66), (X1, K22, ED67), (X1, K22, ED68), (X1, K22, ED69), (X1, K22, ED70), (X1, K22, ED71), (X1, K22, ED72), (X1, K22, ED73), (X1, K22, ED74), (X1, K22, ED75), (X1, K22, ED76), (X1, K22, ED77), (X1, K22, ED78), (X1, K22, ED79), (X1, K22, ED80), (X1, K22, ED81), (X1, K22, ED82), (X1, K22, ED83), (X1, K22, ED84), (X1, K22, ED85), (X1, K22, ED86), (X1, K22, ED87), (X1, K22, ED88), (X1, K22, ED89), (X1, K22, ED90), (X1, K22, ED91), (X1, K22, ED92), (X1, K23, ED1), (X1, K23, ED2), (X1, K23, ED3), (X1, K23, ED4), (X1, K23, ED5), (X1, K23, ED6), (X1, K23, ED7), (X1, K23, ED8), (X1, K23, ED9), (X1, K23, ED10), (X1, K23, ED11), (X1, K23, ED12), (X1, K23, ED13), (X1, K23, ED14), (X1, K23, ED15), (X1, K23, ED16), (X1, K23, ED17), (X1, K23, ED18), (X1, K23, ED19), (X1, K23, ED20), (X1, K23, ED21), (X1, K23, ED22), (X1, K23, ED23), (X1, K23, ED24), (X1, K23, ED25), (X1, K23, ED26), (X1, K23, ED27), (X1, K23, ED28), (X1, K23, ED29), (X1, K23, ED30), (X1, K23, ED31), (X1, K23, ED32), (X1, K23, ED33), (X1, K23, ED34), (X1, K23, ED35), (X1, K23, ED36), (X1, K23, ED37), (X1, K23, ED38), (X1, K23, ED39), (X1, K23, ED40), (X1, K23, ED41), (X1, K23, ED42), (X1, K23, ED43), (X1, K23, ED44), (X1, K23, ED45), (X1, K23, ED46), (X1, K23, ED47), (X1, K23, ED48), (X1, K23, ED49), (X1, K23, ED50), (X1, K23, ED51), (X1, K23, ED52), (X1, K23, ED53), (X1, K23, ED54), (X1, K23, ED55), (X1, K23, ED56), (X1, K23, ED57), (X1, K23, ED58), (X1, K23, ED59), (X1, K23, ED60), (X1, K23, ED61), (X1, K23, ED62), (X1, K23, ED63), (X1, K23, ED64), (X1, K23, ED65), (X1, K23, ED66), (X1, K23, ED67), (X1, K23, ED62), (X1, K23, ED69), (X1, K23, ED70), (X1, K23, ED71), (X1, K23, ED72), (X1, K23, ED73), (X1, K23, ED74), (X1, K23, ED75), (X1, K23, ED76), (X1, K23, ED77), (X1, K23, ED78), (X1, K23, ED79), (X1, K23, ED80), (X1, K23, ED81), (X1, K23, ED82), (X1, K23, ED83), (X1, K23, ED84), (X1, K23, ED85), (X1, K23, ED86), (X1, K23, ED87), (X1, K23, ED88), (X1, K23, ED89), (X1, K23, ED90), (X1, K23, ED91), (X1, K23, ED92), (X1, K24, ED1), (X1, K24, ED2), (X1, K24, ED3), (X1, K24, ED4), (X1, K24, ED5), (X1, K24, ED6), (X1, K24, ED7), (X1, K24, ED8), (X1, K24, ED9), (X1, K24, ED10), (X1, K24, ED11), (X1, K24, ED12), (X1, K24, ED13), (X1, K24, ED14), (X1, K24, ED15), (X1, K24, ED16), (X1, K24, ED17), (X1, K24, ED18), (X1, K24, ED19), (X1, K24, ED20), (X1, K24, ED21), (X1, K24, ED22), (X1, K24, ED23), (X1, K24, ED24), (X1, K24, ED25), (X1, K24, ED26), (X1, K24, ED27), (X1, K24, ED28), (X1, K24, ED29), (X1, K24, ED30), (X1, K24, ED31), (X1, K24, ED32), (X1, K24, ED33), (X1, K24, ED34), (X1, K24, ED35), (X1, K24, ED36), (X1, K24, ED37), (X1, K24, ED38), (X1, K24, ED39), (X1, K24, ED40), (X1, K24, ED41), (X1, K24, ED42), (X1, K24, ED43), (X1, K24, ED44), (X1, K24, ED45), (X1, K24, ED46), (X1, K24, ED47), (X1, K24, ED48), (X1, K24, ED49), (X1, K24, ED50), (X1, K24, ED51), (X1, K24, ED52), (X1, K24, ED53), (X1, K24, ED54), (X1, K24, ED55), (X1, K24, ED56), (X1, K24, ED57), (X1, K24, ED58), (X1, K24, ED59), (X1, K24, ED60), (X1, K24, ED61), (X1, K24, ED62), (X1, K24, ED63), (X1, K24, ED64), (X1, K24, ED65), (X1, K24, ED66), (X1, K24, ED67), (X1, K24, ED68), (X1, K24, ED69), (X1, K24, ED70), (X1, K24, ED71), (X1, K24, ED72), (X1, K24, ED73), (X1, K24, ED74), (X1, K24, ED75), (X1, K24, ED76), (X1, K24, ED77), (X1, K24, ED78), (X1, K24, ED79), (X1, K24, ED80), (X1, K24, ED81), (X1, K24, ED32), (X1, K24, ED83), (X1, K24, ED84), (X1, K24, ED85), (X1, K24, ED86), (X1, K24, ED87), (X1, K24, ED88), (X1, K24, ED89), (X1, K24, ED90), (X1, K24, ED91), (X1, K24, ED92), (X1, K25, ED1), (X1, K25, ED2), (X1, K25, ED3), (X1, K25, ED4), (X1, K25, ED5), (X1, K25, ED6), (X1, K25, ED7), (X1, K25, ED8), (X1, K25, ED9), (X1, K25, ED10), (X1, K25, ED11), (X1, K25, ED12), (X1, K25, ED13), (X1, K25, ED14), (X1, K25, ED15), (X1, K25, ED16), (X1, K25, ED17), (X1, K25, ED18), (X1, K25, ED19), (X1, K25, ED20), (X1, K25, ED21), (X1, K25, ED22), (X1, K25, ED23), (X1, K25, ED24), (X1, K25, ED25), (X1, K25, ED26), (X1, K25, ED27), (X1, K25, ED28), (X1, K25, ED29), (X1, K25, ED30), (X1, K25, ED31), (X1, K25, ED32), (X1, K25, ED33), (X1, K25, ED34), (X1, K25, ED35), (X1, K25, ED36), (X1, K25, ED37), (X1, K25, ED38), (X1, K25, ED39), (X1, K25, ED40), (X1, K25, ED41), (X1, K25, ED42), (X1, K25, ED43), (X1, K25, ED44), (X1, K25, ED45), (X1, K25, ED46), (X1, K25, ED47), (X1, K25, ED48), (X1, K25, ED49), (X1, K25, ED58), (X1, K25, ED51), (X1, K25, ED52), (X1, K25, ED53), (X1, K25, ED54), (X1, K25, ED55), (X1, K25, ED56), (X1, K25, ED57), (X1, K25, ED58), (X1, K25, ED59), (X1, K25, ED60), (X1, K25, ED61), (X1, K25, ED62), (X1, K25, ED63), (X1, K25, ED64), (X1, K25, ED65), (X1, K25, ED66), (X1, K25, ED67), (X1, K25, ED68), (X1, K25, ED69), (X1, K25, ED70), (X1, K25, ED71), (X1, K25, ED72), (X1, K25, ED73), (X1, K25, ED74), (X1, K25, ED75), (X1, K25, ED76), (X1, K25, ED77), (X1, K25, ED78), (X1, K25, ED79), (X1, K25, ED80), (X1, K25, ED81), (X1, K25, ED82), (X1, K25, ED83), (X1, K25, ED84), (X1, K25, ED85), (X1, K25, ED86), (X1, K25, ED87), (X1, K25, ED88), (X1, K25, ED89), (X1, K25, ED90), (X1, K25, ED91), (X1, K25, ED92), (X1, K26, ED1), (X1, K26, ED2), (X1, K26, ED3), (X1, K26, ED4), (X1, K26, ED5), (X1, K26, ED6), (X1, K26, ED7), (X1, K26, ED8), (X1, K26, ED9), (X1, K26, ED10), (X1, K26, ED11), (X1, K26, ED12), (X1, K26, ED13), (X1, K26, ED14), (X1, K26, ED15), (X1, K26, ED16), (X1, K26, ED17), (X1, K26, ED18), (X1, K26, ED19), (X1, K26, ED20), (X1, K26, ED21), (X1, K26, ED22), (X1, K26, ED23), (X1, K26, ED24), (X1, K26, ED25), (X1, K26, ED26), (X1, K26, ED27), (X1, K26, ED28), (X1, K26, ED29), (X1, K26, ED30), (X1, K26, ED31), (X1, K26, ED32), (X1, K26, ED33), (X1, K26, ED34), (X1, K26, ED35), (X1, K26, ED36), (X1, K26, ED37), (X1, K26, ED38), (X1, K26, ED39), (X1, K26, ED40), (X1, K26, ED41), (X1, K26, ED42), (X1, K26, ED43), (X1, K26, ED44), (X1, K26, ED45), (X1, K26, ED46), (X1, K26, ED47), (X1, K26, ED48), (X1, K26, ED49), (X1, K26, ED50), (X1, K26, ED51), (X1, K26, ED52), (X1, K26, ED53), (X1, K26, ED54), (X1, K26, ED55), (X1, K26, ED56), (X1, K26, ED57), (X1, K26, ED58), (X1, K26, ED59), (X1, K26, ED60), (X1, K26, ED61), (X1, K26, ED62), (X1, K26, ED63), (X1, K26, ED64), (X1, K26, ED65), (X1, K26, ED66), (X1, K26, ED67), (X1, K26, ED68), (X1, K26, ED69), (X1, K26, ED70), (X1, K26, ED71), (X1, K26, ED72), (X1, K26, ED73), (X1, K26, ED74), (X1, K26, ED75), (X1, K26, ED76), (X1, K26, ED77), (X1, K26, ED78), (X1, K26, ED79), (X1, K26, ED80), (X1, K26, ED81), (X1, K26, ED82), (X1, K26, ED83), (X1, K26, ED84), (X1, K26, ED85), (X1, K26, ED86), (X1, K26, ED87), (X1, K26, ED88), (X1, K26, ED89), (X1, K26, ED90), (X1, K26, ED91), (X1, K26, ED92), (X1, K27, ED1), (X1, K27, ED2), (X1, K27, ED3), (X1, K27, ED4), (X1, K27, ED5), (X1, K27, ED6), (X1, K27, ED7), (X1, K27, ED8), (X1, K27, ED9), (X1, K27, ED10), (X1, K27, ED11), (X1, K27, ED12), (X1, K27, ED13), (X1, K27, ED14), (X1, K27, ED15), (X1, K27, ED16), (X1, K27, ED17), (X1, K27, ED18), (X1, K27, ED19), (X1, K27, ED20), (X1, K27, ED21), (X1, K27, ED22), (X1, K27, ED23), (X1, K27, ED24), (X1, K27, ED25), (X1, K27, ED26), (X1, K27, ED27), (X1, K27, ED28), (X1, K27, ED29), (X1, K27, ED30), (X1, K27, ED31), (X1, K27, ED32), (X1, K27, ED33), (X1, K27, ED34), (X1, K27, ED35), (X1, K27, ED36), (X1, K27, ED37), (X1, K27, ED38), (X1, K27, ED39), (X1, K27, ED40), (X1, K27, ED41), (X1, K27, ED42), (X1, K27, ED43), (X1, K27, ED44), (X1, K27, ED45), (X1, K27, ED46), (X1, K27, ED47), (X1, K27, ED48), (X1, K27, ED49), (X1, K27, ED50), (X1, K27, ED51), (X1, K27, ED52), (X1, K27, ED53), (X1, K27, ED54), (X1, K27, ED55), (X1, K27, ED56), (X1, K27, ED57), (X1, K27, ED58), (X1, K27, ED59), (X1, K27, ED60), (X1, K27, ED61), (X1, K27, ED62), (X1, K27, ED63), (X1, K27, ED64), (X1, K27, ED65), (X1, K27, ED66), (X1, K27, ED67), (X1, K27, ED68), (X1, K27, ED69), (X1, K27, ED70), (X1, K27, ED71), (X1, K27, ED72), (X1, K27, ED73), (X1, K27, ED74), (X1, K27, ED75), (X1, K27, ED76), (X1, K27, ED77), (X1, K27, ED78), (X1, K27, ED79), (X1, K27, ED80), (X1, K27, ED81), (X1, K27, ED82), (X1, K27, ED83), (X1, K27, ED84), (X1, K27, ED85), (X1, K27, ED86), (X1, K27, ED87), (X1, K27, ED88), (X1, K27, ED89), (X1, K27, ED90), (X1, K27, ED91), (X1, K27, ED92), (X1, K28, ED1), (X1, K28, ED2), (X1, K28, ED3), (X1, K28, ED4), (X1, K28, ED5), (X1, K28, ED6), (X1, K28, ED7), (X1, K28, ED8), (X1, K28, ED9), (X1, K28, ED10), (X1, K28, ED11), (X1, K28, ED12), (X1, K28, ED13), (X1, K28, ED14), (X1, K28, ED15), (X1, K28, ED16), (X1, K28, ED17), (X1, K28, ED18), (X1, K28, ED19), (X1, K28, ED20), (X1, K28, ED21), (X1, K28, ED22), (X1, K28, ED23), (X1, K28, ED24), (X1, K28, ED25), (X1, K28, ED26), (X1, K28, ED27), (X1, K28, ED28), (X1, K28, ED29), (X1, K28, ED30), (X1, K28, ED31), (X1, K28, ED32), (X1, K28, ED33), (X1, K28, ED34), (X1, K28, ED35), (X1, K28, ED36), (X1, K28, ED37), (X1, K28, ED38), (X1, K28, ED39), (X1, K28, ED40), (X1, K20, ED41), (X1, K28, ED42), (X1, K28, ED43), (X1, K28, ED44), (X1, K28, ED45), (X1, K28, ED46), (X1, K20, ED47), (X1, K28, ED48), (X1, K20, ED49), (X1, K28, ED50), (X1, K28, ED51), (X1, K28, ED52), (X1, K28, ED53), (X1, K28, ED54), (X1, K28, ED55), (X1, K28, ED56), (X1, K28, ED57), (X1, K28, ED58), (X1, K28, ED59), (X1, K28, ED60), (X1, K28, ED61), (X1, K28, ED62), (X1, K28, ED63), (X1, K28, ED64), (X1, K28, ED65), (X1, K28, ED66), (X1, K28, ED67), (X1, K28, ED68), (X1, K28, ED69), (X1, K28, ED70), (X1, K28, ED71), (X1, K28, ED72), (X1, K28, ED73), (X1, K28, ED74), (X1, K28, ED75), (X1, K28, ED76), (X1, K28, ED77), (X1, K28, ED78), (X1, K28, ED79), (X1, K28, ED80), (X1, K28, ED81), (X1, K28, ED82), (X1, K28, ED83), (X1, K28, ED84), (X1, K28, ED85), (X1, K28, ED86), (X1, K28, ED87), (X1, K28, ED88), (X1, K28, ED89), (X1, K28, ED90), (X1, K28, ED91), (X1, K28, ED92), (X1, K29, ED1), (X1, K29, ED2), (X1, K29, ED3), (X1, K29, ED4), (X1, K29, E5), (X1, K29, ED6), (X1, K29, ED7), (X1, K29, ED8), (X1, K29, ED9), (X1, K29, ED10), (X1, K29, ED11), (X1, K29, ED12), (X1, K29, ED13), (X1, K29, ED14), (X1, K29, ED15), (X1, K29, ED16), (X1, K29, ED17), (X1, K29, ED18), (X1, K29, ED19), (X1, K29, ED20), (X1, K29, ED21), (X1, K29, ED22), (X1, K29, ED23), (X1, K29, ED24), (X1, K29, ED25), (X1, K29, ED26), (X1, K29, ED27), (X1, K29, ED28), (X1, K29, ED29), (X1, K29, ED30), (X1, K29, ED31), (X1, K29, ED32), (X1, K29, ED33), (X1, K29, ED34), (X1, K29, ED35), (X1, K29, ED36), (X1, K29, ED37), (X1, K29, ED38), (X1, K29, ED39), (X1, K29, ED40), (X1, K29, ED41), (X1, K29, ED42), (X1, K29, ED43), (X1, K29, ED44), (X1, K29, ED45), (X1, K29, ED46), (X1, K29, ED47), (X1, K29, ED48), (X1, K29, ED49), (X1, K29, ED50), (X1, K29, ED51), (X1, K29, ED52), (X1, K29, ED53), (X1, K29, ED54), (X1, K29, ED55), (X1, K29, ED56), (X1, K29, ED57), (X1, K29, ED58), (X1, K29, ED59), (X1, K29, ED60), (X1, K29, ED61), (X1, K29, ED62), (X1, K29, ED63), (X1, K29, ED64), (X1, K29, ED65), (X1, K29, ED66), (X1, K29, ED67), (X1, K29, ED68), (X1, K29, ED69), (X1, K29, ED70), (X1, K29, ED71), (X1, K29, ED72), (X1, K29, ED73), (X1, K29, ED74), (X1, K29, ED75), (X1, K29, ED76), (X1, K29, ED77), (X1, K29, ED78), (X1, K29, ED79), (X1, K29, ED80), (X1, K29, ED81), (X1, K29, ED82), (X1, K29, ED83), (X1, K29, ED84), (X1, K29, ED85), (X1, K29, ED86), (X1, K29, ED87), (X1, K29, ED88), (X1, K29, ED89), (X1, K29, ED90), (X1, K29, ED91), (X1, K29, ED92), (X1, K30, ED1), (X1, K30, ED2), (X1, K30, ED3), (X1, K30, ED4), (X1, K30, ED5), (X1, K30, ED6), (X1, K30, ED7), (X1, K30, ED8), (X1, K30, ED9), (X1, K30, ED10), (X1, K30, ED11), (X1, K30, ED12), (X1, K30, ED13), (X1, K30, ED14), (X1, K30, ED15), (X1, K30, ED16), (X1, K30, ED17), (X1, K30, ED18), (X1, K30, ED19), (X1, K30, ED20), (X1, K30, ED21), (X1, K30, ED22), (X1, K30, ED23), (X1, K30, ED24), (X1, K30, ED25), (X1, K30, ED26), (X1, K30, ED27), (X1, K30, ED28), (X1, K30, ED29), (X1, K30, ED30), (X1, K30, ED31), (X1, K30, ED32), (X1, K30, ED33), (X1, K30, ED34), (X1, K20, ED35), (X1, K20, ED36), (X1, K30, ED37), (X1, K30, ED38), (X1, K30, ED39), (X1, K30, ED40), (X1, K30, ED41), (X1, K30, ED42), (X1, K30, ED43), (X1, K20, ED44), (X1, K30, ED45), (X1, K30, ED46), (X1, K30, ED47), (X1, K30, ED48), (X1, K30, ED49), (X1, K30, ED50), (X1, K30, ED51), (X1, K30, ED52), (X1, K30, ED53), (X1, K30, ED54), (X1, K30, ED55), (X1, K30, ED56), (X1, K30, ED57), (X1, K30, ED58), (X1, K30, ED59), (X1, K30, ED60), (X1, K30, ED61), (X1, K30, ED62), (X1, K30, ED63), (X1, K30, ED64), (X1, K30, ED65), (X1, K30, ED66), (X1, K30, ED67), (X1, K30, ED68), (X1, K30, ED69), (X1, K30, ED70), (X1, K30, ED71), (X1, K30, ED72), (X1, K30, ED73), (X1, K30, ED74), (X1, K30, ED75), (X1, K30, ED76), (X1, K30, ED77), (X1, K30, ED78), (X1, K30, ED79), (X1, K30, ED80), (X1, K30, ED81), (X1, K30, ED82), (X1, K30, ED83), (X1, K30, ED84), (X1, K30, ED85), (X1, K30, ED86), (X1, K30, ED87), (X1, K30, ED88), (X1, K30, ED89), (X1, K30, ED90), (X1, K30, ED91), (X1, K30, ED92), (X1, K31, ED1), (X1, K31, ED2), (X1, K31, ED3), (X1, K31, ED4), (X1, K31, ED5), (X1, K31, ED6), (X1, K31, ED7), (X1, K31, ED8), (X1, K31, ED9), (X1, K31, ED10), (X1, K31, ED11), (X1, K31, ED12), (X1, K31, ED13), (X1, K31, ED14), (X1, K31, ED15), (X1, K31, ED16), (X1, K31, ED17), (X1, K31, ED18), (X1, K31, ED19), (X1, K31, ED20), (X1, K31, ED21), (X1, K31, ED22), (X1, K31, ED23), (X1, K31, ED24), (X1, K31, ED25), (X1, K31, ED26), (X1, K31, ED27), (X1, K31, ED28), (X1, K31, ED29), (X1, K31, ED30), (X1, K31, ED31), (X1, K31, ED32), (X1, K31, ED33), (X1, K31, ED34), (X1, K31, ED35), (X1, K31, ED36), (X1, K31, ED37), (X1, K31, ED38), (X1, K31, ED39), (X1, K31, ED40), (X1, K31, ED41), (X1, K31, ED42), (X1, K31, ED43), (X1, K31, ED44), (X1, K31, ED45), (X1, K31, ED46), (X1, K31, ED47), (X1, K31, ED48), (X1, K31, ED49), (X1, K31,

ED50), (X1, K31, ED51), (X1, K31, ED52), (X1, K31, ED53), (X1, K31, ED54), (X1, K31, ED55), (X1, K31, ED56), (X1, K31, ED57), (X1, K31, ED58), (X1, K31, ED59), (X1, K31, ED60), (X1, K31, ED61), (X1, K31, ED62), (X1, K31, ED63), (X1, K31, ED64), (X1, K31, ED65), (X1, K31, ED66), (X1, K31, ED67), (X1, K31, ED68), (X1, K31, ED69), (X1, K31, ED70), (X1, K31, ED71), (X1, K31, ED72), (X1, K31, ED73), (X1, K31, ED74), (X1, K31, ED75), (X1, K31, ED76), (X1, K31, ED77), (X1, K31, ED78), (X1, K31, ED79), (X1, K31, ED80), (X1, K31, ED81), (X1, K31, ED82), (X1, K31, ED83), (X1, K31, ED84), (X1, K31, ED85), (X1, K31, ED86), (X1, K31, ED87), (X1, K31, ED88), (X1, K31, ED89), (X1, K31, ED90), (X1, K31, ED91), (X1, K31, ED92), (X2, K1, ED1), (X2, K1, ED2), (X2, K1, ED3), (X2, K1, ED4), (X2, K1, ED5), (X2, K1, ED6), (X2, K1, ED7), (X2, K1, ED8), (X2, K1, ED9), (X2, K1, ED10), (X2, K1, ED11), (X2, K1, ED12), (X2, K1, ED13), (X2, K1, ED14), (X2, K1, ED15), (X2, K1, ED16), (X2, K1, ED17), (X2, K1, ED18), (X2, K1, ED19), (X2, K1, ED20), (X2, K1, ED21), (X2, K1, ED22), (X2, K1, ED23), (X2, K1, ED24), (X2, K1, ED25), (X2, K1, ED26), (X2, K1, ED27), (X2, K1, ED28), (X2, K1, ED29), (X2, K1, ED30), (X2, K1, ED31), (X2, K1, ED32), (X2, K1, ED33), (X2, K1, ED34), (X2, K1, ED35), (X2, K1, ED36), (X2, K1, ED37), (X2, K1, ED38), (X2, K1, ED39), (X2, K1, ED40), (X2, K1, ED41), (X2, K1, ED42), (X2, K1, ED43), (X2, K1, ED44), (X2, K1, ED45), (X2, K1, ED46), (X2, K1, ED47), (X2, K1, ED48), (X2, K1, ED49), (X2, K1, ED50), (X2, K1, ED51), (X2, K1, ED52), (X2, K1, ED53), (X2, K1, ED54), (X2, K1, ED55), (X2, K1, ED56), (X2, K1, ED57), (X2, K1, ED58), (X2, K1, ED59), (X2, K1, ED60), (X2, K1, ED61), (X2, K1, ED62), (X2, K1, ED63), (X2, K1, ED64), (X2, K1, ED65), (X2, K1, ED66), (X2, K1, ED67), (X2, K1, ED68), (X2, K1, ED69), (X2, K1, ED70), (X2, K1, ED71), (X2, K1, ED72), (X2, K1, ED73), (X2, K1, ED74), (X2, K1, ED75), (X2, K1, ED76), (X2, K1, ED77), (X2, K1, ED78), (X2, K1, ED79), (X2, K1, ED80), (X2, K1, ED81), (X2, K1, ED82), (X2, K1, ED83), (X2, K1, ED84), (X2, K1, ED85), (X2, K1, ED86), (X2, K1, ED87), (X2, K1, ED88), (X2, K1, ED89), (X2, K1, ED90), (X2, K1, ED91), (X2, K1, ED92), (X2, K2, ED1), (X2, K2, ED2), (X2, K2, ED3), (X2, K2, ED4), (X2, K2, ED5), (X2, K2, ED6), (X2, K2, ED7), (X2, K2, ED8), (X2, K2, ED9), (X2, K2, ED10), (X2, K2, ED11), (X2, K2, ED12), (X2, K2, ED13), (X2, K2, ED14), (X2, K2, ED15), (X2, K2, ED16), (X2, K2, ED17), (X2, K2, ED18), (X2, K2, ED19), (X2, K2, ED20), (X2, K2, ED21), (X2, K2, ED22), (X2, K2, ED23), (X2, K2, ED24), (X2, K2, ED25), (X2, K2, ED26), (X2, K2, ED27), (X2, K2, ED28), (X2, K2, ED29), (X2, K2, ED30), (X2, K2, ED31), (X2, K2, ED32), (X2, K2, ED33), (X2, K2, ED34), (X2, K2, ED35), (X2, K2, ED36), (X2, K2, ED37), (X2, K2, ED38), (X2, K2, ED39), (X2, K2, ED40), (X2, K2, ED41), (X2, K2, ED42), (X2, K2, ED43), (X2, K2, ED44), (X2, K2, ED45), (X2, K2, ED46), (X2, K2, ED47), (X2, K2, ED48), (X2, K2, ED49), (X2, K2, ED50), (X2, K2, ED51), (X2, K2, ED52), (X2, K2, ED53), (X2, K2, ED54), (X2, K2, ED55), (X2, K2, ED56), (X2, K2, ED57), (X2, K2, ED58), (X2, K2, ED59), (X2, K2, ED60), (X2, K2, ED61), (X2, K2, ED62), (X2, K2, ED63), (X2, K2, ED64), (X2, K2, ED65), (X2, K2, ED66), (X2, K2, ED67), (X2, K2, ED68), (X2, K2, ED69), (X2, K2, ED70), (X2, K2, ED71), (X2, K2, ED72), (X2, K2, ED73), (X2, K2, ED74), (X2, K2, ED75), (X2, K2, ED76), (X2, K2, ED77), (X2, K2, ED78), (X2, K2, ED79), (X2, K2, ED80), (X2, K2, ED81), (X2, K2, ED82), (X2, K2, ED83), (X2, K2, ED84), (X2, K2, ED85), (X2, K2, ED86), (X2, K2, ED87), (X2, K2, ED88), (X2, K2, ED89), (X2, K2, ED90), (X2, K2, ED91), (X2, K2, ED92), (X2, K3, ED1), (X2, K3, ED2), (X2, K3, ED3), (X2, K3, ED4), (X2, K3, ED5), (X2, K3, ED6), (X2, K3, ED7), (X2, K3, ED8), (X2, K3, ED9), (X2, K3, ED10), (X2, K3, ED11), (X2, K3, ED12), (X2, K3, ED13), (X2, K3, ED14), (X2, K3, ED15), (X2, K3, ED16), (X2, K3, ED17), (X2, K3, ED18), (X2, K3, ED19), (X2, K3, ED20), (X2, K3, ED21), (X2, K3, ED22), (X2, K3, ED23), (X2, K3, ED24), (X2, K3, ED25), (X2, K3, ED26), (X2, K3, ED27), (X2, K3, ED28), (X2, K3, ED29), (X2, K3, ED30), (X2, K3, ED31), (X2, K3, ED32), (X2, K3, ED33), (X2, K3, ED34), (X2, K3, ED35), (X2, K3, ED36), (X2, K3, ED37), (X2, K3, ED38), (X2, K3, ED39), (X2, K3, ED40), (X2, K3, ED41), (X2, K3, ED42), (X2, K3, ED43), (X2, K3, ED44), (X2, K3, ED45), (X2, K3, ED46), (X2, K3, ED47), (X2, K3, ED48), (X2, K3, ED49), (X2, K3, ED50), (X2, K3, ED51), (X2, K3, ED52), (X2, K3, ED53), (X2, K3, ED54), (X2, K3, ED55), (X2, K3, ED56), (X2, K3, ED57), (X2, K3, ED58), (X2, K3, ED59), (X2, K3, ED60), (X2, K3, ED61), (X2, K3, ED62), (X2, K3, ED63), (X2, K3, ED64), (X2, K3, ED65), (X2, K3, ED66), (X2, K3, ED67), (X2, K3, ED68), (X2, K3, ED69), (X2, K3, ED70), (X2, K3, ED71), (X2, K3, ED72), (X2, K3, ED73), (X2, K3, ED74), (X2, K3, ED75), (X2, K3, ED76), (X2, K3, ED77), (X2, K3, ED78), (X2, K3, ED79), (X2, K3, ED80), (X2, K3, ED81), (X2, K3, ED82), (X2, K3, ED83), (X2, K3, ED84), (X2, K3, ED85), (X2, K3, ED86), (X2, K3, ED87), (X2, K3, ED88), (X2, K3, ED89), (X2, K3, ED90), (X2, K3, ED91), (X2, K3, ED92), (X2, K6, ED1), (X2, K4, ED2), (X2, K4, ED3) (X2, K4, ED4), (X2, K4, ED5), (X2, K6, ED6), (X2, K4, ED7), (X2, K6, ED8), (X2, K4, ED9), (X2, K4, ED10), (X2, K4, ED11), (X2, K4, ED12), (X2, K4, ED13), (X2, K4, ED14), (X2, K4, ED15), (X2, K6, ED16), (X2, K4, ED17), (X2, K4, ED18), (X2, K4, ED19), (X2, K4, ED20), (X2, K4, ED21), (X2, K4, ED22), (X2, K4, ED23), (X2, K4, ED24), (X2, K4, ED25), (X2, K4, ED26), (X2, K4, ED27), (X2, K4, ED28), (X2, K4, ED29), (X2, K4, ED30), (X2, K4, ED31), (X2, K4, ED32), (X2, K4, ED33), (X2, K4, ED34), (X2, K4, ED35), (X2, K4, ED36), (X2, K4, ED37), (X2, K4, ED38), (X2, K4, ED39), (X2, K6, ED40), (X2, K6, ED41), (X2, K4, ED42), (X2, K4, ED43), (X2, K6, ED44), (X2, K4, ED45), (X2, K4, ED46), (X2, K4, ED47), (X2, K4, ED48), (X2, K4, ED49), (X2, K4, ED50), (X2, K4, ED51), (X2, K4, ED52), (X2, K4, ED53), (X2, K4, ED54), (X2, K4, ED55), (X2, K4, ED56), (X2, K4, ED57), (X2, K4, ED58), (X2, K4, ED59), (X2, K4, ED60), (X2, K4, ED61), (X2, K4, ED62), (X2, K4, ED63), (X2, K4, ED64), (X2, K4, ED65), (X2, K4, ED66), (X2, K4, ED67), (X2, K4, ED68), (X2, K4, ED69), (X2, K4, ED70), (X2, K4, ED71), (X2, K4, ED72), (X2, K4, ED73), (X2, K4, ED74), (X2, K4, ED75), (X2, K4, ED76), (X2, K4, ED77), (X2, K4, ED78), (X2, K4, ED79), (X2, K4, ED80), (X2, K6, ED81), (X2, K4, ED82), (X2, K4, ED83), (X2, K1, ED84), (X2, K6, ED85), (X2, K6, ED86), (X2, K6, ED87), (X2, K6, ED88), (X2, K4, ED89), (X2, K4, ED90), (X2, K4, ED91), (X2, K4, ED92), (X2, K5, ED1), (X2, K5, ED2), (X2, K5, ED3), (X2, K5, EN), (X2, K5, ED5), (X2, K5, ED6), (X2, K5, ED7), (X2, K5, ED8), (X2, K5, ED9), (X2, K5, ED10), (X2, K5, ED11), (X2, K5, ED12), (X2, K5, ED13), (X2, K5, ED14), (X2, K5, ED15), (X2, K5, ED16), (X2, K5, ED17), (X2, K5, ED18), (X2, K5, ED19), (X2, K5, ED20), (X2, K5, ED21), (X2, K5, ED22), (X2, K5, ED23), (X2, K5, ED24), (X2, K5, ED25), (X2, K5, ED26), (X2, K5, ED27), (X2, K5, ED28), (X2, K5, ED29), (X2, K5, ED38), (X2, K5, ED31), (X2, K5, ED32), (X2, K5, ED33), (X2, K5, ED34), (X2, K5, ED35), (X2, K5, ED36), (X2, K5, ED37), (X2, K5, ED38), (X2, K5, ED39), (X2, K5, ED40), (X2, K5, ED41), (X2, K5, ED42), (X2, K5, ED43), (X2, K5, ED44), (X2, K5, ED45), (X2, K5, ED46), (X2, K5, ED47), (X2, K5, ED48), (X2, K5, ED49), (X2, K5, ED50), (X2, K5, ED51), (X2, K5, ED52), (X2, K5, ED53), (X2, K5, ED54), (X2, K5, ED55), (X2, K5, ED56), (X2, K5, ED57), (X2, K5, ED58), (X2, K5, ED59), (X2, K5, ED60), (X2, K5, ED61), (X2, K5, ED62), (X2, K5, ED63), (X2, K5, ED64), (X2, K5, ED65), (X2, K5, ED66), (X2, K5, ED67), (X2, K5, ED68), (X2, K5, ED69), (X2, K5, ED70), (X2, K5, ED71), (X2, K5, ED72), (X2, K5, ED73), (X2, K5, ED74), (X2, K5, ED75), (X2, K5, ED76), (X2, K5, ED77), (X2, K5, ED78), (X2, K5, ED79), (X2, K5, ED80), (X2, K5, ED81), (X2, K5, ED82), (X2, K5, ED83), (X2, K5, ED84), (X2, K5, ED85), (X2, K5, ED86), (X2, K5, ED87), (X2, K5, ED88), (X2, K5, ED89), (X2, K5, ED90), (X2, K5, ED91), (X2, K5, ED92), (X2, K6, ED1), (X2, K6, ED2), (X2, K6, ED3), (X2, K6, ED4), (X2, K6, ED5), (X2, K6, ED6), (X2, K6, ED7), (X2, K6, ED8), (X2, K6, ED9), (X2, K6, ED10), (X2, K6, ED11), (X2, K6, ED12), (X2, K6, ED13), (X2, K6, ED14), (X2, K6, ED15), (X2, K6, ED16), (X2, K6, ED17), (X2, K6, ED18), (X2, K6, ED19), (X2, K6, ED20), (X2, K6, ED21), (X2, K6, ED22), (X2, K6, ED23), (X2, K6, ED24), (X2, K6, ED25), (X2, K6, ED26), (X2, K6, ED27), (X2, K6, ED28), (X2, K6, ED29), (X2, K6, ED30), (X2, K6, ED31), (X2, K6, ED32), (X2, K6, ED33), (X2, K6, ED34), (X2, K6, ED35), (X2, K6, ED36), (X2, K6, ED37), (X2, K6, ED38), (X2, K6, ED39), (X2, K6, ED40), (X2, K6, ED41), (X2, K6, ED42), (X2, K6, ED43), (X2, K6, ED44), (X2, K6, ED45), (X2, K6, ED46), (X2, K6, ED47), (X2, K6, ED48), (X2, K6, ED49), (X2, K6, ED50), (X2, K6, ED51), (X2, K6, ED52), (X2, K6, ED53), (X2, K6, ED54), (X2, K6, ED55), (X2, K6, ED56), (X2, K6, ED57), (X2, K6, ED58), (X2, K6, ED59), (X2, K6, ED60), (X2, K6, ED61), (X2, K6, ED62), (X2, K6, ED63), (X2, K6, ED64), (X2, K6, ED65), (X2, K6, ED66), (X2, K6, ED67), (X2, K6, ED68), (X2, K6, ED69), (X2, K6, ED70), (X2, K6, ED71), (X2, K6, ED72), (X2, K6, ED73), (X2, K6, ED74), (X2, K6, ED75), (X2, K6, ED76), (X2, (6, ED77), (X2, K6, ED78), (X2, K6, ED79), (X2, K6, ED80), (X2, K6, ED81), (X2, K6, ED82), (X2, K6, ED83), (X2, K6, ED84), (X2, K6, ED85), (X2, K6, ED86), (X2, K6, ED87), (X2, K6, ED88), (X2, K6, ED89), (X2, K6, ED90), (X2, K6, ED91), (X2, K6, ED92), (X2, K7, ED1), (X2, K7, ED2), (X2, K7, ED3), (X2, K7, ED4), (X2, K7, ED5), (X2, K7, ED6), (X2, K7, ED7), (X2, K7, ED8), (X2, K7, ED9), (X2, K7, ED10), (X2, K7, ED11), (X2, K7, ED12), (X2, K7, ED13), (X2, K7, ED14), (X2, K7, ED15), (X2, K7, ED16), (X2, K7, ED17), (X2, K7, ED18), (X2, K7, ED19), (X2, K7, ED20), (X2, K7, ED21), (X2, K7, ED22), (X2, K7, ED23), (X2, K7, ED24), (X2, K7, ED25), (X2, K7, ED26), (X2, K7, ED27), (X2, K7, ED28), (X2, K7, ED29), (X2, K7, ED30), (X2, K7, ED31), (X2, K7, ED32), (X2, K7, ED33), (X2, K7, ED34), (X2, K7, ED35), (X2, K7, ED36), (X2, K7, ED37), (X2, K7, ED38), (X2, K7, ED39), (X2, K7, ED40), (X2, K7, ED41), (X2, K7, ED42), (X2, K7, ED43), (X2, K7, ED44), (X2, K7, ED45), (X2, K7, ED46), (X2, K7, ED47), (X2, K7, ED48), (X2, K7, ED49), (X2, K7, ED50), (X2, K7, ED51), (X2, K7, ED52), (X2, K7, ED53), (X2, K7, ED54), (X2, K7, ED55), (X2, K7, ED56), (X2, K7, ED57), (X2, K7, ED58), (X2, K7, ED59), (X2, K7, ED60), (X2, K7, ED61), (X2, K7, ED62), (X2, K7, ED63), (X2, K7, ED64), (X2, K7, ED65), (X2, K7, ED66), (X2, K7, ED67), (X2, K7, ED68), (X2, K7, ED69), (X2, K7, ED70), (X2, K7, ED71), (X2, K7, ED72), (X2, K7, ED73), (X2, K7, ED74), (X2, K7, ED75), (X2, K7, ED76), (X2, K7, ED77), (X2, K7, ED78), (X2, K7, ED79), (X2, K7, ED80), (X2, K7, ED81), (X2, K7, ED82), (X2, K7, ED83), (X2, K7, ED84), (X2, K7, ED85), (X2, K7, ED86), (X2, K7, ED87), (X2, K7, ED88), (X2, K7, ED89), (X2, K7, ED90), (X2, K7, ED91), (X2, K7, ED92), (X2, K8, ED1), (X2, K8, ED2), (X2, K8, ED3), (X2, K8, ED4), (X2, K8, ED5), (X2, K8, ED6), (X2, K8, ED7), (X2, K8, ED8), (X2, K8, ED9), (X2, K8, ED10), (X2, K8, ED11), (X2, K8, ED12), (X2, K8, ED13), (X2, K8, ED14), (X2, K8, ED15), (X2, K8, ED16), (X2, K8, ED17), (X2, K8, ED18), (X2, K8, ED19), (X2, K8, ED20), (X2, K8, ED21), (X2, K8, ED22), (X2, K8, ED23), (X2, K8, ED24), (X2, K8, ED25), (X2, K8, ED26), (X2, K8, ED27), (X2, K8, ED28), (X2, K8, ED29), (X2, K8, ED30), (X2, K8, ED31), (X2, K8, ED32), (X2, K8, ED33), (X2, K8, ED34), (X2, K8, ED35), (X2, K8, ED36), (X2, K8, ED37), (X2, K8, ED38), (X2, K8, ED39), (X2, K8, ED40), (X2, K8, ED41), (X2, K8, ED42), (X2, K8, ED43), (X2, K8, ED44), (X2, K8, ED45), (X2, K8, ED46), (X2, K8, ED47), (X2, K8, ED48), (X2, K8, ED49), (X2, K8, ED50), (X2, K8, ED51), (X2, K8, ED52), (X2, K8, ED53), (X2, K8, ED54), (X2, K8, ED55), (X2, K8, ED56), (X2, K8, ED57), (X2, K8, ED58), (X2, K8, ED59), (X2, K8, ED60), (X2, K8, ED61), (X2, K8, ED62), (X2, K8, ED63), (X2, K8, ED64), (X2, X8, ED65), (X2, K8, ED66), (X2, K8, ED67), (X2, K8, ED68), (X2, K8, ED69), (X2, K8, ED70), (X2, K8, ED71), (X2, K8, ED72), (X2, K8, ED73), (X2, K8, ED74), (X2, K8, ED75), (X2, K8, ED76), (X2, K8, ED77), (X2, K8, ED78), (X2, K8, ED79), (X2, K8, ED80), (X2, K8, ED81), (X2, K8, ED82), (X2, K8, ED83), (X2, K8, ED84), (X2, K8, ED85), (X2, K8, ED86), (X2, K8, ED87), (X2, K8, ED88), (X2, K8, ED89), (X2, K8, ED90), (X2, K8, ED91), (X2, K8, ED92), (X2, K9, ED1), (X2, K9, ED2), (X2, K9, ED3), (X2, K9, ED4), (X2, K9, ED5), (X2, K9, ED6), (X2, K9, ED7), (X2, K9, ED8), (X2, K9, ED9), (X2, K9, ED10), (X2, K9, ED11), (X2, K9, ED12), (X2, K9, ED13), (X2, K9, ED14), (X2, K9, ED15), (X2, K9, ED16), (X2, K9, ED17), (X2, K9, ED18), (X2, K9, ED19), (X2, K9, ED20), (X2, K9, ED21), (X2, K9, ED22), (X2, K9, ED23), (X2, K9, ED24), (X2, K9, ED25), (X2, K9, ED26), (X2, K9, ED27), (X2, K9, ED28), (X2, K9, ED29), (X2, K9, ED30), (X2, K9, ED31), (X2, K9, ED32), (X2, K9, ED33), (X2, K9, ED34), (X2, K9, ED35), (X2, K9, ED36), (X2, K5, ED37), (X2, K9, ED38), (X2, K9, ED39), (X2, K9, ED40), (X2, K9, ED41), (X2, K9, ED42), (X2, K9, ED43), (X2, K9, ED44), (X2, K9, ED45), (X2, K9, ED46), (X2, K9, ED47), (X2, K9, ED48), (X2, K9, ED49), (X2, K9, ED50), (X2, K9, ED51), (X2, K9, ED52), (X2, K9, ED53), (X2, K9, ED54), (X2, K9, ED55), (X2, K9, ED56), (X2, K9, ED57), (X2, K9, ED58), (X2, K9, ED59), (X2, K9, ED60), (X2, K9, ED61), (X2, K9, ED62), (X2, K9, ED63), (X2, K9, ED64), (X2, K9, ED65), (X2, K9, ED66), (X2, K9, ED67), (X2, K9, ED68), (X2, K9, ED69), (X2, K9, ED70), (X2, K9, ED71), (X2, K9, ED72), (X2, K9, ED73), (X2, K9, ED74), (X2, K9, ED75), (X2, K9, ED76), (X2, K9, ED77), (X2, K9, ED78), (X2, K9, ED79), (X2, K9, ED80), (X2, K9, ED81), (X2, K9, ED82), (X2, K9, ED83), (X2, K9, ED84), (X2, K9, ED85), (X2, K9, ED86), (X2, K9, ED87), (X2, K9, ED88), (X2, K9, ED89), (X2, K9, ED90), (X2, K9, ED91), (X2, K9, ED92), (X2, K10, ED1), (X2, K10, ED2), (X2, K10, ED3), (X2, K10, ED4), (X2, K10, ED5), (X2, K10, ED6), (X2, K10, ED7), (X2, K10, ED8), (X2, K10, ED9), (X2, K10, ED10), (X2, K10, ED11), (X2, K10, ED12), (X2, K10, ED13), (X2, K10, ED14), (X2, K10, ED15), (X2, K10, ED16), (X2, K10, ED17), (X2, K10, ED18), (X2, K10, ED19), (X2, K10, ED20), (X2, K10, ED21), (X2, K10, ED22), (X2, K10, ED23), (X2, K10, ED24), (X2, K10, ED25), (X2, K10, ED26), (X2, K10, ED27), (X2, K10, ED28), (X2, K10, ED29), (X2, K10, ED30), (X2, K10, ED31), (X2, K10, ED32), (X2, K10, ED33), (X2, K10, ED34), (X2, K10, ED35), (X2, K10, ED36), (X2, K10, ED37), (X2, K10, ED38), (X2, K10, ED39), (X2, K10, ED40), (X2, K10, ED41), (X2, K10, ED42), (X2, K10, ED43), (X2, K10, ED44), (X2, K10, ED45), (X2, K10, ED46), (X2, K10, ED47), (X2, K10, ED48), (X2, K10, ED49), (X2, K10, ED50), (X2, K10, ED51), (X2, K10, ED52), (X2, K10,

ED53), (X2, K10, ED54), (X2, K10, ED55), (X2, K10, ED56), (X2, K10, ED57), (X2, K10, ED58), (X2, K10, ED59), (X2, K10, ED60), (X2, K10, ED61), (X2, K10, ED62), (X2, K10, ED63), (X2, K10, ED64), (X2, K10, ED65), (X2, K10, ED66), (X2, K10, ED67), (X2, K10, ED68), (X2, K10, ED69), (X2, K10, ED70), (X2, K10, ED71), (X2, K10, ED72), (X2, K10, ED73), (X2, K10, ED74), (X2, K10, ED75), (X2, K10, ED76), (X2, K10, ED77), (X2, K10, ED78), (X2, K10, ED79), (X2, K10, ED80), (X2, K10, ED81), (X2, K10, ED82), (X2, K10, ED83), (X2, K10, ED84), (X2, K10, ED85), (X2, K10, ED86), (X2, K10, ED87), (X2, K10, ED88), (X2, K10, ED89), (X2, K10, ED90), (X2, K10, ED91), (X2, K10, ED92), (X2, K11, ED1), (X2, K11, ED2), (X2, K11, ED3), (X2, K11, ED4), (X2, K11, ED5), (X2, K11, ED6), (X2, K11, ED7), (X2, K11, ED8), (X2, K11, ED9), (X2, K11, ED10), (X2, K11, ED11), (X2, K11, ED12), (X2, K11, ED13), (X2, K11, ED14), (X2, K11, ED15), (X2, K11, ED16), (X2, K11, ED17), (X2, K11, ED18), (X2, K11, ED19), (X2, K11, ED20), (X2, K11, ED21), (X2, K11, ED22), (X2, K11, ED23), (X2, K11, ED24), (X2, K11, ED25), (X2, K11, ED26), (X2, K11, ED27), (X2, K11, ED28), (X2, K11, ED29), (X2, K11, ED30), (X2, K11, ED31), (X2, K11, ED32), (X2, K11, ED33), (X2, K11, ED34), (X2, K11, ED35), (X2, K11, ED36), (X2, K11, ED37), (X2, K11, ED38), (X2, K11, ED39), (X2, K11, ED40), (X2, K11, ED41), (X2, K11, ED42), (X2, K11, ED43), (X2, K11, ED44), (X2, K11, ED45), (X2, K11, ED46), (X2, K11, ED47), (X2, K11, ED48), (X2, K11, ED49), (X2, K11, ED50), (X2, K11, ED51), (X2, K11, ED52), (X2, K11, ED53), (X2, K11, ED54), (X2, K11, ED55), (X2, K11, ED56), (X2, K11, ED57), (X2, K11, ED58), (X2, K11, ED59), (X2, K11, ED60), (X2, K11, ED61), (X2, K11, ED62), (X2, K11, ED63), (X2, K11, ED64), (X2, K11, ED65), (X2, K11, ED66), (X2, K11, ED67), (X2, K11, ED68), (X2, K11, ED69), (X2, K11, ED70), (X2, K11, ED71), (X2, K11, ED72), (X2, K11, ED73), (X2, K11, ED74), (X2, K11, ED75), (X2, K11, ED76), (X2, K11, ED77), (X2, K11, ED78), (X2, K11, ED79), (X2, K11, ED80), (X2, K11, ED81), (X2, K11, ED82), (X2, K11, ED83), (X2, K11, ED84), (X2, K11, ED85), (X2, K11, ED86), (X2, K11, ED87), (X2, K11, ED88), (X2, K11, ED89), (X2, K11, ED90), (X2, K11, ED91), (X2, K11, ED92), (X2, K12, ED1), (X2, K12, ED2), (X2, K12, ED3), (X2, K12, ED4), (X2, K12, ED5), (X2, K12, ED6), (X2, K12, ED7), (X2, K12, ED8), (X2, K12, ED9), (X2, K12, ED10), (X2, K12, ED11), (X2, K12, ED12), (X2, K12, ED13), (X2, K12, ED14), (X2, K12, ED5), (X2, K12, ED16), (X2, K12, ED17), (X2, K12, ED18), (X2, K12, ED19), (X2, K12, ED20), (X2, K12, ED21), (X2, K12, ED22), (X2, K12, £023), (X2, K12, ED24), (X2, K12, ED25), (X2, K12, ED26), (X2, K12, £027), (X2, K12, ED28), (X2, K12, ED29), (X2, K12, ED30), (X2, K12, ED31), (X2, K12, ED32), (X2, K12, ED33), (X2, K12, ED34), (X2, K12, ED35), (X2, K12, ED36), (X2, K12, ED37), (X2, K12, ED38), (X2, K12, ED39), (X2, K12, ED40), (X2, K12, ED41), (X2, K12, ED42), (X2, K12, ED43), (X2, K12, ED44), (X2, K12, ED45), (X2, K12, ED46), (X2, K12, ED47), (X2, K12, ED48), (X2, K12, ED49), (X2, K12, ED50), (X2, K12, ED51), (X2, K12, ED52), (X2, K12, ED53), (X2, K12, ED54), (X2, K12, ED55), (X2, K12, ED56), (X2, K12, ED57), (X2, K12, ED58), (X2, K12, ED59), (X2, K12, ED60), (X2, K12, ED61), (X2, K12, ED62), (X2, K12, ED63), (X2, K12, ED64), (X2, K12, ED65), (X2, K12, ED66), (X2, K12, ED67), (X2, K12, ED68), (X2, K12, ED69), (X2, K12, ED70), (X2, K12, ED71), (X2, K12, ED72), (X2, K12, ED73), (X2, K12, ED74), (X2, K12, ED75), (X2, K12, ED76), (X2, K12, ED77), (X2, K12, ED78), (X2, K12, ED79), (X2, K12, ED80), (X2, K12, ED81), (X2, K12, ED82), (X2, K12, ED83), (X2, K12, ED84), (X2, K12, ED85), (X2, K12, ED86), (X2, K12, ED87), (X2, K12, ED88), (X2, K12, ED89), (X2, K12, ED90), (X2, K12, ED91), (X2, K12, ED92), (X2, K13, ED1), (X2, K13, ED2), (X2, K13, ED3), (X2, K13, ED4), (X2, K13, ED5), (X2, K13, ED6), (X2, K13, ED7), (X2, K13, ED8), (X2, K13, ED9), (X2, K13, ED10), (X2, K13, ED11), (X2, K13, ED12), (X2, K13, ED13), (X2, K13, ED14), (X2, K13, ED15), (X2, K13, ED16), (X2, K13, ED17), (X2, K13, ED18), (X2, K13, ED19), (X2, K13, ED20), (X2, K13, ED21), (X2, K13, ED22), (X2, K13, ED23), (X2, K13, ED24), (X2, K13, ED25), (X2, K13, ED26), (X2, K13, ED27), (X2, K13, ED22), (X2, K13, ED29), (X2, K13, ED30), (X2, K13, ED31), (X2, K13, ED32), (X2, K13, ED33), (X2, K13, ED34), (X2, K13, ED35), (X2, K13, ED36), (X2, K13, ED37), (X2, K13, ED38), (X2, K13, ED39), (X2, K13, ED40), (X2, K13, ED41), (X2, K13, ED42), (X2, K13, ED43), (X2, K13, ED44), (X2, K13, ED45), (X2, K13, ED46), (X2, K13, ED47), (X2, K13, ED48), (X2, K13, ED49), (X2, K13, ED50), (X2, K13, ED51), (X2, K13, ED52), (X2, K13, ED53), (X2, K13, ED54), (X2, K13, ED55), (X2, K13, ED56), (X2, K13, ED57), (X2, K13, ED58), (X2, K13, ED59), (X2, K13, ED60), (X2, K13, ED61), (X2, K13, ED62), (X2, K13, ED63), (X2, K13, ED64), (X2, K13, ED65), (X2, K13, ED66), (X2, K13, ED67), (X2, K13, ED68), (X2, K13, ED69), (X2, K13, ED70), (X2, K13, ED71), (X2, K13, ED72), (X2, K13, ED73), (X2, K13, ED74), (X2, K13, ED75), (X2, K13, ED76), (X2, K13, ED77), (X2, K13, ED78), (X2, K13, ED79), (X2, K13, ED80), (X2, K13, ED81), (X2, K13, ED82), (X2, K13, ED83), (X2, K13, ED84), (X2, K13, ED85), (X2, K13, ED86), (X2, K13, ED87), (X2, K13, ED88), (X2, K13, ED89), (X2, K13, ED90), (X2, K13, ED91), (X2, K13, ED92), (X2, K14, ED1), (X2, K14, ED2), (X2, K14, ED3), (X2, K14, ED4), (X2, K14, ED5), (X2, K14, ED6), (X2, K14, ED7), (X2, K14, ED8), (X2, K14, ED9), (X2, K14, ED10), (X2, K14, ED11), (X2, K14, ED12), (X2, K14, ED13), (X2, K14, ED14), (X2, K14, ED15), (X2, K14, ED16), (X2, K14, ED17), (X2, K14, ED18), (X2, K14, ED19), (X2, K14, ED20), (X2, K14, ED21), (X2, K14, ED22), (X2, K14, ED23), (X2, K14, ED24), (X2, K14, ED25), (X2, K14, ED26), (X2, K14, ED27), (X2, K14, ED28), (X2, K14, ED29), (X2, K14, ED30), (X2, K14, ED31), (X2, K14, ED32), (X2, K14, ED33), (X2, K14, ED34), (X2, K14, ED35), (X2, K14, ED36), (X2, K14, ED37), (X2, K14, ED38), (X2, K14, ED39), (X2, K14, ED40), (X2, K14, ED41), (X2, K14, ED42), (X2, K14, ED43), (X2, K14, ED44), (X2, K14, ED45), (X2, K14, ED46), (X2, K14, ED47), (X2, K14, ED48), (X2, K14, ED49), (X2, K14, ED50), (X2, K14, ED51), (X2, K14, ED52), (X2, K14, ED53), (X2, K14, ED54), (X2, K14, ED55), (X2, K14, ED56), (X2, K14, ED57), (X2, K14, ED58), (X2, K14, ED59), (X2, K14, ED60), (X2, K14, ED61), (X2, K14, ED62), (X2, K14, ED63), (X2, K14, ED64), (X2, K14, ED65), (X2, K14, ED66), (X2, K14, ED67), (X2, K14, ED68), (X2, K14, ED69), (X2, K14, ED70), (X2, K14, ED71), (X2, K14, ED72), (X2, K14, ED73), (X2, K14, ED74), (X2, K14, ED75), (X2, K14, ED76), (X2, K14, ED77), (X2, K14, ED78), (X2, K14, ED79), (X2, K14, ED80), (X2, K14, ED81), (X2, K14, ED82), (X2, K14, ED83), (X2, K14, ED84), (X2, K14, ED85), (X2, K14, ED86), (X2, K14, ED87), (X2, K14, ED88), (X2, K14, ED89), (X2, K14, ED90), (X2, K14, ED91), (X2, K14, ED92), (X2, K15, ED1), (X2, K15, ED2), (X2, K15, ED3), (X2, K15, ED4), (X2, K15, ED5), (X2, K15, ED6), (X2, K15, ED7), (X2, K15, ED8), (X2, K15, ED9), (X2, K15, ED10), (X2, K15, ED11), (X2, K15, ED12), (X2, K15, ED13), (X2, K15, ED14), (X2, K15, ED15), (X2, K15, ED16), (X2, K15, ED17), (X2, K15, ED18), (X2, K15, ED19), (X2, K15, ED20), (X2, K15, ED21), (X2, K15, ED22), (X2, K15, ED23), (X2, K15, ED24), (X2, X15, ED25), (X2, K15, ED26), (X2, K15, ED27), (X2, K15, ED28), (X2, K15, ED29), (X2, K15, ED30), (X2, K15, ED31), (X2, K15, ED32), (X2, X15, ED33), (X2, K15, ED34), (X2, K15, ED35), (X2, K15, ED36), (X2, K15, ED37), (X2, K15, ED38), (X2, K15, ED39), (X2, K15, ED40), (X2, K15, ED41), (X2, K15, ED42), (X2, K15, ED43), (X2, K15, ED44), (X2, K15, ED45), (X2, K15, ED46), (X2, K15, ED47), (X2, K15, ED48), (X2, K15, ED49), (X2, K15, ED50), (X2, K15, ED51), (X2, K15, ED52), (X2, K15, ED53), (X2, K15, ED54), (X2, K15, ED55), (X2, K15, ED56), (X2, K15, ED57), (X2, K15, ED58), (X2, K15, ED59), (X2, K15, ED60), (X2, K15, ED61), (X2, K15, ED62), (X2, K15, ED63), (X2, K15, ED64), (X2, K15, ED65), (X2, K15, ED66), (X2, K15, ED67), (X2, K15, ED66), (X2, K15, ED69), (X2, K15, ED70), (X2, K15, ED71), (X2, K15, ED72), (X2, K15, ED73), (X2, K15, ED74), (X2, K15, ED75), (X2, K15, ED76), (X2, K15, ED77), (X2, K15, ED78), (X2, K15, ED79), (X2, K15, ED80), (X2, K15, ED81), (X2, K15, ED82), (X2, K15, ED83), (X2, K15, ED84), (X2, K15, ED85), (X2, K15, ED86), (X2, K15, ED87), (X2, K15, ED86), (X2, K15, ED89), (X2, K15, ED90), (X2, K15, ED91), (X2, K15, ED92), (X2, K16, ED1), (X2, K16, ED2), (X2, K16, ED3), (X2, K16, ED4), (X2, K16, ED5), (X2, K16, ED6), (X2, K16, E7), (X2, K16, ED8), (X2, K16, ED9), (X2, K16, ED10), (X2, K16, ED11), (X2, K16, ED12), (X2, K16, ED12), (X2, K16, ED14), (X2, K16, ED15), (X2, K16, ED16), (X2, K16, ED17), (X2, K16, ED18), (X2, K16, ED19), (X2, K16, ED20), (X2, K16, ED21), (X2, K16, ED22), (X2, K16, ED23), (X2, K16, ED24), (X2, K16, ED25), (X2, K16, ED26), (X2, K16, ED27), (X2, K16, ED28), (X2, K16, ED29), (X2, X16, ED30), (X2, K16, ED31), (X2, K16, ED32), (X2, K16, ED33), (X2, K16, ED34), (X2, K16, ED35), (X2, K16, ED36), (X2, K16, ED37), (X2, K16, ED38), (X2, K16, ED39), (X2, K16, ED40), (X2, K16, ED41), (X2, K16, ED42), (X2, K16, ED43), (X2, K16, ED44), (X2, K16, ED45), (X2, K16, ED46), (X2, K16, ED47), (X2, K16, ED48), (X2, K16, ED49), (X2, K16, ED50), (X2, K16, ED51), (X2, K16, ED52), (X2, K16, ED53), (X2, K16, ED54), (X2, K16, ED55), (X2, K16, ED56), (X2, K16, ED57), (X2, K16, ED58), (X2, K16, ED59), (X2, K16, ED60), (X2, K16, ED61), (X2, K16, ED62), (X2, K16, ED63), (X2, K16, ED64), (X2, K16, ED65), (X2, K16, ED66), (X2, K16, ED67), (X2, K16, ED68), (X2, K16, ED69), (X2, K16, ED70), (X2, K16, ED71), (X2, K16, ED72), (X2, K16, ED73), (X2, K16, ED74), (X2, K16, ED75), (X2, K16, ED76), (X2, K16, ED77), (X2, K16, ED78), (X2, K16, ED79), (X2, K16, ED80), (X2, K16, ED81), (X2, K16, ED82), (X2, K16, ED83), (X2, K16, ED84), (X2, K16, ED85), (X2, K16, ED86), (X2, K16, ED87), (X2, K16, ED88), (X2, K16, ED89), (X2, K16, ED90), (X2, K16, ED91), (X2, K16, ED92), (X2, K17, ED1), (X2, K17, ED2), (X2, K17, ED3), (X2, K17, ED4), (X2, K17, ED5), (X2, K17, ED6), (X2, K17, ED7), (X2, K17, ED8), (X2, K17, ED9), (X2, K17, ED10), (X2, K17, ED11), (X2, K17, ED12), (X2, K17, ED13), (X2, K17, ED14), (X2, K17, ED15), (X2, K17, ED16), (X2, K17, ED17), (X2, K17, ED18), (X2, K17, ED19), (X2, K17, ED20), (X2, K17, ED21), (X2, K17, ED22), (X2, K17, ED23), (X2, K17, ED24), (X2, K17, ED25), (X2, K17, ED26), (X2, K17, ED27), (X2, K17, ED28), (X2, K17, ED29), (X2, K17, ED30), (X2, K17, ED31), (X2, K17, ED32), (X2, K17, ED33), (X2, K17, ED34), (X2, K17, ED35), (X2, K17, ED36), (X2, K17, ED37), (X2, K17, ED38), (X2, K17, ED39), (X2, K17, ED40), (X2, K17, ED41), (X2, K17, ED42), (X2, K17, ED43), (X2, K17, ED44), (X2, K17, ED45), (X2, K17, ED46), (X2, K17, ED47), (X2, K17 ED48), (X2, K17, ED49), (X2, K17, ED50), (X2, K17, ED51), (X2, K17, ED52), (X2, K17, ED53), (X2, K17, ED54), (X2, K17, ED55), (X2, K17, ED56), (X2, K17, ED57), (X2, K17, ED58), (X2, K17, ED59), (X2, K17, ED60), (X2, K17, ED61), (X2, K17, ED62), (X2, K17, ED63), (X2, K17, ED64), (X2, K17, ED65), (X2, K17, ED66), (X2, K17, ED67), (X2, K17, ED68), (X2, K17, ED69), (X2, K17, ED70), (X2, K17, ED71), (X2, K17, ED72), (X2, K17, ED73), (X2, K17, ED74), (X2, K17, ED75), (X2, K17, ED76), (X2, K17, ED77), (X2, K17, ED78), (X2, K17, ED79), (X2, K17, ED80), (X2, K17, ED81), (X2, K17, ED82), (X2, K17, ED83), (X2, K17, ED84), (X2, K17, ED85), (X2, K17, ED86), (X2, K17, ED87), (X2, K17, ED88), (X2, K17, ED89), (X2, K17, ED90), (X2, K17, ED91), (X2, K17, ED92), (X2, K18, ED1), (X2, K18, ED2), (X2, K18, ED3), (X2, K18, ED4), (X2, K18, ED5), (X2, K18, ED6), (X2, K18, ED7), (X2, K18, ED8), (X2, K18, ED9), (X2, K18, ED10), (X2, K18, ED11), (X2, K18, ED12), (X2, K18, ED13), (X2, K18, ED14), (X2, K18, ED15), (X2, K18, ED16), (X2, K18, ED17), (X2, K18, ED18), (X2, K18, ED19), (X2, K18, ED20), (X2, K18, ED21), (X2, K18, ED22), (X2, K18, ED23), (X2, K18, ED24), (X2, K18, ED25), (X2, K18, ED26), (X2, K18, ED27), (X2, K18, ED28), (X2, K18, ED29), (X2, K18, ED30), (X2, K18, ED31), (X2, K18, ED32), (X2, K18, ED33), (X2, K18, ED34), (X2, K18, ED35), (X2, K18, ED36), (X2, K18, ED37), (X2, K18, ED38), (X2, K18, ED39), (X2, K18, ED40), (X2, K18, ED41), (X2, K18, ED42), (X2, K18, ED43), (X2, K18, ED44), (X2, K18, ED45), (X2, K18, ED46), (X2, K18, ED47), (X2, K18, ED48), (X2, K18, ED49), (X2, K18, ED50), (X2, K18, ED51), (X2, K18, ED52), (X2, K18, ED53), (X2, K18, ED54), (X2, K18, ED55), (X2, K18, ED56), (X2, K18, ED57), (X2, K18, ED58), (X2, K18, ED59), (X2, K18, ED60), (X2, K18, ED61), (X2, K18, ED62), (X2, K18, ED63), (X2, K18, ED64), (X2, K18, ED65), (X2, K18, ED66), (X2, K18, ED67), (X2, K18, ED68), (X2, K18, ED69), (X2, K18, ED70), (X2, K18, ED71), (X2, K18, ED72), (X2, K18, ED73), (X2, X18, ED74), (X2, K18, ED75), (X2, K18, ED76), (X2, K18, ED77), (X2, K18, ED78), (X2, K18, ED79), (X2, K18, ED80), (X2, K18, ED81), (X2, X18, ED82), (X2, K18, ED83), (X2, K18, ED84), (X2, K18, ED85), (X2, K18, ED86), (X2, K18, ED87), (X2, K18, ED88), (X2, K18, ED89), (X2, X18, ED90), (X2, K18, ED91), (X2, K18, ED92), (X2, K19, ED1), (X2, K19, ED2), (X2, K19, ED3), (X2, K19, ED4), (X2, K19, ED5), (X2, K19, ED6), (X2, K19, ED7), (X2, K19, ED8), (X2, K19, ED9), (X2, K19, ED10), (X2, K19, ED11), (X2, K19, ED12), (X2, K19, ED13), (X2, K19, ED14), (X2, K19, ED15), (X2, K19, ED16), (X2, K19, ED17), (X2, K19, ED18), (X2, K19, ED19), (X2, K19, ED20), (X2, K19, ED21), (X2, K19, ED22), (X2, K19, ED23), (X2, K19, ED24), (X2, K19, ED25), (X2, K19, ED26), (X2, K19, ED27), (X2, K19, ED28), (X2, K19, ED29), (X2, K19, ED30), (X2, K19, ED31), (X2, K19, ED32), (X2, K19, ED33), (X2, K19, ED34), (X2, K19, ED35), (X2, K19, ED36), (X2, K19, ED37), (X2, K19, ED38), (X2, K19, ED39), (X2, K19, ED40), (X2, K19, ED41), (X2, K19, ED42), (X2, K19, ED43), (X2, K19, ED44), (X2, K19, ED45), (X2, K19, ED46), (X2, K19,

ED47), (X2, K19, ED48), (X2, K19, ED49), (X2, K19, ED50), (X2, K19, ED51), (X2, K19, ED52), (X2, K19, ED53), (X2, K19, ED54), (X2, K19, ED55), (X2, K19, ED56), (X2, K19, ED57), (X2, K19, ED58), (X2, K19, ED59), (X2, K19, ED60), (X2, K19, ED61), (X2, K19, ED62), (X2, K19, ED63), (X2, K19, ED64), (X2, K19, ED65), (X2, K19, ED66), (X2, K19, ED67), (X2, K19, ED68), (X2, K19, ED69), (X2, K19, ED70), (X2, K19, ED71), (X2, K19, ED72), (X2, K19, ED73), (X2, K19, ED74), (X2, K19, ED75), (X2, K19, ED76), (X2, K19, ED77), (X2, K19, ED78), (X2, K19, ED79), (X2, K19, ED80), (X2, K19, ED81), (X2, K19, ED82), (X2, K19, ED83), (X2, K19, ED84), (X2, K19, ED85), (X2, K19, ED86), (X2, K19, ED87), (X2, K19, ED88), (X2, K19, ED89), (X2, K19, ED90), (X2, K19, ED91), (X2, K19, ED92), (X2, K20, ED1), (X2, K20, ED2), (X2, K20, ED3), (X2, K20, ED4), (X2, K20, ED5), (X2, K20, ED6), (X2, K20, ED7), (X2, K20, ED8), (X2, K20, ED9), (X2, K20, ED10), (X2, K20, ED11), (X2, K20, ED12), (X2, K20, ED13), (X2, K20, ED14), (X2, K20, ED15), (X2, K20, ED16), (X2, K20, ED17), (X2, K20, ED18), (X2, K20, ED19), (X2, K20, ED20), (X2, K20, ED21), (X2, K20, ED22), (X2, K20, ED23), (X2, K20, ED24), (X2, K20, ED25), (X2, K20, ED26), (X2, K20, ED27), (X2, K20, ED28), (X2, K20, ED29), (X2, K20, ED30), (X2, K20, ED31), (X2, K20, ED32), (X2, K20, ED33), (X2, K20, ED34), (X2, K20, ED35), (X2, K20, ED36), (X2, K20, ED37), (X2, K20, ED38), (X2, K20, ED39), (X2, K20, ED40), (X2, K20, ED41), (X2, K20, ED42), (X2, K20, ED43), (X2, K20, ED44), (X2, K20, ED45), (X2, K20, ED46), (X2, K20, ED47), (X2, K20, ED48), (X2, K20, ED49), (X2, K20, ED50), (X2, K20, ED51), (X2, K20, ED52), (X2, K20, ED53), (X2, K20, ED54), (X2, K20, ED55), (X2, K20, ED56), (X2, K20, ED57), (X2, K20, ED58), (X2, K20, ED59), (X2, K20, ED60), (X2, K20, ED61), (X2, K20, ED62), (X2, K20, ED63), (X2, K20, ED64), (X2, K20, ED65), (X2, K20, ED66), (X2, K20, ED67), (X2, K20, ED68), (X2, K20, ED69), (X2, K20, ED70), (X2, K20, ED71), (X2, K20, ED72), (X2, K20, ED73), (X2, K20, ED74), (X2, K20, ED75), (X2, K20, ED76), (X2, K20, ED77), (X2, K20, ED78), (X2, K20, ED79), (X2, K20, ED80), (X2, K20, ED81), (X2, K20, ED82), (X2, K20, ED83), (X2, K20, ED84), (X2, K20, ED85), (X2, K20, ED86), (X2, K20, ED87), (X2, K20, ED88), (X2, K20, ED89), (X2, K20, ED90), (X2, K20, ED91), (X2, K20, ED92), (X2, K21, ED1), (X2, K21, ED2), (X2, K21, En), (X2, K21, ED4), (X2, K21, ED5), (X2, K21, ED6), (X2, K21, ED7), (X2, K21, ED8), (X2, K21, ED9), (X2, K21, ED10), (X2, K21, ED11), (X2, K21, ED12), (X2, K21, ED13), (X2, K21, ED14), (X2, K21, ED15), (X2, K21, ED16), (X2, K21, ED17), (X2, K21, ED18), (X2, K21, ED19), (X2, K21, ED20), (X2, K21, ED21), (X2, K21, ED22), (X2, K21, ED23), (X2, K21, ED24), (X2, K22, ED25), (X2, K21, ED26), (X2, K21, ED27), (X2, K21, ED28), (X2, K21, ED29), (X2, K21, ED30), (X2, K21, ED31), (X2, K21, ED32), (X2, K21, ED33), (X2, K21, ED34), (X2, K21, ED35), (X2, K21, ED36), (X2, K21, ED37), (X2, K21, ED38), (X2, K21, ED38), (X2, K21, ED40), (X2, K21, ED41), (X2, K21, ED42), (X2, K21, ED43), (X2, K21, ED44), (X2, K21, ED45), (X2, K21, ED46), (X2, K21, ED47), (X2, K21, ED48), (X2, K21, ED49), (X2, K21, ED50), (X2, K21, ED51), (X2, K21, ED52), (X2, K21, ED53), (X2, K21, ED54), (X2, K21, ED55), (X2, K21, ED56), (X2, K21, ED57), (X2, K21, ED58), (X2, K21, ED59), (X2, K21, ED60), (X2, K21, ED61), (X2, K21, ED62), (X2, K21, ED63), (X2, K21, ED64), (X2, K21, ED65), (X2, K21, ED66), (X2, K21, ED67), (X2, K21, ED68), (X2, K21, ED69), (X2, K21, ED70), (X2, K21, ED71), (X2, K21, ED72), (X2, K21, ED73), (X2, K21, ED74), (X2, K21, ED75), (X2, K21, ED76), (X2, K21, ED77), (X2, K21, ED78), (X2, K21, ED79), (X2, K21, ED80), (X2, K21, ED81), (X2, K21, ED82), (X2, K21, ED83), (X2, K21, ED84), (X2, K21, ED85), (X2, K21, ED86), (X2, K21, ED87), (X2, K21, ED88), (X2, K21, ED89), (X2, K21, K21, ED90), (X2, K21, ED91), (X2, K21, ED92), (X2, K22, ED1), (X2, K22, ED2), (X2, K22, ED3), (X2, K22, ED4), (X2, K22, ED5), (X2, K22, ED6), (X2, K22, ED7), (X2, K22, ED8), (X2, K22, ED9), (X2, K22, ED10), (X2, K22, ED11), (X2, K22, ED12), (X2, K22, ED13), (X2, K22, ED14), (X2, K22, ED15), (X2, K22, ED16), (X2, K22, ED17), (X2, K22, ED18), (X2, K22, ED19), (X2, K22, ED20), (X2, K22, ED21), (X2, K22, ED22), (X2, K22, ED23), (X2, K22, ED24), (X2, K22, ED25), (X2, K22, ED26), (X2, K22, ED27), (X2, K22, ED28), (X2, K22, ED29), (X2, K22, ED30), (X2, K22, ED31), (X2, K22, ED32), (X2, K22, ED33), (X2, K22, ED34), (X2, K22, ED35), (X2, K22, ED36), (X2, K22, ED37), (X2, K22, ED38), (X2, K22, ED39), (X2, X22, ED40), (X2, K22, ED41), (X2, K22, ED42), (X2, K22, ED43), (X2, K22, ED44), (X2, K22, ED45), (X2, K22, ED46), (X2, K22, ED47), (X2, X22, ED48), (X2, K22, ED49), (X2, K22, ED50), (X2, K22, ED51), (X2, K22, ED52), (X2, K22, ED53), (X2, K22, ED54), (X2, K22, ED55), (X2, K22, ED56), (X2, K22, ED57), (X2, K22, ED58), (X2, K22, ED59), (X2, K22, ED60), (X2, K22, ED61), (X2, K22, ED62), (X2, K22, ED63), (X2, K22, ED64), (X2, K22, ED65), (X2, K22, ED66), (X2, K22, ED67), (X2, K22, ED68), (X2, K22, ED69), (X2, K22, ED70), (X2, K22, ED71), (X2, K22, ED72), (X2, K22, ED73), (X2, K22, ED74), (X2, K22, ED75), (X2, K22, ED76), (X2, K22, ED77), (X2, K22, ED78), (X2, K22, ED79), (X2, K22, ED80), (X2, K22, ED81), (X2, K22, ED82), (X2, K22, ED83), (X2, K22, ED84), (X2, K22, ED85), (X2, K22, ED86), (X2, K22, ED87), (X2, K22, ED88), (X2, K22, ED89), (X2, K22, ED90), (X2, K22, ED91), (X2, K22, ED92), (X2, K23, ED1), (X2, K23, ED2), (X2, K23, ED3), (X2, K23, ED4), (X2, K23, ED5), (X2, K23, ED6), (X2, K23, ED7), (X2, K23, ED8), (X2, K23, ED9), (X2, K23, ED10), (X2, K23, ED11), (X2, K23, ED12), (X2, K23, ED13), (X2, K23, ED14), (X2, K23, ED15), (X2, K23, ED16), (X2, K23, ED17), (X2, K23, ED18), (X2, K23, ED19), (X2, K23, ED20), (X2, K23, ED21), (X2, K23, ED22), (X2, K23, ED23), (X2, K23, ED24), (X2, K23, ED25), (X2, K23, ED26), (X2, K23, ED27), (X2, K23, ED28), (X2, K23, ED29), (X2, K23, ED30), (X2, K23, ED31), (X2, K23, ED32), (X2, K23, ED33), (X2, K23, ED34), (X2, K23, ED35), (X2, K23, ED36), (X2, K23, ED37), (X2, K23, ED38), (X2, K23, ED39), (X2, K23, ED40), (X2, K23, ED41), (X2, K23, ED42), (X2, K23, ED43), (X2, K23, ED44), (X2, X23, ED45), (X2, K23, ED46), (X2, K23, ED47), (X2, K23, ED48), (X2, K23, ED49), (X2, K23, ED50), (X2, K23, ED51), (X2, K23, ED52), (X2, K23, ED53), (X2, K23, ED54), (X2, K23, ED55), (X2, K23, ED56), (X2, K23, ED57), (X2, K23, ED58), (X2, K23, ED59), (X2, K23, ED60), (X2, K23, ED61), (X2, K23, ED62), (X2, K23, ED63), (X2, K23, ED64), (X2, K23, ED65), (X2, K23, ED66), (X2, K23, ED67), (X2, K23, ED68), (X2, K23, ED69), (X2, K23, ED70), (X2, K23, ED71), (X2, K23, ED72), (X2, K23, ED73), (X2, K23, ED74), (X2, K23, ED75), (X2, K23, ED76), (X2, K23, ED77), (X2, K23, ED78), (X2, K23, ED79), (X2, K23, ED80), (X2, K23, ED81), (X2, K23, ED82), (X2, K23, ED83), (X2, K23, ED84), (X2, K23, ED85), (X2, K23,

ED86), (X2, K23, ED87), (X2, K23, ED88), (X2, K23, ED89), (X2, K23, ED90), (X2, K23, ED91), (X2, K23, ED92), (X2, K24, ED1), (X2, K24, ED2), (X2, K24, ED3), (X2, K24, ED4), (X2, K24, ED5), (X2, K24, ED6), (X2, K24, ED7), (X2, K24, ED8), (X2, K24, ED9), (X2, K24, ED10), (X2, K24, ED11), (X2, K24, ED12), (X2, K24, ED13), (X2, K24, ED14), (X2, K24, ED15), (X2, K24, ED16), (X2, K24, ED17), (X2, K24, ED18), (X2, K24, ED19), (X2, K24, ED20), (X2, K24, ED21), (X2, K24, ED22), (X2, K24, ED23), (X2, K24, ED24), (X2, K24, ED25), (X2, K24, ED26), (X2, K24, ED27), (X2, K24, ED28), (X2, K24, ED29), (X2, K24, ED30), (X2, K24, ED31), (X2, K24, ED32), (X2, K24, ED33), (X2, K24, ED34), (X2, K24, ED35), (X2, K24, ED36), (X2, K24, ED37), (X2, K24, ED38), (X2, K24, ED39), (X2, K24, ED40), (X2, K24, ED41), (X2, K24, ED42), (X2, K24, ED43), (X2, K24, ED44), (X2, K24, ED45), (X2, K24, ED46), (X2, K24, ED47), (X2, K24, ED18), (X2, K24, ED49), (X2, K24, ED50), (X2, K24, ED51), (X2, K24, ED52), (X2, K24, ED53), (X2, K24, ED54), (X2, K24, ED55), (X2, K24, ED56), (X2, K24, ED57), (X2, K24, ED58), (X2, K24, ED59), (X2, K24, ED60), (X2, K24, ED61), (X2, K24, ED62), (X2, K24, ED63), (X2, K24, ED61), (X2, K24, ED65), (X2, K24, ED66), (X2, K24, ED67), (X2, K24, ED68), (X2, K24, ED69), (X2, K24, ED70), (X2, K24, ED71), (X2, K24, ED72), (X2, K24, ED73), (X2, K24, ED74), (X2, K24, ED75), (X2, K24, ED76), (X2, K24, ED77), (X2, K24, ED78), (X2, K24, ED79), (X2, K24, ED80), (X2, K24, ED81), (X2, K24, ED82), (X2, K24, ED83), (X2, K24, ED81), (X2, K24, ED85), (X2, K24, ED86), (X2, K24, ED87), (X2, K24, ED88), (X2, K24, ED89), (X2, K24, ED90), (X2, K24, ED91), (X2, K24, ED92), (X2, K25, ED1), (X2, K25, ED2), (X2, K25, ED3), (X2, K25, ED4), (X2, K25, ED5), (X2, K25, ED6), (X2, K25, ED7), (X2, K25, ED8), (X2, K25, ED9), (X2, K25, ED10), (X2, K25, ED11), (X2, K25, ED12), (X2, K25, ED13), (X2, K25, ED14), (X2, K25, ED15), (X2, K25, ED16), (X2, K25, ED17), (X2, K25, ED18), (X2, K25, ED19), (X2, K25, ED20), (X2, K25, ED21), (X2, K25, ED22), (X2, K25, ED23), (X2, K25, ED24), (X2, K25, ED25), (X2, K25, ED26), (X2, K25, ED27), (X2, K25, ED28), (X2, X25, ED29), (X2, K25, ED30), (X2, K25, ED31), (X2, K25, ED32), (X2, K25, ED33), (X2, K25, ED34), (X2, K25, ED35), (X2, K25, ED36), (X2, X25, ED37), (X2, K25, ED38), (X2, K25, ED39), (X2, K25, ED40), (X2, K25, ED41), (X2, K25, ED42), (X2, K25, ED43), (X2, K25, ED44), (X2, K25, ED45), (X2, K25, ED46), (X2, K25, ED47), (X2, K25, ED48), (X2, K25, ED49), (X2, K25, ED50), (X2, K25, ED51), (X2, K25, ED52), (X2, K25, ED53), (X2, K25, ED54), (X2, K25, ED55), (X2, K25, ED56), (X2, K25, ED57), (X2, K25, ED58), (X2, K25, ED59), (X2, K25, ED60), (X2, K25, ED61), (X2, K25, ED62), (X2, K25, ED63), (X2, K25, ED64), (X2, K25, ED65), (X2, K25, ED66), (X2, K25, ED67), (X2, K25, ED68), (X2, K25, ED69), (X2, K25, ED70), (X2, K25, ED71), (X2, K25, ED72), (X2, K25, ED73), (X2, K25, ED74), (X2, K25, ED75), (X2, K25, ED76), (X2, K25, ED77), (X2, K25, ED78), (X2, K25, ED79), (X2, K25, ED80), (X2, K25, ED81), (X2, K25, ED82), (X2, K25, ED83), (X2, K25, ED84), (X2, K25, ED85), (X2, K25, ED86), (X2, K25, ED87), (X2, K25, ED88), (X2, K25, ED89), (X2, K25, ED90), (X2, K25, ED91), (X2, K25, ED92), (X2, K26, ED1), (X2, K26, ED2), (X2, K26, ED3), (X2, K26, ED4), (X2, K26, ED5), (X2, K26, ED6), (X2, K26, ED7), (X2, K26, ED8), (X2, K26, ED9), (X2, K26, ED10), (X2, K26, ED11), (X2, K26, ED12), (X2, K26, ED11), (X2, K26, ED14), (X2, K26, ED15), (X2, K26, ED16), (X2, K26, ED17), (X2, K26, ED18), (X2, K26, ED19), (X2, K26, ED20), (X2, K26, ED21), (X2, K26, ED22), (X2, K26, ED23), (X2, K26, ED24), (X2, K26, ED25), (X2, K26, ED26), (X2, K26, ED27), (X2, K26, ED28), (X2, K26, ED29), (X2, K26, ED30), (X2, K26, ED31), (X2, K26, ED32), (X2, K26, ED33), (X2, X26, ED34), (X2, K26, ED35), (X2, K26, ED36), (X2, K26, ED37), (X2, K26, ED38), (X2, K26, ED39), (X2, K26, ED40), (X2, K26, ED41), (X2, K26, ED42), (X2, K26, ED43), (X2, K26, ED44), (X2, K26, ED45), (X2, K26, ED46), (X2, K26, ED47), (X2, K26, ED48), (X2, K26, ED49), (X2, K26, ED50), (X2, K26, ED51), (X2, K26, ED52), (X2, K26, ED53), (X2, K26, ED54), (X2, K26, ED55), (X2, K26, ED56), (X2, K26, ED57), (X2, K26, ED58), (X2, K26, ED59), (X2, K26, ED60), (X2, K26, ED61), (X2, K26, ED62), (X2, K26, ED63), (X2, K26, ED64), (X2, K26, ED65), (X2, K26, ED66), (X2, K26, ED67), (X2, K26, ED68), (X2, K26, ED69), (X2, K26, ED70), (X2, K26, ED71), (X2, K26, ED72), (X2, K26, ED73), (X2, K26, ED74), (X2, K26, ED75), (X2, K26, ED76), (X2, K26, ED77), (X2, K26, ED78), (X2, K26, ED79), (X2, K26, ED80), (X2, K26, ED81), (X2, K26, ED82), (X2, K26, ED83), (X2, K26, ED84), (X2, K26, ED85), (X2, K26, ED86), (X2, K26, ED87), (X2, K26, ED88), (X2, K26, ED89), (X2, K26, ED90), (X2, K26, ED91), (X2, K26, ED92), (X2, K27, ED1), (X2, K27, ED2), (X2, K27, ED3), (X2, K27, ED4), (X2, K27, ED5), (X2, K27, ED6), (X2, K27, ED7), (X2, K27, ED8), (X2, K27, ED9), (X2, X27, ED10), (X2, K27, ED11), (X2, K27, ED12), (X2, K27, ED13), (X2, K27, ED14), (X2, K27, ED15), (X2, K27, ED16), (X2, K27, ED17), (X2, K27, ED18), (X2, K27, ED19), (X2, K27, ED20), (X2, K27, ED21), (X2, K27, ED22), (X2, K27, ED23), (X2, K27, ED24), (X2, K27, ED25), (X2, K27, ED26), (X2, K27, ED27), (X2, K27, ED28), (X2, K27, ED29), (X2, K27, ED30), (X2, K27, ED31), (X2, K27, ED32), (X2, K27, ED33), (X2, K27, ED34), (X2, K27, ED35), (X2, K27, ED36), (X2, K27, ED37), (X2, K27, ED38), (X2, K27, ED39), (X2, K27, ED40), (X2, K27, ED41), (X2, K27, ED42), (X2, K27, ED43), (X2, K27, ED44), (X2, K27, ED45), (X2, K27, ED46), (X2, K27, ED47), (X2, K27, ED48), (X2, K27, ED49), (X2, K27, ED50), (X2, K27, ED51), (X2, K27, ED52), (X2, K27, ED53), (X2, K27, ED54), (X2, K27, ED55), (X2, K27, ED56), (X2, K27, ED57), (X2, K27, ED58), (X2, K27, ED59), (X2, K27, ED60), (X2, K27, ED61), (X2, K27, ED62), (X2, K27, ED63), (X2, K27, ED64), (X2, K27, ED65), (X2, K27, ED66), (X2, K27, ED67), (X2, K27, ED68), (X2, K27, ED69), (X2, K27, ED70), (X2, K27, ED71), (X2, K27, ED72), (X2, K27, ED73), (X2, K27, ED74), (X2, K27, ED75), (X2, K27, ED76), (X2, K27, ED77), (X2, K27, ED78), (X2, K27, ED79), (X2, K27, ED80), (X2, K27, ED81), (X2, K27, ED82), (X2, K27, ED83), (X2, K27, ED84), (X2, K27, ED85), (X2, K27, ED86), (X2, K27, ED87), (X2, K27, ED88), (X2, K27, ED89), (X2, K27, ED90), (X2, K27, ED91), (X2, K27, ED92), (X2, K28, ED1), (X2, K28, ED2), (X2, K28, ED3), (X2, K28, ED4), (X2, K28, ED5), (X2, K28, ED6), (X2, K28, ED7), (X2, K28, ED8), (X2, K28, ED9), (X2, K28, ED10), (X2, K28, ED11), (X2, K23, ED12), (X2, K28, ED13), (X2, K23, ED14), (X2, K28, ED15), (X2, K28, ED16), (X2, K28, ED17), (X2, X28, ED18), (X2, K28, ED19), (X2, K28, ED23), (X2, K28, ED21), (X2, K28, ED22), (X2, K28, ED23), (X2, K28, ED24), (X2, K28, ED25), (X2, X28, ED26), (X2, K28, ED27), (X2, K28, ED28), (X2, K23, ED29), (X2, K28, ED30), (X2, K28, ED31), (X2, K28, ED32), (X2, K28, ED33), (X2, K28, ED34), (X2, K28, ED35), (X2, K28, ED36), (X2, K28, ED37), (X2, K28,

ED38), (X2, K28, ED39), (X2, K28, ED40), (X2, K28, ED41), (X2, K28, ED42), (X2, K23, ED43), (X2, K28, ED44), (X2, K28, ED45), (X2, K28, ED46), (X2, K28, ED47), (X2, K28, ED48), (X2, K28, ED49), (X2, K28, ED58), (X2, K28, ED51), (X2, K28, ED52), (X2, K28, ED53), (X2, K28, ED54), (X2, K28, ED55), (X2, K28, ED56), (X2, K28, ED57), (X2, K28, ED58), (X2, K28, ED59), (X2, K28, ED60), (X2, K28, ED61), (X2, K26, ED62), (X2, K28, ED63), (X2, K26, ED64), (X2, K28, ED65), (X2, K28, ED66), (X2, K28, ED67), (X2, K28, ED66), (X2, K28, ED69), (X2, K28, ED70), (X2, K28, ED71), (X2, K28, ED72), (X2, K28, ED73), (X2, K28, ED74), (X2, K28, ED75), (X2, K28, ED76), (X2, K23, ED77), (X2, K28, ED78), (X2, K28, ED79), (X2, K26, ED80), (X2, K28, ED81), (X2, X28, ED82), (X2, K28, ED83), (X2, K28, ED84), (X2, K28, ED65), (X2, X28, ED86), (X2, K28, ED87), (X2, K26, ED88), (X2, K23, ED89), (X2, K28, ED90), (X2, K23, ED91), (X2, K28, ED92), (X2, K29, ED1), (X2, K29, ED2), (X2, K29, ED3), (X2, K29, ED4), (X2, K29, ED5), (X2, K29, ED6), (X2, K29, ED7), (X2, K29, ED8), (X2, K29, ED9), (X2, K29, ED10), (X2, K29, ED11), (X2, K29, ED12), (X2, K29, ED13), (X2, K29, ED14), (X2, K29, ED15), (X2, K29, ED16), (X2, K29, ED17), (X2, K29, ED18), (X2, K29, ED19), (X2, K29, ED20), (X2, K29, ED21), (X2, K29, ED22), (X2, K29, ED23), (X2, K29, ED24), (X2, K29, ED25), (X2, K29, ED26), (X2, K29, ED27), (X2, K29, ED28), (X2, K29, ED29), (X2, K29, ED30), (X2, K29, ED31), (X2, K29, ED32), (X2, K29, ED33), (X2, K29, ED34), (X2, K29, ED35), (X2, K29, ED36), (X2, K29, ED37), (X2, K29, ED38), (X2, K29, ED39), (X2, K29, ED40), (X2, K29, ED41), (X2, K29, ED42), (X2, K29, ED43), (X2, K29, ED44), (X2, K29, ED45), (X2, K29, ED46), (X2, K29, ED47), (X2, K29, ED48), (X2, K29, ED49), (X2, K29, ED50), (X2, K29, ED51), (X2, K29, ED52), (X2, K29, ED53), (X2, K29, ED54), (X2, K29, ED55), (X2, K29, ED56), (X2, K29, ED57), (X2, K29, ED58), (X2, K29, ED59), (X2, K29, ED60), (X2, K29, ED61), (X2, K29, ED62), (X2, K29, ED63), (X2, K29, ED64), (X2, K29, ED65), (X2, K29, ED66), (X2, K29, ED67), (X2, K29, ED68), (X2, K29, ED69), (X2, K29, ED70), (X2, K29, ED71), (X2, K29, ED72), (X2, K29, ED73), (X2, K29, ED74), (X2, K29, ED75), (X2, K29, ED76), (X2, K29, ED77), (X2, K29, ED78), (X2, K29, ED79), (X2, K29, ED80), (X2, K29, ED81), (X2, K29, ED82), (X2, K29, ED83), (X2, K29, ED84), (X2, K29, ED85), (X2, K29, ED86), (X2, K29, ED87), (X2, K29, ED88), (X2, K29, ED89), (X2, K29, ED90), (X2, K29, ED91), (X2, K29, ED92), (X2, K30, ED1), (X2, K30, ED2), (X2, K30, ED3), (X2, K30, ED4), (X2, K30, ED5), (X2, K30, ED6), (X2, K30, ED7), (X2, K30, ED8), (X2, K30, ED9), (X2, K30, ED10), (X2, K30, ED11), (X2, K30, ED12), (X2, K30, ED13), (X2, K30, ED14), (X2, K30, ED15), (X2, K30, ED16), (X2, K30, ED17), (X2, K30, ED18), (X2, K30, ED19), (X2, K30, ED20), (X2, K30, ED21), (X2, K30, ED22), (X2, K30, ED23), (X2, K30, ED24), (X2, K30, ED25), (X2, K30, ED26), (X2, K30, ED27), (X2, K30, ED28), (X2, K30, ED29), (X2, K30, ED30), (X2, K30, ED31), (X2, K30, ED32), (X2, K30, ED33), (X2, K30, ED34), (X2, K30, ED35), (X2, K30, ED36), (X2, K30, ED37), (X2, K30, ED38), (X2, K30, ED39), (X2, K30, ED40), (X2, K30, ED41), (X2, K30, ED42), (X2, K30, ED43), (X2, K30, ED44), (X2, K20, ED45), (X2, K30, ED46), (X2, K30, ED47), (X2, K30, ED48), (X2, K30, ED49), (X2, K30, ED50), (X2, K30, ED51), (X2, K30, ED52), (X2, K20, ED53), (X2, K30, ED54), (X2, K30, ED55), (X2, K30, ED56), (X2, K30, ED57), (X2, K30, ED58), (X2, K30, ED59), (X2, K30, ED60), (X2, K30, ED61), (X2, K30, ED62), (X2, K30, ED63), (X2, K30, ED64), (X2, K30, ED65), (X2, K30, ED66), (X2, K30, ED67), (X2, K30, ED68), (X2, K30, ED69), (X2, K30, ED70), (X2, K30, ED71), (X2, K30, ED72), (X2, K30, ED73), (X2, K30, ED74), (X2, K30, ED75), (X2, K30, ED76), (X2, K30, ED77), (X2, K30, ED78), (X2, K30, ED79), (X2, K30, ED80), (X2, K30, ED81), (X2, K30, ED82), (X2, K30, ED83), (X2, K30, ED84), (X2, K30, ED85), (X2, K30, ED86), (X2, K30, ED87), (X2, K30, ED88), (X2, K30, ED89), (X2, K30, ED90), (X2, K30, ED91), (X2, K30, ED92), (X2, K31, ED1), (X2, K31, ED2), (X2, K31, ED3), (X2, K31, ED4), (X2, K31, ED5), (X2, K31, ED6), (X2, K31, ED7), (X2, K31, ED8), (X2, K31, ED9), (X2, K31, ED10), (X2, K31, ED11), (X2, K31, ED12), (X2, K31, ED13), (X2, K31, ED14), (X2, K31, ED15), (X2, K31, ED16), (X2, K31, ED17), (X2, K31, ED18), (X2, K31, ED19), (X2, K31, ED20), (X2, K31, ED21), (X2, K31, ED22), (X2, K31, ED23), (X2, K31, ED24), (X2, K31, ED25), (X2, K31, ED26), (X2, K31, ED27), (X2, K31, ED28), (X2, K31, ED29), (X2, K31, ED30), (X2, K31, ED31), (X2, K31, ED32), (X2, K31, ED33), (X2, K31, ED34), (X2, K31, ED35), (X2, K31, ED36), (X2, K31, ED37), (X2, K31, ED38), (X2, K31, ED39), (X2, K31, ED40), (X2, K31, ED41), (X2, K31, ED42), (X2, K31, ED43), (X2, K31, ED44), (X2, K31, ED45), (X2, K31, ED46), (X2, K31, ED47), (X2, K31, ED48), (X2, K31, ED49), (X2, K31, ED50), (X2, K31, ED51), (X2, K31, ED52), (X2, K31, ED53), (X2, K31, ED54), (X2, K31, ED55), (X2, K31, ED56), (X2, K31, ED57), (X2, K31, ED58), (X2, K31, ED59), (X2, K31, ED60), (X2, K31, ED61), (X2, K31, ED62), (X2, K31, ED63), (X2, K31, ED64), (X2, K31, ED65), (X2, K31, ED66), (X2, K31, ED67), (X2, K31, ED68), (X2, K31, ED69), (X2, K31, ED70), (X2, K31, ED71), (X2, K31, ED72), (X2, K31, ED73), (X2, K31, ED74), (X2, K31, ED75), (X2, K31, ED76), (X2, K31, ED77), (X2, K31, ED78), (X2, K31, ED79), (X2, K31, ED80), (X2, K31, ED81), (X2, K31, ED82), (X2, K31, ED82), (X2, K31, ED84), (X2, K31, ED85), (X2, K31, ED86), (X2, K31, ED87), (X2, K31, ED88), (X2, K31, ED89), (X2, K31, ED90), (X2, K31, ED91), (X2, K31, ED92), (X3, K1, ED1), (X3, K1, ED2), (X3, K1, ED3), (X3, K1, ED4), (X3, K1, ED5), (X3, K1, ED6), (X3, K1, ED7), (X3, K1, ED8), (X3, K1, ED9), (X3, K1, ED10), (X3, K1, ED11), (X3, K1, ED12), (X3, K1, ED13), (X3, K1, ED14), (X3, K1, ED15), (X3, K1, ED16), (X3, K1, ED17), (X3, K1, ED18), (X3, K1, ED19), (X3, K1, ED20), (X3, K1, ED21), (X3, K1, ED22), (X3, K1, ED23), (X3, K1, ED24), (X3, K1, ED25), (X3, K1, ED26), (X3, K1, ED27), (X3, K1, ED28), (X3, K1, ED29), (X3, K1, ED30), (X3, K1, ED31), (X3, K1, ED32), (X3, K1, ED33), (X3, K1, ED34), (X3, K1, ED35), (X3, K1, ED36), (X3, K1, ED37), (X3, K1, ED38), (X3, K1, ED39), (X3, K1, ED40), (X3, K1, ED41), (X3, K1, ED42), (X3, K1, ED43), (X3, K1, ED44), (X3, K1, ED45), (X3, K1, ED46), (X3, K1, ED47), (X3, K1, ED48), (X3, K1, ED49), (X3, K1, ED50), (X3, K1, ED51), (X3, K1, ED52), (X3, K1, ED53), (X3, K1, ED54), (X3, K1, ED55), (X3, K1, ED56), (X3, K1, ED57), (X3, K1, ED58), (X3, K1, ED59), (X3, K1, ED60), (X3, K1, ED61), (X3, K1, ED62), (X3, K1, ED63), (X3, K1, ED64), (X3, K1, ED65), (X3, K1, ED66), (X3, K1, ED67), (X3, K1, ED68), (X3, K1, ED69), (X3, K1, ED70), (X3, K1, ED71), (X3, K1, ED72), (X3, K1, ED73), (X3, K1, ED74), (X3, K1, ED75), (X3, K1, ED76), (X3, K1, ED77), (X3, K1, ED78), (X3, K1, ED79), (X3, K1, ED80), (X3, K1, ED81), (X3, K1, ED82), (X3, K1, ED83), (X3, K1, ED84), (X3, K1,

ED85), (X3, K1, ED86), (X3, K1, ED87), (X3, K1, ED88), (X3, K1, ED89), (X3, K1, ED90), (X3, K1, ED91), (X3, K1, ED92), (X3, K2, ED1), (X3, K2, ED2), (X3, K2, ED3), (X3, K2, ED4), (X3, K2, ED5), (X3, K2, ED6), (X3, K2, ED7), (X3, K2, ED8), (X3, K2, ED9), (X3, K2, ED10), (X3, K2, ED11), (X3, K2, ED12), (X3, K2, ED13), (X3, K2, ED14), (X3, K2, ED15), (X3, K2, ED16), (X3, K2, ED17), (X3, K2, ED18), (X3, K2, ED19), (X3, K2, ED20), (X3, K2, ED21), (X3, K2, ED22), (X3, K2, ED23), (X3, K2, ED24), (X3, K2, ED25), (X3, K2, ED26), (X3, K2, ED27), (X3, K2, ED28), (X3, K2, ED29), (X3, K2, ED30), (X3, K2, ED31), (X3, K2, ED32), (X3, K2, ED33), (X3, K2, ED34), (X3, K2, ED35), (X3, K2, ED36), (X3, K2, ED37), (X3, K2, ED38), (X3, K2, ED39), (X3, K2, ED40), (X3, K2, ED41), (X3, K2, ED42), (X3, K2, ED43), (X3, K2, ED44), (X3, K2, ED45), (X3, K2, ED46), (X3, K2, ED47), (X3, K2, ED48), (X3, K2, ED49), (X3, K2, ED50), (X3, K2, ED51), (X3, K2, ED52), (X3, K2, ED53), (X3, K2, ED54), (X3, K2, ED55), (X3, K2, ED56), (X3, K2, ED57), (X3, K2, ED58), (X3, K2, ED59), (X3, K2, ED60), (X3, K2, ED61), (X3, K2, ED62), (X3, K2, ED63), (X3, K2, ED64), (X3, K2, ED65), (X3, K2, ED66), (X3, K2, ED67), (X3, K2, ED68), (X3, K2, ED69), (X3, K2, ED70), (X3, K2, ED71), (X3, K2, ED72), (X3, K2, ED73), (X3, K2, ED74), (X3, K2, ED75), (X3, K2, ED76), (X3, K2, ED77), (X3, K2, ED78), (X3, K2, ED79), (X3, K2, ED80), (X3, K2, ED81), (X3, K2, ED82), (X3, K2, ED83), (X3, K2, ED84), (X3, K2, ED85), (X3, K2, ED86), (X3, K2, ED87), (X3, K2, ED88), (X3, K2, ED89), (X3, K2, ED90), (X3, K2, ED91), (X3, K2, ED92), (X3, K3, ED1), (X3, K3, ED2), (X3, K3, ED3), (X3, K3, ED4), (X3, K3, ED5), (X3, K3, ED6), (X3, K3, ED7), (X3, K3, ED8), (X3, K3, ED9), (X3, K3, ED10), (X3, K3, ED11), (X3, K3, ED12), (X3, K3, ED13), (X3, K3, ED14), (X3, K3, ED15), (X3, K3, ED16), (X3, K3, ED17), (X3, K3, ED18), (X3, K3, ED19), (X3, K3, ED20), (X3, K3, ED21), (X3, K3, ED22), (X3, K3, ED23), (X3, K3, ED24), (X3, K3, ED25), (X3, K3, ED26), (X3, K3, ED27), (X3, K3, ED28), (X3, K3, ED29), (X3, K3, ED30), (X3, K3, ED31), (X3, K3, ED32), (X3, K3, ED33), (X3, K3, ED34), (X3, K3, ED35), (X3, K3, ED36), (X3, K3, ED37), (X3, K3, ED38), (X3, K3, ED39), (X3, K3, ED40), (X3, K3, ED41), (X3, K3, ED42), (X3, K3, ED43), (X3, K3, ED44), (X3, K3, ED45), (X3, K3, ED46), (X3, K3, ED47), (X3, K3, ED48), (X3, K3, ED49), (X3, K3, ED50), (X3, K3, ED51), (X3, K3, ED52), (X3, K3, ED53), (X3, K3, ED54), (X3, K3, ED55), (X3, K3, ED56), (X3, K3, ED57), (X3, K3, ED58), (X3, K3, ED59), (X3, K3, ED60), (X3, K3, ED61), (X3, K3, ED62), (X3, K3, ED63), (X3, K3, ED64), (X3, K3, ED65), (X3, K3, ED66), (X3, K3, ED67), (X3, K3, ED68), (X3, K3, ED69), (X3, K3, ED70), (X3, K3, ED71), (X3, K3, ED72), (X3, K3, ED73), (X3, K3, ED74), (X3, K3, ED75), (X3, K3, ED76), (X3, K3, ED77), (X3, K3, ED78), (X3, K3, ED79), (X3, K3, ED80), (X3, K3, ED81), (X3, K3, ED82), (X3, K3, ED83), (X3, K3, ED84), (X3, K3, ED85), (X3, K3, ED86), (X3, K3, ED87), (X3, K3, ED88), (X3, K3, ED89), (X3, K3, ED90), (X3, K3, ED91), (X3, K3, ED92), (X3, K4, ED1), (X3, K4, ED2), (X3, K4, ED3), (X3, K4, ED4), (X3, K4, ED5), (X3, K4, ED6), (X3, K4, ED7), (X3, K4, ED8), (X3, K4, ED9), (X3, K4, ED10), (X3, K4, ED11), (X3, K4, ED12), (X3, K4, ED13), (X3, K6, ED14), (X3, K6, ED15), (X3, K4, ED16), (X3, K4, ED17), (X3, K6, ED18), (X3, K4, ED19), (X3, K4, ED20), (X3, K4, ED21), (X3, K4, ED22), (X3, K4, ED23), (X3, K4, ED24), (X3, K4, ED25), (X3, K4, ED26), (X3, K4, ED27), (X3, K4, ED28), (X3, K4, ED29), (X3, K4, ED30), (X3, K4, ED31), (X3, K4, ED32), (X3, K4, ED33), (X3, K4, ED34), (X3, K4, ED35), (X3, K4, ED36), (X3, K4, ED37), (X3, K4, ED38), (X3, K4, ED39), (X3, K4, ED40), (X3, K4, ED41), (X3, K4, ED42), (X3, K4, ED43), (X3, K4, ED44), (X3, K4, ED45), (X3, K4, ED46), (X3, K4, ED47), (X3, K4, ED48), (X3, K4, ED49), (X3, K4, ED50), (X3, K4, ED51), (X3, K4, ED52), (X3, K4, ED53), (X3, K4, ED54), (X3, K6, ED55), (X3, K4, ED56), (X3, K4, ED57), (X3, K1, ED58), (X3, K6, ED59), (X3, K6, ED60), (X3, K6, ED61), (X3, K6, ED62), (X3, K4, ED63), (X3, K4, ED64), (X3, K4, ED65), (X3, K4, ED66), (X3, K4, ED67), (X3, K4, ED68), (X3, K4, ED69), (X3, K4, ED70), (X3, K4, ED71), (X3, K4, ED72), (X3, K4, ED73), (X3, K4, ED74), (X3, K4, ED75), (X3, K4, ED76), (X3, K4, ED77), (X3, K4, ED78), (X3, K4, ED79), (X3, K4, ED80), (X3, K4, ED81), (X3, K4, ED82), (X3, K4, ED83), (X3, K4, ED84), (X3, K4, ED85), (X3, K4, ED86), (X3, K4, ED87), (X3, K4, ED88), (X3, K4, ED89), (X3, K4, ED90), (X3, K4, ED91), (X3, K4, ED92), (X3, K5, ED1), (X3, K5, ED2), (X3, K5, ED3), (X3, K5, ED4), (X3, K5, ED5), (X3, K5, ED6), (X3, K5, ED7), (X3, K5, ED8), (X3, K5, ED9), (X3, K5, ED10), (X3, K5, ED11), (X3, K5, ED12), (X3, K5, ED13), (X3, K5, ED14), (X3, K5, ED15), (X3, K5, ED16), (X3, K5, ED17), (X3, K5, ED18), (X3, K5, ED19), (X3, K5, ED20), (X3, K5, ED21), (X3, K5, ED22), (X3, K5, ED23), (X3, K5, ED24), (X3, K5, ED25), (X3, K5, ED26), (X3, K5, ED27), (X3, K5, ED28), (X3, K5, ED29), (X3, K5, ED30), (X3, K5, ED31), (X3, K5, ED32), (X3, K5, ED33), (X3, K5, ED34), (X3, K5, ED35), (X3, K5, ED36), (X3, K5, ED37), (X3, K5, ED38), (X3, K5, ED39), (X3, K5, ED40), (X3, K5, ED41), (X3, K5, ED42), (X3, K5, ED43), (X3, K5, ED44), (X3, K5, ED45), (X3, K5, ED46), (X3, K5, ED47), (X3, K5, ED48), (X3, K5, ED49), (X3, K5, ED50), (X3, K5, ED51), (X3, K5, ED52), (X3, K5, ED53), (X3, K5, ED54), (X3, K5, ED55), (X3, K5, ED56), (X3, K5, ED57), (X3, K5, ED58), (X3, K5, ED59), (X3, K5, ED60), (X3, K5, ED61), (X3, K5, ED62), (X3, K5, ED63), (X3, K5, ED64), (X3, K5, ED65), (X3, K5, ED66), (X3, K5, ED67), (X3, K5, ED68), (X3, K5, ED69), (X3, K5, ED70), (X3, K5, ED71), (X3, K5, ED72), (X3, K5, ED73), (X3, K5, ED74), (X3, K5, ED75), (X3, K5, ED76), (X3, K5, ED77), (X3, K5, ED78), (X3, K5, ED79), (X3, K5, ED80), (X3, K5, ED81), (X3, K5, ED82), (X3, K5, ED83), (X3, K5, ED84), (X3, K5, ED85), (X3, K5, ED86), (X3, K5, ED87), (X3, K5, ED88), (X3, K5, ED89), (X3, K5, ED90), (X3, K5, ED91), (X3, K5, ED92), (X3, K6, ED1), (X3, K6, ED2), (X3, K6, ED3), (X3, K6, ED4), (X3, K6, ED5), (X3, K6, ED6), (X3, K6, ED7), (X3, K6, ED8), (X3, K6, ED9), (X3, K6, ED10), (X3, K6, ED11), (X3, K6, ED12), (X3, K6, ED13), (X3, K6, ED14), (X3, K6, ED15), (X3, K6, ED16), (X3, K6, ED17), (X3, K6, ED18), (X3, K6, ED19), (X3, K6, ED20), (X3, K6, ED21), (X3, K6, ED22), (X3, K6, ED23), (X3, K6, ED24), (X3, K6, ED25), (X3, K6, ED26), (X3, K6, ED27), (X3, K6, ED28), (X3, K6, ED29), (X3, K6, ED30), (X3, K6, ED31), (X3, K6, ED32), (X3, K6, ED33), (X3, K6, ED34), (X3, K6, ED35), (X3, K6, ED36), (X3, K6, ED37), (X3, K6, ED38), (X3, K6, ED39), (X3, K6, ED40), (X3, K6, ED41), (X3, K6, ED42), (X3, K6, ED43), (X3, K6, ED44), (X3, K6, ED45), (X3, K6, ED46), (X3, K6, ED47), (X3, K6, ED48), (X3, K6, ED49), (X3, K6, ED50), (X3, K6, ED51), (X3, K6, ED52), (X3, K6, ED53), (X3, K6, ED54), (X3, K6, ED55), (X3, K6, ED56), (X3, K6, ED57), (X3, K6, ED58), (X3, K6, ED59), (X3, K6, ED60), (X3, K6, ED61), (X3, K6, ED62), (X3, K6, ED63), (X3, K6, ED64), (X3, K6, ED65), (X3, K6, ED66), (X3, K6, ED67), (X3, K6, ED6.8), (X3, K6, ED69), (X3, K6, ED70), (X3, K6, ED71), (X3, K6, ED72), (X3, K6, ED73), (X3, K6, ED74), (X3, K6, ED75), (X3, K6, ED76), (X3, K6, ED77), (X3, K6, ED78), (X3, K6, ED79), (X3, K6, ED80), (X3, K6, ED81), (X3, K6, ED82), (X3, K6, ED83), (X3, K6, ED84), (X3, K6, ED85), (X3, K6, ED86), (X3, K6, ED87), (X3, K6, ED88), (X3, K6, ED89), (X3, K6, ED90), (X3, K6, ED91), (X3, K6, ED92), (X3, K7, ED1), (X3, K7, ED2), (X3, K7, ED3), (X3, K7, ED4), (X3,

K7, ED5), (X3, K7, ED6), (X3, K7, ED7), (X3, K7, ED8), (X3, K7, ED9), (X3, K7, ED10), (X3, K7, ED11), (X3, K7, ED12), (X3, K7, ED13), (X3, K7, ED14), (X3, K7, ED15), (X3, K7, ED16), (X3, K7, ED17), (X3, K7, ED18), (X3, K7, ED19), (X3, K7, ED20), (X3, K7, ED21), (X3, K7, ED22), (X3, K7, ED23), (X3, K7, ED24), (X3, K7, ED25), (X3, K7, ED26), (X3, K7, ED27), (X3, K7, ED28), (X3, K7, ED29), (X3, K7, ED30), (X3, K7, ED31), (X3, K7, ED32), (X3, K7, ED33), (X3, K7, ED34), (X3, K7, ED35), (X3, K7, ED36), (X3, K7, ED37), (X3, K7, ED38), (X3, K7, ED39), (X3, K7, ED40), (X3, K7, ED41), (X3, K7, ED42), (X3, K7, ED43), (X3, K7, ED44), (X3, K7, ED45), (X3, K7, ED46), (X3, K1, ED47), (X3, K7, ED48), (X3, K7, ED49), (X3, K7, ED50), (X3, K7, ED51), (X3, K7, ED52), (X3, K7, ED53), (X3, K7, ED54), (X3, K7, ED55), (X3, K7, ED56), (X3, K7, ED57), (X3, K7, ED58), (X3, K7, ED59), (X3, K7, ED60), (X3, K7, ED61), (X3, K7, ED62), (X3, K7, ED63), (X3, K7, ED64), (X3, K7, ED65), (X3, K7, ED66), (X3, K7, ED67), (X3, K7, ED68), (X3, K7, ED69), (X3, K7, ED70), (X3, K7, ED71), (X3, K7, ED72), (X3, K7, ED73), (X3, K7, ED74), (X3, K7, ED75), (X3, K7, ED76), (X3, K7, ED77), (X3, K7, ED78), (X3, K7, ED79), (X3, K7, ED80), (X3, K7, ED81), (X3, K7, ED82), (X3, K7, ED83), (X3, K7, ED84), (X3, K7, ED85), (X3, K7, ED86), (X3, K7, ED87), (X3, K7, ED88), (X3, K7, ED89), (X3, K7, ED90), (X3, K7, ED91), (X3, K7, ED92), (X3, K8, ED1), (X3, K8, ED2), (X3, K8, ED3), (X3, K8, ED4), (X3, K8, ED5), (X3, K8, ED6), (X3, K8, ED7), (X3, K8, ED8), (X3, K8, ED9), (X3, K8, ED10), (X3, K8, ED11), (X3, K8, ED12), (X3, K8, ED13), (X3, K8, ED14), (X3, K8, ED15), (X3, K8, ED16), (X3, K8, ED17), (X3, K8, ED18), (X3, K8, ED19), (X3, K8, ED20), (X3, K8, ED21), (X3, K8, ED22), (X3, K8, ED23), (X3, K8, ED24), (X3, K8, ED25), (X3, K8, ED26), (X3, K8, ED27), (X3, K8, ED28), (X3, K8, ED29), (X3, K8, ED30), (X3, K8, ED31), (X3, K8, ED32), (X3, K8, ED33), (X3, K8, ED34), (X3, K8, ED35), (X3, K8, ED36), (X3, K8, ED37), (X3, K8, ED38), (X3, K8, ED39), (X3, K8, ED40), (X3, K8, ED41), (X3, K8, ED42), (X3, K8, ED43), (X3, K8, ED44), (X3, K8, ED45), (X3, K8, ED46), (X3, K8, ED47), (X3, K8, ED48), (X3, K8, ED49), (X3, K8, ED50), (X3, K8, ED51), (X3, K8, ED52), (X3, K8, ED53), (X3, K8, ED54), (X3, K8, ED55), (X3, K8, ED56), (X3, K8, ED57), (X3, K8, ED58), (X3, K8, ED59), (X3, K8, ED60), (X3, K8, ED61), (X3, K8, ED62), (X3, K8, ED63), (X3, K8, ED64), (X3, K8, ED65), (X3, K8, ED66), (X3, K8, ED67), (X3, K8, ED68), (X3, K8, ED69), (X3, K8, ED70), (X3, K8, ED71), (X3, K8, ED72), (X3, K8, ED73), (X3, K8, ED74), (X3, K8, ED75), (X3, K8, ED76), (X3, K8, ED77), (X3, K8, ED78), (X3, K8, ED79), (X3, K8, ED80), (X3, K8, ED81), (X3, K8, ED82), (X3, K8, ED83), (X3, K8, ED84), (X3, K8, ED85), (X3, K8, ED86), (X3, K8, ED87), (X3, K8, ED88), (X3, K8, ED89), (X3, K8, ED90), (X3, K8, ED91), (X3, K8, ED92), (X3, K9, ED1), (X3, K9, ED2), (X3, K9, ED3), (X3, K9, ED4), (X3, K9, ED5), (X3, K9, ED6), (X3, K9, ED7), (X3, K9, ED8), (X3, K9, ED9), (X3, K9, ED10), (X3, K9, ED11), (X3, K9, ED12), (X3, K9, ED13), (X3, K9, ED14), (X3, K9, ED15), (X3, K9, ED16), (X3, K9, ED17), (X3, K9, ED18), (X3, K9, ED19), (X3, K9, ED20), (X3, K9, ED21), (X3, K9, ED22), (X3, K9, ED23), (X3, K9, ED24), (X3, K9, ED25), (X3, K9, ED26), (X3, K9, ED27), (X3, K9, ED28), (X3, K9, ED29), (X3, K9, ED30), (X3, K9, ED31), (X3, K9, ED32), (X3, K9, ED33), (X3, K9, ED34), (X3, K9, ED35), (X3, K9, ED36), (X3, K9, ED37), (X3, K9, ED38), (X3, K9, ED39), (X3, K9, ED40), (X3, K9, ED41), (X3, K9, ED42), (X3, K9, ED43), (X3, K9, ED44), (X3, K9, ED45), (X3, K9, ED46), (X3, K9, ED47), (X3, K9, ED48), (X3, K9, ED49), (X3, K9, ED50), (X3, K9, ED51), (X3, K9, ED52), (X3, K9, ED53), (X3, K9, ED54), (X3, K9, ED55), (X3, K9, ED56), (X3, K9, ED57), (X3, K9, ED58), (X3, K9, ED59), (X3, K9, ED60), (X3, K9, ED61), (X3, K9, ED62), (X3, K9, ED63), (X3, K9, ED64), (X3, K9, ED65), (X3, K9, ED66), (X3, K9, ED67), (X3, K9, ED68), (X3, K9, ED69), (X3, K9, ED70), (X3, K9, ED71), (X3, K9, ED72), (X3, K9, ED73), (X3, K9, ED74), (X3, K9, ED75), (X3, K9, ED76), (X3, K9, ED77), (X3, K9, ED78), (X3, K9, ED79), (X3, K9, ED80), (X3, K9, ED81), (X3, K9, ED82), (X3, K9, ED83), (X3, K9, ED84), (X3, K9, ED85), (X3, K9, ED86), (X3, K9, ED87), (X3, K9, ED88), (X3, K9, ED89), (X3, K9, ED90), (X3, K9, ED91), (X3, K9, ED92), (X3, K10, ED1), (X3, K10, ED2), (X3, K10, ED3), (X3, K10, ED4), (X3, K10, ED5), (X3, K10, ED6), (X3, K10, ED7), (X3, K10, ED8), (X3, K10, ED9), (X3, K10, ED10), (X3, K10, ED11), (X3, K10, ED12), (X3, K10, ED13), (X3, K10, ED14), (X3, K10, ED15), (X3, K10, ED16), (X3, K10, ED17), (X3, K10, ED18), (X3, K10, ED19), (X3, K10, ED20), (X3, K10, ED21), (X3, K10, ED22), (X3, K10, ED23), (X3, K10, ED24), (X3, K10, ED25), (X3, K10, ED26), (X3, K10, ED27), (X3, K10, ED28), (X3, K10, ED29), (X3, K10, ED30), (X3, K10, ED31), (X3, K10, ED32), (X3, K10, ED33), (X3, K10, ED34), (X3, K10, ED35), (X3, K10, ED36), (X3, K10, ED37), (X3, K10, ED38), (X3, K10, ED39), (X3, K10, ED40), (X3, K10, ED41), (X3, K10, ED42), (X3, K10, ED43), (X3, K10, ED44), (X3, K10, ED45), (X3, K10, ED46), (X3, K10, ED47), (X3, K10, ED48), (X3, K10, ED49), (X3, K10, ED50), (X3, K10, ED51), (X3, K10, ED52), (X3, K10, ED53), (X3, K10, ED54), (X3, K10, ED55), (X3, K10, ED56), (X3, K10, ED57), (X3, K10, ED58), (X3, K10, ED59), (X3, K10, ED60), (X3, K10, ED61), (X3, K10, ED62), (X3, K10, ED63), (X3, K10, ED64), (X3, K10, ED65), (X3, K10, ED66), (X3, K10, ED67), (X3, K10, ED68), (X3, K10, ED69), (X3, K10, ED70), (X3, K10, ED71), (X3, K10, ED72), (X3, K10, ED73), (X3, K10, ED71), (X3, K10, ED75), (X3, K10, ED76), (X3, K10, ED77), (X3, K10, ED78), (X3, K10, ED79), (X3, K10, ED80), (X3, K10, ED81), (X3, K10, ED82), (X3, K10, ED83), (X3, K10, ED84), (X3, K10, ED85), (X3, K10, ED86), (X3, K10, ED87), (X3, K10, ED88), (X3, K10, ED89), (X3, K10, ED90), (X3, K10, ED91), (X3, K10, ED92), (X3, K11, ED1), (X3, K11, ED2), (X3, K11, ED3), (X3, K11, ED4), (X3, K11, ED5), (X3, K11, ED6), (X3, K11, ED7), (X3, K11, ED8), (X3, K11, ED9), (X3, K11, ED10), (X3, K11, ED11), (X3, K11, ED12), (X3, K11, ED13), (X3, K11, ED14), (X3, K11, ED15), (X3, K11, ED16), (X3, K11, ED17), (X3, K11, ED18), (X3, K11, ED19), (X3, K11, ED20), (X3, K11, ED21), (X3, K11, ED22), (X3, K11, ED23), (X3, K11, ED24), (X3, K11, ED25), (X3, K11, ED26), (X3, K11, ED27), (X3, K11, ED28), (X3, K11, ED29), (X3, K11, ED30), (X3, K11, ED31), (X3, K11, ED32), (X3, K11, ED33), (X3, K11, ED34), (X3, K11, ED35), (X3, K11, ED36), (X3, K11, ED37), (X3, K11, ED38), (X3, K11, ED39), (X3, K11, ED40), (X3, K11, ED41), (X3, K11, ED42), (X3, K11, ED43), (X3, K11, ED44), (X3, K11, ED45), (X3, K11, ED46), (X3, K11, ED47), (X3, K11, ED48), (X3, K11, ED49), (X3, K11, ED50), (X3, K11, ED51), (X3, K11, ED52), (X3, K11, ED53), (X3, K11, ED54), (X3, K11, ED55), (X3, K11, ED56), (X3, K11, ED57), (X3, K11, ED58), (X3, K11, ED59), (X3, K11, ED60), (X3, K11, ED61), (X3, K11, ED62), (X3, K11, ED63), (X3, K11, ED64), (X3, K11, ED65), (X3, K11, ED66), (X3, K11, ED67), (X3, K11, ED68), (X3, K11, ED69), (X3, K11, ED70), (X3, K11, ED71), (X3, K11, ED72), (X3, K11, ED73), (X3, K11, ED74), (X3, K11, ED75), (X3, K11, ED76), (X3, K11, ED77), (X3, K11, ED78), (X3, K11, ED79), (X3, K11,

ED80), (X3, K11, ED81), (X3, K11, ED82), (X3, K11, ED83), (X3, K11, ED84), (X3, K11, ED85), (X3, K11, ED86), (X3, K11, ED87), (X3, K11, ED88), (X3, K11, ED89), (X3, K11, ED90), (X3, K11, ED91), (X3, K11, ED92), (X3, K12, ED1), (X3, K12, ED2), (X3, K12, ED3), (X3, K12, ED4), (X3, K12, ED5), (X3, K12, ED6), (X3, K12, ED7), (X3, K12, ED8), (X3, K12, ED9), (X3, K12, ED10), (X3, K12, ED11), (X3, K12, ED12), (X3, K12, ED13), (X3, K12, ED14), (X3, K12, ED15), (X3, K12, ED16), (X3, K12, ED17), (X3, K12, ED18), (X3, K12, ED19), (X3, K12, ED20), (X3, K12, ED21), (X3, K12, ED22), (X3, K12, ED23), (X3, K12, ED24), (X3, K12, ED25), (X3, K12, ED26), (X3, K12, ED27), (X3, K12, ED28), (X3, K12, ED29), (X3, K12, ED30), (X3, K12, ED31), (X3, K12, ED32), (X3, K12, ED33), (X3, K12, ED34), (X3, K12, ED35), (X3, K12, ED36), (X3, K12, ED37), (X3, K12, ED38), (X3, K12, ED39), (X3, K12, ED40), (X3, K12, ED41), (X3, K12, ED42), (X3, K12, ED43), (X3, K12, ED44), (X3, K12, ED45), (X3, K12, ED46), (X3, K12, ED47), (X3, K12, ED48), (X3, K12, ED49), (X3, K12, ED50), (X3, K12, ED51), (X3, K12, ED52), (X3, K12, ED53), (X3, K12, ED54), (X3, K12, ED55), (X3, K12, ED56), (X3, K12, ED57), (X3, K12, ED58), (X3, K12, ED59), (X3, K12, ED60), (X3, K12, ED61), (X3, K12, ED62), (X3, K12, ED63), (X3, K12, ED64), (X3, K12, ED65), (X3, K12, ED66), (X3, K12, ED67), (X3, K12, ED68), (X3, K12, ED69), (X3, K12, ED70), (X3, K12, ED71), (X3, K12, ED72), (X3, K12, ED73), (X3, K12, ED74), (X3, K12, ED75), (X3, K12, ED76), (X3, K12, ED77), (X3, K12, ED78), (X3, K12, ED79), (X3, K12, ED80), (X3, K12, ED81), (X3, K12, ED82), (X3, K12, ED83), (X3, K12, ED84), (X3, K12, ED85), (X3, K12, ED86), (X3, K12, ED87), (X3, K12, ED88), (X3, K12, ED89), (X3, K12, ED90), (X3, K12, ED91), (X3, K12, ED92), (X3, K13, ED1), (X3, K13, ED2), (X3, K13, ED3), (X3, K13, ED4), (X3, K13, ED5), (X3, K13, ED6), (X3, K13, ED7), (X3, K13, ED8), (X3, K13, ED9), (X3, K13, ED10), (X3, K13, ED11), (X3, K13, ED12), (X3, K13, ED13), (X3, K13, ED14), (X3, K13, ED15), (X3, K13, ED16), (X3, K13, ED17), (X3, K13, ED18), (X3, K13, ED19), (X3, K13, ED20), (X3, K13, ED21), (X3, K13, ED22), (X3, K13, ED23), (X3, K13, ED24), (X3, K13, ED25), (X3, K13, ED26), (X3, K13, ED27), (X3, K13, ED28), (X3, K13, ED29), (X3, K13, ED30), (X3, K13, ED31), (X3, K13, ED32), (X3, K13, ED33), (X3, K13, ED34), (X3, K13, ED35), (X3, K13, ED36), (X3, K13, ED37), (X3, K13, ED38), (X3, K13, ED39), (X3, K13, ED40), (X3, K13, ED41), (X3, K13, ED42), (X3, K13, ED43), (X3, K13, ED44), (X3, K13, ED45), (X3, K13, ED46), (X3, K13, ED47), (X3, K13, ED48), (X3, K13, ED49), (X3, K13, ED50), (X3, K13, ED51), (X3, K13, ED52), (X3, K13, ED53), (X3, K13, ED54), (X3, K13, ED55), (X3, K13, ED56), (X3, K13, ED57), (X3, K13, ED58), (X3, K13, ED59), (X3, K13, ED60), (X3, K13, ED61), (X3, K13, ED62), (X3, K13, ED63), (X3, K13, ED61), (X3, K13, ED65), (X3, K13, ED66), (X3, K13, ED67), (X3, K13, ED68), (X3, K13, ED69), (X3, K13, ED70), (X3, K13, ED71), (X3, K13, ED72), (X3, K13, ED73), (X3, K13, ED74), (X3, K13, ED75), (X3, K13, ED76), (X3, K13, ED77), (X3, K13, ED78), (X3, K13, ED79), (X3, K13, ED80), (X3, K13, ED81), (X3, K13, ED82), (X3, K13, ED83), (X3, K13, ED84), (X3, K13, ED85), (X3, K13, ED86), (X3, K13, ED87), (X3, K13, ED88), (X3, K13, ED89), (X3, K13, ED90), (X3, K13, ED91), (X3, K13, ED92), (X3, K14, ED1), (X3, K14, ED2), (X3, K14, ED3), (X3, K14, ED4), (X3, K14, ED5), (X3, K14, ED6), (X3, K14, ED7), (X3, K14, ED8), (X3, K14, ED9), (X3, K14, ED10), (X3, K14, ED11), (X3, K14, ED12), (X3, K14, ED13), (X3, K14, ED14), (X3, K14, ED15), (X3, K14, ED16), (X3, K14, ED17), (X3, K14, ED18), (X3, K14, ED19), (X3, K14, ED20), (X3, K14, ED21), (X3, K14, ED22), (X3, K14, ED23), (X3, K14, ED24), (X3, K14, ED25), (X3, K14, ED26), (X3, K14, ED27), (X3, K14, ED28), (X3, K14, ED29), (X3, K14, ED30), (X3, K14, ED31), (X3, K14, ED32), (X3, K14, ED33), (X3, K14, ED34), (X3, K14, ED35), (X3, K14, ED36), (X3, K14, ED37), (X3, K14, ED38), (X3, K14, ED39), (X3, K14, ED40), (X3, K14, ED41), (X3, K14, ED42), (X3, K14, ED43), (X3, K14, ED44), (X3, K14, ED45), (X3, K14, ED46), (X3, K14, ED47), (X3, K14, ED48), (X3, K14, ED49), (X3, K14, ED50), (X3, K14, ED51), (X3, K14, ED52), (X3, K14, ED53), (X3, K14, ED54), (X3, K14, ED55), (X3, K14, ED56), (X3, K14, ED57), (X3, K14, ED58), (X3, K14, ED59), (X3, K14, ED60), (X3, K14, ED61), (X3, K14, ED62), (X3, K14, ED63), (X3, K14, ED64), (X3, K14, ED65), (X3, K14, ED66), (X3, K14, ED67), (X3, K14, ED68), (X3, K14, ED69), (X3, K14, ED70), (X3, K14, ED71), (X3, K14, ED72), (X3, K14, ED73), (X3, K14, ED74), (X3, K14, ED75), (X3, K14, ED76), (X3, K14, ED77), (X3, K14, ED78), (X3, K14, ED79), (X3, K14, ED80), (X3, K14, ED81), (X3, K14, ED82), (X3, K14, ED83), (X3, K14, ED84), (X3, K14, ED85), (X3, K14, ED86), (X3, K14, ED87), (X3, K14, ED88), (X3, K14, ED89), (X3, K14, ED90), (X3, K14, ED91), (X3, K14, ED92), (X3, K15, ED1), (X3, K15, ED2), (X3, K15, ED3), (X3, K15, ED4), (X3, K15, ED5), (X3, K13, ED6), (X3, K15, ED7), (X3, K15, ED8), (X3, K15, ED9), (X3, K15, ED10), (X3, K15, ED11), (X3, K15, ED12), (X3, K15, ED13), (X3, K15, ED14), (X3, K15, ED15), (X3, K15, ED16), (X3, K15, ED17), (X3, K15, ED18), (X3, K15, ED219), (X3, K15, ED20), (X3, K15, ED21), (X3, K15, ED22), (X3, K15, ED23), (X3, K15, ED24), (X3, K15, ED25), (X3, K15, ED26), (X3, K15, ED27), (X3, K15, ED28), (X3, K15, ED29), (X3, K15, ED30), (X3, K15, ED31), (X3, K15, n32), (X3, K15, ED33), (X3, K15, ED34), (X3, K15, ED35), (X3, K15, ED36), (X3, K15, ED37), (X3, K15, ED38), (X3, K15, ED39), (X3, K15, ED40), (X3, K15, ED41), (X3, K15, ED42), (X3, K15, ED43), (X3, K15, ED44), (X3, K15, ED45), (X3, K15, ED46), (X3, K15, ED47), (X3, K15, ED48), (X3, K15, ED49), (X3, K15, ED50), (X3, K15, ED51), (X3, K15, ED52), (X3, K15, ED53), (X3, K15, ED54), (X3, K15, ED55), (X3, K15, ED56), (X3, K15, ED57), (X3, K15, ED58), (X3, K15, ED59), (X3, K15, ED60), (X3, K15, ED61), (X3, K15, ED62), (X3, K15, ED63), (X3, K15, ED64), (X3, K15, ED65), (X3, K15, ED66), (X3, K15, ED67), (X3, K15, ED68), (X3, K15, ED69), (X3, K15, ED70), (X3, K15, ED71), (X3, K15, ED72), (X3, K15, ED73), (X3, K15, ED74), (X3, K15, ED75), (X3, K15, ED76), (X3, K15, ED77), (X3, K15, ED78), (X3, K15, ED79), (X3, K15, ED80), (X3, K15, ED81), (X3, K15, ED82), (X3, K15, ED83), (X3, K15, ED84), (X3, K15, ED85), (X3, K15, ED86), (X3, K15, ED87), (X3, K15, ED88), (X3, K15, ED89), (X3, K15, ED90), (X3, K15, ED91), (X3, K15, ED92), (X3, K16, ED1), (X3, K16, ED2), (X3, K16, ED3), (X3, K16, ED4), (X3, K16, ED5), (X3, K16, ED6), (X3, K16, ED7), (X3, K16, ED8), (X3, K16, ED9), (X3, K16, ED10), (X3, K16, ED11) (X3, K16, ED12), (X3, K16, ED13), (X3, K16, ED14), (X3, K16, ED15) (X3, K16, ED16), (X3, K16, ED17), (X3, K16, ED18), (X3, K16, ED19) (X3, K16, ED20), (X3, K16, ED21), (X3, K16, ED22), (X3, K16, ED23), (X3, K16, ED24), (X3, K16, ED25), (X3, K16, ED26), (X3, K16, ED27) (X3, K16, ED28), (X3, K16, ED29), (X3, K16, ED30), (X3, K16, ED31), (X3, K16, ED32), (X3, K16,

ED33), (X3, K16, ED34), (X3, K16, ED35) (X3, K16, ED36), (X3, K16, ED37), (X3, K16, ED38), (X3, K16, ED39), (X3, K16, ED40), (X3, K16, ED41), (X3, K16, ED42), (X3, K16, ED43), (X3, K16, ED44), (X3, K16, ED45), (X3, K16, ED46), (X3, K16, ED47), (X3, K16, ED48), (X3, K16, ED49), (X3, K16, ED50), (X3, K16, ED51), (X3, K16, ED52), (X3, K16, ED53), (X3, K16, ED54), (X3, K16, ED55), (X3, K16, ED56), (X3, K16, ED57), (X3, K16, ED58), (X3, K16, ED59), (X3, K16, ED60) (X3, K16, ED61), (X3, K16, ED62), (X3, K16, ED63), (X3, K16, ED64) (X3, K16, ED65), (X3, K16, ED66), (X3, K16, ED67), (X3, K16, ED68) (X3, K16, ED69), (X3, K16, ED70), (X3, K16, ED71), (X3, K16, ED72) (X3, K16, ED73), (X3, K16, ED74), (X3, K16, ED75), (X3, K16, ED76) (X3, K16, ED77), (X3, K16, ED78), (X3, K16, ED79), (X3, K16, ED80) (X3, K16, ED81), (X3, K16, ED82), (X3, K16, ED83), (X3, K16, ED84) (X3, K16, ED85), (X3, K16, ED86), (X3, K16, ED87), (X3, K16, ED88) (X3, K16, ED89), (X3, K16, ED90), (X3, K16, ED91), (X3, K16, ED92), (X3, K17, ED1), (X3, K17, ED2), (X3, K17, ED3), (X3, K17, ED4), (X3, K17, ED5), (X3, K17, ED6), (X3, K17, ED7), (X3, K17, ED8), (X3, K17, ED9), (X3, K17, ED10), (X3, K17, ED11), (X3, K17, ED12), (X3, K17, ED13), (X3, K17, ED14), (X3, K17, ED15), (X3, K17, ED16), (X3, K17, ED17), (X3, K17, ED18), (X3, K17, ED19), (X3, K17, ED20), (X3, K17, ED21), (X3, K17, ED22), (X3, K17, ED23), (X3, K17, ED24), (X3, K17, ED25), (X3, K17, ED26), (X3, K17, ED27), (X3, K17, ED28), (X3, K17, ED29), (X3, K17, ED30), (X3, K17, ED31), (X3, K17, ED32), (X3, K17, ED33), (X3, K17, ED34), (X3, K17, ED35), (X3, K17, ED36), (X3, K17, ED37), (X3, K17, ED38), (X3, K17, ED39), (X3, K17, ED40), (X3, K17, ED41), (X3, K17, ED42), (X3, K17, ED43), (X3, K17, ED44), (X3, K17, ED45), (X3, K17, ED46), (X3, K17, ED47), (X3, K17, ED48), (X3, K17, ED49), (X3, K17, ED50), (X3, K17, ED51), (X3, K17, ED52), (X3, K17, ED53), (X3, K17, ED54), (X3, K17, ED55), (X3, K17, ED56), (X3, K17, ED57), (X3, K17, ED58), (X3, K17, ED59), (X3, K17, ED60), (X3, K17, ED61), (X3, K17, ED62), (X3, K17, ED63), (X3, K17, ED64), (X3, K17, ED65), (X3, K17, ED66), (X3, K17, ED67), (X3, K17, ED68), (X3, K17, ED69), (X3, K17, ED70), (X3, K17, ED71), (X3, K17, ED72), (X3, K17, ED73), (X3, K17, ED74), (X3, K17, ED75), (X3, K17, ED76), (X3, K17, ED77), (X3, K17, ED78), (X3, K17, ED79), (X3, K17, ED80), (X3, K17, ED81), (X3, K17, ED82), (X3, K17, ED83), (X3, K17, ED84), (X3, K17, ED85), (X3, K17, ED86), (X3, K17, ED87), (X3, K17, ED88), (X3, K17, ED89), (X3, K17, ED90), (X3, K17, ED91), (X3, K17, ED92), (X3, K18, ED1), (X3, K18, ED2), (X3, K18, ED3), (X3, K18, ED4), (X3, K18, ED5), (X3, K18, ED6), (X3, K18, ED7), (X3, K18, ED8), (X3, K18, ED9), (X3, K18, ED10), (X3, K18, ED11), (X3, K18, ED12), (X3, K18, ED13), (X3, K18, ED14), (X3, K18, ED15), (X3, K18, ED16), (X3, K18, ED17), (X3, K18, ED18), (X3, K18, ED19), (X3, K18, ED20), (X3, K18, ED21), (X3, K18, ED22), (X3, K18, ED23), (X3, K18, ED24), (X3, K18, ED25), (X3, K18, ED26), (X3, K18, ED27), (X3, K18, ED28), (X3, K18, ED29), (X3, K18, ED30), (X3, K18, ED31), (X3, K18, ED32), (X3, K18, ED33), (X3, K18, ED34), (X3, K18, ED35), (X3, K18, ED36), (X3, K18, ED37), (X3, K18, ED38), (X3, K18, ED39), (X3, K18, ED40), (X3, K18, ED41), (X3, K18, ED42), (X3, K18, ED43), (X3, K18, ED44), (X3, K18, ED45), (X3, K18, ED46), (X3, K18, ED47), (X3, K18, ED48), (X3, K18, ED49), (X3, K18, ED50), (X3, K18, ED51), (X3, K18, ED52), (X3, K18, ED53), (X3, K18, ED54), (X3, K18, ED55), (X3, K18, ED56), (X3, K18, ED57), (X3, K18, ED58), (X3, K18, ED59), (X3, K18, ED60), (X3, K18, ED61), (X3, K18, ED62), (X3, K18, ED63), (X3, K18, ED64), (X3, K18, ED65), (X3, K18, ED66), (X3, K18, ED67), (X3, K18, ED68), (X3, K18, ED69), (X3, K18, ED70), (X3, K18, ED71), (X3, K18, ED72), (X3, K18, ED73), (X3, K18, ED74), (X3, K18, ED75), (X3, K18, ED76), (X3, K18, ED77), (X3, K18, ED78), (X3, K18, ED79), (X3, K18, ED80), (X3, K18, ED81), (X3, K18, ED82), (X3, K18, ED83), (X3, K18, ED84), (X3, K18, ED85), (X3, K18, ED86), (X3, K18, ED87), (X3, K18, ED88), (X3, K18, ED89), (X3, K18, ED90), (X3, K18, ED91), (X3, K18, ED92), (X3, K19, ED1), (X3, K19, ED2), (X3, K19, ED3), (X3, K19, ED4), (X3, K19, ED5), (X3, K19, ED6), (X3, K19, ED7), (X3, K19, ED8) (X3, K19, ED9), (X3, K19, ED10), (X3, K19, ED11), (X3, K19, ED12) (X3, K19, ED13), (X3, K19, ED14), (X3, K19, ED15), (X3, K19, ED16), (X3, K19, ED17), (X3, K19, ED18), (X3, K19, ED19), (X3, K19, ED20), (X3, K19, ED21), (X3, K19, ED22), (X3, K19, ED23), (X3, K19, ED24) (X3, K19, ED25), (X3, K19, ED26), (X3, K19, ED27), (X3, K19, ED28), (X3, K19, ED29), (X3, K19, ED30), (X3, K19, ED31), (X3, K19, ED32), (X3, K19, ED33), (X3, K19, ED34), (X3, K19, ED35), (X3, K19, ED36), (X3, K19, ED37), (X3, K19, ED38), (X3, K19, ED39), (X3, K19, ED40), (X3, K19, ED41), (X3, K19, ED42), (X3, K19, ED43), (X3, K19, ED44), (X3, K19, ED45), (X3, K19, ED46), (X3, K19, ED47), (X3, K19, ED48), (X3, K19, ED49), (X3, K19, ED50), (X3, K19, ED51), (X3, K19, ED52), (X3, K19, ED53), (X3, K19, ED54), (X3, K19, ED55), (X3, K19, ED56), (X3, K19, ED57), (X3, K19, ED58), (X3, K19, ED59), (X3, K19, ED60), (X3, K19, ED61), (X3, K19, ED62), (X3, K19, ED63), (X3, K19, ED64), (X3, K19, ED65), (X3, K19, ED66), (X3, K19, ED67), (X3, K19, ED68), (X3, K19, ED69), (X3, K19, ED70), (X3, K19, ED71), (X3, K19, ED72), (X3, K19, ED73), (X3, K19, ED74), (X3, K19, ED75), (X3, K19, ED76), (X3, K19, ED77), (X3, K19, ED78), (X3, K19, ED79), (X3, K19, ED80), (X3, K19, ED81), (X3, K19, ED82), (X3, K19, ED83), (X3, K19, ED84), (X3, K19, ED85), (X3, K19, ED86), (X3, K19, ED87), (X3, K19, ED88), (X3, K19, ED89), (X3, K19, ED90), (X3, K19, ED91), (X3, K19, ED92), (X3, K20, ED1), (X3, K20 ED2), (X3, K20, ED3), (X3, K20, ED4), (X3, K20, ED5), (X3, K20, ED6), (X3, K20, ED7), (X3, K20, ED8), (X3, K20, ED9), (X3, K20, ED10), (X3, K20, ED11), (X3, K20, ED12), (X3, K20, ED13), (X3, K20, ED14), (X3, K20, ED15), (X3, K20, ED16), (X3, K20, ED17), (X3, K20, ED18), (X3, K20, ED19), (X3, K20, ED20), (X3, K20, ED21), (X3, K20, ED22), (X3, K20, ED23), (X3, K20, ED24), (X3, K20, ED25), (X3, K20, ED26), (X3, K20, ED27), (X3, K20, ED28), (X3, K20, ED29), (X3, K20, ED30), (X3, K20, ED31), (X3, K20, ED32), (X3, K20, ED33), (X3, K20, ED34), (X3, K20, ED35), (X3, K20, ED36), (X3, K20, ED37), (X3, K20, ED38), (X3, K20, ED39), (X3, K20, ED40), (X3, K20, ED41), (X3, K20, ED42), (X3, K20, ED43), (X3, K20, ED44), (X3, K20, ED45), (X3, K20, ED46), (X3, K20, ED47), (X3, K20, ED48), (X3, K20, ED49), (X3, K20, ED50), (X3, K20, ED51), (X3, K20, ED52), (X3, K20, ED53), (X3, K20, ED54), (X3, K20, ED55), (X3, K20, ED56), (X3, K20, ED57), (X3, K20, ED58), (X3, K20, ED59), (X3, K20, ED60), (X3, K20, ED61), (X3, K20, ED62), (X3, K20, ED63), (X3, K20, ED64), (X3, K20, ED65), (X3, K20, ED66), (X3, K20, ED67), (X3, K20, ED68), (X3, K20, ED69), (X3, K20, ED70), (X3, K20, ED71), (X3, K20, ED72), (X3, K20, ED73), (X3, K20,

ED74), (X3, K20, ED75), (X3, K20, ED76), (X3, K20, ED77), (X3, K20, ED78), (X3, K20, ED79), (X3, K20, ED80), (X3, K20, ED81), (X3, K20, ED82), (X3, K20, ED83), (X3, K20, ED84), (X3, K20, ED85), (X3, K20, ED86), (X3, K20, ED87), (X3, K20, ED88), (X3, K20, ED89), (X3, K20, ED90), (X3, K20, ED91), (X3, K20, ED92), (X3, K21, ED1), (X3, K21, ED2), (X3, K21, ED3), (X3, K21, ED4), (X3, K21, ED5), (X3, K21, ED6), (X3, K21, ED7), (X3, K21, ED8), (X3, K21, ED9), (X3, K21, ED10), (X3, K21, ED11), (X3, K21, ED12), (X3, K21, ED13), (X3, K21, ED14), (X3, K21, ED15), (X3, K21, ED16), (X3, K21, ED17), (X3, K21, ED18), (X3, K21, ED19), (X3, K21, ED20), (X3, K21, ED21), (X3, K21, ED22), (X3, K21, ED23), (X3, K21, ED24), (X3, K21, ED25), (X3, K21, ED26), (X3, K21, ED27), (X3, K21, ED28), (X3, K21, ED29), (X3, K21, ED30), (X3, K21, ED31), (X3, K21, ED32), (X3, K21, ED33), (X3, K21, ED34), (X3, K21, ED35), (X3, K21, ED36), (X3, K21, ED37), (X3, K21, ED38), (X3, K21, ED39), (X3, K21, ED40), (X3, K21, ED41), (X3, K21, ED42), (X3, K21, ED43), (X3, K21, ED44), (X3, K21, ED45), (X3, K21, ED46), (X3, K21, ED47), (X3, K21, ED48), (X3, K21, ED49), (X3, K21, ED50), (X3, K21, ED51), (X3, K21, ED52), (X3, K21, ED53), (X3, K21, ED54), (X3, K21, ED55), (X3, K21, ED56), (X3, K21, ED57), (X3, K21, ED58), (X3, K21, ED59), (X3, K21, ED60), (X3, K21, ED61), (X3, K21, ED62), (X3, K21, ED63), (X3, K21, ED64), (X3, K21, ED65), (X3, K21, ED66), (X3, K21, ED67), (X3, K21, ED68), (X3, K21, ED69), (X3, K21, ED70), (X3, K21, ED71), (X3, K21, ED72), (X3, K21, ED73), (X3, K21, ED74), (X3, K21, ED75), (X3, K21, ED76), (X3, K21, ED77), (X3, K21, ED78), (X3, K21, ED79), (X3, K21, ED80), (X3, K21, ED81), (X3, K21, ED82), (X3, K21, ED83), (X3, K21, ED84), (X3, K21, ED85), (X3, K21, ED86), (X3, K21, ED87), (X3, K21, ED88), (X3, K21, ED89), (X3, K21, ED90), (X3, K21, ED91), (X3, K21, ED92), (X3, K22, ED1), (X3, K22, ED2), (X3, K22, ED3), (X3, K22, ED4), (X3, K22, ED5), (X3, K22, ED6), (X3, K22, ED7), (X3, K22, ED8), (X3, K22, ED9), (X3, K22, ED10), (X3, K22, ED11), (X3, K22, ED12), (X3, K22, ED13), (X3, K22, ED14), (X3, K22, ED15), (X3, K22, ED16), (X3, K22, ED17), (X3, K22, ED18), (X3, K22, ED19), (X3, K22, ED20), (X3, K22, ED21), (X3, K22, ED22), (X3, K22, ED23), (X3, K22, ED24), (X3, K22, ED25), (X3, K22, ED26), (X3, K22, ED27), (X3, K22, ED28), (X3, K22, ED29), (X3, K22, ED30), (X3, K22, ED31), (X3, K272, ED32), (X3, K22, ED33), (X3, K22, ED34), (X3, K22, ED35), (X3, K22, ED36), (X3, K22, ED37), (X3, K22, ED38), (X3, K22, ED39), (X3, K22, ED40), (X3, K22, ED41), (X3, K22, ED42), (X3, K22, ED43), (X3, K22, ED44), (X3, K22, ED45), (X3, K22, ED46), (X3, K22, ED47), (X3, K22, ED48), (X3, K22, ED49), (X3, K22, ED50), (X3, K22, ED51), (X3, K22, ED52), (X3, K22, ED53), (X3, K22, ED54), (X3, K22, ED55), (X3, K22, ED56), (X3, K22, ED57), (X3, K22, ED58), (X3, K22, ED59), (X3, K22, ED60), (X3, K22, ED61), (X3, K22, ED62), (X3, K22, ED63), (X3, K22, ED64), (X3, K22, ED65), (X3, K22, ED66), (X3, K22, ED67), (X3, K22, ED68), (X3, K22, ED69), (X3, K22, ED70), (X3, K22, ED71), (X3, K22, ED72), (X3, K22, ED73), (X3, K22, ED74), (X3, K22, ED75), (X3, K22, ED76), (X3, K22, ED77), (X3, K22, ED78), (X3, K22, ED79), (X3, K22, ED80), (X3, K22, ED81), (X3, K22, ED82), (X3, K22, ED83), (X3, K22, ED84), (X3, K22, ED85), (X3, K22, ED86), (X3, K22, ED87), (X3, K22, ED88), (X3, K22, ED89), (X3, K22, ED90), (X3, K22, ED91), (X3, K22, ED92), (X3, K23, ED1), (X3, K23, ED2), (X3, K23, ED3), (X3, K23, ED4), (X3, K23, ED5), (X3, K23, ED6), (X3, K23, ED7), (X3, K23, ED8), (X3, K23, ED9), (X3, K23, ED10), (X3, K23, ED11), (X3, K23, ED12), (X3, K23, ED13), (X3, K23, ED14), (X3, K23, ED15), (X3, K23, ED16), (X3, K23, ED17), (X3, K23, ED18), (X3, K23, ED19), (X3, K23, ED20), (X3, K23, ED21), (X3, K23, ED22), (X3, K23, ED23), (X3, K23, ED24), (X3, K23, ED25), (X3, K23, ED26), (X3, K23, ED27), (X3, K23, ED28), (X3, K23, ED29), (X3, K23, ED30), (X3, K23, ED31), (X3, K23, ED32), (X3, K23, ED33), (X3, K23, ED34), (X3, K23, ED35), (X3, K23, ED36), (X3, K23, ED37), (X3, K23, ED38), (X3, K23, ED39), (X3, K23, ED40), (X3, K23, ED41), (X3, K23, ED42), (X3, K23, ED43), (X3, K23, ED44), (X3, K23, ED45), (X3, K23, ED46), (X3, K23, ED47), (X3, K23, ED48), (X3, K23, ED49), (X3, K23, ED50), (X3, K23, ED51), (X3, K23, ED52), (X3, K23, ED53), (X3, K23, ED54), (X3, K23, ED55), (X3, K23, ED56), (X3, K23, ED57), (X3, K23, ED58), (X3, K23, ED59), (X3, K23, ED60), (X3, K23, ED61), (X3, K23, ED62), (X3, K23, ED63), (X3, K23, ED64), (X3, K23, ED65), (X3, K23, ED66), (X3, K23, ED67), (X3, K23, ED68), (X3, K23, ED69), (X3, K23, ED70), (X3, K23, ED71), (X3, K23, ED72), (X3, K23, ED73), (X3, K23, ED74), (X3, K23, ED75), (X3, K23, ED76), (X3, K23, ED77), (X3, K23, ED78), (X3, K23, ED79), (X3, K23, ED80), (X3, K23, ED81), (X3, K23, ED82), (X3, K23, ED83), (X3, K23, ED84), (X3, K23, ED85), (X3, K23, ED86), (X3, K23, ED87), (X3, K23, ED82), (X3, K23, ED89), (X3, K23, ED90), (X3, K23, ED91), (X3, K23, ED92), (X3, K24, En), (X3, K24, ED2), (X3, K24, ED3), (X3, K24, ED4), (X3, K24, ED5), (X3, K24, ED6), (X3, K24, ED7), (X3, K24, ED8), (X3, K24, ED9), (X3, K24, ED10), (X3, K24, ED11), (X3, K24, ED12), (X3, K24, ED13), (X3, K24, ED14), (X3, K24, ED15), (X3, K24, ED16), (X3, K24, ED17), (X3, K24, ED18), (X3, K24, ED19), (X3, K24, ED20), (X3, K24, ED21), (X3, K24, ED22), (X3, K24, ED23), (X3, K24, ED21), (X3, K24, ED25), (X3, K24, ED26), (X3, K24, ED27), (X3, K24, ED28), (X3, K24, ED29), (X3, K24, ED30), (X3, K24, ED31), (X3, K24, ED32), (X3, K24, ED33), (X3, K24, ED34), (X3, K24, ED35), (X3, K24, ED36), (X3, K24, ED37), (X3, K24, ED38), (X3, K24, ED39), (X3, K24, ED40), (X3, K24, ED41), (X3, K24, ED42), (X3, K24, ED43), (X3, K24, ED44), (X3, K24, ED45), (X3, K24, ED46), (X3, K24, ED47), (X3, K24, ED48), (X3, K24, ED49), (X3, K24, ED50), (X3, K24, ED51), (X3, K24, ED52), (X3, K24, ED53), (X3, K24, ED54), (X3, K24, ED55), (X3, K24, ED56), (X3, K24, ED57), (X3, K24, ED58), (X3, K24, ED59), (X3, K24, ED60), (X3, K24, ED61), (X3, K24, ED62), (X3, K24, ED63), (X3, K24, ED64), (X3, K24, ED65), (X3, K24, ED66), (X3, K24, ED67), (X3, K24, ED68), (X3, K24, ED69), (X3, K24, ED70), (X3, K24, ED71), (X3, K24, ED72), (X3, K24, ED73), (X3, K24, ED74), (X3, K24, ED75), (X3, K24, ED76), (X3, K24, ED77), (X3, K24, ED78), (X3, K24, ED79), (X3, K24, ED80), (X3, K24, ED81), (X3, K24, ED82), (X3, K24, ED83), (X3, K24, ED84), (X3, K24, ED85), (X3, K24, ED86), (X3, K24, ED87), (X3, K24, ED88), (X3, K24, ED89), (X3, K24, ED90), (X3, K24, ED91), (X3, K24, ED92), (X3, K25, ED1), (X3, K25, ED2), (X3, K25, ED3), (X3, K25, ED4), (X3, K25, ED5), (X3, K25, ED6), (X3, K25, ED7), (X3, K25, ED8), (X3, K25, ED9), (X3, K23, ED10), (X3, K23, ED11), (X3, K25, ED12), (X3, K25, ED13), (X3, K25, ED14), (X3, K25, ED15), (X3, K25, ED16), (X3, K25, ED17), (X3, K25, ED18), (X3, K25, ED19), (X3, K25, ED20), (X3, K25, ED21), (X3, K25, ED22), (X3, K25, ED23), (X3, K25, ED24), (X3, K25, ED25), (X3, K25,

ED26), (X3, K25, ED27), (X3, K25, ED28), (X3, K25, ED29), (X3, K25, ED30), (X3, K25, ED31), (X3, K25, ED32), (X3, K25, ED33), (X3, K25, ED34), (X3, K25, ED35), (X3, K25, ED36), (X3, K25, ED37), (X3, K25, ED38), (X3, K25, ED39), (X3, K25, ED40), (X3, K25, ED41), (X3, K25, ED42), (X3, K25, ED43), (X3, K25, ED44), (X3, K25, ED45), (X3, K25, ED46), (X3, K25, ED47), (X3, K25, ED48), (X3, K25, ED49), (X3, K25, ED50), (X3, K25, ED51), (X3, K25, ED52), (X3, K25, ED53), (X3, K25, ED54), (X3, K25, ED55), (X3, K25, ED56), (X3, K25, ED57), (X3, K25, ED58), (X3, K25, ED59), (X3, K25, ED60), (X3, K25, ED61), (X3, K25, ED62), (X3, K25, ED63), (X3, K25, ED64), (X3, K25, ED65), (X3, K25, ED66), (X3, K25, ED67), (X3, K25, ED68), (X3, K25, ED69), (X3, K25, ED70), (X3, K25, ED71), (X3, K25, ED72), (X3, K25, ED73), (X3, K25, ED74), (X3, K25, ED75), (X3, K25, ED76), (X3, K25, ED77), (X3, K25, ED78), (X3, K25, ED79), (X3, K25, ED80), (X3, K25, ED81), (X3, K25, ED82), (X3, K25, ED83), (X3, K25, ED84), (X3, K25, ED85), (X3, K25, ED86), (X3, K25, ED87), (X3, K25, ED88), (X3, K25, ED89), (X3, K25, ED90), (X3, K25, ED91), (X3, K25, ED92), (X3, K26, ED1), (X3, K26, ED2), (X3, K26, ED3), (X3, K26, ED4), (X3, K26, ED5), (X3, K26, ED6), (X3, K26, ED7), (X3, K26, ED8), (X3, K26, ED9), (X3, K26, ED10), (X3, K26, ED11), (X3, K26, ED12), (X3, K26, ED13), (X3, K26, ED14), (X3, K26, ED15), (X3, K26, ED16), (X3, K26, ED17), (X3, K26, ED18), (X3, K26, ED19), (X3, K26, ED20), (X3, K26, ED21), (X3, K26, ED22), (X3, K26, ED23), (X3, K26, ED24), (X3, K26, ED25), (X3, K26, ED26), (X3, K26, ED27), (X3, K26, ED28), (X3, K26, ED29), (X3, K26, ED30), (X3, K26, ED31), (X3, K26, ED32), (X3, K26, ED33), (X3, K26, ED34), (X3, K26, ED35), (X3, K26, ED36), (X3, K26, ED37), (X3, K26, ED38), (X3, K26, ED39), (X3, K26, ED40), (X3, K26, ED42), (X3, K26, ED42), (X3, K26, ED43), (X3, K26, ED44), (X3, K26, ED45), (X3, K26, ED46), (X3, K26, ED47), (X3, K26, ED48), (X3, K26, ED49), (X3, K26, ED50), (X3, K26, ED51), (X3, K26, ED52), (X3, K26, ED53), (X3, K26, ED54), (X3, K26, ED55), (X3, K26, ED56), (X3, K26, ED57), (X3, K26, ED58), (X3, K26, ED59), (X3, K26, ED60), (X3, K26, ED61), (X3, K26, ED62), (X3, K26, ED63), (X3, K26, ED64), (X3, K26, ED65), (X3, K26, ED66), (X3, K26, ED67), (X3, K26, ED68), (X3, K26, ED69), (X3, K26, ED70), (X3, K26, ED71), (X3, K26, ED72), (X3, K26, ED73), (X3, K26, ED74), (X3, K26, ED75), (X3, K26, ED76), (X3, K26, ED77), (X3, K26, ED78), (X3, K26, ED79), (X3, K26, ED80), (X3, K26, ED81), (X3, K26, ED82), (X3, K26, ED83), (X3, K26, ED84), (X3, K26, ED85), (X3, K26, ED86), (X3, K26, ED87), (X3, K26, ED88), (X3, K26, ED89), (X3, K26, ED90), (X3, K26, ED91), (X3, K26, ED92), (X3, K27, ED1), (X3, K27, ED2), (X3, K27, ED3), (X3, K27, ED4), (X3, K27, ED5), (X3, K27, ED6), (X3, K27, ED7), (X3, K27, ED8), (X3, K27, ED9), (X3, K27, ED10), (X3, K27, ED11), (X3, K27, ED12), (X3, K27, ED13), (X3, K27, ED14), (X3, K27, ED15), (X3, K27, ED16), (X3, K27, ED17), (X3, K27, ED18), (X3, K27, ED19), (X3, K27, ED20), (X3, K27, ED21), (X3, K27, ED22), (X3, K27, ED23), (X3, K27, ED24), (X3, K27, ED25), (X3, K27, ED26), (X3, K27, ED27), (X3, K27, ED28), (X3, K27, ED29), (X3, K27, ED30), (X3, K27, ED31), (X3, K27, ED32), (X3, K27, ED33), (X3, K27, ED34), (X3, K27, ED35), (X3, K27, ED36), (X3, K27, ED37), (X3, K27, ED38), (X3, K27, ED39), (X3, K27, ED40), (X3, K27, ED41), (X3, K27, ED42), (X3, K27, ED43), (X3, K27, ED44), (X3, K27, ED45), (X3, K27, ED46), (X3, K27, ED47), (X3, K27, ED48), (X3, K27, ED49), (X3, K27, ED50), (X3, K27, ED51), (X3, K27, ED52), (X3, K27, ED53), (X3, K27, ED54), (X3, K27, ED55), (X3, K27, ED56), (X3, K27, ED57), (X3, K27, ED58), (X3, K27, ED59), (X3, K27, ED60), (X3, K27, ED61), (X3, K27, ED62), (X3, K27, ED63), (X3, K27, ED64), (X3, K27, ED65), (X3, K27, ED66), (X3, K27, ED67), (X3, K27, ED68), (X3, K27, ED69), (X3, K27, ED70), (X3, K27, ED71), (X3, K27, ED72), (X3, K27, ED73), (X3, K27, ED74), (X3, K27, ED75), (X3, K27, ED76), (X3, K27, ED77), (X3, K27, ED78), (X3, K27, ED79), (X3, K27, ED80), (X3, K27, ED81), (X3, K27, ED82), (X3, K27, ED83), (X3, K27, ED84), (X3, K27, ED85), (X3, K27, ED86), (X3, K27, ED87), (X3, K27, ED88), (X3, K27, ED89), (X3, K27, ED90), (X3, K27, ED91), (X3, K27, ED92), (X3, K28, ED1), (X3, K28, ED2), (X3, K28, ED3), (X3, K28, ED4), (X3, K28, ED5), (X3, K28, ED6), (X3, K28, ED7), (X3, K28, ED8), (X3, K28, ED9), (X3, K28, ED10), (X3, K28, ED11), (X3, K28, ED12), (X3, K28, ED13), (X3, K28, ED14), (X3, K28, ED15), (X3, K28, ED16), (X3, K28, ED17), (X3, K28, ED18), (X3, K28, ED19), (X3, K28, ED20), (X3, K28, ED21), (X3, K28, ED22), (X3, K28, ED23), (X3, K28, ED24), (X3, K28, ED25), (X3, K28, ED26), (X3, K28, ED27), (X3, K28, ED28), (X3, K28, ED29), (X3, K28, ED30), (X3, K28, ED31), (X3, K28, ED32), (X3, K28, ED33), (X3, K28, ED34), (X3, K28, ED35), (X3, K28, ED36), (X3, K28, ED37), (X3, K28, ED38), (X3, K28, ED39), (X3, K28, ED40), (X3, K28, ED41), (X3, K28, ED42), (X3, K28, ED43), (X3, K28, ED44), (X3, K28, ED45), (X3, K28, ED46), (X3, K28, ED47), (X3, K28, ED48), (X3, K28, ED49), (X3, K28, ED50), (X3, K28, ED51), (X3, K28, ED52), (X3, K28, ED53), (X3, K28, ED54), (X3, K28, ED55), (X3, K28, ED56), (X3, K28, ED57), (X3, K28, ED58), (X3, K28, ED59), (X3, K28, ED60), (X3, K28, ED61), (X3, K28, ED62), (X3, K28, ED63), (X3, K28, ED64), (X3, K28, ED65), (X3, K28, ED66), (X3, K28, ED67), (X3, K28, ED68), (X3, K28, ED69), (X3, K28, ED70), (X3, K28, ED71), (X3, K28, ED72), (X3, K28, ED73), (X3, K28, ED74), (X3, K28, ED75), (X3, K28, ED76), (X3, K28, ED77), (X3, K28, ED78), (X3, K28, ED79), (X3, K28, ED80), (X3, K28, ED81), (X3, K28, ED82), (X3, K28, ED83), (X3, K28, ED84), (X3, K28, ED85), (X3, K28, ED86), (X3, K28, ED87), (X3, K28, ED88), (X3, K28, ED89), (X3, K28, ED90), (X3, K28, ED91), (X3, K28, ED92), (X3, K29, ED1), (X3, K29, ED2), (X3, K29, ED3), (X3, K29, ED4), (X3, K29, ED5), (X3, K29, ED6), (X3, K29, ED7), (X3, K29, ED8), (X3, K29, ED9), (X3, K29, ED10), (X3, K29, ED11), (X3, K29, ED12), (X3, K29, ED13), (X3, K29, ED14), (X3, K29, ED15), (X3, K29, ED16), (X3, K29, ED17), (X3, K29, ED18), (X3, K29, ED19), (X3, K29, ED20), (X3, K29, ED21), (X3, K29, ED22), (X3, K29, ED23), (X3, K29, ED24), (X3, K29, ED25), (X3, K29, ED26), (X3, K29, ED27), (X3, K29, ED28), (X3, K29, ED29), (X3, K29, ED30), (X3, K29, ED31), (X3, K29, ED32), (X3, K29, ED33), (X3, K29, ED34), (X3, K29, ED35), (X3, K29, ED36), (X3, K29, ED37), (X3, K29, ED38), (X3, K29, ED39), (X3, K29, ED40), (X3, K29, ED41), (X3, K29, ED42), (X3, K29, ED43), (X3, K29, ED44), (X3, K29, ED45), (X3, K29, ED46), (X3, K29, ED47), (X3, K29, ED48), (X3, K29, ED49), (X3, K29, ED50), (X3, K29, ED51), (X3, K29, ED52), (X3, K29, ED53), (X3, K29, ED54), (X3, K29, ED55), (X3, K29, ED56), (X3, K29, ED57), (X3, K29, ED58), (X3, K29, ED59), (X3, K29, ED60), (X3, K29, ED61), (X3, K29, ED62), (X3, K29, ED63), (X3, K29, ED64), (X3, K29, ED65), (X3, K29, ED66), (X3, K29, ED67), (X3, K29,

ED68), (X3, K29, ED69), (X3, K29, ED70), (X3, K29, ED71), (X3, K29, ED72), (X3, K29, ED73), (X3, K29, ED74), (X3, K29, ED75), (X3, K29, ED76), (X3, K29, ED77), (X3, K29, ED78), (X3, K29, ED79), (X3, K29, ED80), (X3, K29, ED81), (X3, K29, ED82), (X3, K29, ED83), (X3, K29, ED84), (X3, K29, ED85), (X3, K29, ED86), (X3, K29, ED87), (X3, K29, ED88), (X3, K29, ED89), (X3, K29, ED90), (X3, K29, ED91), (X3, K29, ED92), (X3, K30, ED1), (X3, K30, ED2), (X3, K30, ED3), (X3, K30, ED4), (X3, K30, ED5), (X3, K30, ED6), (X3, K30, ED7), (X3, K30, ED8), (X3, K30, ED9), (X3, K30, ED10), (X3, K30, ED11), (X3, K30, ED12), (X3, K30, ED13), (X3, K30, ED14), (X3, K30, ED15), (X3, K30, ED16), (X3, K30, ED17), (X3, K30, ED18), (X3, K30, ED19), (X3, K30, ED20), (X3, K30, ED21), (X3, K30, ED22), (X3, K30, ED23), (X3, K30, ED24), (X3, K30, ED25), (X3, K30, ED26), (X3, K30, ED27), (X3, K30, ED28), (X3, K30, ED29), (X3, K30, ED30), (X3, K30, ED31), (X3, K30, ED32), (X3, K30, ED33), (X3, K30, ED34), (X3, K30, ED35), (X3, K30, ED36), (X3, K30, ED37), (X3, K30, ED38), (X3, K30, ED39), (X3, K30, ED40), (X3, K30, ED41), (X3, K30, ED42), (X3, K30, ED43), (X3, K30, ED44), (X3, K30, ED45), (X3, K30, ED46), (X3, K30, ED47), (X3, K30, ED48), (X3, K30, ED49), (X3, K30, ED50), (X3, K30, ED51), (X3, K30, ED52), (X3, K30, ED53), (X3, K30, ED54), (X3, K30, ED55), (X3, K30, ED56), (X3, K30, ED57), (X3, K30, ED58), (X3, K30, ED59), (X3, K30, ED60), (X3, K30, ED61), (X3, K30, ED62), (X3, K30, ED63), (X3, K30, ED64), (X3, K30, ED65), (X3, K30, ED66), (X3, K30, ED67), (X3, K30, ED68), (X3, K30, ED69), (X3, K30, ED70), (X3, K30, ED71), (X3, K30, ED72), (X3, K30, ED73), (X3, K30, ED74), (X3, K30, ED75), (X3, K30, ED76), (X3, K30, ED77), (X3, K30, ED78), (X3, K30, ED79), (X3, K30, ED80), (X3, K30, ED81), (X3, K30, ED82), (X3, K30, ED83), (X3, K30, ED84), (X3, K30, ED85), (X3, K30, ED86), (X3, K30, ED87), (X3, K30, ED8), (X3, K30, ED89), (X3, K30, ED90), (X3, K30, ED91), (X3, K30, ED92), (X3, K31, ED1), (X3, K31, ED2), (X3, K31, ED3), (X3, K31, ED4), (X3, K31, ED5), (X3, K31, ED6), (X3, K31, ED7), (X3, K31, ED8), (X3, K31, ED9), (X3, K31, ED10), (X3, K31, ED11), (X3, K31, ED12), (X3, K31, ED13), (X3, K31, ED14), (X3, K31, ED15), (X3, K31, ED16), (X3, K31, ED17), (X3, K31, ED18), (X3, K31, ED19), (X3, K31, ED20), (X3, K31, ED21), (X3, K31, ED22), (X3, K31, ED23), (X3, K31, ED24), (X3, K31, ED25), (X3, K31, ED26), (X3, K31, ED27), (X3, K31, ED28), (X3, K31, ED29), (X3, K31, ED30), (X3, K31, ED31), (X3, K31, ED32), (X3, K31, ED33), (X3, K31, ED34), (X3, K31, ED35), (X3, K31, ED36), (X3, K31, ED37), (X3, K31, ED38), (X3, K31, ED39), (X3, K31, ED40), (X3, K31, ED41), (X3, K31, ED42), (X3, K31, ED43), (X3, K31, ED44), (X3, K31, ED45), (X3, K31, ED46), (X3, K31, ED47), (X3, K31, ED48), (X3, K31, ED49), (X3, K31, ED50), (X3, K31, ED51), (X3, K31, ED52), (X3, K31, ED53), (X3, K31, ED54), (X3, K31, ED55), (X3, K31, ED56), (X3, K31, ED57), (X3, K31, ED58), (X3, K31, ED59), (X3, K31, ED60), (X3, K31, ED61), (X3, K31, ED62), (X3, K31, ED63), (X3, K31, ED64), (X3, K31, ED65), (X3, K31, ED66), (X3, K31, ED67), (X3, K31, ED68), (X3, K31, ED69), (X3, K31, ED70), (X3, K31, ED71), (X3, K31, ED72), (X3, K31, ED73), (X3, K31, ED74), (X3, K31, ED75), (X3, K31, ED76), (X3, K31, ED77), (X3, K31, ED78), (X3, K31, ED79), (X3, K31, ED80), (X3, K31, ED81), (X3, K31, ED82), (X3, K31, ED83), (X3, K31, ED84), (X3, K31, ED85), (X3, K31, ED86), (X3, K31, ED87), (X3, K31, ED88), (X3, K31, ED89), (X3, K31, ED90), (X3, K31, ED91), (X3, K31, ED92).

Test Example 1

Compound (I) of the subject invention has been investigated for in vitro antimicrobial activity thereof.
(Test Methods)
(Microbe/Strain Species Nos. 1-4):
Measurement of Minimum Inhibitory Concentration (MIC: microgram/ml) was conducted according to the standard method of the Japan Society for Chemotherapy, and the amount of bacteria for inoculation was 1000 cfu/spot, and sensitive disc medium was used as the test medium, and conducted using agar plate incubation.
(Microbe/Strain Species Nos. 5):
Measurement of Minimum Inhibitory Concentration (MIC, microgram/ml) was conducted according to the CLSI (Clinical and Laboratory Standards Institute) and the amount of bacteria for inoculation was 10000 cfu/spot, and Mueller-Hinton agar medium was used as the test medium, and conducted using agar plate incubation.
Test results are shown in Table 10 and 11. In the tables, the unit of the values of inhibitory activity is microgram/ml (μg/ml)

TABLE 10

| Bacteria Strain No. | Bacteria Species | Strain Name | Compound (I-2) | Compound (I-4) | Compound (I-6) | Compound (I-8) |
|---|---|---|---|---|---|---|
| 1 | Klebsiella pneumoniae | ATCC 700603 | 1 | 0.25 | 0.25 | 0.5 |
| 2 | Pseudomonas aeruginosa | SR24 | 0.125 | 0.063 | 0.063 | 0.125 |
| 3 | Pseudomonas aeruginosa | SR27060 | 1 | 0.25 | 0.25 | 0.5 |
| 4 | Acinetobacter baumannii | SR24395 | 1 | 0.5 | 0.25 | 0.5 |
| 5 | Stenotrohomonas maltophilia | SR21970 | | 1 | 1 | 2 |

TABLE 11

| Bacteria Strain No. | Bacteria Species | Strain Name | Compound (1-11) | Compound (1-18) |
|---|---|---|---|---|
| 1 | Klebsiella pneumoniae | ATCC 700603 | 0.5 | 0.5 |
| 2 | Pseudomonas aeruginosa | SR24 | 0.25 | 0.25 |
| 3 | Pseudomonas aeruginosa | SR27060 | 1 | 0.5 |
| 4 | Acinetobacter baumannii | SR24396 | 0.25 | 0.25 |
| 5 | Stenotrohomonas maltophilia | SR21970 | 1 | 1 |

Description of the bacterial species in the above tables, enzymes (beta-lactamase) produced thereby, and the strain types are shown in Table 12 below.

TABLE 12

| Bacteria Species | Strain Name | Enzyme Produced | Strain Type |
|---|---|---|---|
| K. pneumoniae | ATCC700603 | SHV-18 | ESBL producing strain |
| P. aeruginosa | SR24 | None | Ceftazidime sensitive strain |
| P. aeruginosa | SR27060 | IMP-1 | MBL producing strain (carbapenem resistant strain) |
| A. baumannii | SR24396 | None | |
| S. maltophilia | SR21970 | L-1 | MBL producing strain (carbapenem resistant strain) |

Test Example 2

Compound (I) of the subject invention has been investigated for in vitro antimicrobial activity thereof.

(Test Methods)

Mice (ICR series, male, 5-week-aged) were inoculated intraperitoneally with P. aeruginosa SR27001 (multidrug-resistant Pseudomonas aeruginosa; IMP-1 producing strain) to raise infection. One and half hours after, mice were treated with intravenous administration in twice, and then the ED50 value was calculated based on the survival rate after 7 days.

Test Results: The Compound (I) of the subject invention exhibited efficacy in vivo.

As shown in the above results, the compounds of the subject invention were shown to have a wide antimicrobial spectrum, in particular, potent antimicrobial spectrum against Gram negative bacteria, and/or effectiveness against multidrug resistant bacteria, and exhibited high stability against beta-lactamase producing Gram negative bacteria. In comparison to cefepime hydrochloride hydrate (CFPM) commercially available as beta-lactamase resistant cephalosporin antibiotics having a similar structure, it was shown that the compounds of the subject invention have more potent antimicrobial activity. Consequently, it was shown that the compounds of the subject invention are useful as pharmaceutical products.

Formulation Example 1

Powder of the compounds of the subject invention is loaded to prepare a formulation for injection.

INDUSTRIAL APPLICABILITY

The compounds of the subject invention have a wide antimicrobial spectrum, and are effective as an antimicrobial drug having high stability against beta-lactamase producing Gram negative bacteria. Moreover, the subject compounds have good bioavailability, and high water solubility, and thus particularly useful for injectable formulation.

The invention claimed is:

1. A compound of the formula:

[Formula 1]

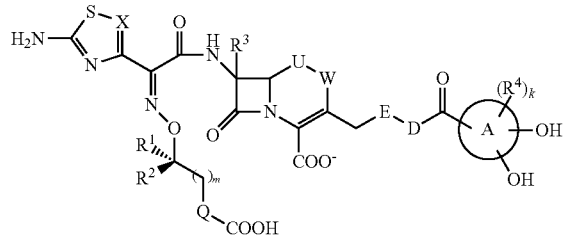

(I)

or an ester, a protected compound at the amino on the ring in the 7-side chain, or a pharmaceutically acceptable salt thereof, wherein X is $-N=$, $-CH=$, $-C(-R^5)=$, $-C(-Br)=$ or $-C(-Cl)=$;

$R^5$ is lower alkyl or halo(lower)alkyl;

W is $-CH_2-$, $-S-$ or $-O-$;

U is $-CH_2-$, $-S-$ or $-O-$ when W is $-CH_2-$, or U is $-CH_2-$ when W is $-S-$ or $-O-$;

$R^1$ and $R^2$ are each independently hydrogen atom, halogen, hydroxy, carboxy, optionally substituted lower alkyl, optionally substituted carbocyclic group or optionally substituted heterocyclic group; or $R^1$ and $R^2$ taken together with a neighboring atom may form an optionally substituted carbocyclic group or an optionally substituted heterocyclic group;

Q is a single bond, optionally substituted carbocyclic group, or an optionally substituted heterocyclic group;

ring A is a 6-membered aromatic heterocyclic group having 1 nitrogen atom;

$R^3$ is hydrogen atom, $-OCH_3$ or $-NH-CH(=O)$;

k is an integer from 0 to 2;

m is an integer from 0 to 2;

each $R^4$ is independently hydrogen atom, halogen, hydroxy, $-CN$, $-C(=O)-R^6$, $-C(=O)-OH$, or $-OR^6$;

$R^6$ is lower alkyl or halo(lower)alkyl;

with regard to D and E, a) D is a single bond, $-N(R^8)-$ or $-R^7-N(R^8)-$ wherein $R^7$ is an optionally substituted lower alkylene and $R^8$ is a hydrogen or lower alkyl, and E is an optionally substituted cyclic group selected from the following formulae (1) to (8), (10), (11), (13), (15) and (25) to (31); or b) D is the formula:

[Formula 2]

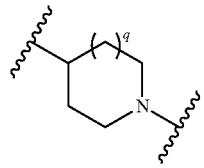

wherein q is 0 or 1, and
E is a group of formula (10) or (41) in the following formulae:
[Formula 3]
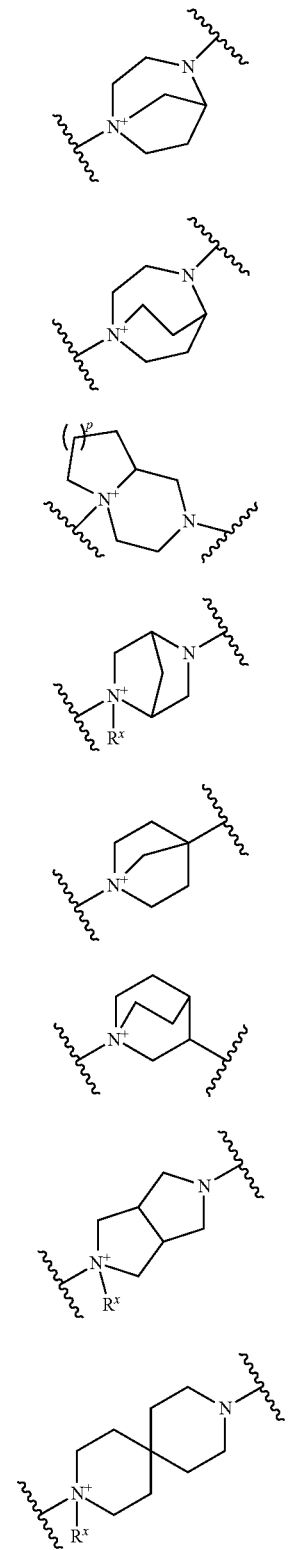
(1)
(2)
(3)
(4)
(5)
(6)
(7)
(8)
-continued
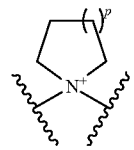
(10)
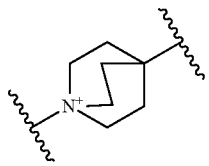
(11)
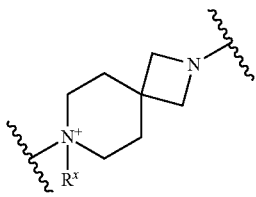
(13)
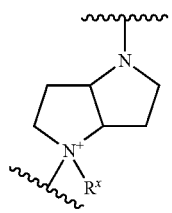
(15)
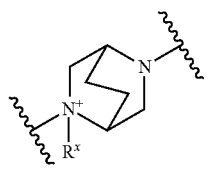
(25)
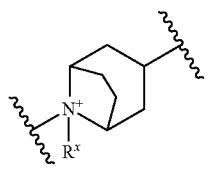
(26)
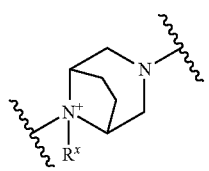
(27)
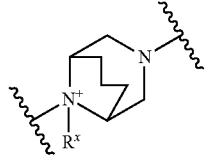
(28)

-continued

(29)
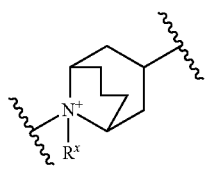

(30)
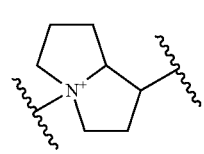

(31)
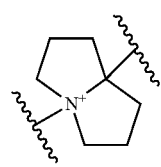

(41)
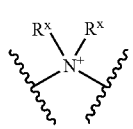

wherein p is an integer from 1 to 3; and $R^x$ is an optionally substituted lower alkyl.

2. The compound, or an ester, a protected compound at the amino on the ring in the 7-side chain, or a pharmaceutically acceptable salt thereof according to claim 1, wherein D is a single bond, —NH— or —$R^7$—NH—, $R^7$ is a lower alkylene, and E is selected from the formulae (1) to (8), (10), (11), (13), (15) and (25) to (31).

3. The compound, or an ester, a protected compound at the amino on the ring in the 7-side chain, or a pharmaceutically acceptable salt thereof according to claim 2, wherein D is —NH—, —$CH_2$—NH— or —$CH_2$—$CH_2$—NH—.

4. The compound, or an ester, a protected compound at the amino on the ring in the 7-side chain, or a pharmaceutically acceptable salt thereof according to claim 2, wherein D is a single bond.

5. The compound, or an ester, a protected compound at the amino on the ring in the 7-side chain, or a pharmaceutically acceptable salt thereof according to claim 1, wherein D is the formula:

[Formula 5]
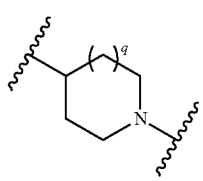

wherein q is as defined in claim 1.

6. The compound, or an ester, a protected compound at the amino on the ring in the 7-side chain, or a pharmaceutically acceptable salt thereof according to claim 1, wherein U is —S—.

7. The compound, or an ester, a protected compound at the amino on the ring in the 7-side chain, or a pharmaceutically acceptable salt thereof according to claim 1, wherein W is —$CH_2$—.

8. The compound, or an ester, a protected compound at the amino on the ring in the 7-side chain, or a pharmaceutically acceptable salt thereof according to claim 1, wherein $R^3$ is hydrogen atom or —$OCH_3$.

9. The compound, or an ester, a protected compound at the amino on the ring in the 7-side chain, or a pharmaceutically acceptable salt thereof according to claim 1, wherein X is —N=, —CH= or —C(—Cl)=.

10. The compound, or an ester, a protected compound at the amino on the ring in the 7-side chain, or a pharmaceutically acceptable salt thereof according to claim 1, wherein the formula:

[Formula 8]
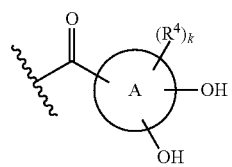

is selected from the formula:

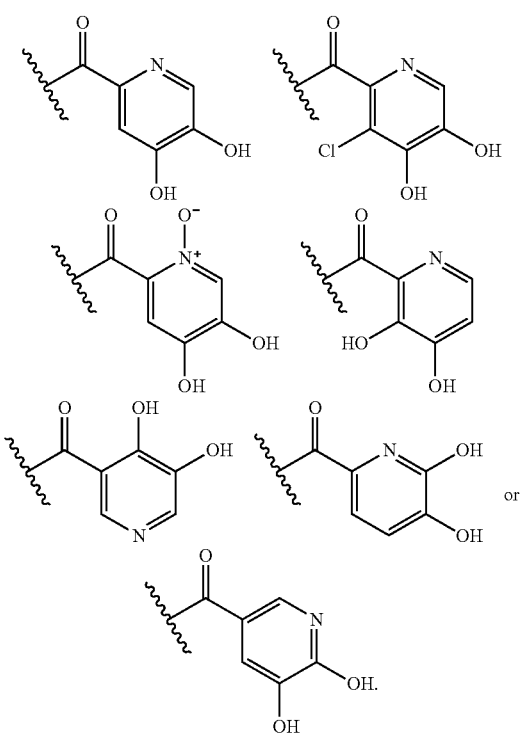

11. The compound, or an ester, a protected compound at the amino on the ring in the 7-side chain, or a pharmaceutically acceptable salt thereof according to claim 1, wherein Q is a single bond or an optionally substituted phenylene.

12. The compound, or an ester, a protected compound at the amino on the ring in the 7-side chain, or a pharmaceutically acceptable salt thereof according to claim 11, wherein $R^1$ is an optionally substituted lower alkyl and $R^2$ is a hydrogen atom.

13. The compound, or an ester, a protected compound at the amino on the ring in the 7-side chain, or a pharmaceutically acceptable salt thereof according to claim 11, wherein $R^1$ is hydrogen atom and $R^2$ is an optionally substituted lower alkyl.

14. The compound, or an ester, a protected compound at the amino on the ring in the 7-side chain, or a pharmaceutically acceptable salt thereof according to claim 11, wherein $R^1$ and $R^2$ are each independently lower alkyl.

15. The compound, or an ester, a protected compound at the amino on the ring in the 7-side chain, or a pharmaceutically acceptable salt thereof according to claim 12, wherein m is 0.

16. A pharmaceutical composition, which comprises a compound, or an ester, a protected compound at the amino on the ring in the 7-side chain, or a pharmaceutically acceptable salt thereof according to claim 1.

17. The pharmaceutical composition according to claim 16, which possesses antimicrobial activity.

18. A method for treating a bacterial infection, characterized in that the compound, or an ester, a protected compound at the amino on the ring in the 7-side chain, or a pharmaceutically acceptable salt thereof according to claim 1 is administered.

19. The compound, or an ester, a protected compound at the amino on the ring in the 7-side chain, or a pharmaceutically acceptable salt thereof according to claim 1, wherein E is a group selected from the formulae (1) to (7), (10), (11), (15), (25) to (31) and (41).

20. The compound, or an ester, a protected compound at the amino on the ring in the 7-side chain, or a pharmaceutically acceptable salt thereof according to claim 1, wherein E is a group selected from the formulae (1) to (6), (10), (11), (15), (25) to (29) and (41).

21. The compound, or an ester, a protected compound at the amino on the ring in the 7-side chain, or a pharmaceutically acceptable salt thereof according to claim 1, wherein E is a group selected from the formulae (1) to (6), (10), (11), (15), (26), (29) and (41).

22. The compound, or an ester, a protected compound at the amino on the ring in the 7-side chain, or a pharmaceutically acceptable salt thereof according to claim 1, wherein E is a group selected from the formulae (2) to (3), (10), (11), (26) and (41).

* * * * *